US011851694B1

(12) United States Patent
Mauger et al.

(10) Patent No.: US 11,851,694 B1
(45) Date of Patent: Dec. 26, 2023

(54) HIGH FIDELITY IN VITRO TRANSCRIPTION

(71) Applicant: ModernaTX, Inc., Cambridge, MA (US)

(72) Inventors: David Mauger, Arlington, MA (US); Vladimir Presnyak, Manchester, NH (US); Amy E. Rabideau, Waltham, MA (US); Iain Mcfadyen, Arlington, MA (US)

(73) Assignee: ModernaTX, Inc., Cambridge, MA (US)

( * ) Notice: Subject to any disclaimer, the term of this patent is extended or adjusted under 35 U.S.C. 154(b) by 632 days.

(21) Appl. No.: 16/794,318

(22) Filed: Feb. 19, 2020

Related U.S. Application Data

(60) Provisional application No. 62/808,099, filed on Feb. 20, 2019.

(51) Int. Cl.
C12P 19/34 (2006.01)
C12N 15/11 (2006.01)

(52) U.S. Cl.
CPC .............. *C12P 19/34* (2013.01); *C12N 15/11* (2013.01)

(58) Field of Classification Search
CPC .................................. C12P 19/34; C12N 15/11
See application file for complete search history.

(56) References Cited

U.S. PATENT DOCUMENTS

| | | | |
|---|---|---|---|
| 7,335,471 B2 | 2/2008 | Guillerez et al. |
| 8,710,200 B2 | 4/2014 | Schrum et al. |
| 8,754,062 B2 | 6/2014 | De Fougerolles et al. |
| 8,822,663 B2 | 9/2014 | Schrum et al. |
| 8,999,380 B2 | 4/2015 | Bancel et al. |
| 9,045,740 B2 | 6/2015 | Martin et al. |
| 9,163,246 B2 | 10/2015 | Barnes |
| 9,221,891 B2 | 12/2015 | Bancel et al. |
| 9,283,287 B2 | 3/2016 | Bancel et al. |
| 9,303,079 B2 | 4/2016 | Bancel et al. |
| 9,464,124 B2 | 10/2016 | Bancel et al. |
| 9,512,456 B2 | 12/2016 | Wang et al. |
| 9,597,380 B2 | 3/2017 | Chakraborty et al. |
| 9,868,691 B2 | 1/2018 | Benenato et al. |
| 9,872,900 B2 | 1/2018 | Ciaramella et al. |
| 10,064,934 B2 | 9/2018 | Ciaramella et al. |
| 10,064,935 B2 | 9/2018 | Ciaramella et al. |
| 10,124,055 B2 | 11/2018 | Ciaramella et al. |
| 10,207,010 B2 | 2/2019 | Besin et al. |
| 10,273,269 B2 | 4/2019 | Ciaramella |
| 10,449,244 B2 | 10/2019 | Ciaramella et al. |
| 10,465,190 B1 | 11/2019 | Chen et al. |
| 10,493,143 B2 | 12/2019 | Ciaramella et al. |
| 10,526,629 B2 | 1/2020 | Rabideau et al. |
| 10,653,712 B2 | 5/2020 | Hoge |
| 10,653,767 B2 | 5/2020 | Ciaramella et al. |
| 10,695,419 B2 | 6/2020 | Ciaramella et al. |
| 10,925,958 B2 | 2/2021 | Ciaramella |
| 11,045,540 B2 | 6/2021 | Ciaramella |
| 11,103,578 B2 | 8/2021 | Ciaramella et al. |
| 11,351,242 B1 | 6/2022 | Lori et al. |
| 2007/0037245 A1 | 2/2007 | Endo et al. |
| 2013/0059344 A1* | 3/2013 | Striedner ............... C12N 15/70 435/254.2 |
| 2013/0102034 A1 | 4/2013 | Schrum et al. |
| 2013/0236974 A1 | 9/2013 | De Fougerolles |
| 2013/0245103 A1 | 9/2013 | De Fougerolles et al. |
| 2013/0259923 A1 | 10/2013 | Bancel et al. |
| 2013/0266640 A1 | 10/2013 | De Fougerolles et al. |
| 2014/0147432 A1 | 5/2014 | Bancel et al. |
| 2014/0148502 A1 | 5/2014 | Bancel et al. |
| 2014/0193482 A1 | 7/2014 | Bancel et al. |
| 2014/0206752 A1 | 7/2014 | Afeyan et al. |
| 2014/0378538 A1 | 12/2014 | Bancel |
| 2015/0051268 A1 | 2/2015 | Bancel et al. |
| 2015/0056253 A1 | 2/2015 | Bancel et al. |
| 2015/0141499 A1 | 5/2015 | Bancel et al. |
| 2015/0307542 A1 | 10/2015 | Roy et al. |
| 2015/0315541 A1 | 11/2015 | Bancel et al. |
| 2015/0376581 A1 | 12/2015 | Brakmann et al. |
| 2016/0024140 A1 | 1/2016 | Issa et al. |
| 2016/0024141 A1 | 1/2016 | Issa et al. |
| 2016/0032261 A1 | 2/2016 | Sobek et al. |
| 2016/0032273 A1 | 2/2016 | Shahrokh et al. |
| 2016/0038612 A1 | 2/2016 | Hoge et al. |
| 2016/0243221 A1 | 8/2016 | Hoge et al. |
| 2016/0317647 A1 | 11/2016 | Ciaramella et al. |
| 2017/0043037 A1 | 2/2017 | Kariko et al. |
| 2017/0202979 A1 | 7/2017 | Chakraborty et al. |

(Continued)

FOREIGN PATENT DOCUMENTS

WO  WO 2013/050609 A1  4/2013
WO  WO-2014152027 A1 * 9/2014 ........... C12N 15/101

(Continued)

OTHER PUBLICATIONS

Singh RK et al. Protein Engineering Approaches in the Post-Genomic Era. 2017. Current Protein and Peptide Science. 18, 1-11. (Year: 2017).*
Zhang M et al. Propagated Perturbations from a Peripheral Mutation Show Interactions Supporting WW Domain Thermostability. 2018. Structure. 26, 1474-1485. (Year: 2018).*
U.S. Appl. No. 16/036,318, filed Jul. 16, 2018, Ciaramella et al.
U.S. Appl. No. 16/048,154, filed Jul. 27, 2018, Ciaramella et al.
U.S. Appl. No. 16/144,394, filed Sep. 27, 2018, Ciaramella et al.
U.S. Appl. No. 90/014,395, filed Oct. 24, 2019, Ciaramella et al.
U.S. Appl. No. 15/748,773, filed Jan. 30, 2018, Ciaramella et al.
U.S. Appl. No. 15/753,293, filed Feb. 17, 2018, Smith.
U.S. Appl. No. 15/753,297, filed Feb. 17, 2018, Thompson.
U.S. Appl. No. 15/748,782, filed Jan. 30, 2018, Mousavi et al.
U.S. Appl. No. 15/767,587, filed Apr. 11, 2018, Ciaramella.
U.S. Appl. No. 16/450,882, filed Jun. 24, 2019, Ciaramella.
U.S. Appl. No. 16/833,409, filed Mar. 27, 2020, Ciaramella.

(Continued)

*Primary Examiner* — Paul J Holland
(74) *Attorney, Agent, or Firm* — Wolf, Greenfield & Sacks, P.C.

(57) ABSTRACT

The present disclosure provides methods and compositions for high fidelity in vitro transcription reactions.

15 Claims, 5 Drawing Sheets

Specification includes a Sequence Listing.

(56) References Cited

U.S. PATENT DOCUMENTS

| | | |
|---|---|---|
| 2017/0204152 A1 | 7/2017 | Nelson et al. |
| 2017/0130255 A1 | 10/2017 | Wang et al. |
| 2018/0000953 A1 | 1/2018 | Almarsson et al. |
| 2018/0002393 A1 | 1/2018 | Bancel et al. |
| 2018/0028664 A1 | 2/2018 | Besin et al. |
| 2018/0237849 A1 | 8/2018 | Thompson |
| 2018/0243225 A1 | 8/2018 | Ciaramella |
| 2018/0243230 A1 | 8/2018 | Smith |
| 2018/0256628 A1 | 9/2018 | Hoge et al. |
| 2018/0271795 A1 | 9/2018 | Martini et al. |
| 2018/0271970 A1 | 9/2018 | Ciaramella et al. |
| 2018/0273977 A1 | 9/2018 | Mousavi et al. |
| 2018/0274009 A1 | 9/2018 | Marquardt et al. |
| 2018/0280496 A1 | 10/2018 | Ciaramella et al. |
| 2018/0289792 A1 | 10/2018 | Ciaramella et al. |
| 2018/0303929 A1 | 10/2018 | Ciaramella et al. |
| 2018/0311336 A1 | 11/2018 | Ciaramella et al. |
| 2018/0311343 A1 | 11/2018 | Huang et al. |
| 2018/0318409 A1 | 11/2018 | Valiante et al. |
| 2018/0363019 A1 | 12/2018 | Hoge |
| 2018/0369374 A1 | 12/2018 | Frederick et al. |
| 2018/0371047 A1 | 12/2018 | Ticho et al. |
| 2019/0002890 A1 | 1/2019 | Martini et al. |
| 2019/0008938 A1 | 1/2019 | Ciaramella et al. |
| 2019/0085368 A1 | 3/2019 | Bancel et al. |
| 2019/0099481 A1 | 4/2019 | Ciaramella et al. |
| 2019/0175517 A1 | 6/2019 | Martini et al. |
| 2019/0175727 A1 | 6/2019 | Huang et al. |
| 2019/0192646 A1 | 6/2019 | Cohen et al. |
| 2019/0192653 A1 | 6/2019 | Hoge et al. |
| 2019/0275170 A1 | 9/2019 | Benenato et al. |
| 2019/0298657 A1 | 10/2019 | Martini et al. |
| 2019/0298658 A1 | 10/2019 | Benenato |
| 2019/0300906 A1 | 10/2019 | Martini et al. |
| 2019/0314292 A1 | 10/2019 | Benenato et al. |
| 2019/0314493 A1 | 10/2019 | Ciaramella et al. |
| 2019/0336452 A1 | 11/2019 | Brader |
| 2019/0336595 A1 | 11/2019 | Ciaramella |
| 2019/0351040 A1 | 11/2019 | Valiante et al. |
| 2019/0382774 A1 | 12/2019 | Hoge et al. |
| 2019/0390181 A1 | 12/2019 | Benenato et al. |
| 2020/0030432 A1 | 1/2020 | Ciaramella et al. |
| 2020/0032274 A1 | 1/2020 | Mauger et al. |
| 2020/0038499 A1 | 2/2020 | Narayanan et al. |
| 2020/0054737 A1 | 2/2020 | Ciaramella et al. |
| 2020/0069599 A1 | 3/2020 | Smith et al. |
| 2020/0069793 A1 | 3/2020 | Ciaramella |
| 2020/0069794 A1 | 3/2020 | Ciaramella et al. |
| 2020/0071689 A1 | 3/2020 | Miracco |
| 2020/0085916 A1 | 3/2020 | Martini et al. |
| 2020/0109420 A1 | 4/2020 | Brito et al. |
| 2020/0129608 A1 | 4/2020 | Ciaramella et al. |
| 2020/0129615 A1 | 4/2020 | Ciaramella et al. |
| 2020/0239869 A1 | 7/2020 | Issa et al. |
| 2020/0254086 A1 | 8/2020 | Hoge et al. |
| 2020/0282047 A1 | 9/2020 | Ciaramella et al. |
| 2021/0046173 A1 | 2/2021 | Ciaramella et al. |
| 2021/0163919 A1 | 6/2021 | Issa et al. |
| 2021/0187097 A1 | 6/2021 | Ciaramella et al. |
| 2021/0217484 A1 | 7/2021 | Giessel et al. |
| 2021/0228707 A1 | 7/2021 | Mektar et al. |
| 2021/0268086 A1 | 9/2021 | Zhong et al. |
| 2021/0309976 A1 | 10/2021 | Dousis et al. |
| 2022/0031631 A1 | 2/2022 | Almarsson et al. |
| 2022/0047518 A1 | 2/2022 | Hennessy et al. |
| 2022/0054653 A1 | 2/2022 | Martini et al. |
| 2022/0062408 A1 | 3/2022 | Kramarczyk et al. |
| 2022/0125899 A1 | 4/2022 | Ashburn et al. |
| 2022/0145381 A1 | 5/2022 | Elich et al. |

FOREIGN PATENT DOCUMENTS

| | | |
|---|---|---|
| WO | WO 2016/164762 A1 | 10/2016 |
| WO | WO 2016/201377 A1 | 12/2016 |
| WO | WO 2017/011773 A1 | 1/2017 |
| WO | WO 2017/015457 A1 | 1/2017 |
| WO | WO 2017/020026 A1 | 2/2017 |
| WO | WO 2017/062513 A1 | 4/2017 |
| WO | WO 2017/066789 A1 | 4/2017 |
| WO | WO 2017/070601 A1 | 4/2017 |
| WO | WO 2017/127750 A1 | 7/2017 |
| WO | WO 2017/201333 A1 | 11/2017 |
| WO | WO 2017/201340 A1 | 11/2017 |
| WO | WO 2017/201342 A1 | 11/2017 |
| WO | WO 2017/201347 A1 | 11/2017 |
| WO | WO 2018/053209 A1 | 3/2018 |
| WO | WO 2018/075980 A1 | 4/2018 |
| WO | WO 2018/081459 A1 | 5/2018 |
| WO | WO 2018/089851 A1 | 5/2018 |
| WO | WO 2018/107088 A1 | 6/2018 |
| WO | WO 2018/111967 A1 | 6/2018 |
| WO | WO 2018/144082 A1 | 8/2018 |
| WO | WO 2018/144778 A1 | 8/2018 |
| WO | WO 2018/170245 A1 | 9/2018 |
| WO | WO 2018/170256 A1 | 9/2018 |
| WO | WO 2018/170260 A1 | 9/2018 |
| WO | WO 2018/170270 A1 | 9/2018 |
| WO | WO 2018/170347 A1 | 9/2018 |
| WO | WO 2018/175783 A1 | 9/2018 |
| WO | WO 2018/187590 A2 | 10/2018 |
| WO | WO 2018/200737 A2 | 11/2018 |
| WO | WO 2018/232355 A1 | 12/2018 |
| WO | WO 2018/232357 A1 | 12/2018 |
| WO | WO 2019/005540 A1 | 1/2019 |
| WO | WO 2019/036670 A1 | 2/2019 |
| WO | WO 2019/036683 A1 | 2/2019 |
| WO | WO 2019/036685 A1 | 2/2019 |
| WO | WO 2019/103993 A1 | 5/2019 |
| WO | WO 2018/157009 A1 | 8/2019 |
| WO | WO 2019/148101 A1 | 8/2019 |
| WO | WO 2020/006242 A1 | 1/2020 |
| WO | WO 2020/056370 A1 | 3/2020 |
| WO | WO 2020/061284 A1 | 3/2020 |
| WO | WO 2020/061295 A1 | 3/2020 |
| WO | WO 2020/061367 A1 | 3/2020 |
| WO | WO 2020/146814 A1 | 7/2020 |
| WO | WO 2020/190750 A1 | 9/2020 |
| WO | WO 2020/243561 A1 | 12/2020 |
| WO | WO 2021/030533 A1 | 2/2021 |
| WO | WO 2021/050864 A1 | 3/2021 |
| WO | WO 2021/055811 A1 | 3/2021 |
| WO | WO 2021/155243 A1 | 8/2021 |
| WO | WO 2021/159040 A2 | 8/2021 |
| WO | WO 2021/159130 A2 | 8/2021 |
| WO | WO 2021/211343 A1 | 10/2021 |
| WO | WO 2021/222304 A1 | 11/2021 |
| WO | WO 2021/231929 A1 | 11/2021 |
| WO | WO 2021/231963 A1 | 11/2021 |
| WO | WO 2021/237084 A1 | 11/2021 |
| WO | WO 2021/247817 A1 | 12/2021 |
| WO | WO 2022/067010 A1 | 3/2022 |

OTHER PUBLICATIONS

U.S. Appl. No. 15/767,600, filed Apr. 11, 2018, Ciaramella et al.
U.S. Appl. No. 15/769,710, filed Apr. 19, 2018, Ciaramella et al.
U.S. Appl. No. 15/767,609, filed Apr. 11, 2018, Ciaramella et al.
U.S. Appl. No. 15/767,613, filed Apr. 11, 2018, Ciaramella et al.
U.S. Appl. No. 15/767,618, filed Apr. 11, 2018, Ciaramella et al.
U.S. Appl. No. 16/136,503, filed Sep. 20, 2018, Ciaramella et al.
U.S. Appl. No. 16/853,973, filed Apr. 21, 2020, Ciaramella et al.
U.S. Appl. No. 16/850,519, filed Apr. 16, 2020, Ciaramella et al.
U.S. Appl. No. 15/746,286, filed Jan. 19, 2018, Ciaramella et al.
U.S. Appl. No. 16/009,880, filed Jun. 15, 2018, Ciaramella et al.
U.S. Appl. No. 15/981,762, filed May 16, 2018, Bancel et al.
U.S. Appl. No. 16/582,621, filed Sep. 25, 2019, Chen et al.
U.S. Appl. No. 16/599,661, filed Oct. 11, 2019, Besin et al.
U.S. Appl. No. 16/001,786, filed Jun. 6, 2018, Hoge et al.
U.S. Appl. No. 16/333,330, filed Mar. 14, 2019, Hoge et al.
U.S. Appl. No. 16/839,278, filed Apr. 3, 2020, Hoge et al.
U.S. Appl. No. 16/389,545, filed Apr. 19, 2019, Ciaramella et al.
U.S. Appl. No. 16/864,566, filed May 1, 2020, Ciaramella et al.

(56) References Cited

OTHER PUBLICATIONS

U.S. Appl. No. 16/368,270, filed Mar. 28, 2019, Ciaramella et al.
U.S. Appl. No. 16/805,587, filed Feb. 28, 2020, Ciaramella et al.
U.S. Appl. No. 16/468,838, filed Jun. 12, 2019, Miracco.
U.S. Appl. No. 16/001,765, filed Jun. 6, 2018, Marquardt et al.
U.S. Appl. No. 16/348,943, filed May 10, 2019, Ciaramella.
U.S. Appl. No. 16/467,142, filed Jun. 6, 2019, Ciaramella et al.
U.S. Appl. No. 16/603,111, filed Oct. 4, 2019, Brito et al.
U.S. Appl. No. 16/482,844, filed Aug. 1, 2019, Valiante et al.
U.S. Appl. No. 16/496,135, filed Sep. 20, 2019, Narayanan et al.
U.S. Appl. No. 16/483,012, filed Aug. 1, 2019, Mauger et al.
U.S. Appl. No. 16/657,122, filed Oct. 18, 2019, Rabideau et al.
U.S. Appl. No. 16/362,366, filed Mar. 22, 2019, Ciaramella.
U.S. Appl. No. 16/493,986, filed Sep. 13, 2019, Ciaramella et al.
U.S. Appl. No. 16/494,130, filed Sep. 13, 2019, Ciaramella et al.
U.S. Appl. No. 16/494,103, filed Sep. 13, 2019, Ciaramella et al.
U.S. Appl. No. 16/494,162, filed Sep. 13, 2019, Ciaramella.
U.S. Appl. No. 16/494,988, filed Sep. 17, 2019, Ciaramella et al.
U.S. Appl. No. 16/639,265, filed Feb. 14, 2020, Issa et al.
U.S. Appl. No. 16/639,305, filed Feb. 14, 2020, Issa et al.
U.S. Appl. No. 16/302,607, filed Nov. 16, 2018, Benenato et al.
U.S. Appl. No. 16/623,069, filed Dec. 16, 2019, Hoge et al.
U.S. Appl. No. 16/639,403, filed Feb. 14, 2020, Hoge et al.
U.S. Appl. No. 16/131,793, filed Sep. 14, 2018, Ciaramella et al.
U.S. Appl. No. 16/848,318, filed Apr. 14, 2020, Ciaramella et al.
U.S. Appl. No. 16/608,451, filed Oct. 25, 2019, Ciaramella et al.
U.S. Appl. No. 16/788,182, filed Feb. 11, 2020, Panther et al.
Mellits, K.H. et al., Removal of double-stranded contaminants from RNA transcripts: synthesis of adenovirus VA RNAI from a T7 vector. Nucleic Acids Res. Sep. 25, 1990;18(18):5401-6.
Mignone, F. et al., Untranslated regions of mRNAs. Genome Biol. 2002;3(3):REVIEWS0004. Epub Feb. 28, 2002. pp. 1-10.

\* cited by examiner

HIGH FIDELITY IN VITRO TRANSCRIPTION

RELATED APPLICATION

This application claims the benefit under 35 U.S.C. § 119(e) of U.S. provisional application No. 62/808,099, filed Feb. 20, 2019, which is incorporated by reference herein in its entirety.

REFERENCE TO A SEQUENCE LISTING SUBMITTED AS A TEXT FILE VIA EFS-WEB

The instant application contains a Sequence Listing which has been submitted in ASCII format via EFS-Web and is hereby incorporated by reference in its entirety. Said ASCII copy, created on Nov. 17, 2022, is named M137870119US01-SUBSEQ-MSB and is 347,140 bytes in size.

SUMMARY

Provided herein, in some aspects, are methods and compositions for high fidelity in vitro transcription (IVT) reactions. In vitro transcription reactions are often contaminated with various RNA species, such as truncated species, the presence of which decreases the yield of intended full-length RNA product. Data provided herein shows unexpectedly that many of these truncated RNA species resulting from early termination are the result of the presence of a non-canonical terminator sequence in the starting DNA. Modification of this non-canonical terminator sequence, even a simple 1-2 nucleotide mutation, is sufficient to reduce and/or prevent early termination of the intended full-length RNA product (see, e.g., Example 3 and FIG. 6).

Surprisingly, the data provided herein also shows that the level of IVT contamination varies with the type of RNA polymerase used, and that this variation depends at least in part on the presence of the non-canonical termination motif in the starting DNA. For example, as shown in FIG. 1, the percentage of truncated RNA species produced in an in vitro transcription reaction varied significantly between an IVT reaction that used wild-type T7 RNA polymerase and an IVT reaction that used a T7 RNA polymerase variant. With wild-type polymerase, only 7.2% of the RNA includes truncated species. By contrast, with variant polymerase, 33.2% of the RNA included truncated species.

Thus, some aspects of the present disclosure provide methods of producing a messenger RNA (mRNA), the method comprising (a) identifying a non-canonical terminator motif NNATCTGTTNN (SEQ ID NO: 50) in a DNA encoding a mRNA that encodes a polypeptide, wherein Nat each position of the non-canonical terminator motif is any nucleotide selected from A, T, C, and G, (b) producing a modified DNA comprising at least one codon substitution in the non-canonical terminator motif that preserves the amino acid sequence of the polypeptide; and (c) optionally producing a modified mRNA in an in vitro transcription reaction that comprises the modified DNA. In some embodiments, the methods comprise producing a modified DNA comprising at least one codon substitution in the non-canonical terminator motif that preserves the amino acid sequence of the polypeptide, and producing a modified mRNA in an in vitro transcription reaction that comprises the modified DNA.

Other aspects of the present disclosure provide a modified DNA comprising at least one codon substitution in a non-canonical terminator motif NNATCTGTTNN (SEQ ID NO: 50), relative to a reference DNA that comprises the non-canonical terminator motif, wherein the reference DNA encodes a mRNA that encodes a polypeptide, wherein the substitution in the non-canonical terminator motif preserves the amino acid sequence of the polypeptide, and wherein Nat each position of the non-canonical terminator motif is any nucleotide selected from A, T, C, and G.

Still other aspects of the present disclosure provide a modified mRNA comprising at least one codon substitution in a non-canonical terminator motif NNAUCUGUUNN (SEQ ID NO: 51), relative to a reference mRNA that comprises the non-canonical terminator motif, wherein the reference mRNA encodes a polypeptide, wherein the substitution in the non-canonical terminator motif preserves the amino acid sequence of the polypeptide, and wherein Nat each position of the non-canonical terminator motif is any nucleotide selected from A, U, C, and G.

In some embodiments, the polypeptide comprises an amino acid sequence X1-Ser-Val, and X1 is selected from the group consisting of Ile, Leu, Val, Ala, Gly, Pro, Thr, Ser, Gln, Glu, Lys, and Arg.

In some embodiments, X1 is Ile, and the at least one codon substitution comprises: a substitution of codon NNA to ATT or ATC; a substitution of codon TCT to TCC, TCA, TCG, AGT, or AGC; and/or a substitution of codon GTT to GTC, GTA, or GTG.

In some embodiments, X1 is Leu, and the at least one codon substitution comprises: a substitution of codon NNA to CTT, CTC, CTG, CTA, TTA, or TTG; a substitution of codon TCT to TCC, TCA, TCG, AGT, or AGC; and/or a substitution of codon GTT to GTC, GTA, or GTG.

In some embodiments, X1 is Val, and the at least one codon substitution comprises: a substitution of codon NNA to GTT, GTC, or GTG; a substitution of codon TCT to TCC, TCA, TCG, AGT, or AGC; and/or a substitution of codon GTT to GTC, GTA, or GTG.

In some embodiments, X1 is Ala, and the at least one codon substitution comprises: a substitution of codon NNA to GCT, GCC, or GCG; a substitution of codon TCT to TCC, TCA, TCG, AGT, or AGC; and/or a substitution of codon GTT to GTC, GTA, or GTG.

In some embodiments, X1 is Gly, and the at least one codon substitution comprises: a substitution of codon NNA to GGT, GGC, or GGG; a substitution of codon TCT to TCC, TCA, TCG, AGT, or AGC; and/or a substitution of codon GTT to GTC, GTA, or GTG.

In some embodiments, the at least one codon substitution comprises: a substitution of codon NNA to CCT, CCC, or CCG; a substitution of codon TCT to TCC, TCA, TCG, AGT, or AGC; and/or a substitution of codon GTT to GTC, GTA, or GTG.

In some embodiments, X1 is Thr, and the at least one codon substitution comprises: a substitution of codon NNA to ACT, ACC, or ACG; a substitution of codon TCT to TCC, TCA, TCG, AGT, or AGC; and/or a substitution of codon GTT to GTC, GTA, or GTG.

In some embodiments, X1 is Ser, and the at least one codon substitution comprises: a substitution of codon NNA to TCT, TCC, TCA, TCG, AGT, or AGC; a substitution of codon TCT to TCC, TCA, TCG, AGT, or AGC; and/or a substitution of codon GTT to GTC, GTA, or GTG.

In some embodiments, X1 is Gln, and the at least one codon substitution comprises: a substitution of codon NNA to GTT, GTC, GTG; a substitution of codon TCT to TCC, TCA, TCG, AGT, or AGC; and/or a substitution of codon GTT to GTC, GTA, or GTG.

In some embodiments, X1 is Glu, and the at least one codon substitution comprises: a substitution of codon NNA to CAG; a substitution of codon TCT to TCC, TCA, TCG, AGT, or AGC; and/or a substitution of codon GTT to GTC, GTA, or GTG.

In some embodiments, X1 is Lys, and the at least one codon substitution comprises: a substitution of codon NNA to AAG; a substitution of codon TCT to TCC, TCA, TCG, AGT, or AGC; and/or a substitution of codon GTT to GTC, GTA, or GTG.

In some embodiments, X1 is Arg, and the at least one codon substitution comprises: a substitution of codon NNA to CGT, CGC, CGA, CGG, AGA, or AGG; a substitution of codon TCT to TCC, TCA, TCG, AGT, or AGC; and/or a substitution of codon GTT to GTC, GTA, or GTG.

In some embodiments, the polypeptide comprises an amino acid sequence X2-Leu-Phe, and X2 is selected from the group consisting of Tyr, His, Asn, and Asp.

In some embodiments, X2 is Tyr, and the at least one codon substitution comprises: a substitution of codon NAT to TAC; a substitution of codon CTG to CTT, CTC, CTA, TTA, or TTG; and/or a substitution of codon TTC to TTN, or TTN to TTC.

In some embodiments, X2 is His, and the at least one codon substitution comprises: a substitution of codon NAT to CAC; a substitution of codon CTG to CTT, CTC, CTA, TTA, or TTG; and/or a substitution of codon TTC to TTN, or TTN to TTC.

In some embodiments, X2 is Asn, and the at least one codon substitution comprises: a substitution of codon NAT to AAC; a substitution of codon CTG to CTT, CTC, CTA, TTA, or TTG; and/or a substitution of codon TTC to TTN, or TTN to TTC.

In some embodiments, X2 is Asp, and the at least one codon substitution comprises: a substitution of codon NAT to GAC; a substitution of codon CTG to CTT, CTC, CTA, TTA, or TTG; and/or a substitution of codon TTC to TTN, or TTN to TTC.

In some embodiments, the polypeptide comprises an amino acid sequence X2-Leu-Leu, and X2 is selected from the group consisting of Tyr, His, Asn, and Asp.

In some embodiments, X2 is Tyr, and the at least one codon substitution comprises: a substitution of codon NAT to TAC; a substitution of codon CTG to CTT, CTC, CTA, TTA, or TTG; and/or a substitution of codon TTA to TTG, or TTG to TTA.

In some embodiments, X2 is His, and the at least one codon substitution comprises: a substitution of codon NAT to CAC; a substitution of codon CTG to CTT, CTC, CTA, TTA, or TTG; and/or a substitution of codon TTA to TTG, or TTG to TTA.

In some embodiments, wherein X2 is Asn, and the at least one codon substitution comprises: a substitution of codon NAT to AAC; a substitution of codon CTG to CTT, CTC, CTA, TTA, or TTG; and/or a substitution of codon TTA to TTG, or TTG to TTA.

In some embodiments, X2 is Asp, and the at least one codon substitution comprises: a substitution of codon NAT to GAC; a substitution of codon CTG to CTT, CTC, CTA, TTA, or TTG; and/or a substitution of codon TTA to TTG, or TTG to TTA.

In some embodiments, the polypeptide comprises an amino acid sequence Ile-Cys-X3, and X3 is selected from the group consisting of Leu, Phe, Cys, Ser, Tyr, and Trp.

In some embodiments, X3 is Leu, and the at least one codon substitution comprises: a substitution of codon ATC to ATT or ATA; a substitution of codon TGT to TGC; and/or a substitution of codon TNN to CTT, CTC, CTA, CTG, TTA, or TTG.

In some embodiments, X3 is Phe, and the at least one codon substitution comprises: a substitution of codon ATC to ATT or ATA; and/or a substitution of codon TGT to TGC.

In some embodiments, X3 is Cys, and the at least one codon substitution comprises: a substitution of codon ATC to ATT or ATA; and/or a substitution of codon TGT to TGC.

In some embodiments, X3 is Ser, and the at least one codon substitution comprises: a substitution of codon ATC to ATT or ATA; a substitution of codon TGT to TGC; and/or a substitution of codon TNN to TCT, TCC, TCA, TCG, AGT, or AGC.

In some embodiments, X3 is Tyr, and the at least one codon substitution comprises: a substitution of codon ATC to ATT or ATA; and/or a substitution of codon TGT to TGC.

In some embodiments, X3 is Trp, and the at least one codon substitution comprises: a substitution of codon ATC to ATT or ATA; and/or a substitution of codon TGT to TGC.

In some embodiments, the methods comprise producing a modified mRNA in an in vitro transcription reaction that comprises the modified DNA and further comprises dNTPs and a RNA polymerase.

In some embodiments, the RNA polymerase is a T7 RNA polymerase. For example, the T7 RNA polymerase may be a wild-type T7 RNA polymerase. In some embodiments, the wild-type T7 RNA polymerase comprises the amino acid sequence of SEQ ID NO: 1.

In some embodiments, the RNA polymerase is a T7 RNA polymerase variant.

In some embodiments, the T7 RNA polymerase variant comprises an amino acid modification that causes increased transcription efficiency, relative to wild-type RNA polymerase. In some embodiments, the amino acid modification causes a loop structure of the RNA polymerase variant to undergo a conformational change to a helix structure as the RNA polymerase variant transitions from an initiation complex to an elongation complex. In some embodiments, the amino acid modification comprises an amino acid substitution at position 47, relative to the wild-type RNA polymerase, wherein the wild-type RNA polymerase comprises the amino acid sequence of SEQ ID NO: 1. In some embodiments, the amino acid substitution at position 47 is G47A.

In some embodiments, the amino acid modification comprises an additional C-terminal amino acid, relative to the wild-type RNA polymerase. In some embodiments, the additional C-terminal amino acid is selected from glycine, threonine, serine, alanine, and proline. In some embodiments, the additional C-terminal amino acid is glycine.

In some embodiments, the T7 RNA polymerase variant further comprises an amino acid substitution at a binding site residue for de novo RNA synthesis. In some embodiments, the amino acid substitution at the binding site residue is a substitution at a position selected from positions 350, 351, 387, 394, 425, 427, 437, 441, 632, 811, and 880, relative to the wild-type RNA polymerase, wherein the wild-type RNA polymerase comprises the amino acid sequence of SEQ ID NO: 1.

In some embodiments, the amino acid substitution at the binding site residue is at position 350, and the additional amino acid substitution at position 350 is selected from E350K, E350N, E350A, and E350W.

In some embodiments, the amino acid substitution at the binding site residue is at position 351, and the additional amino acid substitution at position 351 is D351V.

In some embodiments, the amino acid substitution at the binding site residue is at position 387, and the additional amino acid substitution at position 387 is selected from K387H, K387N, and K387S.

In some embodiments, the amino acid substitution at the binding site residue is at position 437, and the additional amino acid substitution at position 437 is selected from N437T, N437I, N437Y, and N437F.

In some embodiments, the amino acid substitution at the binding site residue is at position 441, and the additional amino acid substitution at position 441 is selected from K441R.

In some embodiments, the amino acid substitution at the binding site residue is at position 880, and the additional amino acid substitution at position 880 is F880Y.

In some embodiments, the in vitro transcription reaction of (c) comprises less than 20% of a truncated species of the modified mRNA. For example, the in vitro transcription reaction of (c) may comprise less than 10% of a truncated species of the modified mRNA. In some embodiments, the in vitro transcription reaction of (c) comprises less than 5% of a truncated species of the modified mRNA.

DETAILED DESCRIPTION

Figure 1A:
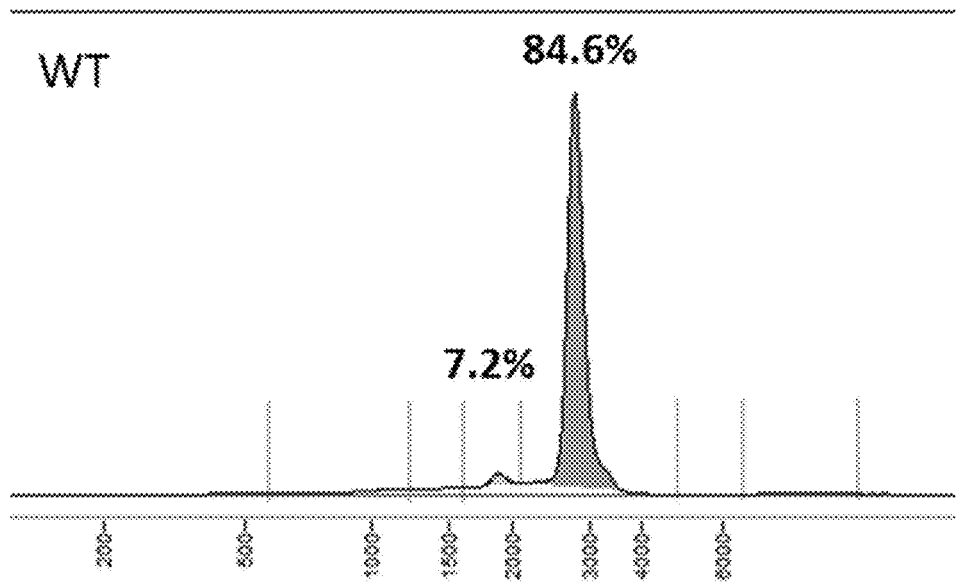
FIGS. 1A-1B show capillary electropherograms of RNA products following in vitro transcription of a DNA template (Template A) comprising a non-canonical terminator sequence (ATCTGTT) using the WT T7 polymerase (FIG. 1A) or the G47A+C-terminal G T7 polymerase variant (FIG. 1B). 84.6% of total RNA products generated using the WT polymerase were full-length RNA transcripts (~2800 nucleotides); 7.2% of total RNA products were truncated transcripts (~2000 nucleotides). 54.9% of total RNA products generated using the G47A+C-terminal G polymerase were full-length RNA transcripts (~2800 nucleotides); 33.2% of total RNA products were truncated transcripts (~2000 nucleotides).

Some aspects of the present disclosure provide methods of producing a messenger RNA (mRNA), the methods comprising (a) identifying a non-canonical terminator motif NNATCTGTTNN (SEQ ID NO: 50) in a DNA encoding a mRNA that encodes a polypeptide, wherein N at each position of the non-canonical terminator motif is any nucleotide selected from A, T, C, and G, (b) producing a modified DNA comprising at least one codon substitution in the non-canonical terminator motif that preserves the amino acid sequence of the polypeptide; and (c) optionally producing a modified mRNA in an in vitro transcription reaction that comprises the modified DNA.

A terminator motif (also referred to as a terminator sequence) is a section of a nucleic acid sequence that mediates transcriptional termination by providing signals in a newly synthesized transcript RNA that trigger processes that release the transcript RNA from the transcriptional complex (e.g., RNA polymerase and related transcriptional machinery). These processes include the direct interaction of the mRNA secondary structure with the complex and/or the indirect activities of recruited termination factors. Canonical terminator motifs include one of three stop codons—TAG, TAA, or TGA in DNA, or UAG, UAA, or UGA in RNA. The non-canonical terminator motif described herein comprises the sequence NNATCTGTTNN (SEQ ID NO: 50) in DNA or NNAUCUGUUNN (SEQ ID NO: 51) in RNA, wherein N at each position of the non-canonical terminator motif is any nucleotide selected from adenine (A), thymine (T), cytosine (C), and guanine (G).

Any amino acid substitution(s) made in the non-canonical terminator motif is designed such that the amino acid sequence of the polypeptide encoded by the nucleic acid (DNA and/or RNA) comprising the modified non-canonical terminator motif does not change as a result of the amino acid substitution(s). For example, if the nucleic acid encodes a polypeptide comprising tyrosine(Tyr)-leucine(Leu)-phenylalanine(Phe), and the nucleic acid comprises the non-canonical terminator motif TAT-CTG-TTT, then the following substitutions may be used to preserve the amino acid sequence of the polypeptide: a substitution of TAT to TAC, a substitution of CTG to CTT, CTC, CTA, TTA, or TTG, and/or a substitution of TTT to TTC. Thus, the entire non-canonical terminator motif TAT-CTG-TTT may be replaced by one of the following sequences in which a single codon substitution is made to preserve the amino acid sequence of the polypeptide: TAC-CTG-TTT, TAT-CTT-TTT, TAT-CTC-TTT, TAT-CTA-TTT, TAT-TTA-TTT, TAT-TTG-TTT, or TAT-CTG-TTC. It should be understood that more than one codon substitution can be made, in some embodiments, while still preserving the amino acid sequence of the polypeptide. For example, with the foregoing example, TAT may be changed to TAC, and CTG may be changed to any one of CTT, CTC, CTA, TTA, or TTG, while TTT remains unchanged. Likewise, all three codons may be substituted. For example, TAT may be changed to TAC, and CTG may be changed to any one of CTT, CTC, CTA, TTA, or TTG, and TTT may be changed to TTC. In each of the foregoing examples, each polypeptide encoded by the nucleic acids comprising the modified non-canonical terminator motif comprises Tyr-Leu-Phe.

Other aspects of the present disclosure provide a modified DNA comprising at least one codon substitution in a non-canonical terminator motif NNATCTGTTNN (SEQ ID NO: 50), relative to a reference DNA that comprises the non-canonical terminator motif, wherein the reference DNA encodes a mRNA that encodes a polypeptide, wherein the substitution in the non-canonical terminator motif preserves the amino acid sequence of the polypeptide, and wherein N at each position of the non-canonical terminator motif is any nucleotide selected from A, T, C, and G.

Still other aspects of the present disclosure provide a modified mRNA comprising at least one codon substitution in a non-canonical terminator motif NNAUCUGUUNN (SEQ ID NO: 51), relative to a reference mRNA that comprises the non-canonical terminator motif, wherein the reference mRNA encodes a polypeptide, wherein the substitution in the non-canonical terminator motif preserves the amino acid sequence of the polypeptide, and wherein N at each position of the non-canonical terminator motif is any nucleotide selected from A, U, C, and G.

Termination Motif I

The non-canonical termination motif described herein may occur in one of three reading frames. Termination motif I (reading frame 1) includes codons NNA-TCT-GTT; termination motif II (reading frame 2) includes codons NAT-CTG-TTN; and termination motif III (reading frame 3) includes codons ATC-TGT-TNN; wherein N at each position of the non-canonical terminator motif is any nucleotide selected from A, T, C, and G.

In some embodiments, a nucleic acid of the present disclosure includes termination motif I, which encodes a polypeptide that comprises an amino acid sequence X1-Ser-Val, wherein X1 is selected from the group consisting of Ile, Leu, Val, Ala, Gly, Pro, Thr, Ser, Gln, Glu, Lys, and Arg. Thus, in some embodiments, the polypeptide encoded by a nucleic acid comprising the sequence NNA-TCT-GTT comprises the amino acid sequence Ile-Ser-Val, Leu-Ser-Val, Val-Ser-Val, Ala-Ser-Val, Gly-Ser-Val, Pro-Ser-Val, Thr-Ser-Val, Ser-Ser-Val, Gln-Ser-Val, Glu-Ser-Val, Lys-Ser-Val, or Arg-Ser-Val.

In some embodiments, X1 is Ile, and the at least one codon substitution comprises a substitution (in the nucleic acid encoding the polypeptide) of codon NNA to ATT. In some embodiments, X1 is Ile, and the at least one codon substitution comprises a substitution (in the nucleic acid encoding the polypeptide) of codon NNA to ATC. In some embodiments, X1 is Ile, and the at least one codon substitution comprises a substitution (in the nucleic acid encoding the polypeptide) of codon TCT to TCC. In some embodiments, X1 is Ile, and the at least one codon substitution comprises a substitution (in the nucleic acid encoding the polypeptide) of codon TCT to TCA. In some embodiments, X1 is Ile, and the at least one codon substitution comprises a substitution (in the nucleic acid encoding the polypeptide) of codon TCT to TCG. In some embodiments, X1 is Ile, and the at least one codon substitution comprises a substitution (in the nucleic acid encoding the polypeptide) of codon TCT to AGT. In some embodiments, X1 is Ile, and the at least one codon substitution comprises a substitution (in the nucleic acid encoding the polypeptide) of codon TCT to AGC. In some embodiments, X1 is Ile, and the at least one codon substitution comprises a substitution (in the nucleic acid encoding the polypeptide) of codon GTT to GTC. In some embodiments, X1 is Ile, and the at least one codon substitution comprises a substitution (in the nucleic acid encoding the polypeptide) of codon GTT to GTA. In some embodiments, X1 is Ile, and the at least one codon substitution comprises a substitution (in the nucleic acid encoding the polypeptide) of codon GTT to GTG.

In some embodiments, X1 is Leu, and the at least one codon substitution comprises a substitution (in the nucleic acid encoding the polypeptide) of codon NNA to CTT. In some embodiments, X1 is Leu, and the at least one codon substitution comprises a substitution (in the nucleic acid encoding the polypeptide) of codon NNA to CTC. In some embodiments, X1 is Leu, and the at least one codon substitution comprises a substitution (in the nucleic acid encoding the polypeptide) of codon NNA to CTG. In some embodiments, X1 is Leu, and the at least one codon substitution comprises a substitution (in the nucleic acid encoding the polypeptide) of codon NNA to TTG. In some embodiments, X1 is Leu, and the at least one codon substitution comprises a substitution (in the nucleic acid encoding the polypeptide) of codon TCT to TCC. In some embodiments, X1 is Leu, and the at least one codon substitution comprises a substitution (in the nucleic acid encoding the polypeptide) of codon TCT to TCA. In some embodiments, X1 is Leu, and the at least one codon substitution comprises a substitution (in the nucleic acid encoding the polypeptide) of codon TCT to TCG. In some embodiments, X1 is Leu, and the at least one codon substitution comprises a substitution (in the nucleic acid encoding the polypeptide) of codon TCT to AGT. In some embodiments, X1 is Leu, and the at least one codon substitution comprises a substitution (in the nucleic acid encoding the polypeptide) of codon TCT to AGC. In some embodiments, X1 is Leu, and the at least one codon substitution comprises a substitution (in the nucleic acid encoding the polypeptide) of codon GTT to GTC. In some embodiments, X1 is Leu, and the at least one codon substitution comprises a substitution (in the nucleic acid encoding the polypeptide) of codon GTT to GTA. In some embodiments, X1 is Leu, and the at least one codon substitution comprises a substitution (in the nucleic acid encoding the polypeptide) of codon GTT to GTG.

In some embodiments, X1 is Val, and the at least one codon substitution comprises a substitution (in the nucleic acid encoding the polypeptide) of codon NNA to GTT. In some embodiments, X1 is Val, and the at least one codon substitution comprises a substitution (in the nucleic acid encoding the polypeptide) of codon NNA to GTC. In some embodiments, X1 is Val, and the at least one codon substitution comprises a substitution (in the nucleic acid encoding the polypeptide) of codon NNA to GTG. In some embodiments, X1 is Val, and the at least one codon substitution comprises a substitution (in the nucleic acid encoding the polypeptide) of codon TCT to TCC. In some embodiments, X1 is Val, and the at least one codon substitution comprises a substitution (in the nucleic acid encoding the polypeptide) of codon TCT to TCA. In some embodiments, X1 is Val, and the at least one codon substitution comprises a substitution (in the nucleic acid encoding the polypeptide) of codon TCT to TCG. In some embodiments, X1 is Val, and the at least one codon substitution comprises a substitution (in the nucleic acid encoding the polypeptide) of codon TCT to AGT. In some embodiments, X1 is Val, and the at least one codon substitution comprises a substitution (in the nucleic acid encoding the polypeptide) of codon TCT to AGC. In some embodiments, X1 is Val, and the at least one codon substitution comprises a substitution (in the nucleic acid encoding the polypeptide) of codon GTT to GTC. In some embodiments, X1 is Val, and the at least one codon substitution comprises a substitution (in the nucleic acid encoding the polypeptide) of codon GTT to GTA. In some embodiments, X1 is Val, and the at least one codon substitution comprises a substitution (in the nucleic acid encoding the polypeptide) of codon GTT to GTG.

In some embodiments, X1 is Ala, and the at least one codon substitution comprises a substitution (in the nucleic acid encoding the polypeptide) of codon NNA to GCT. In some embodiments, X1 is Ala, and the at least one codon substitution comprises a substitution (in the nucleic acid encoding the polypeptide) of codon NNA to GCC. In some embodiments, X1 is Ala, and the at least one codon substitution comprises a substitution (in the nucleic acid encoding the polypeptide) of codon NNA to GCG. In some embodiments, X1 is Ala, and the at least one codon substitution comprises a substitution (in the nucleic acid encoding the polypeptide) of codon TCT to TCC. In some embodiments, X1 is Ala, and the at least one codon substitution comprises a substitution (in the nucleic acid encoding the polypeptide) of codon TCT to TCA. In some embodiments, X1 is Ala, and the at least one codon substitution comprises a substitution (in the nucleic acid encoding the polypeptide) of codon TCT to TCG. In some embodiments, X1 is Ala, and the at least one codon substitution comprises a substitution (in the nucleic acid encoding the polypeptide) of codon TCT to AGT. In some embodiments, X1 is Ala, and the at least one codon substitution comprises a substitution (in the nucleic acid encoding the polypeptide) of codon TCT to AGC. In some embodiments, X1 is Ala, and the at least one codon substitution comprises a substitution (in the nucleic acid encoding the polypeptide) of codon GTT to GTC. In some embodiments, X1 is Ala, and the at least one codon substitution comprises a substitution (in the nucleic acid encoding the polypeptide) of codon GTT to GTA. In some embodiments, X1 is Ala, and the at least one codon substitution comprises a substitution (in the nucleic acid encoding the polypeptide) of codon GTT to GTG.

In some embodiments, X1 is Gly, and the at least one codon substitution comprises a substitution (in the nucleic acid encoding the polypeptide) of codon NNA to GGT. In some embodiments, X1 is Gly, and the at least one codon substitution comprises a substitution (in the nucleic acid encoding the polypeptide) of codon NNA to GGC. In some embodiments, X1 is Gly, and the at least one codon substitution comprises a substitution (in the nucleic acid encoding the polypeptide) of codon NNA to GGG. In some embodiments, X1 is Gly, and the at least one codon substitution comprises a substitution (in the nucleic acid encoding the polypeptide) of codon TCT to TCC. In some embodiments, X1 is Gly, and the at least one codon substitution comprises a substitution (in the nucleic acid encoding the polypeptide) of codon TCT to TCA. In some embodiments, X1 is Gly, and the at least one codon substitution comprises a substitution (in the nucleic acid encoding the polypeptide) of codon TCT to TCG. In some embodiments, X1 is Gly, and the at least one codon substitution comprises a substitution (in the nucleic acid encoding the polypeptide) of codon TCT to AGT. In some embodiments, X1 is Gly, and the at least one codon substitution comprises a substitution (in the nucleic acid encoding the polypeptide) of codon TCT to AGC. In some embodiments, X1 is Gly, and the at least one codon substitution comprises a substitution (in the nucleic acid encoding the polypeptide) of codon GTT to GTC. In some embodiments, X1 is Gly, and the at least one codon substitution comprises a substitution (in the nucleic acid encoding the polypeptide) of codon GTT to GTA. In some embodiments, X1 is Gly, and the at least one codon substitution comprises a substitution (in the nucleic acid encoding the polypeptide) of codon GTT to GTG.

In some embodiments, X1 is Pro, and the at least one codon substitution comprises a substitution (in the nucleic acid encoding the polypeptide) of codon NNA to CCT. In some embodiments, X1 is Pro, and the at least one codon substitution comprises a substitution (in the nucleic acid encoding the polypeptide) of codon NNA to CCC. In some embodiments, X1 is Pro, and the at least one codon substitution comprises a substitution (in the nucleic acid encoding the polypeptide) of codon NNA to CCG. In some embodiments, X1 is Pro, and the at least one codon substitution comprises a substitution (in the nucleic acid encoding the polypeptide) of codon TCT to TCC. In some embodiments, X1 is Pro, and the at least one codon substitution comprises a substitution (in the nucleic acid encoding the polypeptide) of codon TCT to TCA. In some embodiments, X1 is Pro, and the at least one codon substitution comprises a substitution (in the nucleic acid encoding the polypeptide) of codon TCT to TCG. In some embodiments, X1 is Pro, and the at least one codon substitution comprises a substitution (in the nucleic acid encoding the polypeptide) of codon TCT to AGT. In some embodiments, X1 is Pro, and the at least one codon substitution comprises a substitution (in the nucleic acid encoding the polypeptide) of codon TCT to AGC. In some embodiments, X1 is Pro, and the at least one codon substitution comprises a substitution (in the nucleic acid encoding the polypeptide) of codon GTT to GTC. In some embodiments, X1 is Pro, and the at least one codon substitution comprises a substitution (in the nucleic acid encoding the polypeptide) of codon GTT to GTA. In some embodiments, X1 is Pro, and the at least one codon substitution comprises a substitution (in the nucleic acid encoding the polypeptide) of codon GTT to GTG.

In some embodiments, X1 is Thr, and the at least one codon substitution comprises a substitution (in the nucleic acid encoding the polypeptide) of codon NNA to ACT. In some embodiments, X1 is Thr, and the at least one codon substitution comprises a substitution (in the nucleic acid encoding the polypeptide) of codon NNA to ACC. In some embodiments, X1 is Thr, and the at least one codon substitution comprises a substitution (in the nucleic acid encoding the polypeptide) of codon NNA to ACG. In some embodiments, X1 is Thr, and the at least one codon substitution comprises a substitution (in the nucleic acid encoding the polypeptide) of codon TCT to TCC. In some embodiments, X1 is Thr, and the at least one codon substitution comprises a substitution (in the nucleic acid encoding the polypeptide) of codon TCT to TCA. In some embodiments, X1 is Thr, and the at least one codon substitution comprises a substitution (in the nucleic acid encoding the polypeptide) of codon TCT to TCG. In some embodiments, X1 is Thr, and the at least one codon substitution comprises a substitution (in the nucleic acid encoding the polypeptide) of codon TCT to AGT. In some embodiments, X1 is Thr, and the at least one codon substitution comprises a substitution (in the nucleic acid encoding the polypeptide) of codon TCT to AGC. In some embodiments, X1 is Thr, and the at least one codon substitution comprises a substitution (in the nucleic acid encoding the polypeptide) of codon GTT to GTC. In some embodiments, X1 is Thr, and the at least one codon substitution comprises a substitution (in the nucleic acid encoding the polypeptide) of codon GTT to GTA. In some embodiments, X1 is Thr, and the at least one codon substitution comprises a substitution (in the nucleic acid encoding the polypeptide) of codon GTT to GTG.

In some embodiments, X1 is Ser, and the at least one codon substitution comprises a substitution (in the nucleic acid encoding the polypeptide) of codon NNA to TCT. In some embodiments, X1 is Ser, and the at least one codon substitution comprises a substitution (in the nucleic acid encoding the polypeptide) of codon NNA to TCC. In some embodiments, X1 is Ser, and the at least one codon substitution comprises a substitution (in the nucleic acid encoding the polypeptide) of codon NNA to TCG. In some embodiments, X1 is Ser, and the at least one codon substitution comprises a substitution (in the nucleic acid encoding the polypeptide) of codon NNA to AGT. In some embodiments, X1 is Ser, and the at least one codon substitution comprises a substitution (in the nucleic acid encoding the polypeptide) of codon NNA to AGC. In some embodiments, X1 is Ser, and the at least one codon substitution comprises a substitution (in the nucleic acid encoding the polypeptide) of codon TCT to TCC. In some embodiments, X1 is Ser, and the at least one codon substitution comprises a substitution (in the nucleic acid encoding the polypeptide) of codon TCT to TCA. In some embodiments, X1 is Ser, and the at least one codon substitution comprises a substitution (in the nucleic acid encoding the polypeptide) of codon TCT to TCG. In some embodiments, X1 is Ser, and the at least one codon substitution comprises a substitution (in the nucleic acid encoding the polypeptide) of codon TCT to AGT. In some embodiments, X1 is Ser, and the at least one codon substitution comprises a substitution (in the nucleic acid encoding the polypeptide) of codon TCT to AGC. In some embodiments, X1 is Ser, and the at least one codon substitution comprises a substitution (in the nucleic acid encoding the polypeptide) of codon GTT to GTC. In some embodiments, X1 is Ser, and the at least one codon substitution comprises a substitution (in the nucleic acid encoding the polypeptide) of codon GTT to GTA. In some embodiments, X1 is Ser, and the at least one codon substitution comprises a substitution (in the nucleic acid encoding the polypeptide) of codon GTT to GTG.

In some embodiments, X1 is Gln, and the at least one codon substitution comprises a substitution (in the nucleic acid encoding the polypeptide) of codon NNA to GTT. In some embodiments, X1 is Gln, and the at least one codon substitution comprises a substitution (in the nucleic acid encoding the polypeptide) of codon NNA to GTC. In some embodiments, X1 is Gln, and the at least one codon substitution comprises a substitution (in the nucleic acid encoding the polypeptide) of codon NNA to GTG. In some embodiments, X1 is Gln, and the at least one codon substitution comprises a substitution (in the nucleic acid encoding the polypeptide) of codon TCT to TCC. In some embodiments, X1 is Gln, and the at least one codon substitution comprises a substitution (in the nucleic acid encoding the polypeptide) of codon TCT to TCA. In some embodiments, X1 is Gln, and the at least one codon substitution comprises a substitution (in the nucleic acid encoding the polypeptide) of codon TCT to TCG. In some embodiments, X1 is Gln, and the at least one codon substitution comprises a substitution (in the nucleic acid encoding the polypeptide) of codon TCT to AGT. In some embodiments, X1 is Gln, and the at least one codon substitution comprises a substitution (in the nucleic acid encoding the polypeptide) of codon TCT to AGC. In some embodiments, X1 is Gln, and the at least one codon substitution comprises a substitution (in the nucleic acid encoding the polypeptide) of codon GTT to GTC. In some embodiments, X1 is Gln, and the at least one codon substitution comprises a substitution (in the nucleic acid encoding the polypeptide) of codon GTT to GTA. In some embodiments, X1 is Gln, and the at least one codon substitution comprises a substitution (in the nucleic acid encoding the polypeptide) of codon GTT to GTG.

In some embodiments, X1 is Glu, and the at least one codon substitution comprises a substitution (in the nucleic acid encoding the polypeptide) of codon NNA to CAG. In some embodiments, X1 is Glu, and the at least one codon substitution comprises a substitution (in the nucleic acid encoding the polypeptide) of codon TCT to TCC. In some embodiments, X1 is Glu, and the at least one codon substitution comprises a substitution (in the nucleic acid encoding the polypeptide) of codon TCT to TCA. In some embodiments, X1 is Glu, and the at least one codon substitution comprises a substitution (in the nucleic acid encoding the polypeptide) of codon TCT to TCG. In some embodiments, X1 is Glu, and the at least one codon substitution comprises a substitution (in the nucleic acid encoding the polypeptide) of codon TCT to AGT. In some embodiments, X1 is Glu, and the at least one codon substitution comprises a substitution (in the nucleic acid encoding the polypeptide) of codon TCT to AGC. In some embodiments, X1 is Glu, and the at least one codon substitution comprises a substitution (in the nucleic acid encoding the polypeptide) of codon GTT to GTC. In some embodiments, X1 is Glu, and the at least one codon substitution comprises a substitution (in the nucleic acid encoding the polypeptide) of codon GTT to GTA. In some embodiments, X1 is Glu, and the at least one codon substitution comprises a substitution (in the nucleic acid encoding the polypeptide) of codon GTT to GTG.

In some embodiments, X1 is Lys, and the at least one codon substitution comprises a substitution (in the nucleic acid encoding the polypeptide) of codon NNA to AAG. In some embodiments, X1 is Lys, and the at least one codon substitution comprises a substitution (in the nucleic acid encoding the polypeptide) of codon TCT to TCC. In some embodiments, X1 is Lys, and the at least one codon substitution comprises a substitution (in the nucleic acid encoding the polypeptide) of codon TCT to TCA. In some embodiments, X1 is Lys, and the at least one codon substitution comprises a substitution (in the nucleic acid encoding the polypeptide) of codon TCT to TCG. In some embodiments, X1 is Lys, and the at least one codon substitution comprises a substitution (in the nucleic acid encoding the polypeptide) of codon TCT to AGT. In some embodiments, X1 is Lys, and the at least one codon substitution comprises a substitution (in the nucleic acid encoding the polypeptide) of codon TCT to AGC. In some embodiments, X1 is Lys, and the at least one codon substitution comprises a substitution (in the nucleic acid encoding the polypeptide) of codon GTT to GTC. In some embodiments, X1 is Lys, and the at least one codon substitution comprises a substitution (in the nucleic acid encoding the polypeptide) of codon GTT to GTA. In some embodiments, X1 is Lys, and the at least one codon substitution comprises a substitution (in the nucleic acid encoding the polypeptide) of codon GTT to GTG.

In some embodiments, X1 is Arg, and the at least one codon substitution comprises a substitution (in the nucleic acid encoding the polypeptide) of codon NNA to CGT. In some embodiments, X1 is Arg, and the at least one codon substitution comprises a substitution (in the nucleic acid encoding the polypeptide) of codon NNA to CGC. In some embodiments, X1 is Arg, and the at least one codon substitution comprises a substitution (in the nucleic acid encoding the polypeptide) of codon NNA to CGA. In some embodiments, X1 is Arg, and the at least one codon substitution comprises a substitution (in the nucleic acid encoding the polypeptide) of codon NNA to CGG. In some embodiments, X1 is Arg, and the at least one codon substitution comprises a substitution (in the nucleic acid encoding the polypeptide) of codon NNA to AGG. In some embodiments, X1 is Arg, and the at least one codon substitution comprises a substitution (in the nucleic acid encoding the polypeptide) of codon TCT to TCC. In some embodiments, X1 is Arg, and the at least one codon substitution comprises a substitution (in the nucleic acid encoding the polypeptide) of codon TCT to TCA. In some embodiments, X1 is Arg, and the at least one codon substitution comprises a substitution (in the nucleic acid encoding the polypeptide) of codon TCT to TCG. In some embodiments, X1 is Arg, and the at least one codon substitution comprises a substitution (in the nucleic acid encoding the polypeptide) of codon TCT to AGT. In some embodiments, X1 is Arg, and the at least one codon substitution comprises a substitution (in the nucleic acid encoding the polypeptide) of codon TCT to AGC. In some embodiments, X1 is Arg, and the at least one codon substitution comprises a substitution (in the nucleic acid encoding the polypeptide) of codon GTT to GTC. In some embodiments, X1 is Arg, and the at least one codon substitution comprises a substitution (in the nucleic acid encoding the polypeptide) of codon GTT to GTA. In some embodiments, X1 is Arg, and the at least one codon substitution comprises a substitution (in the nucleic acid encoding the polypeptide) of codon GTT to GTG.

Termination Motif II

In some embodiments, a nucleic acid of the present disclosure includes termination motif II, and encodes a polypeptide that comprises an amino acid sequence X2-Leu-Phe, wherein X2 is selected from the group consisting of Tyr, His, Asn, and Asp. Thus, in some embodiments, the polypeptide encoded by a nucleic acid comprising the sequence NAT-CTG-TTN comprises the amino acid sequence Tyr-Leu-Phe, His-Leu-Phe, Asn-Leu-Phe, or Asp-Leu-Phe.

In some embodiments, X2 is Tyr, and the at least one codon substitution comprises a substitution of codon NAT to TAC. In some embodiments, X2 is Tyr, and the at least one codon substitution comprises a substitution of codon CTG to CTT. In some embodiments, X2 is Tyr, and the at least one codon substitution comprises a substitution of codon CTG to CTC. In some embodiments, X2 is Tyr, and the at least one codon substitution comprises a substitution of codon CTG to CTA. In some embodiments, X2 is Tyr, and the at least one codon substitution comprises a substitution of codon CTG to TTA. In some embodiments, X2 is Tyr, and the at least one codon substitution comprises a substitution of codon CTG to TTG. In some embodiments, X2 is Tyr, and the at least one codon substitution comprises a substitution of codon TTN to TTC. In some embodiments, X2 is Tyr, and the at least one codon substitution comprises a substitution of codon TTN to TTN.

In some embodiments, X2 is His, and the at least one codon substitution comprises a substitution of codon NAT to CAC. In some embodiments, X2 is His, and the at least one codon substitution comprises a substitution of codon CTG to CTT. In some embodiments, X2 is His, and the at least one codon substitution comprises a substitution of codon CTG to CTC. In some embodiments, X2 is His, and the at least one codon substitution comprises a substitution of codon CTG to CTA. In some embodiments, X2 is His, and the at least one codon substitution comprises a substitution of codon CTG to TTA. In some embodiments, X2 is His, and the at least one codon substitution comprises a substitution of codon CTG to TTG. In some embodiments, X2 is His, and the at least one codon substitution comprises a substitution of codon TTN to TTC. In some embodiments, X2 is His, and the at least one codon substitution comprises a substitution of codon TTN to TTN.

In some embodiments, X2 is Asn, and the at least one codon substitution comprises a substitution of codon NAT to AAC. In some embodiments, X2 is Asn, and the at least one codon substitution comprises a substitution of codon CTG to CTT. In some embodiments, X2 is Asn, and the at least one codon substitution comprises a substitution of codon CTG to CTC. In some embodiments, X2 is Asn, and the at least one codon substitution comprises a substitution of codon CTG to CTA. In some embodiments, X2 is Asn, and the at least one codon substitution comprises a substitution of codon CTG to TTA. In some embodiments, X2 is Asn, and the at least one codon substitution comprises a substitution of codon CTG to TTG. In some embodiments, X2 is Asn, and the at least one codon substitution comprises a substitution of codon TTN to TTC. In some embodiments, X2 is Asn, and the at least one codon substitution comprises a substitution of codon TTN to TTN.

In some embodiments, X2 is Asp, and the at least one codon substitution comprises a substitution of codon NAT to GAC. In some embodiments, X2 is Asp, and the at least one codon substitution comprises a substitution of codon CTG to CTT. In some embodiments, X2 is Asp, and the at least one codon substitution comprises a substitution of codon CTG to CTC. In some embodiments, X2 is Asp, and the at least one codon substitution comprises a substitution of codon CTG to CTA. In some embodiments, X2 is Asp, and the at least one codon substitution comprises a substitution of codon CTG to TTA. In some embodiments, X2 is Asp, and the at least one codon substitution comprises a substitution of codon CTG to TTG. In some embodiments, X2 is Asp, and the at least one codon substitution comprises a substitution of codon TTN to TTC. In some embodiments, X2 is Asp, and the at least one codon substitution comprises a substitution of codon TTN to TTN.

In some embodiments, a nucleic acid of the present disclosure include termination motif II, and encodes a polypeptide that comprises an amino acid sequence X2-Leu-Leu, wherein X2 is selected from the group consisting of Tyr, His, Asn, and Asp. Thus, in some embodiments, the polypeptide encoded by a nucleic acid comprising the sequence NAT-CTG-TTN comprises the amino acid sequence Tyr-Leu-Leu, His-Leu-Leu, Asn-Leu-Leu, or Asp-Leu-Leu.

In some embodiments, X2 is Tyr, and the at least one codon substitution comprises a substitution of codon NAT to TAC. In some embodiments, X2 is Tyr, and the at least one codon substitution comprises a substitution of codon CTG to CTT. In some embodiments, X2 is Tyr, and the at least one codon substitution comprises a substitution of codon CTG to CTT. In some embodiments, X2 is Tyr, and the at least one codon substitution comprises a substitution of codon CTG to CTC. In some embodiments, X2 is Tyr, and the at least one codon substitution comprises a substitution of codon CTG to CTA. In some embodiments, X2 is Tyr, and the at least one codon substitution comprises a substitution of codon CTG to TTA. In some embodiments, X2 is Tyr, and the at least one codon substitution comprises a substitution of codon CTG to TTG. In some embodiments, X2 is Tyr, and the at least one codon substitution comprises a substitution of codon TTN to TTA. In some embodiments, X2 is Tyr, and the at least one codon substitution comprises a substitution of codon TTN to TTG.

In some embodiments, X2 is His, and the at least one codon substitution comprises a substitution of codon NAT to CAC. In some embodiments, X2 is His, and the at least one codon substitution comprises a substitution of codon CTG to CTT. In some embodiments, X2 is His, and the at least one codon substitution comprises a substitution of codon CTG to CTC. In some embodiments, X2 is His, and the at least one codon substitution comprises a substitution of codon CTG to CTA. In some embodiments, X2 is His, and the at least one codon substitution comprises a substitution of codon CTG to TTA. In some embodiments, X2 is His, and the at least one codon substitution comprises a substitution of codon CTG to TTG. In some embodiments, X2 is His, and the at least one codon substitution comprises a substitution of codon TTN to TTA. In some embodiments, X2 is His, and the at least one codon substitution comprises a substitution of codon TTN to TTG.

In some embodiments, X2 is Asn, and the at least one codon substitution comprises a substitution of codon NAT to AAC. In some embodiments, X2 is Asn, and the at least one codon substitution comprises a substitution of codon CTG to CTT. In some embodiments, X2 is Asn, and the at least one codon substitution comprises a substitution of codon CTG to CTC. In some embodiments, X2 is Asn, and the at least one codon substitution comprises a substitution of codon CTG to CTA. In some embodiments, X2 is Asn, and the at least one codon substitution comprises a substitution of codon CTG to TTA. In some embodiments, X2 is Asn, and the at least one codon substitution comprises a substitution of codon CTG to TTG. In some embodiments, X2 is Asn, and the at least one codon substitution comprises a substitution of codon TTN to TTA. In some embodiments, X2 is Asn, and the at least one codon substitution comprises a substitution of codon TTN to TTG.

In some embodiments, X2 is Asp, and the at least one codon substitution comprises a substitution of codon NAT to GAC. In some embodiments, X2 is Asp, and the at least one codon substitution comprises a substitution of codon CTG to CTT. In some embodiments, X2 is Asp, and the at least one codon substitution comprises a substitution of codon CTG to CTC. In some embodiments, X2 is Asp, and the at least one codon substitution comprises a substitution of codon CTG to CTA. In some embodiments, X2 is Asp, and the at least one codon substitution comprises a substitution of codon CTG to TTA. In some embodiments, X2 is Asp, and the at least one codon substitution comprises a substitution of codon CTG to TTG. In some embodiments, X2 is Asp, and the at least one codon substitution comprises a substitution of codon TTN to TTA. In some embodiments, X2 is Asp, and the at least one codon substitution comprises a substitution of codon TTN to TTG.

Termination Motif III

In some embodiments, a nucleic acid of the present disclosure includes termination motif III, which encodes a polypeptide that comprises an amino acid sequence Ile-Cys-X3, wherein X3 is selected from the group consisting of Leu, Phe, Cys, Ser, Tyr, and Trp. Thus, in some embodiments, the polypeptide encoded by a nucleic acid comprising the sequence ATC-TGT-TNN comprises the amino acid sequence Ile-Cys-Leu, Ile-Cys-Phe, Ile-Cys-Cys, Ile-Cys-Ser, Ile-Cys-Tyr, or Ile-Cys-Trp.

In some embodiments, X3 is Leu, and the at least one codon substitution comprises a substitution of codon ATC to ATT. In some embodiments, X3 is Leu, and the at least one codon substitution comprises a substitution of codon ATC to ATA. In some embodiments, X3 is Leu, and the at least one codon substitution comprises a substitution of codon TGT to TGC. In some embodiments, X3 is Leu, and the at least one codon substitution comprises a substitution of codon TNN to CTT. In some embodiments, X3 is Leu, and the at least one codon substitution comprises a substitution of codon TNN to CTC. In some embodiments, X3 is Leu, and the at least one codon substitution comprises a substitution of codon TNN to CTA. In some embodiments, X3 is Leu, and the at least one codon substitution comprises a substitution of codon TNN to CTG.

In some embodiments, X3 is Phe, and the at least one codon substitution comprises a substitution of codon ATC to ATT. In some embodiments, X3 is Phe, and the at least one codon substitution comprises a substitution of codon ATC to ATA. In some embodiments, X3 is Phe, and the at least one codon substitution comprises a substitution of codon TGT to TGC.

In some embodiments, X3 is Cys, and the at least one codon substitution comprises a substitution of codon ATC to ATT. In some embodiments, X3 is Cys, and the at least one codon substitution comprises a substitution of codon ATC to ATA. In some embodiments, X3 is Cys, and the at least one codon substitution comprises a substitution of codon TGT to TGC.

In some embodiments, X3 is Ser, and the at least one codon substitution comprises a substitution of codon ATC to ATT. In some embodiments, X3 is Ser, and the at least one codon substitution comprises a substitution of codon ATC to ATA. In some embodiments, X3 is Ser, and the at least one codon substitution comprises a substitution of codon TGT to TGC. In some embodiments, X3 is Ser, and the at least one codon substitution comprises a substitution of codon TNN to AGT. In some embodiments, X3 is Ser, and the at least one codon substitution comprises a substitution of codon TNN to AGC.

In some embodiments, X3 is Tyr, and the at least one codon substitution comprises a substitution of codon ATC to ATT. In some embodiments, X3 is Tyr, and the at least one codon substitution comprises a substitution of codon ATC to ATA. In some embodiments, X3 is Tyr, and the at least one codon substitution comprises a substitution of codon TGT to TGC.

In some embodiments, X3 is Trp, and the at least one codon substitution comprises a substitution of codon ATC to ATT. In some embodiments, X3 is Trp, and the at least one codon substitution comprises a substitution of codon ATC to ATA. In some embodiments, X3 is Trp, and the at least one codon substitution comprises a substitution of codon TGT to TGC.

In some embodiments, an in vitro transcription reaction that uses DNA modified to eliminate the non-canonical terminator sequence comprises less than 20% of a truncated species of mRNA. For example, the in vitro transcription reaction may comprise less than 15%, less than 10%, less than 5%, less than 4%, less than 3%, less than 2%, less than 1%, less than 0.5%, or less than 0.1% of a truncated species of mRNA. In some embodiments, an in vitro transcription reaction that uses DNA modified to eliminate the non-canonical terminator sequence comprises 0.1%-10%, 0.1%-5%, or 0.1%-1%, 0.5%-10%, 0.5%-5%, or of a truncated species of mRNA.

RNA Polymerases and Variants Thereof

RNA polymerase (DNA-dependent RNA polymerase) is an enzyme that catalyzes the sequential addition of a ribonucleotide to the 3' end of a growing RNA chain (transcription of RNA in the 5'→3' direction), with nucleoside triphosphates (NTPs) acting as substrates for the enzyme and with the sequence of nucleotides specified by a DNA template. Transcription relies on the complementary pairing of bases. The two strands of a double helix separate locally, and one of the separated strands serves as a template (DNA template). RNA polymerase then catalyzes the alignment of free nucleotides on the DNA template by their complementary bases in the template. Thus, a RNA polymerase is considered to have RNA polymerase activity if the polymerase catalyzes the sequential addition of a ribonucleotide to the 3' end of a growing RNA chain.

RNA polymerase variants of the present disclosure include at least one amino acid substitution, relative to the wild type (WT) RNA polymerase. For example, with reference to WT T7 RNAP having an amino acid sequence of SEQ ID NO:1, the glycine at position 47 is considered a "wild-type amino acid," whereas a substitution of the glycine for alanine at position 47 is considered an "amino acid substitution" that has a high-helix propensity. In some embodiments, the RNA polymerase variant is a T7 RNAP variant comprising at least one (one or more) amino acid substitution relative to WT RNAP (e.g., WT T7 RNAP having an amino acid sequence of SEQ ID NO:1).

Use of the RNA polymerase variants of the present disclosure, for example, in an in vitro transcription reaction, in some embodiments, increases transcription efficiency, relative to a control RNA polymerase. For example, use of a RNA polymerase variant may increase the transcription efficiency (e.g., RNA yield and/or rate of transcription) by at least 20%. In some embodiments, use of a RNA polymerase variant increases the transcription efficiency (e.g., yield) by at least 30%, at least 40%, at least 50%, at least 60%, at least 70%, at least 80%, at least 90%, or at least 10%. In some embodiments, use of a RNA polymerase variant increases the transcription efficiency by 20-100%, 20-90%, 20-80%, 20-70%, 20-60%, 20-50%, 30-100%, 30-90%, 30-80%, 30-70%, 30-60%, 30-50%, 40-100%, 40-90%, 40-80%, 40-60%, 40-50%, 50-100%, 50-90%, 50-80%, 50-70%, or 50-60%. In some embodiments, the control RNA polymerase is a wild-type RNA polymerase comprising the amino acid sequence of SEQ ID NO: 1 ("wild-type T7 RNA polymerase"). In other embodiments, the control RNA polymerase is a RNA polymerase variant comprising an amino acid sequence of SEQ ID NO: 1 modified to include G47A substitution and an additional glycine at its C-terminus ("control T7 RNA polymerase variant" or "G47A+C-terminal G T7 RNA polymerase variant").

Some aspects of the present disclosure provide methods that use RNA polymerase variants that comprise multiple amino acid substitutions and/or modifications, relative to wild-type RNA polymerase. In some embodiments, a RNA polymerase variant comprise a RNA polymerase that includes (a) an amino acid substitution at a binding site residue for de novo RNA synthesis, and (b) an amino acid substitution that facilitates the conformational change from the RNAP initiation complex to the RNAP elongation complex.

Wild-Type T7 RNA Polymerase (SEQ ID NO: 1)
MNTINIAKNDFSDIELAAIPENTLADHYGERLAREQLALEHESYEMGEAR

FRKMFERQLKAGEVADNAAAKPLITTLLPKMIARINDWFEEVKAKRGKRP

TAFQFLQEIKPEAVAYITIKTTLACLTSADNTTVQAVASAIGRAIEDEAR

FGRIRDLEAKHFKKNVEEQLNKRVGHVYKKAFMQVVEADMLSKGLLGGEA

WSSWHKEDSIHVGVRCIEMLIESTGMVSLHRQNAGVVGQDSETIELAPEY

AEAIATRAGALAGISPMFQPCVVPPKPWTGITGGGYWANGRRPLALVRTH

SKKALMRYEDVYMPEVYKAINIAQNTAWKINKKVLAVANVITKWKHCPVE

DIPAIEREELPMKPEDIDMNPEALTAWKRAAAAVYRKDKARKSRRISLEF

MLEQANKFANHKAIWFPYNMDWRGRVYAVSMENPQGNDMTKGLLTLAKGK

PIGKEGYYWLKIHGANCAGVDKVPFPERIKFIEENHENIMACAKSPLENT

WWAEQDSPFCFLAFCFEYAGVQHHGLSYNCSLPLAFDGSCSGIQHFSAML

RDEVGGRAVNLLPSETVQDIYGIVAKKVNEILQADAINGTDNEVVTVTDE

NTGEISEKVKLGTKALAGQWLAYGVTRSVTKRSVMTLAYGSKEFGFRQQV

LEDTIQPAIDSGKGLMFTQPNQAAGYMAKLIWESVSVTVVAAVEAMNWLK

SAAKLLAAEVKDKKTGEILRKRCAVHWVTPDGFPVWQEYKKPIQTRLNLM

FLGQFRLQPTINTNKDSEIDAHKQESGIAPNFVHSQDGSHLRKTVVWAHE

KYGIESFALIHDSFGTIPADAANLFKAVRETMVDTYESCDVLADFYDQFA

DQLHESQLDKMPALPAKGNLNLRDILESDFAFA

Control T7 RNA Polymerase Variant (G47A+C-Terminal G)

(SEQ ID NO: 45)
MNTINIAKNDESDIELAAIPENTLADHYGERLAREQLALEHESYEMAEAR

FRKMFERQLKAGEVADNAAAKPLITTLLPKMIARINDWFEEVKAKRGKRP

TAFQFLQEIKPEAVAYITIKTTLACLTSADNTTVQAVASAIGRAIEDEAR

FGRIRDLEAKHFKKNVEEQLNKRVGHVYKKAFMQVVEADMLSKGLLGGEA

WSSWHKEDSIHVGVRCIEMLIESTGMVSLHRQNAGVVGQDSETIELAPEY

AEAIATRAGALAGISPMFQPCVVPPKPWTGITGGGYWANGRRPLALVRTH

SKKALMRYEDVYMPEVYKAINIAQNTAWKINKKVLAVANVITKWKHCPVE

DIPAIEREELPMKPEDIDMNPEALTAWKRAAAAVYRKDKARKSRRISLEF

MLEQANKFANHKAIWFPYNMDWRGRVYAVSMFNPQGNDMTKGLLTLAKGK

PIGKEGYYWLKIHGANCAGVDKVPFPERIKFIEENHENIMACAKSPLENT

WWAEQDSPFCFLAFCFEYAGVQHHGLSYNCSLPLAFDGSCSGIQHFSAML

RDEVGGRAVNLLPSETVQDIYGIVAKKVNEILQADAINGTDNEVVTVTDE

NTGEISEKVKLGTKALAGQWLAYGVTRSVTKRSVMTLAYGSKEFGFRQQV

LEDTIQPAIDSGKGLMFTQPNQAAGYMAKLIWESVSVTVVAAVEAMNWLK

SAAKLLAAEVKDKKTGEILRKRCAVHWVTPDGFPVWQEYKKPIQTRLNLM

FLGQFRLQPTINTNKDSEIDAHKQESGIAPNFVHSQDGSHLRKTVVWAHE

KYGIESFALIHDSFGTIPADAANLFKAVRETMVDTYESCDVLADFYDQFA

DQLHESQLDKMPALPAKGNLNLRDILESDFAFAG

High Helix Propensity Amino Acid Substitutions

Structural studies of T7 RNAP have shown that the conformation of the N-terminal domain changes substantially between the initiation phase and elongation phase of transcription. The N-terminal domain comprises a C-helix subdomain and the promoter binding domain, which includes two segments separated by subdomain H. The promoter binding domain and the bound promoter rotate by approximately 45 degrees upon synthesis of an 8-nt RNA transcript, allowing the promoter contacts to be maintained while the active site is expanded to accommodate a growing heteroduplex. The C-helix subdomain moves modestly toward its elongation conformation, whereas subdomain H remains in its initiation-rather than its elongation-phase location, more than 70 angstroms away. Comparison of the structures of the T7 RNAP initiation and elongation complexes reveal extensive conformational changes within the N-terminal 267 residues (N-terminal domain) and little change in the rest of the RNAP. A rigid body rotation of the promoter binding domain as well as the refolding of the N-terminal C-helix (residues 28-71) and H (residues 151-190) subdomains are responsible for abolishing the promoter binding site, enlarging the active site and creating an exit tunnel for the RNA transcript. The structural changes within the N-terminal domain account for the increased stability and the processivity of the elongation complex (see, e.g., Durniak, K. J. et al., *Science* 322(5901): 553-557, 2008, incorporated herein by reference).

Provided herein, in some aspects, are methods that use RNA polymerase variants (e.g., T7 RNAP variants) that facilitate the conformational change from the RNAP initiation complex to the RNAP elongation complex. In some embodiments, a RNA polymerase variant comprises at least one amino acid modification, relative to wild-type RNA polymerase, that causes at least one three-dimensional loop structure of the RNA polymerase variant to undergo a conformational change to a helix structure as the RNA polymerase variant transitions from an initiation complex to an elongation complex. Thus, in some embodiments, at least one amino acid modification has a high-helix propensity, relative to wild-type amino acid. In some embodiments, a RNA polymerase variant comprises an amino acid substitution at position 47, relative to the wild-type RNA polymerase, wherein the wild-type RNA polymerase comprises the amino acid sequence of SEQ ID NO: 1. The amino acid substitution, in some embodiments, is a high propensity amino acid substitution. Examples of high-helix propensity amino acids include alanine, isoleucine, leucine, arginine, methionine, lysine, glutamine, and/or glutamate. In some embodiments, the amino acid substitution at position 47 is G47A.

Examples of loop structures include but are not limited to amino acid (aa) 42-47 in the C-helix structure (e.g., aa 28-71 of SEQ ID NO:1) of the T7 RNAP initiation complex (IC) conformation and aa 257-262 in the C-linker structure (e.g., aa 258-266 of SEQ ID NO:1) of the IC.

C-terminal RNA Polymerase Variants

Further, the RNA polymerase variants, in some embodiments, include at least one additional amino acid at the C terminus of the polymerase. The at least one additional amino acid, in some embodiments, is selected from alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine. In some embodiments, the at least one additional amino acid is a polar amino acid. In some embodiments, the at least one additional amino acid is a non-polar amino acid. In some embodiments, the at least one additional amino acid is glycine. In some embodiments, the at least one additional amino acid is alanine. In some embodiments, the at least one additional amino acid is serine. In some embodiments, a RNA polymerase variant comprise a RNA polymerase that includes an additional C-terminal amino acid, relative to the wild-type RNA polymerase. The additional C-terminal amino acid, in some embodiments, is selected from glycine, alanine, threonine, proline, glutamine, serine. In some embodiments, the additional C-terminal amino acid (e.g., at position 884 relative to wild-type RNA polymerase comprising the amino acid sequence of SEQ ID NO: 1) is glycine.

Binding Site Amino Acid Substitutions

DNA-directed RNA polymerases are capable of initiating synthesis of RNA without primers; the first catalytic stage of initiation is referred to as de novo RNA synthesis. De novo synthesis is a unique phase in the transcription cycle where the RNA polymerase binds two nucleotides rather than a nascent RNA polymer and a single nucleotide. For bacteriophage T7 RNA polymerase, transcription begins with a marked preference for GTP at the +1 and +2 positions. Initiating nucleotides bind RNA polymerase in locations distinct from those described for elongation complexes (Kennedy W P et al. *J Mol Biol.* 2007; 370(2): 256-68). Selection bias in favor of GTP as an initiating nucleotide is achieved by shape complementarity, extensive protein side-chain, and strong base-stacking interactions for the guanine moiety in the enzyme active site. Thus, an initiating GTP provides the largest stabilization force for the open promoter conformation (Kennedy et al. 2007). The RNA polymerase variants used herein, in some embodiments, comprise one or more amino acid substitution(s) at one or more binding site residue(s) for de novo RNA synthesis, which, without being bound by theory, alters RNA polymerase affinity to the cap analog of an in vitro transcription reaction, for example, such that there is an improvement in capping efficiency at low cap analog concentrations.

Thus, the present disclosure, in some aspects, provides methods that use a RNA polymerase variants that comprises an RNA polymerase that includes an amino acid substitution at a binding site residue for de novo RNA synthesis (see, e.g., Table 1). A RNA polymerase variant is an enzyme having RNA polymerase activity and at least one substitution and/or modification relative to the counterpart wild-type RNA polymerase. In some embodiments, the amino acid substitution at a binding site residue is a substitution at a position selected from positions 350, 351, 387, 394, 425, 427, 437, 441, 632, 811, and 880, relative to the wild-type RNA polymerase, wherein the wild-type RNA polymerase comprises the amino acid sequence of SEQ ID NO: 1.

In some embodiments, a RNA polymerase variant comprises a RNA polymerase that includes (a) an amino acid substitution at a position selected from positions 350, 351, 387, 394, 425, 427, 437, 441, 632, 811, and 880, and (b) an additional amino acid substitution and/or an amino acid modification at the C-terminal end, relative to wild-type RNA polymerase, wherein the wild-type RNA polymerase comprises the amino acid sequence of SEQ ID NO: 1.

In some embodiments, a RNA polymerase variant comprises a RNA polymerase that includes an amino acid substitution at position 47 (e.g., G47A), an amino acid substitution at position 350, and/or an additional amino acid (e.g., G) at the C-terminal end (at position 884), relative to wild-type RNA polymerase, wherein the wild-type RNA polymerase comprises the amino acid sequence of SEQ ID NO: 1. In some embodiments, a RNA polymerase variant comprises a RNA polymerase that includes an amino acid substitution at position 47 (e.g., G47A), a lysine (K) at position 350 (E350K), and/or an additional amino acid (e.g., G) at the C-terminal end (at position 884), relative to wild-type RNA polymerase, wherein the wild-type RNA polymerase comprises the amino acid sequence of SEQ ID NO: 1. In some embodiments, a RNA polymerase variant comprises a RNA polymerase that includes an amino acid substitution at position 47 (e.g., G47A), an asparagine (N) at position 350 (E350N), and/or an additional amino acid (e.g., G) at the C-terminal end (at position 884), relative to wild-type RNA polymerase, wherein the wild-type RNA polymerase comprises the amino acid sequence of SEQ ID NO: 1. In some embodiments, a RNA polymerase variant comprises a RNA polymerase that includes an amino acid substitution at position 47 (e.g., G47A), an alanine (A) at position 350 (E350A), and/or an additional amino acid (e.g., G) at the C-terminal end (at position 884), relative to wild-type RNA polymerase, wherein the wild-type RNA polymerase comprises the amino acid sequence of SEQ ID NO: 1. In some embodiments, a RNA polymerase variant comprises a RNA polymerase that includes an amino acid substitution at position 47 (e.g., G47A), a tryptophan at position 350 (E350W), and/or an additional amino acid (e.g., G) at the C-terminal end (at position 884), relative to wild-type RNA polymerase, wherein the wild-type RNA polymerase comprises the amino acid sequence of SEQ ID NO: 1.

In some embodiments, a RNA polymerase variant comprises a RNA polymerase that includes an amino acid substitution at position 47 (e.g., G47A), an amino acid substitution at position 351, and/or an additional amino acid (e.g., G) at the C-terminal end (at position 884), relative to wild-type RNA polymerase, wherein the wild-type RNA polymerase comprises the amino acid sequence of SEQ ID NO: 1. In some embodiments, a RNA polymerase variant comprises a RNA polymerase that includes an amino acid substitution at position 47 (e.g., G47A), a valine (V) at position 351 (D351V), and/or an additional amino acid (e.g., G) at the C-terminal end (at position 884), relative to wild-type RNA polymerase, wherein the wild-type RNA polymerase comprises the amino acid sequence of SEQ ID NO: 1.

In some embodiments, a RNA polymerase variant comprises a RNA polymerase that includes an amino acid substitution at position 47 (e.g., G47A), an amino acid substitution at position 387, and/or an additional amino acid (e.g., G) at the C-terminal end (at position 884), relative to wild-type RNA polymerase, wherein the wild-type RNA polymerase comprises the amino acid sequence of SEQ ID NO: 1. In some embodiments, a RNA polymerase variant comprises a RNA polymerase that includes an amino acid substitution at position 47 (e.g., G47A), a serine at position 387 (K387S), and/or an additional amino acid (e.g., G) at the C-terminal end (at position 884), relative to wild-type RNA polymerase, wherein the wild-type RNA polymerase comprises the amino acid sequence of SEQ ID NO: 1. In some embodiments, a RNA polymerase variant comprises a RNA polymerase that includes an amino acid substitution at position 47 (e.g., G47A), a histidine (H) at position 387 (K387H), and/or an additional amino acid (e.g., G) at the C-terminal end (at position 884), relative to wild-type RNA polymerase, wherein the wild-type RNA polymerase comprises the amino acid sequence of SEQ ID NO: 1. In some embodiments, a RNA polymerase variant comprises a RNA polymerase that includes an amino acid substitution at position 47 (e.g., G47A), an asparagine at position 387 (K387N), and/or an additional amino acid (e.g., G) at the C-terminal end (at position 884), relative to wild-type RNA polymerase, wherein the wild-type RNA polymerase comprises the amino acid sequence of SEQ ID NO: 1.

In some embodiments, a RNA polymerase variant comprises a RNA polymerase that includes an amino acid substitution at position 47 (e.g., G47A), an amino acid substitution at position 394, and/or an additional amino acid (e.g., G) at the C-terminal end (at position 884), relative to wild-type RNA polymerase, wherein the wild-type RNA polymerase comprises the amino acid sequence of SEQ ID NO: 1.

In some embodiments, a RNA polymerase variant comprises a RNA polymerase that includes an amino acid substitution at position 47 (e.g., G47A), an amino acid substitution at position 425, and/or an additional amino acid (e.g., G) at the C-terminal end (at position 884), relative to wild-type RNA polymerase, wherein the wild-type RNA polymerase comprises the amino acid sequence of SEQ ID NO: 1.

In some embodiments, a RNA polymerase variant comprises a RNA polymerase that includes an amino acid substitution at position 47 (e.g., G47A), an amino acid substitution at position 427, and/or an additional amino acid (e.g., G) at the C-terminal end (at position 884), relative to wild-type RNA polymerase, wherein the wild-type RNA polymerase comprises the amino acid sequence of SEQ ID NO: 1.

In some embodiments, a RNA polymerase variant comprises a RNA polymerase that includes an amino acid substitution at position 47 (e.g., G47A), an amino acid substitution at position 437, and/or an additional amino acid (e.g., G) at the C-terminal end (at position 884), relative to wild-type RNA polymerase, wherein the wild-type RNA polymerase comprises the amino acid sequence of SEQ ID NO: 1. In some embodiments, a RNA polymerase variant comprises a RNA polymerase that includes an amino acid substitution at position 47 (e.g., G47A), a threonine at position 437 (N437T), and/or an additional amino acid (e.g., G) at the C-terminal end (at position 884), relative to wild-type RNA polymerase, wherein the wild-type RNA polymerase comprises the amino acid sequence of SEQ ID NO: 1. In some embodiments, a RNA polymerase variant comprises a RNA polymerase that includes an amino acid substitution at position 47 (e.g., G47A), an isoleucine at position 437 (N437I), and/or an additional amino acid (e.g., G) at the C-terminal end (at position 884), relative to wild-type RNA polymerase, wherein the wild-type RNA polymerase comprises the amino acid sequence of SEQ ID NO: 1. In some embodiments, a RNA polymerase variant comprises a RNA polymerase that includes an amino acid substitution at position 47 (e.g., G47A), a tyrosine at position 437 (N437Y), and/or an additional amino acid (e.g., G) at the C-terminal end (at position 884), relative to wild-type RNA polymerase, wherein the wild-type RNA polymerase comprises the amino acid sequence of SEQ ID NO: 1. In some embodiments, a RNA polymerase variant comprises a RNA polymerase that includes an amino acid substitution at position 47 (e.g., G47A), a phenylalanine at position 437 (N437F), and/or an additional amino acid (e.g., G) at the C-terminal end (at position 884), relative to wild-type RNA polymerase, wherein the wild-type RNA polymerase comprises the amino acid sequence of SEQ ID NO: 1.

In some embodiments, a RNA polymerase variant comprises a RNA polymerase that includes an amino acid substitution at position 47 (e.g., G47A), an amino acid substitution at position 441, and/or an additional amino acid (e.g., G) at the C-terminal end (at position 884), relative to wild-type RNA polymerase, wherein the wild-type RNA polymerase comprises the amino acid sequence of SEQ ID NO: 1. In some embodiments, a RNA polymerase variant comprises a RNA polymerase that includes an amino acid substitution at position 47 (e.g., G47A), an arginine at position 441 (K441R), and/or an additional amino acid (e.g., G) at the C-terminal end (at position 884), relative to wild-type RNA polymerase, wherein the wild-type RNA polymerase comprises the amino acid sequence of SEQ ID NO: 1.

In some embodiments, a RNA polymerase variant comprises a RNA polymerase that includes an amino acid substitution at position 47 (e.g., G47A), an amino acid substitution at position 632, and/or an additional amino acid (e.g., G) at the C-terminal end (at position 884), relative to wild-type RNA polymerase, wherein the wild-type RNA polymerase comprises the amino acid sequence of SEQ ID NO: 1.

In some embodiments, a RNA polymerase variant comprises a RNA polymerase that includes an amino acid substitution at position 47 (e.g., G47A), an amino acid substitution at position 811, and/or an additional amino acid (e.g., G) at the C-terminal end (at position 884), relative to wild-type RNA polymerase, wherein the wild-type RNA polymerase comprises the amino acid sequence of SEQ ID NO: 1.

In some embodiments, a RNA polymerase variant comprises a RNA polymerase that includes an amino acid substitution at position 47 (e.g., G47A), an amino acid substitution at position 880, and/or an additional amino acid (e.g., G) at the C-terminal end (at position 884), relative to wild-type RNA polymerase, wherein the wild-type RNA polymerase comprises the amino acid sequence of SEQ ID NO: 1. In some embodiments, a RNA polymerase variant comprises a RNA polymerase that includes an amino acid substitution at position 47 (e.g., G47A), a tyrosine at position 880 (F880Y), and/or an additional amino acid (e.g., G) at the C-terminal end (at position 884), relative to wild-type RNA polymerase, wherein the wild-type RNA polymerase comprises the amino acid sequence of SEQ ID NO: 1.

In some embodiments, a RNA polymerase variant comprises a RNA polymerase that includes an amino acid substitution at position 47 (e.g., G47A), and an additional amino acid at the C-terminal end (at position 884), relative to wild-type RNA polymerase, wherein the wild-type RNA polymerase comprises the amino acid sequence of SEQ ID NO: 1. In some embodiments, the additional amino acid at the C-terminal end is threonine (T). In some embodiments, the additional amino acid at the C-terminal end is serine (S). In some embodiments, the additional amino acid at the C-terminal end is alanine (A). In some embodiments, the additional amino acid at the C-terminal end is proline (P).

In some embodiments, a RNA polymerase variant comprises a RNA polymerase that comprises an amino acid substitution at position 350, relative to wild-type RNA polymerase, wherein the wild-type RNA polymerase comprises the amino acid sequence of SEQ ID NO: 1. In some embodiments, the amino acid substitution at position 350 is selected from the group consisting of E350R, E350K, E350H, E350D, E350Q, E350N, E350T, E350S, E350C, E350G, E350A, E350V, E350I, E350M, E350P, E350Y, E350W, and E350F. In some embodiments, the amino acid substitution at position 350 is E350R. In some embodiments, the amino acid substitution at position 350 is E350K. In some embodiments, the amino acid substitution at position 350 is E350H. In some embodiments, the amino acid substitution at position 350 is E350D. In some embodiments, the amino acid substitution at position 350 is E350Q. In some embodiments, the amino acid substitution at position 350 is E350N. In some embodiments, the amino acid substitution at position 350 is E350T. In some embodiments, the amino acid substitution at position 350 is E350S. In some embodiments, the amino acid substitution at position 350 is E350C. In some embodiments, the amino acid substitution at position 350 is E350G. In some embodiments, the amino acid substitution at position 350 is E350A. In some embodiments, the amino acid substitution at position 350 is E350V. In some embodiments, the amino acid substitution at position 350 is E350I. In some embodiments, the amino acid substitution at position 350 is E350M. In some embodiments, the amino acid substitution at position 350 is E350P. In some embodiments, the amino acid substitution at position 350 is E350Y. In some embodiments, the amino acid substitution at position 350 is E350W. In some embodiments, the amino acid substitution at position 350 is E350F.

In some embodiments, a RNA polymerase variant comprises a RNA polymerase that comprises an amino acid substitution at position 351, relative to wild-type RNA polymerase, wherein the wild-type RNA polymerase comprises the amino acid sequence of SEQ ID NO: 1. In some embodiments, the amino acid substitution at position 351 is selected from the group consisting of D351R, D351K, D351H, D351E, D351Q, D351N, D351T, D351S, D351C, D351G, D351A, D351V, D351I, D351M, D351P, D351Y, D351W, and D351F. In some embodiments, the amino acid substitution at position 351 is D351R. In some embodiments, the amino acid substitution at position 351 is D351K. In some embodiments, the amino acid substitution at position 351 is D351H. In some embodiments, the amino acid substitution at position 351 is D351E. In some embodiments, the amino acid substitution at position 351 is D351Q. In some embodiments, the amino acid substitution at position 351 is D351N. In some embodiments, the amino acid substitution at position 351 is D351T. In some embodiments, the amino acid substitution at position 351 is D351S. In some embodiments, the amino acid substitution at position 351 is D351C. In some embodiments, the amino acid substitution at position 351 is D351G. In some embodiments, the amino acid substitution at position 351 is D351A. In some embodiments, the amino acid substitution at position 351 is D351V. In some embodiments, the amino acid substitution at position 351 is D351I. In some embodiments, the amino acid substitution at position 351 is D351M. In some embodiments, the amino acid substitution at position 351 is D351P. In some embodiments, the amino acid substitution at position 351 is D351Y. In some embodiments, the amino acid substitution at position 351 is D351W. In some embodiments, the amino acid substitution at position 351 is D351F.

In some embodiments, a RNA polymerase variant comprises a RNA polymerase that comprises an amino acid substitution at position 387, relative to wild-type RNA polymerase, wherein the wild-type RNA polymerase comprises the amino acid sequence of SEQ ID NO: 1. In some embodiments, the amino acid substitution at position 387 is selected from the group consisting of K387R, K387H, K387E, K387D, K387Q, K387N, K387T, K387S, K387C, K387G, K387A, K387V, K387I, K387M, K387P, K387Y, K387W, and K387F. In some embodiments, the amino acid substitution at position 387 is K387R. In some embodiments, the amino acid substitution at position 387 is K387H. In some embodiments, the amino acid substitution at position 387 is K387E. In some embodiments, the amino acid substitution at position 387 is K387D. In some embodiments, the amino acid substitution at position 387 is K387Q. In some embodiments, the amino acid substitution at position 387 is K387N. In some embodiments, the amino acid substitution at position 387 is K387T. In some embodiments, the amino acid substitution at position 387 is K387S. In some embodiments, the amino acid substitution at position 387 is K387C. In some embodiments, the amino acid substitution at position 387 is K387G. In some embodiments, the amino acid substitution at position 387 is K387A. In some embodiments, the amino acid substitution at position 387 is K387V. In some embodiments, the amino acid substitution at position 387 is K387I. In some embodiments, the amino acid substitution at position 387 is K387M. In some embodiments, the amino acid substitution at position 387 is K387P. In some embodiments, the amino acid substitution at position 387 is K387Y. In some embodiments, the amino acid substitution at position 387 is K387W. In some embodiments, the amino acid substitution at position 387 is K387F.

In some embodiments, a RNA polymerase variant comprises a RNA polymerase that comprises an amino acid substitution at position 394, relative to wild-type RNA polymerase, wherein the wild-type RNA polymerase comprises the amino acid sequence of SEQ ID NO: 1. In some embodiments, the amino acid substitution at position 394 is selected from the group consisting of R394K, R394H, R394E, R394D, R394Q, R394N, R394T, R394S, R394C, R394G, R394A, R394V, R394I, R394M, R394P, R394Y, R394W, and R394F. In some embodiments, the amino acid substitution at position 394 is R394K. In some embodiments, the amino acid substitution at position 394 is R394H. In some embodiments, the amino acid substitution at position 394 is R394E. In some embodiments, the amino acid substitution at position 394 is R394D. In some embodiments, the amino acid substitution at position 394 is R394Q. In some embodiments, the amino acid substitution at position 394 is R394N. In some embodiments, the amino acid substitution at position 394 is R394T. In some embodiments, the amino acid substitution at position 394 is R394S. In some embodiments, the amino acid substitution at position 394 is R394C. In some embodiments, the amino acid substitution at position 394 is R394G. In some embodiments, the amino acid substitution at position 394 is R394A. In some embodiments, the amino acid substitution at position 394 is R394V. In some embodiments, the amino acid substitution at position 394 is R394I. In some embodiments, the amino acid substitution at position 394 is R394M. In some embodiments, the amino acid substitution at position 394 is R394P. In some embodiments, the amino acid substitution at position 394 is R394Y. In some embodiments, the amino acid substitution at position 394 is R394W. In some embodiments, the amino acid substitution at position 394 is R394F.

In some embodiments, a RNA polymerase variant comprises a RNA polymerase that comprises an amino acid substitution at position 425, relative to wild-type RNA polymerase, wherein the wild-type RNA polymerase comprises the amino acid sequence of SEQ ID NO: 1. In some embodiments, the amino acid substitution at position 425 is selected from the group consisting of R425K, R425H, R425E, R425D, R425Q, R425N, R425T, R425S, R425C, R425G, R425A, R425V, R425I, R425M, R425P, R425Y, R425W, and R425F. In some embodiments, the amino acid substitution at position 425 is R425K. In some embodiments, the amino acid substitution at position 425 is R425H. In some embodiments, the amino acid substitution at position 425 is R425E. In some embodiments, the amino acid substitution at position 425 is R425D. In some embodiments, the amino acid substitution at position 425 is R425Q. In some embodiments, the amino acid substitution at position 425 is R425N. In some embodiments, the amino acid substitution at position 425 is R425T. In some embodiments, the amino acid substitution at position 425 is R425S. In some embodiments, the amino acid substitution at position 425 is R425C. In some embodiments, the amino acid substitution at position 425 is R425G. In some embodiments, the amino acid substitution at position 425 is R425A. In some embodiments, the amino acid substitution at position 425 is R425V. In some embodiments, the amino acid substitution at position 425 is R425I. In some embodiments, the amino acid substitution at position 425 is R425M. In some embodiments, the amino acid substitution at position 425 is R425P. In some embodiments, the amino acid substitution at position 425 is R425Y. In some embodiments, the amino acid substitution at position 425 is R425W. In some embodiments, the amino acid substitution at position 425 is R425F.

In some embodiments, a RNA polymerase variant comprises a RNA polymerase that comprises an amino acid substitution at position 427, relative to wild-type RNA polymerase, wherein the wild-type RNA polymerase comprises the amino acid sequence of SEQ ID NO: 1. In some embodiments, the amino acid substitution at position 427 is selected from the group consisting of Y427R, Y427K, Y427H, Y427E, Y427D, Y427Q, Y427N, Y427T, Y427S, Y427C, Y427G, Y427A, Y427V, Y427I, Y427M, Y427P, Y427W, and Y427F. In some embodiments, the amino acid substitution at position 427 is Y427R. In some embodiments, the amino acid substitution at position 427 is Y427K. In some embodiments, the amino acid substitution at position 427 is Y427H. In some embodiments, the amino acid substitution at position 427 is Y427E. In some embodiments, the amino acid substitution at position 427 is Y427D. In some embodiments, the amino acid substitution at position 427 is Y427Q. In some embodiments, the amino acid substitution at position 427 is Y427N. In some embodiments, the amino acid substitution at position 427 is Y427T. In some embodiments, the amino acid substitution at position 427 is Y427S. In some embodiments, the amino acid substitution at position 427 is Y427C. In some embodiments, the amino acid substitution at position 427 is Y427G. In some embodiments, the amino acid substitution at position 427 is Y427A. In some embodiments, the amino acid substitution at position 427 is Y427V. In some embodiments, the amino acid substitution at position 427 is Y427I. In some embodiments, the amino acid substitution at position 427 is Y427M. In some embodiments, the amino acid substitution at position 427 is Y427P. In some embodiments, the amino acid substitution at position 427 is Y427W. In some embodiments, the amino acid substitution at position 427 is Y427F.

In some embodiments, a RNA polymerase variant comprises a RNA polymerase that comprises an amino acid substitution at position 437, relative to wild-type RNA polymerase, wherein the wild-type RNA polymerase comprises the amino acid sequence of SEQ ID NO: 1. In some embodiments, the amino acid substitution at position 437 is selected from the group consisting of N437R, N437K, N437H, N437E, N437D, N437Q, N437T, N437S, N437C, N437G, N437A, N437V, N437I, N437M, N437P, N437Y, N437W, and N437F. In some embodiments, the amino acid substitution at position 437 is N437R. In some embodiments, the amino acid substitution at position 437 is N437K. In some embodiments, the amino acid substitution at position 437 is N437H. In some embodiments, the amino acid substitution at position 437 is N437E. In some embodiments, the amino acid substitution at position 437 is N437D. In some embodiments, the amino acid substitution at position 437 is N437Q. In some embodiments, the amino acid substitution at position 437 is N437T. In some embodiments, the amino acid substitution at position 437 is N437S. In some embodiments, the amino acid substitution at position 437 is N437C. In some embodiments, the amino acid substitution at position 437 is N437G. In some embodiments, the amino acid substitution at position 437 is N437A. In some embodiments, the amino acid substitution at position 437 is N437V. In some embodiments, the amino acid substitution at position 437 is N437I. In some embodiments, the amino acid substitution at position 437 is N437M. In some embodiments, the amino acid substitution at position 437 is N437P. In some embodiments, the amino acid substitution at position 437 is N437Y. In some embodiments, the amino acid substitution at position 437 is N437W. In some embodiments, the amino acid substitution at position 437 is N437F.

In some embodiments, a RNA polymerase variant comprises a RNA polymerase that comprises an amino acid substitution at position 441, relative to wild-type RNA polymerase, wherein the wild-type RNA polymerase comprises the amino acid sequence of SEQ ID NO: 1. In some embodiments, the amino acid substitution at position 441 is selected from the group consisting of K441R, K441H, K441E, K441D, K441Q, K441N, K441T, K441S, K441C, K441G, K441A, K441V, K441I, K441M, K441P, K441Y, K441W, and K441F. In some embodiments, the amino acid substitution at position 441 is K441R. In some embodiments, the amino acid substitution at position 441 is K441H. In some embodiments, the amino acid substitution at position 441 is K441E. In some embodiments, the amino acid substitution at position 441 is K441D. In some embodiments, the amino acid substitution at position 441 is K441Q. In some embodiments, the amino acid substitution at position 441 is K441N. In some embodiments, the amino acid substitution at position 441 is K441T. In some embodiments, the amino acid substitution at position 441 is K441S. In some embodiments, the amino acid substitution at position 441 is K441C. In some embodiments, the amino acid substitution at position 441 is K441G. In some embodiments, the amino acid substitution at position 441 is K441A. In some embodiments, the amino acid substitution at position 441 is K441V. In some embodiments, the amino acid substitution at position 441 is K441I. In some embodiments, the amino acid substitution at position 441 is K441M. In some embodiments, the amino acid substitution at position 441 is K441P. In some embodiments, the amino acid substitution at position 441 is K441Y. In some embodiments, the amino acid substitution at position 441 is K441W. In some embodiments, the amino acid substitution at position 441 is K441F.

In some embodiments, a RNA polymerase variant comprises a RNA polymerase that comprises an amino acid substitution at position 632, relative to wild-type RNA polymerase, wherein the wild-type RNA polymerase comprises the amino acid sequence of SEQ ID NO: 1. In some embodiments, the amino acid substitution at position 632 is selected from the group consisting of R632K, R632H, R632E, R632D, R632Q, R632N, R632T, R632S, R632C, R632G, R632A, R632V, R632I, R632M, R632P, R632Y, R632W, and R632F. In some embodiments, the amino acid substitution at position 632 is R632K. In some embodiments, the amino acid substitution at position 632 is R632H. In some embodiments, the amino acid substitution at position 632 is R632E. In some embodiments, the amino acid substitution at position 632 is R632D. In some embodiments, the amino acid substitution at position 632 is R632Q. In some embodiments, the amino acid substitution at position 632 is R632N. In some embodiments, the amino acid substitution at position 632 is R632T. In some embodiments, the amino acid substitution at position 632 is R632S. In some embodiments, the amino acid substitution at position 632 is R632C. In some embodiments, the amino acid substitution at position 632 is R632G. In some embodiments, the amino acid substitution at position 632 is R632A. In some embodiments, the amino acid substitution at position 632 is R632V. In some embodiments, the amino acid substitution at position 632 is R632I. In some embodiments, the amino acid substitution at position 632 is R632M. In some embodiments, the amino acid substitution at position 632 is R632P. In some embodiments, the amino acid substitution at position 632 is R632Y. In some embodiments, the amino acid substitution at position 632 is R632W. In some embodiments, the amino acid substitution at position 632 is R632F.

In some embodiments, a RNA polymerase variant comprises a RNA polymerase that comprises an amino acid substitution at position 811, relative to wild-type RNA polymerase, wherein the wild-type RNA polymerase comprises the amino acid sequence of SEQ ID NO: 1. In some embodiments, the amino acid substitution at position 811 is selected from the group consisting of H811R, H811K, H811E, H811D, H811Q, H811N, H811T, H811S, H811C, H811G, H811A, H811V, H811I, H811M, H811P, H811Y, H811W, and H811F. In some embodiments, the amino acid substitution at position 811 is H811R. In some embodiments, the amino acid substitution at position 811 is H811K. In some embodiments, the amino acid substitution at position 811 is H811E. In some embodiments, the amino acid substitution at position 811 is H811D. In some embodiments, the amino acid substitution at position 811 is H811Q. In some embodiments, the amino acid substitution at position 811 is H811N. In some embodiments, the amino acid substitution at position 811 is H811T. In some embodiments, the amino acid substitution at position 811 is H811S. In some embodiments, the amino acid substitution at position 811 is H811C. In some embodiments, the amino acid substitution at position 811 is H811G. In some embodiments, the amino acid substitution at position 811 is H811A. In some embodiments, the amino acid substitution at position 811 is H811V. In some embodiments, the amino acid substitution at position 811 is H811I. In some embodiments, the amino acid substitution at position 811 is H811M. In some embodiments, the amino acid substitution at position 811 is H811P. In some embodiments, the amino acid substitution at position 811 is H811Y. In some embodiments, the amino acid substitution at position 811 is H811W. In some embodiments, the amino acid substitution at position 811 is H811F.

In some embodiments, a RNA polymerase variant comprises a RNA polymerase that comprises an amino acid substitution at position 880, relative to wild-type RNA polymerase, wherein the wild-type RNA polymerase comprises the amino acid sequence of SEQ ID NO: 1. In some embodiments, the amino acid substitution at position 880 is selected from the group consisting of F880R, F880K, F880H, F880E, F880D, F880Q, F880N, F880T, F880S, F880C, F880G, F880A, F880V, F880I, F880M, F880P, F880Y, and F880W. In some embodiments, the amino acid substitution at position 880 is F880R. In some embodiments, the amino acid substitution at position 880 is F880K. In some embodiments, the amino acid substitution at position 880 is F880H. In some embodiments, the amino acid substitution at position 880 is F880E. In some embodiments, the amino acid substitution at position 880 is F880D. In some embodiments, the amino acid substitution at position 880 is F880Q. In some embodiments, the amino acid substitution at position 880 is F880N. In some embodiments, the amino acid substitution at position 880 is F880T. In some embodiments, the amino acid substitution at position 880 is F880S. In some embodiments, the amino acid substitution at position 880 is F880C. In some embodiments, the amino acid substitution at position 880 is F880G. In some embodiments, the amino acid substitution at position 880 is F880A. In some embodiments, the amino acid substitution at position 880 is F880V. In some embodiments, the amino acid substitution at position 880 is F880I. In some embodiments, the amino acid substitution at position 880 is F880M. In some embodiments, the amino acid substitution at position 880 is F880P. In some embodiments, the amino acid substitution at position 880 is F880Y. In some embodiments, the amino acid substitution at position 880 is F880W.

In should be understood that the RNA polymerase variants of the present disclosure may include more than one (e.g., 2, 3, 4, 5, or more) amino acid substitution and/or modification. It should also be understood that any of the RNA polymerase variants may include a G47A substitution and/or an additional C-terminal amino acid, such as glycine, relative to a wild-type RNA polymerase comprising the amino acid sequence of SEQ ID NO: 1.

In some embodiments, a RNA polymerase variant comprises a RNA polymerase that includes (a) an amino acid substitution at positions 350, 351, and 387, and (b) an additional amino acid substitution and/or an amino acid modification at the C-terminal end, relative to wild-type RNA polymerase, wherein the wild-type RNA polymerase comprises the amino acid sequence of SEQ ID NO: 1. In some embodiments, the additional amino acid substitution at position 350 is E350A. In some embodiments, the additional amino acid substitution at position 350 is E350K. In some embodiments, the additional amino acid substitution at position 350 is E350N. In some embodiments, the additional amino acid substitution at position 350 is E350W. In some embodiments, the additional amino acid substitution at position 351 is D351V. In some embodiments, the additional amino acid substitution at position 387 is K387S. In some embodiments, the additional amino acid substitution at position 387 is K387H. In some embodiments, the additional amino acid substitution at position 387 is K387N. In some embodiments, the RNA polymerase variant comprises a G47A substitution. In some embodiments, the RNA polymerase variant comprises an additional glycine at the C-terminus.

In some embodiments, a RNA polymerase variant comprises a RNA polymerase that includes (a) an amino acid substitution at positions 437 and 441, and (b) an additional amino acid substitution and/or an amino acid modification at the C-terminal end, relative to wild-type RNA polymerase, wherein the wild-type RNA polymerase comprises the amino acid sequence of SEQ ID NO: 1. In some embodiments, the additional amino acid substitution at position 437 is N437T. In some embodiments, the additional amino acid substitution at position 437 is N437Y. In some embodiments, the additional amino acid substitution at position 437 is N437I. In some embodiments, the additional amino acid substitution at position 437 is N437F. In some embodiments, the additional amino acid substitution at position 441 is K441R. In some embodiments, the RNA polymerase variant comprises a G47A substitution. In some embodiments, the RNA polymerase variant comprises an additional glycine at the C-terminus.

In some embodiments, a RNA polymerase variant comprises a RNA polymerase that includes (a) an amino acid substitution at positions 880, and (b) an amino acid modification at the C-terminal end, relative to wild-type RNA polymerase, wherein the wild-type RNA polymerase comprises the amino acid sequence of SEQ ID NO: 1. In some embodiments, the additional amino acid substitution at position 880 is F880Y. In some embodiments, the amino acid modification at the C-terminal end is an additional alanine (A). In some embodiments, the amino acid modification at the C-terminal end is an additional serine (S). In some embodiments, the amino acid modification at the C-terminal end is an additional threonine (T). In some embodiments, the amino acid modification at the C-terminal end is an additional proline (P). In some embodiments, the RNA polymerase variant comprises a G47A substitution.

In some embodiments, a RNA polymerase variant comprises a RNA polymerase that includes (a) an amino acid substitution at positions 632, 653, and 657, and (b) an additional amino acid substitution and/or an amino acid modification at the C-terminal end, relative to wild-type RNA polymerase, wherein the wild-type RNA polymerase comprises the amino acid sequence of SEQ ID NO: 1. In some embodiments, the additional amino acid substitution at position 632 is R632K. In some embodiments, the additional amino acid substitution at position 632 is R632T. In some embodiments, the additional amino acid substitution at position 653 is D653T. In some embodiments, the additional amino acid substitution at position 653 is D653K. In some embodiments, the additional amino acid substitution at position 657 is P657W. In some embodiments, the additional amino acid substitution at position 657 is P657R. In some embodiments, the additional amino acid substitution at position 657 is P657A. In some embodiments, the RNA polymerase variant comprises a G47A substitution. In some embodiments, the RNA polymerase variant comprises an additional glycine at the C-terminus.

It should also be understood that the present disclosure encompasses RNA polymerases that have at least 90%, at least 91%, at least 92%, at least 93%, at least 94%, at least 95%, at least 96%, at least 97%, at least 98%, or at least 99% identity to the RNA polymerase variants of described herein. It should also be understood that any of the RNA polymerase variants described herein may share at least 90%, at least 91%, at least 92%, at least 93%, at least 94%, at least 95% identity with a RNA polymerase comprising the amino acid sequence of SEQ ID NO: 1.

The term "identity" refers to a relationship between the sequences of two or more polypeptides (e.g. enzymes) or polynucleotides (nucleic acids), as determined by comparing the sequences. Identity also refers to the degree of sequence relatedness between or among sequences as determined by the number of matches between strings of two or more amino acid residues or nucleic acid residues. Identity measures the percent of identical matches between the smaller of two or more sequences with gap alignments (if any) addressed by a particular mathematical model or computer program (e.g., "algorithms"). Identity of related proteins or nucleic acids can be readily calculated by known methods. "Percent (%) identity" as it applies to polypeptide or polynucleotide sequences is defined as the percentage of residues (amino acid residues or nucleic acid residues) in the candidate amino acid or nucleic acid sequence that are identical with the residues in the amino acid sequence or nucleic acid sequence of a second sequence after aligning the sequences and introducing gaps, if necessary, to achieve the maximum percent identity. Methods and computer programs for the alignment are well known in the art. It is understood that identity depends on a calculation of percent identity but may differ in value due to gaps and penalties introduced in the calculation. Generally, variants of a particular polynucleotide or polypeptide (e.g., antigen) have at least 40%, 45%, 50%, 55%, 60%, 65%, 70%, 75%, 80%, 85%, 90%, 91%, 92%, 93%, 94%, 95%, 96%, 97%, 98%, 99% but less than 100% sequence identity to that particular reference polynucleotide or polypeptide as determined by sequence alignment programs and parameters described herein and known to those skilled in the art. Such tools for alignment include those of the BLAST suite (Stephen F. Altschul, et al (1997), "Gapped BLAST and PSI-BLAST: a new generation of protein database search programs", *Nucleic Acids Res.* 25:3389-3402). Another popular local alignment technique is based on the Smith-Waterman algorithm (Smith, T. F. & Waterman, M. S. (1981) "Identification of common molecular subsequences." *J. Mol. Biol.* 147:195-197). A general global alignment technique based on dynamic programming is the Needleman-Wunsch algorithm (Needleman, S. B. & Wunsch, C. D. (1970) "A general method applicable to the search for similarities in the amino acid sequences of two proteins." *J. Mol. Biol.* 48:443-453). More recently a Fast Optimal Global Sequence Alignment Algorithm (FOGSAA) has been developed that purportedly produces global alignment of nucleotide and protein sequences faster than other optimal global alignment methods, including the Needleman-Wunsch algorithm.

Trinucleotide Caps

An in vitro transcription reaction, in some embodiments, is a co-transcriptional capping reaction for ribonucleic acid (RNA) synthesis. That is, RNA is produced in a "one-pot" reaction, without the need for a separate capping reaction. Thus, the methods, in some embodiments, comprise reacting a polynucleotide template with a RNA polymerase variant, nucleoside triphosphates, and a cap analog under in vitro transcription reaction conditions to produce RNA transcript.

A cap analog may be, for example, a dinucleotide cap, a trinucleotide cap, or a tetranucleotide cap. In some embodiments, a cap analog is a dinucleotide cap. In some embodiments, a cap analog is a trinucleotide cap. In some embodiments, a cap analog is a tetranucleotide cap.

A trinucleotide cap, in some embodiments, comprises a compound of formula (I)

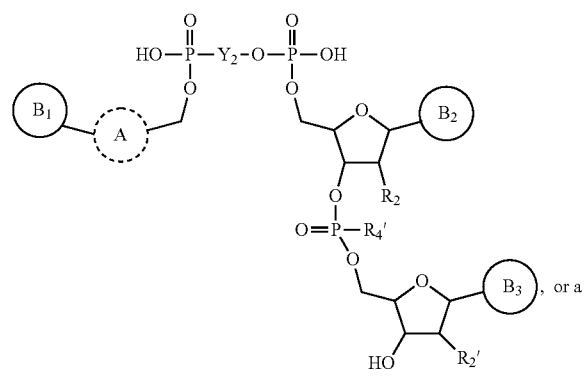

(I)

, or a stereoisomer, tautomer or salt thereof, wherein

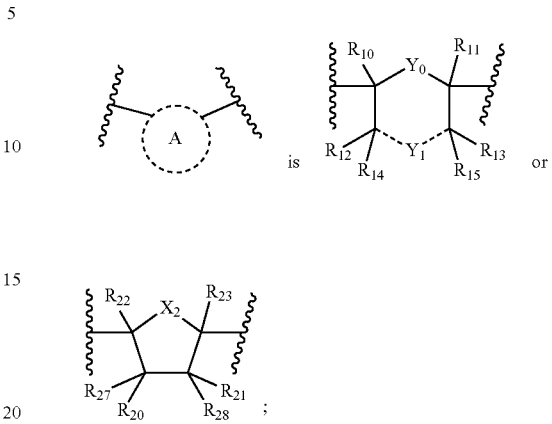

ring $B_1$ is a modified or unmodified Guanine;

ring $B_2$ and ring $B_3$ each independently is a nucleobase or a modified nucleobase;

$X_2$ is O, $S(O)_p$, $NR_{24}$ or $CR_{25}R_{26}$ in which p is 0, 1, or 2;

$Y_0$ is O or $CR_6R_7$;

Y1 is O, $S(O)_n$, $CR_6R_7$, or $NR_8$, in which n is 0, 1, or 2;

each --- is a single bond or absent, wherein when each --- is a single bond, Yi is O, $S(O)_n$, $CR_6R_7$, or $NR_8$; and when each --- is absent, Yi is void;

$Y_2$ is $(OP(O)R_4)_m$ in which m is 0, 1, or 2, or —O—$(CR_{40}R_{41})u$-$Q_0$-$(CR_{42}R_{43})v$-, in which $Q_0$ is a bond, O, $S(O)_r$, $NR_{44}$, or $CR_{45}R_{46}$, r is 0, 1, or 2, and each of u and v independently is 1, 2, 3 or 4;

each $R_2$ and $R_2'$ independently is halo, LNA, or $OR_3$;

each $R_3$ independently is H, $C_1$-$C_6$ alkyl, $C_2$-$C_6$ alkenyl, or $C_2$-$C_6$ alkynyl and $R_3$, when being $C_1$-$C_6$ alkyl, $C_2$-$C_6$ alkenyl, or $C_2$-$C_6$ alkynyl, is optionally substituted with one or more of halo, OH and $C_1$-$C_6$ alkoxyl that is optionally substituted with one or more OH or OC(O)—$C_1$-$C_6$ alkyl;

each $R_4$ and $R_4'$ independently is H, halo, $C_1$-$C_6$ alkyl, OH, SH, SeH, or $BH_3^-$;

each of $R_6$, $R_7$, and $R_8$, independently, is -$Q_1$-$T_1$, in which $Q_1$ is a bond or $C_1$-$C_3$ alkyl linker optionally substituted with one or more of halo, cyano, OH and $C_1$-$C_6$ alkoxy, and $T_1$ is H, halo, OH, COOH, cyano, or $R_{s1}$, in which $R_{s1}$ is $C_1$-$C_3$ alkyl, $C_2$-$C_6$ alkenyl, $C_2$-$C_6$ alkynyl, $C_1$-$C_6$ alkoxyl, C(O)O—$C_1$-$C_6$ alkyl, $C_3$-$C_8$ cycloalkyl, $C_6$-$C_{10}$ aryl, $NR_{31}R_{32}$, $(NR_{31}R_{32}R_{33})^+$, 4 to 12-membered heterocycloalkyl, or 5- or 6-membered heteroaryl, and $R_{s1}$ is optionally substituted with one or more substituents selected from the group consisting of halo, OH, oxo, $C_1$-$C_6$ alkyl, COOH, C(O)O—$C_1$-$C_6$ alkyl, cyano, $C_1$-$C_6$ alkoxyl, $NR_{31}R_{32}$, $(NR_{31}R_{32}R_{33})^+$, $C_3$-$C_8$ cycloalkyl, $C_6$-$C_{10}$ aryl, 4 to 12-membered heterocycloalkyl, and 5- or 6-membered heteroaryl;

each of $R_{10}$, $R_{11}$, $R_{12}$, $R_{13}$, $R_{14}$, and $R_{15}$, independently, is -$Q_2$-$T_2$, in which $Q_2$ is a bond or $C_1$-$C_3$ alkyl linker optionally substituted with one or more of halo, cyano, OH and $C_1$-$C_6$ alkoxy, and $T_2$ is H, halo, OH, $NH_2$, cyano, $NO_2$, $N_3$, $R_{s2}$, or $OR_{s2}$, in which $R_{s2}$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, NHC(O)—

$C_1$-$C_6$ alkyl, $NR_{31}R_{32}$, $(NR_{31}R_{32}R_{33})^+$, 4 to 12-membered heterocycloalkyl, or 5- or 6-membered heteroaryl, and $R_{s2}$ is optionally substituted with one or more substituents selected from the group consisting of halo, OH, oxo, $C_1$-$C_6$ alkyl, COOH, C(O)O—$C_1$-$C_6$ alkyl, cyano, $C_1$-$C_6$ alkoxyl, $NR_{31}R_{32}$, $(NR_{31}R_{32}R_{33})^+$, $C_3$-$C_8$ cycloalkyl, $C_6$-$C_{10}$ aryl, 4 to 12-membered heterocycloalkyl, and 5- or 6-membered heteroaryl; or alternatively Ru together with $R_{14}$ is oxo, or $R_{13}$ together with $R_{15}$ is oxo, each of $R_{20}$, $R_{21}$, $R_{22}$, and $R_{23}$ independently is -$Q_3$-$T_3$, in which $Q_3$ is a bond or $C_1$-$C_3$ alkyl linker optionally substituted with one or more of halo, cyano, OH and $C_1$-$C_6$ alkoxy, and $T_3$ is H, halo, OH, $NH_2$, cyano, $NO_2$, $N_3$, $R_{S3}$, or $OR_{S3}$, in which $R_{S3}$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, NHC(O)—$C_1$-$C_6$ alkyl, mono-$C_1$-$C_6$ alkylamino, di-$C_1$-$C_6$ alkylamino, 4 to 12-membered heterocycloalkyl, or 5- or 6-membered heteroaryl, and $Rs_3$ is optionally substituted with one or more substituents selected from the group consisting of halo, OH, oxo, $C_1$-$C_6$ alkyl, COOH, C(O)O—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl;

each of $R_{24}$, $R_{25}$, and $R_{26}$ independently is H or $C_1$-$C_6$ alkyl;

each of $R_{27}$ and $R_{28}$ independently is H or $OR_{29}$; or $R_{27}$ and $R_{28}$ together form O—$R_{30}$—O; each $R_{29}$ independently is H, $C_1$-$C_6$ alkyl, $C_2$-$C_6$ alkenyl, or $C_2$-$C_6$ alkynyl and $R_{29}$, when being $C_1$-$C_6$ alkyl, $C_2$-$C_6$ alkenyl, or $C_2$-$C_6$ alkynyl, is optionally substituted with one or more of halo, OH and $C_1$-$C_6$ alkoxyl that is optionally substituted with one or more OH or OC(O)—$C_1$-$C_6$ alkyl;

$R_{30}$ is $C_1$-$C_6$ alkylene optionally substituted with one or more of halo, OH and $C_1$-$C_6$ alkoxyl;

each of $R_{31}$, $R_{32}$, and $R_{33}$, independently is H, $C_1$-$C_6$ alkyl, $C_3$-$C_8$ cycloalkyl, $C_6$-$C_{10}$ aryl, 4 to 12-membered heterocycloalkyl, or 5- or 6-membered heteroaryl;

each of $R_{40}$, $R_{41}$, $R_{42}$, and $R_{43}$ independently is H, halo, OH, cyano, $N_3$, $OP(O)R_{47}R_{48}$, or $C_1$-$C_6$ alkyl optionally substituted with one or more $OP(O)R_{47}R_{48}$, or one $R_{41}$ and one $R_{43}$, together with the carbon atoms to which they are attached and $Q_0$, form $C_4$-$C_{10}$ cycloalkyl, 4- to 14-membered heterocycloalkyl, $C_6$-$C_{10}$ aryl, or 5- to 14-membered heteroaryl, and each of the cycloalkyl, heterocycloalkyl, phenyl, or 5- to 6-membered heteroaryl is optionally substituted with one or more of OH, halo, cyano, $N_3$, oxo, $OP(O)R_{47}R_{48}$, $C_1$-$C_6$ alkyl, $C_1$-$C_6$ haloalkyl, COOH, C(O)O—$C_1$-$C_6$ alkyl, $C_1$-$C_6$ alkoxyl, $C_1$-$C_6$ haloalkoxyl, amino, mono-$C_1$-$C_6$ alkylamino, and di-$C_1$-$C_6$ alkylamino;

$R_{44}$ is H, $C_1$-$C_6$ alkyl, or an amine protecting group;

each of $R_{45}$ and $R_{46}$ independently is H, $OP(O)R_{47}R_{48}$, or $C_1$-$C_6$ alkyl optionally substituted with one or more $OP(O)R_{47}R_{48}$, and each of $R_{47}$ and $R_{48}$, independently is H, halo, $C_1$-$C_6$ alkyl, OH, SH, SeH, or $BH_3$.

It should be understood that a cap analog, as provided herein, may include any of the cap analogs described in international publication WO 2017/066797, published on 20 Apr. 2017, incorporated by reference herein in its entirety.

In some embodiments, the B2 middle position can be a non-ribose molecule, such as arabinose.

In some embodiments $R_2$ is ethyl-based.

Thus, in some embodiments, a trinucleotide cap comprises the following structure:

(II)

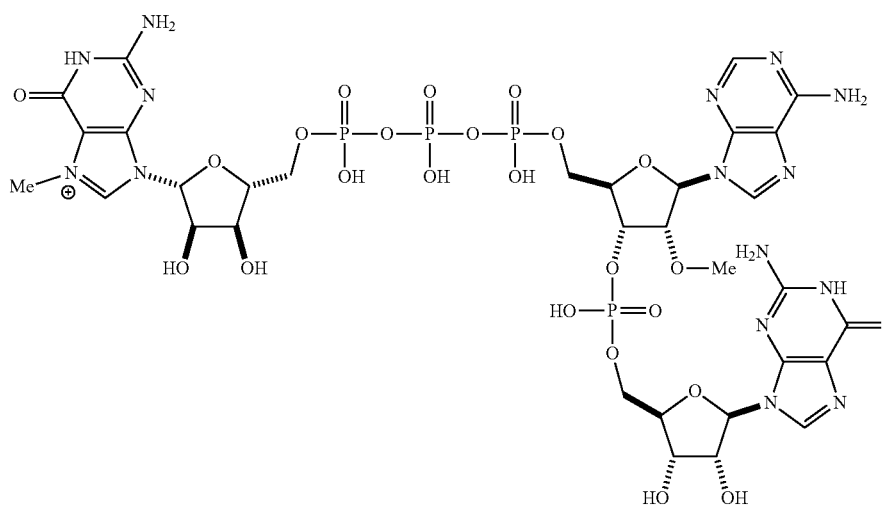

In other embodiments, a trinucleotide cap comprises the following structure:
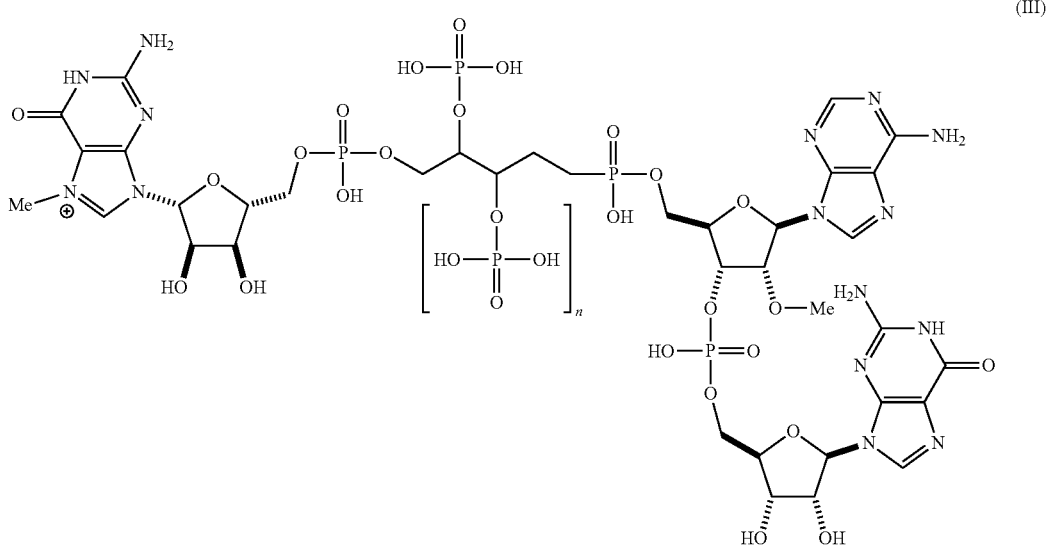
(III)
In yet other embodiments, a trinucleotide cap comprises the following structure:
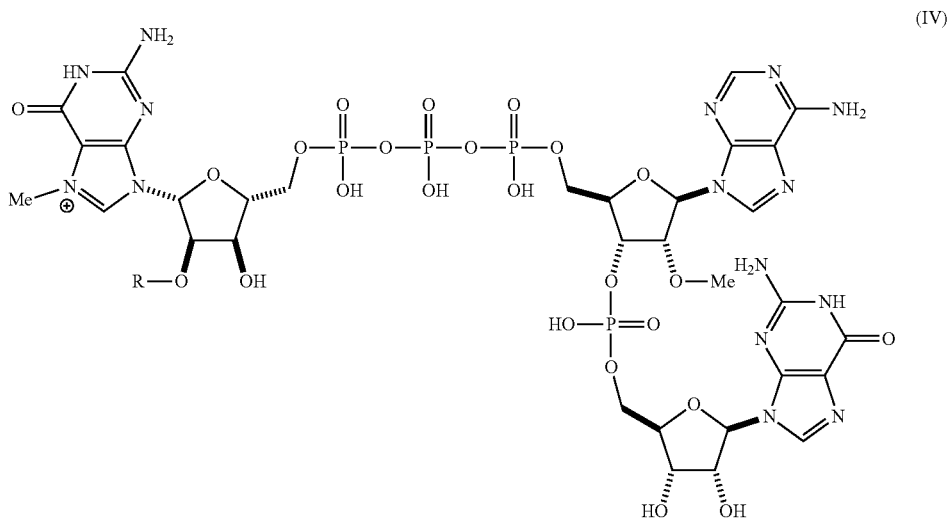
(IV)

In still other embodiments, a trinucleotide cap comprises the following structure:

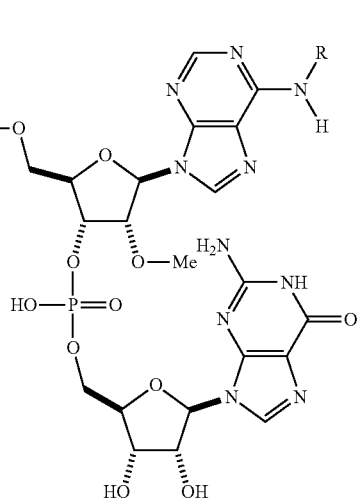

(V)

A trinucleotide cap, in some embodiments, comprises a sequence selected from the following sequences: GAA, GAC, GAG, GAU, GCA, GCC, GCG, GCU, GGA, GGC, GGG, GGU, GUA, GUC, GUG, and GUU. In some embodiments, a trinucleotide cap comprises GAA. In some embodiments, a trinucleotide cap comprises GAC. In some embodiments, a trinucleotide cap comprises GAG. In some embodiments, a trinucleotide cap comprises GAU. In some embodiments, a trinucleotide cap comprises GCA. In some embodiments, a trinucleotide cap comprises GCC. In some embodiments, a trinucleotide cap comprises GCG. In some embodiments, a trinucleotide cap comprises GCU. In some embodiments, a trinucleotide cap comprises GGA. In some embodiments, a trinucleotide cap comprises GGC. In some embodiments, a trinucleotide cap comprises GGG. In some embodiments, a trinucleotide cap comprises GGU. In some embodiments, a trinucleotide cap comprises GUA.

In some embodiments, a trinucleotide cap comprises GUC. In some embodiments, a trinucleotide cap comprises GUG. In some embodiments, a trinucleotide cap comprises GUU.

In some embodiments, a trinucleotide cap comprises a sequence selected from the following sequences: $m^7$GpppApA, $m^7$GpppApC, $m^7$GpppApG, $m^7$GpppApU, $m^7$GpppCpA, $m^7$GpppCpC, $m^7$GpppCpG, $m^7$GpppCpU, $m^7$GpppGpA, $m^7$GpppGpC, $m^7$GpppGpG, $m^7$GpppGpU, $m^7$GpppUpA, $m^7$GpppUpC, $m^7$GpppUpG, and $m^7$GpppUpU.

In some embodiments, a trinucleotide cap comprises $m^7$GpppApA. In some embodiments, a trinucleotide cap comprises $m^7$GpppApC. In some embodiments, a trinucleotide cap comprises $m^7$GpppApG. In some embodiments, a trinucleotide cap comprises $m^7$GpppApU. In some embodiments, a trinucleotide cap comprises $m^7$GpppCpA. In some embodiments, a trinucleotide cap comprises $m^7$GpppCpC. In some embodiments, a trinucleotide cap comprises $m^7$GpppCpG. In some embodiments, a trinucleotide cap comprises $m^7$GpppCpU. In some embodiments, a trinucleotide cap comprises $m^7$GpppGpA. In some embodiments, a trinucleotide cap comprises $m^7$GpppGpC. In some embodiments, a trinucleotide cap comprises $m^7$GpppGpG. In some embodiments, a trinucleotide cap comprises $m^7$GpppGpU. In some embodiments, a trinucleotide cap comprises $m^7$GpppUpA. In some embodiments, a trinucleotide cap comprises $m^7$GpppUpC. In some embodiments, a trinucleotide cap comprises $m^7$GpppUpG. In some embodiments, a trinucleotide cap comprises $m^7$GpppUpU.

A trinucleotide cap, in some embodiments, comprises a sequence selected from the following sequences: $m^7G_{3'OMe}$pppApA, $m^7G_{3'OMe}$pppApC, $m^7G_{3'OMe}$pppApG, $m^7G_{3'OMe}$pppApU, $m^7G_{3'OMe}$pppCpA, $m^7G_{3'OMe}$pppCpC, $m^7G_{3'OMe}$pppCpG, $m^7G_{3'OMe}$pppCpU, $m^7G_{3'OMe}$pppGpA, $m^7G_{3'OMe}$pppGpC, $m^7G_{3'OMe}$pppGpG, $m^7G_{3'OMe}$pppGpU, $m^7G_{3'OMe}$pppUpA, $m^7G_{3'OMe}$pppUpC, $m^7G_{3'OMe}$pppUpG, and $m^7G_{3'OMe}$pppUpU.

In some embodiments, a trinucleotide cap comprises $m^7G_{3'OMe}$pppApA. In some embodiments, a trinucleotide cap comprises $m^7G_{3'OMe}$pppApC. In some embodiments, a trinucleotide cap comprises $m^7G_{3'OMe}$pppApG. In some embodiments, a trinucleotide cap comprises $m^7G_{3'OMe}$pppApU. In some embodiments, a trinucleotide cap comprises $m^7G_{3'OMe}$pppCpA. In some embodiments, a trinucleotide cap comprises $m^7G_{3'OMe}$pppCpC. In some embodiments, a trinucleotide cap comprises $m^7G_{3'OMe}$pppCpG. In some embodiments, a trinucleotide cap comprises $m^7G_{3'OMe}$pppCpU. In some embodiments, a trinucleotide cap comprises $m^7G_{3'OMe}$pppGpA. In some embodiments, a trinucleotide cap comprises $m^7G_{3'OMe}$pppGpC. In some embodiments, a trinucleotide cap comprises $m^7G_{3'OMe}$pppGpG. In some embodiments, a trinucleotide cap comprises $m^7G_{3'OMe}$pppGpU. In some embodiments, a trinucleotide cap comprises $m^7G_{3'OMe}$pppUpA. In some embodiments, a trinucleotide cap comprises $m^7G_{3'OMe}$pppUpC. In some embodiments, a trinucleotide cap comprises $m^7G_{3'OMe}$pppUpG. In some embodiments, a trinucleotide cap comprises $m^7G_{3'OMe}$pppUpU.

A trinucleotide cap, in other embodiments, comprises a sequence selected from the following sequences: $m^7G_{3'OMe}$pppA$_{2'OMe}$pA, $m^7G_{3'OMe}$pppA$_{2'OMe}$pC, $m^7G_{3'OMe}$pppA$_{2'OMe}$pG, $m^7G_{3'OMe}$pppA$_{2'OMe}$pU, $m^7G_{3'OMe}$pppC$_{2'OMe}$pA, $m^7G_{3'OMe}$pppC$_{2'OMe}$pC, $m^7G_{3'OMe}pppC_{2'OMe}pG$, $m^7G_{3'OMe}pppC_{2'OMe}pU$, $m^7G_{3'OMe}pppG_{2'OMe}pA$, $m^7G_{3'OMe}pppG_{2'OMe}pC$, $m^7G_{3'OMe}pppG_{2'OMe}pG$, $m^7G_{3'OMe}pppG_{2'OMe}pU$, $m^7G_{3'OMe}pppU_{2'OMe}pA$, $m^7G_{3'OMe}pppU_{2'OMe}pC$, $m^7G_{3'OMe}pppU_{2'OMe}pG$, and $m^7G_{3'OMe}pppU_{2'OMe}pU$.

In some embodiments, a trinucleotide cap comprises $m^7G_{3'OMe}pppA_{2'OMe}pA$. In some embodiments, a trinucleotide cap comprises $m^7G_{3'OMe}pppA_{2'OMe}pC$. In some embodiments, a trinucleotide cap comprises $m^7G_{3'OMe}pppA_{2'OMe}pG$. In some embodiments, a trinucleotide cap comprises $m^7G_{3'OMe}pppA_{2'OMe}pU$. In some embodiments, a trinucleotide cap comprises $m^7G_{3'OMe}pppC_{2'OMe}pA$. In some embodiments, a trinucleotide cap comprises $m^7G_{3'OMe}pppC_{2'OMe}pC$. In some embodiments, a trinucleotide cap comprises $m^7G_{3'OMe}pppC_{2'OMe}pG$. In some embodiments, a trinucleotide cap comprises $m^7G_{3'OMe}pppC_{2'OMe}pU$. In some embodiments, a trinucleotide cap comprises $m^7G_{3'OMe}pppG_{2'OMe}pA$. In some embodiments, a trinucleotide cap comprises $m^7G_{3'OMe}pppG_{2'OMe}pC$. In some embodiments, a trinucleotide cap comprises $m^7G_{3'OMe}pppG_{2'OMe}pG$. In some embodiments, a trinucleotide cap comprises $m^7G_{3'OMe}pppG_{2'OMe}pU$. In some embodiments, a trinucleotide cap comprises $m^7G_{3'OMe}pppU_{2'OMe}pA$. In some embodiments, a trinucleotide cap comprises $m^7G_{3'OMe}pppU_{2'OMe}pC$. In some embodiments, a trinucleotide cap comprises $m^7G_{3'OMe}pppU_{2'OMe}pG$. In some embodiments, a trinucleotide cap comprises $m^7G_{3'OMe}pppU_{2'OMe}pU$.

A trinucleotide cap, in still other embodiments, comprises a sequence selected from the following sequences: $m^7GpppA_{2'OMe}pA$, $m^7GpppA_{2'OMe}pC$, $m^7GpppA_{2'OMe}pG$, $m^7GpppA_{2'OMe}pU$, $m^7GpppC_{2'OMe}pA$, $m^7GpppC_{2'OMe}pC$, $m^7GpppC_{2'OMe}pG$, $m^7GpppC_{2'OMe}pU$, $m^7GpppG_{2'OMe}pA$, $m^7GpppG_{2'OMe}pC$, $m^7GpppG_{2'OMe}pG$, $m^7GpppG_{2'OMe}pU$, $m^7GpppU_{2'OMe}pA$, $m^7GpppU_{2'OMe}pC$, $m^7GpppU_{2'OMe}pG$, and $m^7GpppU_{2'OMe}pU$.

In some embodiments, a trinucleotide cap comprises $m^7GpppA_{2'OMe}pA$. In some embodiments, a trinucleotide cap comprises $m^7GpppA_{2'OMe}pC$. In some embodiments, a trinucleotide cap comprises $m^7GpppA_{2'OMe}pG$. In some embodiments, a trinucleotide cap comprises $m^7GpppA_{2'OMe}pU$. In some embodiments, a trinucleotide cap comprises $m^7GpppC_{2'OMe}pA$. In some embodiments, a trinucleotide cap comprises $m^7GpppC_{2'OMe}pC$. In some embodiments, a trinucleotide cap comprises $m^7GpppC_{2'OMe}pG$. In some embodiments, a trinucleotide cap comprises $m^7GpppC_{2'OMe}pU$. In some embodiments, a trinucleotide cap comprises $m^7GpppG_{2'OMe}pA$. In some embodiments, a trinucleotide cap comprises $m^7GpppG_{2'OMe}pC$. In some embodiments, a trinucleotide cap comprises $m^7GpppG_{2'OMe}pG$. In some embodiments, a trinucleotide cap comprises $m^7GpppG_{2'OMe}pU$. In some embodiments, a trinucleotide cap comprises $m^7GpppU_{2'OMe}pA$. In some embodiments, a trinucleotide cap comprises $m^7GpppU_{2'OMe}pC$. In some embodiments, a trinucleotide cap comprises $m^7GpppU_{2'OMe}pG$. In some embodiments, a trinucleotide cap comprises $m^7GpppU_{2'OMe}pU$.

In some embodiments, a trinucleotide cap comprises GAG. In some embodiments, a trinucleotide cap comprises GCG. In some embodiments, a trinucleotide cap comprises GUG. In some embodiments, a trinucleotide cap comprises GGG.

In Vitro Transcription Methods

Some aspects of the present disclosure provide methods of producing (synthesizing) a RNA transcript (e.g., mRNA transcript) comprising contacting a DNA template with a RNA polymerase (e.g., a T7 RNA polymerase) under conditions that result in the production of RNA transcript.

In some aspects, the present disclosure provides methods of performing an IVT reaction, comprising contacting a DNA template with the RNA polymerase (e.g., a T7 RNA polymerase, in the presence of nucleoside triphosphates and buffer under conditions that result in the production of RNA transcripts.

Other aspects of the present disclosure provide co-transcriptional capping methods that comprise reacting a DNA template with a T7 RNA polymerase variant, nucleoside triphosphates, and a cap analog under in vitro transcription reaction conditions to produce RNA transcript.

In some embodiments, a co-transcriptional capping method for RNA synthesis comprises reacting a DNA template with (a) a T7 RNA polymerase (e.g., wild-type or varian), (b) nucleoside triphosphates, and (c) a cap analog (e.g., a trinucleotide cap comprising sequence $GpppA_{2'OMe}pG$), under in vitro transcription reaction conditions to produce RNA transcript, optionally wherein the polynucleotide template includes a 2'-deoxythymidine residue at template position +1.

IVT conditions typically require a purified linear DNA template containing a promoter, nucleoside triphosphates, a buffer system that includes dithiothreitol (DTT) and magnesium ions, and a RNA polymerase. The exact conditions used in the transcription reaction depend on the amount of RNA needed for a specific application. Typical IVT reactions are performed by incubating a DNA template with a RNA polymerase and nucleoside triphosphates, including GTP, ATP, CTP, and UTP (or nucleotide analogs) in a transcription buffer. A RNA transcript having a 5' terminal guanosine triphosphate is produced from this reaction.

A deoxyribonucleic acid (DNA) is simply a nucleic acid template for RNA polymerase. A DNA template may include a polynucleotide encoding a polypeptide of interest (e.g., an antigenic polypeptide). A DNA template, in some embodiments, includes a RNA polymerase promoter (e.g., a T7 RNA polymerase promoter) located 5' from and operably linked to polynucleotide encoding a polypeptide of interest. A DNA template may also include a nucleotide sequence encoding a polyadenylation (polyA) tail located at the 3' end of the gene of interest.

Polypeptides of interest include, but are not limited to, biologics, antibodies, antigens (vaccines), and therapeutic proteins. The term "protein" encompasses peptides.

A RNA transcript, in some embodiments, is the product of an IVT reaction. A RNA transcript, in some embodiments, is a messenger RNA (mRNA) that includes a nucleotide sequence encoding a polypeptide of interest linked to a polyA tail. In some embodiments, the mRNA is modified mRNA (mmRNA), which includes at least one modified nucleotide.

A nucleotide includes a nitrogenous base, a five-carbon sugar (ribose or deoxyribose), and at least one phosphate group. Nucleotides include nucleoside monophosphates, nucleoside diphosphates, and nucleoside triphosphates. A nucleoside monophosphate (NMP) includes a nucleobase linked to a ribose and a single phosphate; a nucleoside diphosphate (NDP) includes a nucleobase linked to a ribose and two phosphates; and a nucleoside triphosphate (NTP) includes a nucleobase linked to a ribose and three phosphates. Nucleotide analogs are compounds that have the general structure of a nucleotide or are structurally similar to a nucleotide. Nucleotide analogs, for example, include an analog of the nucleobase, an analog of the sugar and/or an analog of the phosphate group(s) of a nucleotide.

A nucleoside includes a nitrogenous base and a 5-carbon sugar. Thus, a nucleoside plus a phosphate group yields a nucleotide. Nucleoside analogs are compounds that have the general structure of a nucleoside or are structurally similar to a nucleoside. Nucleoside analogs, for example, include an analog of the nucleobase and/or an analog of the sugar of a nucleoside.

It should be understood that the term "nucleotide" includes naturally-occurring nucleotides, synthetic nucleotides and modified nucleotides, unless indicated otherwise. Examples of naturally-occurring nucleotides used for the production of RNA, e.g., in an IVT reaction, as provided herein include adenosine triphosphate (ATP), guanosine triphosphate (GTP), cytidine triphosphate (CTP), uridine triphosphate (UTP), and 5-methyluridine triphosphate ($m^5$UTP). In some embodiments, adenosine diphosphate (ADP), guanosine diphosphate (GDP), cytidine diphosphate (CDP), and/or uridine diphosphate (UDP) are used.

Examples of nucleotide analogs include, but are not limited to, antiviral nucleotide analogs, phosphate analogs (soluble or immobilized, hydrolyzable or non-hydrolyzable), dinucleotide, trinucleotide, tetranucleotide, e.g., a cap analog, or a precursor/substrate for enzymatic capping (vaccinia or ligase), a nucleotide labeled with a functional group to facilitate ligation/conjugation of cap or 5' moiety (IRES), a nucleotide labeled with a 5' $PO_4$ to facilitate ligation of cap or 5' moiety, or a nucleotide labeled with a functional group/protecting group that can be chemically or enzymatically cleaved. Examples of antiviral nucleotide/nucleoside analogs include, but are not limited, to Ganciclovir, Entecavir, Telbivudine, Vidarabine and Cidofovir.

Modified nucleotides may include modified nucleobases. For example, a RNA transcript (e.g., mRNA transcript) of the present disclosure may include a modified nucleobase selected from pseudouridine (ψ), 1-methylpseudouridine (m1ψ), 1-ethylpseudouridine, 2-thiouridine, 4'-thiouridine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methyluridine, 5-methoxyuridine (mo5U) and 2'-O-methyl uridine. In some embodiments, a RNA transcript (e.g., mRNA transcript) includes a combination of at least two (e.g., 2, 3, 4 or more) of the foregoing modified nucleobases.

The nucleoside triphosphates (NTPs) as provided herein may comprise unmodified or modified ATP, modified or unmodified UTP, modified or unmodified GTP, and/or modified or unmodified CTP. In some embodiments, NTPs of an IVT reaction comprise unmodified ATP. In some embodiments, NTPs of an IVT reaction comprise modified ATP. In some embodiments, NTPs of an IVT reaction comprise unmodified UTP. In some embodiments, NTPs of an IVT reaction comprise modified UTP. In some embodiments, NTPs of an IVT reaction comprise unmodified GTP. In some embodiments, NTPs of an IVT reaction comprise modified GTP. In some embodiments, NTPs of an IVT reaction comprise unmodified CTP. In some embodiments, NTPs of an IVT reaction comprise modified CTP.

The concentration of nucleoside triphosphates and cap analog present in an IVT reaction may vary. In some embodiments, NTPs and cap analog are present in the reaction at equimolar concentrations. In some embodiments, the molar ratio of cap analog (e.g., trinucleotide cap) to nucleoside triphosphates in the reaction is greater than 1:1. For example, the molar ratio of cap analog to nucleoside triphosphates in the reaction may be 2:1, 3:1, 4:1, 5:1, 6:1, 7:1, 8:1, 9:1, 10:1, 15:1, 20:1, 25:1, 50:1, or 100:1. In some embodiments, the molar ratio of cap analog (e.g., trinucleotide cap) to nucleoside triphosphates in the reaction is less than 1:1. For example, the molar ratio of cap analog (e.g., trinucleotide cap) to nucleoside triphosphates in the reaction may be 1:2, 1:3, 1:4, 1:5, 1:6, 1:7, 1:8, 1:9, 1:10, 1:15, 1:20, 1:25, 1:50, or 1:100.

The composition of NTPs in an IVT reaction may also vary. For example, ATP may be used in excess of GTP, CTP and UTP. As a non-limiting example, an IVT reaction may include 7.5 millimolar GTP, 7.5 millimolar CTP, 7.5 millimolar UTP, and 3.75 millimolar ATP. The same IVT reaction may include 3.75 millimolar cap analog (e.g., trinucleotide cap). In some embodiments, the molar ratio of G:C:U:A:cap is 1:1:1:0.5:0.5. In some embodiments, the molar ratio of G:C:U:A:cap is 1:1:0.5:1:0.5. In some embodiments, the molar ratio of G:C:U:A:cap is 1:0.5:1:1:0.5. In some embodiments, the molar ratio of G:C:U:A:cap is 0.5:1:1:1:0.5.

In some embodiments, a RNA transcript (e.g., mRNA transcript) includes a modified nucleobase selected from pseudouridine (ψ), 1-methylpseudouridine ($m^1$ψ), 5-methoxyuridine ($mo^5$U), 5-methylcytidine ($m^5$C), α-thio-guanosine and α-thio-adenosine. In some embodiments, a RNA transcript (e.g., mRNA transcript) includes a combination of at least two (e.g., 2, 3, 4 or more) of the foregoing modified nucleobases.

In some embodiments, a RNA transcript (e.g., mRNA transcript) includes pseudouridine (ψ). In some embodiments, a RNA transcript (e.g., mRNA transcript) includes 1-methylpseudouridine ($m^1$ψ). In some embodiments, a RNA transcript (e.g., mRNA transcript) includes 5-methoxyuridine ($mo^5$U). In some embodiments, a RNA transcript (e.g., mRNA transcript) includes 5-methylcytidine ($m^5$C). In some embodiments, a RNA transcript (e.g., mRNA transcript) includes α-thio-guanosine. In some embodiments, a RNA transcript (e.g., mRNA transcript) includes α-thio-adenosine.

In some embodiments, the polynucleotide (e.g., RNA polynucleotide, such as mRNA polynucleotide) is uniformly modified (e.g., fully modified, modified throughout the entire sequence) for a particular modification. For example, a polynucleotide can be uniformly modified with 1-methylpseudouridine ($m^1$ψ), meaning that all uridine residues in the mRNA sequence are replaced with 1-methylpseudouridine ($m^1$ψ). Similarly, a polynucleotide can be uniformly modified for any type of nucleoside residue present in the sequence by replacement with a modified residue such as any of those set forth above. Alternatively, the polynucleotide (e.g., RNA polynucleotide, such as mRNA polynucleotide) may not be uniformly modified (e.g., partially modified, part of the sequence is modified). Each possibility represents a separate embodiment of the present invention.

In some embodiments, the buffer system contains tris. The concentration of tris used in an IVT reaction, for example, may be at least 10 mM, at least 20 mM, at least 30 mM, at least 40 mM, at least 50 mM, at least 60 mM, at least 70 mM, at least 80 mM, at least 90 mM, at least 100 mM or at least 110 mM phosphate. In some embodiments, the concentration of phosphate is 20-60 mM or 10-100 mM.

In some embodiments, the buffer system contains dithiothreitol (DTT). The concentration of DTT used in an IVT reaction, for example, may be at least 1 mM, at least 5 mM, or at least 50 mM. In some embodiments, the concentration of DTT used in an IVT reaction is 1-50 mM or 5-50 mM. In some embodiments, the concentration of DTT used in an IVT reaction is 5 mM.

In some embodiments, the buffer system contains magnesium. In some embodiments, the molar ratio of NTP to magnesium ions ($Mg^{2+}$; e.g., $MgCl_2$) present in an IVT reaction is 1:1 to 1:5. For example, the molar ratio of NTP to magnesium ions may be 1:1, 1:2, 1:3, 1:4 or 1:5.

In some embodiments, the molar ratio of NTP plus cap analog (e.g., trinucleotide cap, such as GAG) to magnesium ions ($Mg^{2+}$; e.g., $MgCl_2$) present in an IVT reaction is 1:1 to 1:5. For example, the molar ratio of NTP+trinucleotide cap (e.g., GAG) to magnesium ions may be 1:1, 1:2, 1:3, 1:4 or 1:5.

In some embodiments, the buffer system contains Tris-HCl, spermidine (e.g., at a concentration of 1-30 mM), TRITON® X-100 (polyethylene glycol p-(1,1,3,3-tetramethylbutyl)-phenyl ether) and/or polyethylene glycol (PEG).

The addition of nucleoside triphosphates (NTPs) to the 3' end of a growing RNA strand is catalyzed by a polymerase, such as T7 RNA polymerase, for example, any one or more of the T7 RNA polymerase variants of the present disclosure. In some embodiments, the RNA polymerase (e.g., T7 RNA polymerase variant) is present in a reaction (e.g., an IVT reaction) at a concentration of 0.01 mg/ml to 1 mg/ml. For example, the RNA polymerase may be present in a reaction at a concentration of 0.01 mg/mL, 0.05 mg/ml, 0.1 mg/ml, 0.5 mg/ml or 1.0 mg/ml.

DNA (e.g., cDNA) encoding the polynucleotides described herein may be transcribed using an in vitro transcription (IVT) system. In vitro transcription of RNA is known in the art and is described in International Publication WO/2014/152027, which is incorporated by reference herein in its entirety.

In some embodiments, the RNA transcript is generated using a non-amplified, linearized DNA template in an in vitro transcription reaction to generate the RNA transcript. In some embodiments, the template DNA is isolated DNA. In some embodiments, the template DNA is cDNA. In some embodiments, the cDNA is formed by reverse transcription of a RNA polynucleotide.

In some embodiments, an in vitro transcription template encodes a 5' untranslated (UTR) region, contains an open reading frame, and encodes a 3' UTR and a polyA tail. The particular nucleic acid sequence composition and length of an in vitro transcription template will depend on the mRNA encoded by the template.

A "5' untranslated region" (UTR) refers to a region of an mRNA that is directly upstream (i.e., 5') from the start codon (i.e., the first codon of an mRNA transcript translated by a ribosome) that does not encode a polypeptide. When RNA transcripts are being generated, the 5' UTR may comprise a promoter sequence. Such promoter sequences are known in the art. It should be understood that such promoter sequences will not be present in RNA of the disclosure.

A "3' untranslated region" (UTR) refers to a region of an mRNA that is directly downstream (i.e., 3') from the stop codon (i.e., the codon of an mRNA transcript that signals a termination of translation) that does not encode a polypeptide.

An "open reading frame" is a continuous stretch of DNA beginning with a start codon (e.g., methionine (ATG)), and ending with a stop codon (e.g., TAA, TAG or TGA) and encodes a polypeptide.

A "polyA tail" is a region of mRNA that is downstream, e.g., directly downstream (i.e., 3'), from the 3' UTR that contains multiple, consecutive adenosine monophosphates. A polyA tail may contain 10 to 300 adenosine monophosphates. For example, a polyA tail may contain 10, 20, 30, 40, 50, 60, 70, 80, 90, 100, 110, 120, 130, 140, 150, 160, 170, 180, 190, 200, 210, 220, 230, 240, 250, 260, 270, 280, 290 or 300 adenosine monophosphates. In some embodiments, a polyA tail contains 50 to 250 adenosine monophosphates. In a relevant biological setting (e.g., in cells, in vivo) the poly(A) tail functions to protect mRNA from enzymatic degradation, e.g., in the cytoplasm, and aids in transcription termination, and/or export of the mRNA from the nucleus and translation.

In some embodiments, a nucleic acid includes 200 to 3,000 nucleotides. For example, a nucleic acid may include 200 to 500, 200 to 1000, 200 to 1500, 200 to 3000, 500 to 1000, 500 to 1500, 500 to 2000, 500 to 3000, 1000 to 1500, 1000 to 2000, 1000 to 3000, 1500 to 3000, or 2000 to 3000 nucleotides).

An in vitro transcription system typically comprises a transcription buffer, nucleotide triphosphates (NTPs), an RNase inhibitor and a polymerase.

The NTPs may be manufactured in house, may be selected from a supplier, or may be synthesized as described herein. The NTPs may be selected from, but are not limited to, those described herein including natural and unnatural (modified) NTPs.

Any number of RNA polymerases or variants may be used in the method of the present disclosure. The polymerase may be selected from, but is not limited to, a phage RNA polymerase, e.g., a T7 RNA polymerase, a T3 RNA polymerase, a SP6 RNA polymerase, and/or mutant polymerases such as, but not limited to, polymerases able to incorporate modified nucleic acids and/or modified nucleotides, including chemically modified nucleic acids and/or nucleotides. Some embodiments exclude the use of DNase.

In some embodiments, the RNA transcript is capped via enzymatic capping. In some embodiments, the RNA comprises 5' terminal cap, for example, 7mG(5')ppp(5')NlmpNp.

Purification

Purification of the nucleic acids described herein may include, but is not limited to, nucleic acid clean-up, quality assurance and quality control. Clean-up may be performed by methods known in the arts such as, but not limited to, AGENCOURT® beads (Beckman Coulter Genomics, Danvers, MA), poly-T beads, LNA™ oligo-T capture probes (EXIQON® Inc, Vedbaek, Denmark) or HPLC based purification methods such as, but not limited to, strong anion exchange HPLC, weak anion exchange HPLC, reverse phase HPLC (RP-HPLC), and hydrophobic interaction HPLC (HIC-HPLC). The term "purified" when used in relation to a nucleic acid such as a "purified nucleic acid" refers to one that is separated from at least one contaminant. A "contaminant" is any substance that makes another unfit, impure or inferior. Thus, a purified nucleic acid (e.g., DNA and RNA) is present in a form or setting different from that in which it is found in nature, or a form or setting different from that which existed prior to subjecting it to a treatment or purification method.

A quality assurance and/or quality control check may be conducted using methods such as, but not limited to, gel electrophoresis, UV absorbance, or analytical HPLC.

In some embodiments, the nucleic acids may be sequenced by methods including, but not limited to reverse-transcriptase-PCR.

Quantification

In some embodiments, the nucleic acids of the present disclosure may be quantified in exosomes or when derived from one or more bodily fluid. Bodily fluids include peripheral blood, serum, plasma, ascites, urine, cerebrospinal fluid (CSF), sputum, saliva, bone marrow, synovial fluid, aqueous humor, amniotic fluid, cerumen, breast milk, broncheoalveolar lavage fluid, semen, prostatic fluid, cowper's fluid or pre-ejaculatory fluid, sweat, fecal matter, hair, tears, cyst fluid, pleural and peritoneal fluid, pericardial fluid, lymph, chyme, chyle, bile, interstitial fluid, menses, pus, sebum, vomit, vaginal secretions, mucosal secretion, stool water, pancreatic juice, lavage fluids from sinus cavities, bronchopulmonary aspirates, blastocyl cavity fluid, and umbilical cord blood. Alternatively, exosomes may be retrieved from an organ selected from the group consisting of lung, heart, pancreas, stomach, intestine, bladder, kidney, ovary, testis, skin, colon, breast, prostate, brain, esophagus, liver, and placenta.

Assays may be performed using construct specific probes, cytometry, qRT-PCR, real-time PCR, PCR, flow cytometry, electrophoresis, mass spectrometry, or combinations thereof while the exosomes may be isolated using immunohistochemical methods such as enzyme linked immunosorbent assay (ELISA) methods. Exosomes may also be isolated by size exclusion chromatography, density gradient centrifugation, differential centrifugation, nanomembrane ultrafiltration, immunoabsorbent capture, affinity purification, microfluidic separation, or combinations thereof.

These methods afford the investigator the ability to monitor, in real time, the level of nucleic acids remaining or delivered. This is possible because the nucleic acids of the present disclosure, in some embodiments, differ from the endogenous forms due to the structural or chemical modifications.

In some embodiments, the nucleic acid may be quantified using methods such as, but not limited to, ultraviolet visible spectroscopy (UV/Vis). A non-limiting example of a UV/Vis spectrometer is a NANODROP® spectrometer (ThermoFisher, Waltham, MA). The quantified nucleic acid may be analyzed in order to determine if the nucleic acid may be of proper size, check that no degradation of the nucleic acid has occurred. Degradation of the nucleic acid may be checked by methods such as, but not limited to, agarose gel electrophoresis, HPLC based purification methods such as, but not limited to, strong anion exchange HPLC, weak anion exchange HPLC, reverse phase HPLC (RP-HPLC), and hydrophobic interaction HPLC (HIC-HPLC), liquid chromatography-mass spectrometry (LCMS), capillary electrophoresis (CE) and capillary gel electrophoresis (CGE).

Lipid Nanoparticles (LNPs)

In some embodiments, RNA of the disclosure is formulated in a lipid nanoparticle (LNP). Lipid nanoparticles typically comprise ionizable cationic lipid, non-cationic lipid, sterol and PEG lipid components along with the nucleic acid cargo of interest. The lipid nanoparticles of the disclosure can be generated using components, compositions, and methods as are generally known in the art, see for example PCT/US2016/052352; PCT/US2016/068300; PCT/US2017/037551; PCT/US2015/027400; PCT/US2016/047406; PCT/US2016000129; PCT/US2016/014280; PCT/US2016/014280; PCT/US2017/038426; PCT/US2014/027077; PCT/US2014/055394; PCT/US2016/52117; PCT/US2012/069610; PCT/US2017/027492; PCT/US2016/059575 and PCT/US2016/069491 all of which are incorporated by reference herein in their entirety.

RNA of the disclosure is typically formulated in lipid nanoparticle. In some embodiments, the lipid nanoparticle comprises at least one ionizable cationic lipid, at least one non-cationic lipid, at least one sterol, and/or at least one polyethylene glycol (PEG)-modified lipid.

In some embodiments, the lipid nanoparticle comprises a molar ratio of 20-60% ionizable cationic lipid. For example, the lipid nanoparticle may comprise a molar ratio of 20-50%, 20-40%, 20-30%, 30-60%, 30-50%, 30-40%, 40-60%, 40-50%, or 50-60% ionizable cationic lipid. In some embodiments, the lipid nanoparticle comprises a molar ratio of 20%, 30%, 40%, 50, or 60% ionizable cationic lipid.

In some embodiments, the lipid nanoparticle comprises a molar ratio of 5-25% non-cationic lipid. For example, the lipid nanoparticle may comprise a molar ratio of 5-20%, 5-15%, 5-10%, 10-25%, 10-20%, 10-25%, 15-25%, 15-20%, or 20-25% non-cationic lipid. In some embodiments, the lipid nanoparticle comprises a molar ratio of 5%, 10%, 15%, 20%, or 25% non-cationic lipid.

In some embodiments, the lipid nanoparticle comprises a molar ratio of 25-55% sterol. For example, the lipid nanoparticle may comprise a molar ratio of 25-50%, 25-45%, 25-35%, 25-30%, 30-55%, 30-50%, 30-45%, 30-40%, 30-35%, 35-55%, 35-50%, 35-40%, 40-55%, 40-50%, 40-45%, 45-55%, 45-50%, or 50-55% sterol. In some embodiments, the lipid nanoparticle comprises a molar ratio of 25%, 30%, 35%, 40%, 45%, 50%, or 55% sterol.

In some embodiments, the lipid nanoparticle comprises a molar ratio of 0.5-15% PEG-modified lipid. For example, the lipid nanoparticle may comprise a molar ratio of 0.5-10%, 0.5-5%, 1-15%, 1-10%, 1-5%, 2-15%, 2-10%, 2-5%, 5-15%, 5-10%, or 10-15%. In some embodiments, the lipid nanoparticle comprises a molar ratio of 0.5%, 1%, 2%, 3%, 4%, 5%, 6%, 7%, 8%, 9%, 10%, 11%, 12%, 13%, 14%, or 15% PEG-modified lipid.

In some embodiments, the lipid nanoparticle comprises a molar ratio of 20-60% ionizable cationic lipid, 5-25% non-cationic lipid, 25-55% sterol, and 0.5-15% PEG-modified lipid.

In some embodiments, an ionizable cationic lipid of the disclosure comprises a compound having structure:

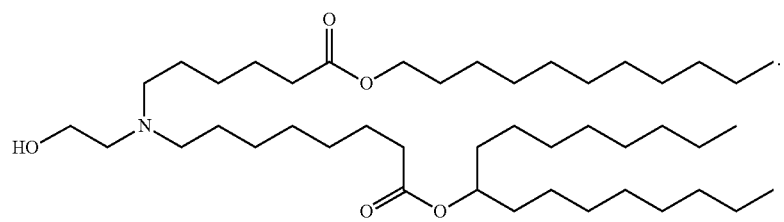

(Compound 1)

In some embodiments, an ionizable cationic lipid of the disclosure comprises a compound having structure:

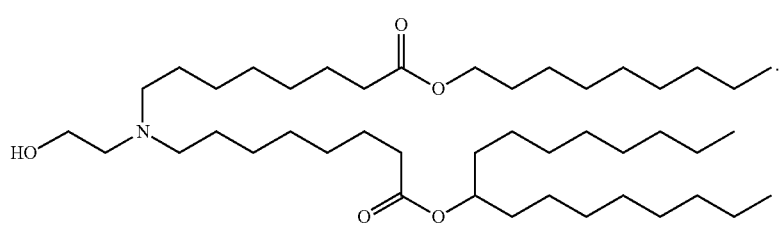

(Compound 2)

In some embodiments, a non-cationic lipid of the disclosure comprises 1,2-distearoyl-sn-glycero-3-phosphocholine (DSPC), 1,2-dioleoyl-sn-glycero-3-phosphoethanolamine (DOPE), 1,2-dilinoleoyl-sn-glycero-3-phosphocholine (DLPC), 1,2-dimyristoyl-sn-gly cero-phosphocholine (DMPC), 1,2-dioleoyl-sn-glycero-3-phosphocholine (DOPC), 1,2-dipalmitoyl-sn-glycero-3-phosphocholine (DPPC), 1,2-diundecanoyl-sn-glycero-phosphocholine (DUPC), 1-palmitoyl-2-oleoyl-sn-glycero-3-phosphocholine (POPC), 1,2-di-(18:0 Diether PC), 1-oleoyl-2 cholesterylhemisuccinoyl-sn-glycero-3-phosphocholine (OChemsPC), 1-hexadecyl-sn-glycero-3-phosphocholine (C16 Ly so PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-diphytanoyl-sn-glycero-3-phosphoethanolamine (ME 16.0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), sphingomyelin, and mixtures thereof.

In some embodiments, a PEG modified lipid of the disclosure comprises a PEG-modified phosphatidylethanolamine, a PEG-modified phosphatidic acid, a PEG-modified ceramide, a PEG-modified dialkylamine, a PEG-modified diacylglycerol, a PEG-modified dialkylglycerol, and mixtures thereof. In some embodiments, the PEG-modified lipid is PEG-DMG, PEG-c-DOMG (also referred to as PEG-DOMG), PEG-DSG and/or PEG-DPG.

In some embodiments, a sterol of the disclosure comprises cholesterol, fecosterol, sitosterol, ergosterol, campesterol, stigmasterol, brassicasterol, tomatidine, ursolic acid, alpha-tocopherol, and mixtures thereof.

In some embodiments, a LNP of the disclosure comprises an ionizable cationic lipid of Compound 1, wherein the non-cationic lipid is DSPC, the structural lipid that is cholesterol, and the PEG lipid is PEG-DMG.

In some embodiments, a LNP of the disclosure comprises an N:P ratio of from about 2:1 to about 30:1.

In some embodiments, a LNP of the disclosure comprises an N:P ratio of about 6:1.

In some embodiments, a LNP of the disclosure comprises an N:P ratio of about 3:1.

In some embodiments, a LNP of the disclosure comprises a wt/wt ratio of the ionizable cationic lipid component to the RNA of from about 10:1 to about 100:1.

In some embodiments, a LNP of the disclosure comprises a wt/wt ratio of the ionizable cationic lipid component to the RNA of about 20:1.

In some embodiments, a LNP of the disclosure comprises a wt/wt ratio of the ionizable cationic lipid component to the RNA of about 10:1.

In some embodiments, a LNP of the disclosure has a mean diameter from about 50 nm to about 150 nm.

In some embodiments, a LNP of the disclosure has a mean diameter from about 70 nm to about 120 nm.

Applications

The RNA transcripts produced according to the present disclosure include mRNA (including modified mRNA and/or unmodified RNA), lncRNA, self-replicating RNA, circular RNA, CRISPR guide RNA, and the like. In embodiments, the RNA is RNA (e.g., mRNA or self-replicating RNA) that encodes a polypeptide (e.g., a therapeutic polypeptide). Thus, the RNA transcripts produced using RNA polymerase variants of the present disclosure may be used in a myriad of applications.

For example, the RNA transcripts may be used to produce polypeptides of interest, e.g., therapeutic proteins, vaccine antigen, and the like. In some embodiments, the RNA transcripts are therapeutic RNAs. A therapeutic mRNA is an mRNA that encodes a therapeutic protein (the term 'protein' encompasses peptides). Therapeutic proteins mediate a variety of effects in a host cell or in a subject to treat a disease or ameliorate the signs and symptoms of a disease. For example, a therapeutic protein can replace a protein that is deficient or abnormal, augment the function of an endogenous protein, provide a novel function to a cell (e.g., inhibit or activate an endogenous cellular activity, or act as a delivery agent for another therapeutic compound (e.g., an antibody-drug conjugate). Therapeutic mRNA may be useful for the treatment of the following diseases and conditions: bacterial infections, viral infections, parasitic infections, cell proliferation disorders, genetic disorders, and autoimmune disorders. Other diseases and conditions are encompassed herein.

A protein of interest encoded by an mRNA as provided herein can be essentially any protein. In some embodiments, the therapeutic protein is a cytokine, a growth factor, an antibody or a fusion protein. Non-limiting examples of therapeutic proteins include blood factors (such as Factor VIII and Factor VII), complement factors, Low Density Lipoprotein Receptor (LDLR) and MUT1. Non-limiting examples of cytokines include interleukins, interferons, chemokines, lymphokines and the like. Non-limiting examples of growth factors include erythropoietin, EGFs, PDGFs, FGFs, TGFs, IGFs, TNFs, CSFs, MCSFs, GMCSFs and the like. Non-limiting examples of antibodies include adalimumab, infliximab, rituximab, ipilimumab, tocilizumab, canakinumab, itolizumab, tralokinumab. Non-limiting examples of fusion proteins include, for example, etanercept, abatacept and belatacept.

In some embodiments, the protein of interest is human erythropoietin, LDLR (for use in inhibiting cholesterol), or MUT1 (for use in the treatment of methylmalonic acidemia (MMA)). In other embodiments, the protein of interest encoded by the mRNA is a therapeutic antibody, including but not limited to the antibodies listed above.

A RNA transcript produced using a RNA polymerase variant as disclosed herein may encode one or more biologics. A biologic is a polypeptide-based molecule that may be used to treat, cure, mitigate, prevent, or diagnose a serious or life-threatening disease or medical condition. Biologics include, but are not limited to, allergenic extracts (e.g. for allergy shots and tests), blood components, gene therapy products, human tissue or cellular products used in transplantation, vaccines, monoclonal antibodies, cytokines, growth factors, enzymes, thrombolytics, and immunomodulators, among others.

One or more biologics currently being marketed or in development may be encoded by the RNA of the present invention. While not wishing to be bound by theory, it is believed that incorporation of the encoding polynucleotides of a known biologic into the RNA of the present disclosure will result in improved therapeutic efficacy due at least in part to the specificity, purity and/or selectivity of the construct designs.

A RNA transcript produced using a RNA polymerase variant as disclosed herein may encode one or more antibodies. The term "antibody" includes monoclonal antibodies (including full length antibodies which have an immunoglobulin Fc region), antibody compositions with polyepitopic specificity, multispecific antibodies (e.g., bispecific antibodies, diabodies, and single-chain molecules), as well as antibody fragments. The term "immunoglobulin" (Ig) is used interchangeably with "antibody" herein. A monoclonal antibody is an antibody obtained from a population of substantially homogeneous antibodies, i.e., the individual antibodies comprising the population are identical except for possible naturally occurring mutations and/or post-translation modifications (e.g., isomerizations, amidations) that may be present in minor amounts. Monoclonal antibodies are highly specific, being directed against a single antigenic site.

Monoclonal antibodies specifically include chimeric antibodies (immunoglobulins) in which a portion of the heavy and/or light chain is identical with or homologous to corresponding sequences in antibodies derived from a particular species or belonging to a particular antibody class or subclass, while the remainder of the chain(s) is(are) identical with or homologous to corresponding sequences in antibodies derived from another species or belonging to another antibody class or subclass, as well as fragments of such antibodies, so long as they exhibit the desired biological activity. Chimeric antibodies include, but are not limited to, "primatized" antibodies comprising variable domain antigen-binding sequences derived from a non-human primate (e.g., Old World Monkey, Ape etc.) and human constant region sequences.

Antibodies encoded in the RNA of the present disclosure may be utilized to treat conditions or diseases in many therapeutic areas such as, but not limited to, blood, cardiovascular, CNS, poisoning (including antivenoms), dermatology, endocrinology, gastrointestinal, medical imaging, musculoskeletal, oncology, immunology, respiratory, sensory and anti-infective.

A RNA transcript produced using a RNA polymerase variant as disclosed herein may encode one or more vaccine antigens. A vaccine antigen is a biological preparation that improves immunity to a particular disease or infectious agent. One or more vaccine antigens currently being marketed or in development may be encoded by the RNA of the present disclosure. Vaccine antigens encoded in the RNA may be utilized to treat conditions or diseases in many therapeutic areas such as, but not limited to, cancer, allergy and infectious disease. In some embodiments, a cancer vaccine may be a personalized cancer vaccine in the form of a concatemer or individual RNAs encoding peptide epitopes or a combination thereof.

A RNA transcript produced using a RNA polymerase variant as disclosed herein may be designed to encode on or more antimicrobial peptides (AMP) or antiviral peptides (AVP). AMPs and AVPs have been isolated and described from a wide range of animals such as, but not limited to, microorganisms, invertebrates, plants, amphibians, birds, fish, and mammals. The anti-microbial polypeptides may block cell fusion and/or viral entry by one or more enveloped viruses (e.g., HIV, HCV). For example, the anti-microbial polypeptide can comprise or consist of a synthetic peptide corresponding to a region, e.g., a consecutive sequence of at least about 5, 10, 15, 20, 25, 30, 35, 40, 45, 50, 55, or 60 amino acids of the transmembrane subunit of a viral envelope protein, e.g., HIV-1 gp120 or gp41. The amino acid and nucleotide sequences of HIV-1 gp120 or gp41 are described in, e.g., Kuiken et al., (2008). "HIV Sequence Compendium," Los Alamos National Laboratory.

In some embodiments, RNA transcripts are used as radiolabeled RNA probes. In some embodiments, RNA transcripts are used for non-isotopic RNA labeling. In some embodiments, RNA transcripts are used as guide RNA (gRNA) for gene targeting. In some embodiments, RNA transcripts (e.g., mRNA) are used for in vitro translation and micro injection. In some embodiments, RNA transcripts are used for RNA structure, processing and catalysis studies. In some embodiments, RNA transcripts are used for RNA amplification. In some embodiments, RNA transcripts are used as anti-sense RNA for gene expression experiment. Other applications are encompassed by the present disclosure.

TABLE 1

RNA Polymerase Variants

| RNA Polymerase Variants | Amino Acid Sequence | SEQ ID NO |
|---|---|---|
| | For the amino acid sequences of SEQ ID NO: 2-14, X may be any amino acid selected from R, K, H, E, D, Q, N, T, S, C, G, A, V, L, I, M, P, Y, W, and F. | |
| G47X | MNTINIAKNDFSDIELAAIPFNTLADHYGERLAREQLALEHESYEMXEARF RKMFERQLKAGEVADNAAAKPLITTLLPKMIARINDWFEEVKAKRGKRPTA FQFLQEIKPEAVAYITIKTTLACLTSADNTTVQAVASAIGRAIEDEARFGR | 2 |

TABLE 1-continued

RNA Polymerase Variants

| RNA Polymerase Variants | Amino Acid Sequence | SEQ ID NO |
|---|---|---|
|  | IRDLEAKHFKKNVEEQLNKRVGHVYKKAFMQVVEADMLSKGLLGGEAWSSW HKEDSIHVGVRCIEMLIESTGMVSLHRQNAGVVGQDSETIELAPEYAEAIA TRAGALAGISPMFQPCVVPPKPWTGITGGGYWANGRRPLALVRTHSKKALM RYEDVYMPEVYKAINIAQNTAWKINKKVLAVANVITKWKHCPVEDIPAIER EELPMKPEDIDMNPEALTAWKRAAAAVYRKDKARKSRRISLEFMLEQANKE ANHKAIWFPYNMDWRGRVYAVSMFNPQGNDMTKGLLTLAKGKPIGKEGYYW LKIHGANCAGVDKVPFPERIKFIEENHENIMACAKSPLENTWWAEQDSPFC FLAFCFEYAGVQHHGLSYNCSLPLAFDGSCSGIQHFSAMLRDEVGGRAVNL LPSETVQDIYGIVAKKVNEILQADAINGTDNEVVTVTDENTGEISEKVKLG TKALAGQWLAYGVTRSVTKRSVMTLAYGSKEFGFRQQVLEDTIQPAIDSGK GLMFTQPNQAAGYMAKLIWESVSVTVVAAVEAMNWLKSAAKLLAAEVKDKK TGEILRKRCAVHWVTPDGFPVWQEYKKPIQTRLNLMFLGQFRLQPTININK DSEIDAHKQESGIAPNFVHSQDGSHLRKTVVWAHEKYGIESFALIHDSFGT IPADAANLFKAVRETMVDTYESCDVLADFYDQFADQLHESQLDKMPALPAK GNLNLRDILESDFAFA |  |
| E350X | MNTINIAKNDFSDIELAAIPENTLADHYGERLAREQLALEHESYEMGEARF RKMFERQLKAGEVADNAAAKPLITTLLPKMIARINDWFEEVKAKRGKRPTA FQFLQEIKPEAVAYITIKTTLACLTSADNTTVQAVASAIGRAIEDEARFGR IRDLEAKHFKKNVEEQLNKRVGHVYKKAFMQVVEADMLSKGLLGGEAWSSW HKEDSIHVGVRCIEMLIESTGMVSLHRQNAGVVGQDSETIELAPEYAEAIA TRAGALAGISPMFQPCVVPPKPWTGITGGGYWANGRRPLALVRTHSKKALM RYEDVYMPEVYKAINIAQNTAWKINKKVLAVANVITKWKHCPVXDIPAIER EELPMKPEDIDMNPEALTAWKRAAAAVYRKDKARKSRRISLEFMLEQANKE ANHKAIWFPYNMDWRGRVYAVSMFNPQGNDMTKGLLTLAKGKPIGKEGYYW LKIHGANCAGVDKVPFPERIKFIEENHENIMACAKSPLENTWWAEQDSPFC FLAFCFEYAGVQHHGLSYNCSLPLAFDGSCSGIQHFSAMLRDEVGGRAVNL LPSETVQDIYGIVAKKVNEILQADAINGTDNEVVTVTDENTGEISEKVKLG TKALAGQWLAYGVTRSVTKRSVMTLAYGSKEFGFRQQVLEDTIQPAIDSGK GLMFTQPNQAAGYMAKLIWESVSVTVVAAVEAMNWLKSAAKLLAAEVKDKK TGEILRKRCAVHWVTPDGFPVWQEYKKPIQTRLNLMFLGQFRLQPTINTNK DSEIDAHKQESGIAPNFVHSQDGSHLRKTVVWAHEKYGIESFALIHDSFGT IPADAANLFKAVRETMVDTYESCDVLADFYDQFADQLHESQLDKMPALPAK GNLNLRDILESDFAFA | 3 |
| D351X | MNTINIAKNDFSDIELAAIPENTLADHYGERLAREQLALEHESYEMGEARF RKMFERQLKAGEVADNAAAKPLITTLLPKMIARINDWFEEVKAKRGKRPTA FQFLQEIKPEAVAYITIKTTLACLTSADNTTVQAVASAIGRAIEDEARFGR IRDLEAKHFKKNVEEQLNKRVGHVYKKAFMQVVEADMLSKGLLGGEAWSSW HKEDSIHVGVRCIEMLIESTGMVSLHRQNAGVVGQDSETIELAPEYAEAIA TRAGALAGISPMFQPCVVPPKPWTGITGGGYWANGRRPLALVRTHSKKALM RYEDVYMPEVYKAINIAQNTAWKINKKVLAVANVITKWKHCPVEXIPAIER EELPMKPEDIDMNPEALTAWKRAAAAVYRKDKARKSRRISLEFMLEQANKE ANHKAIWFPYNMDWRGRVYAVSMFNPQGNDMTKGLLTLAKGKPIGKEGYYW LKIHGANCAGVDKVPFPERIKFIEENHENIMACAKSPLENTWWAEQDSPFC FLAFCFEYAGVQHHGLSYNCSLPLAFDGSCSGIQHFSAMLRDEVGGRAVNL LPSETVQDIYGIVAKKVNEILQADAINGTDNEVVTVTDENTGEISEKVKLG TKALAGQWLAYGVTRSVTKRSVMTLAYGSKEFGFRQQVLEDTIQPAIDSGK GLMFTQPNQAAGYMAKLIWESVSVTVVAAVEAMNWLKSAAKLLAAEVKDKK TGEILRKRCAVHWVTPDGFPVWQEYKKPIQTRLNLMFLGQFRLQPTININK DSEIDAHKQESGIAPNFVHSQDGSHLRKTVVWAHEKYGIESFALIHDSFGT IPADAANLFKAVRETMVDTYESCDVLADFYDQFADQLHESQLDKMPALPAK GNLNLRDILESDFAFA | 4 |
| K387X | MNTINIAKNDFSDIELAAIPENTLADHYGERLAREQLALEHESYEMGEARF RKMFERQLKAGEVADNAAAKPLITTLLPKMIARINDWFEEVKAKRGKRPTA FQFLQEIKPEAVAYITIKTTLACLTSADNTTVQAVASAIGRAIEDEARFGR IRDLEAKHFKKNVEEQLNKRVGHVYKKAFMQVVEADMLSKGLLGGEAWSSW HKEDSIHVGVRCIEMLIESTGMVSLHRQNAGVVGQDSETIELAPEYAEAIA TRAGALAGISPMFQPCVVPPKPWTGITGGGYWANGRRPLALVRTHSKKALM RYEDVYMPEVYKAINIAQNTAWKINKKVLAVANVITKWKHCPVEDIPAIER EELPMKPEDIDMNPEALTAWKRAAAAVYRXDKARKSRRISLEFMLEQANKE ANHKAIWFPYNMDWRGRVYAVSMFNPQGNDMTKGLLTLAKGKPIGKEGYYW LKIHGANCAGVDKVPFPERIKFIEENHENIMACAKSPLENTWWAEQDSPFC FLAFCFEYAGVQHHGLSYNCSLPLAFDGSCSGIQHFSAMLRDEVGGRAVNL LPSETVQDIYGIVAKKVNEILQADAINGTDNEVVTVTDENTGEISEKVKLG TKALAGQWLAYGVTRSVTKRSVMTLAYGSKEFGFRQQVLEDTIQPAIDSGK GLMFTQPNQAAGYMAKLIWESVSVTVVAAVEAMNWLKSAAKLLAAEVKDKK TGEILRKRCAVHWVTPDGFPVWQEYKKPIQTRLNLMFLGQFRLQPTININK DSEIDAHKQESGIAPNFVHSQDGSHLRKTVVWAHEKYGIESFALIHDSFGT IPADAANLFKAVRETMVDTYESCDVLADFYDQFADQLHESQLDKMPALPAK GNLNLRDILESDFAFA | 5 |
| R394X | MNTINIAKNDFSDIELAAIPFNTLADHYGERLAREQLALEHESYEMGEARF RKMFERQLKAGEVADNAAAKPLITTLLPKMIARINDWFEEVKAKRGKRPTA FQFLQEIKPEAVAYITIKTTLACLTSADNTTVQAVASAIGRAIEDEARFGR IRDLEAKHFKKNVEEQLNKRVGHVYKKAFMQVVEADMLSKGLLGGEAWSSW HKEDSIHVGVRCIEMLIESTGMVSLHRQNAGVVGQDSETIELAPEYAEAIA | 6 |

TABLE 1-continued

RNA Polymerase Variants

| RNA Polymerase Variants | Amino Acid Sequence | SEQ ID NO |
|---|---|---|
| | TRAGALAGISPMFQPCVVPPKPWTGITGGGYWANGRRPLALVRTHSKKALM RYEDVYMPEVYKAINIAQNTAWKINKKVLAVANVITKWKHCPVEDIPAIER EELPMKPEDIDMNPEALTAWKRAAAAVYRKDKARKSXRISLEFMLEQANKE ANHKAIWFPYNMDWRGRVYAVSMFNPQGNDMTKGLLTLAKGKPIGKEGYYW LKIHGANCAGVDKVPFPERIKFIEENHENIMACAKSPLENTWWAEQDSPFC FLAFCFEYAGVQHHGLSYNCSLPLAFDGSCSGIQHFSAMLRDEVGGRAVNL LPSETVQDIYGIVAKKVNEILQADAINGTDNEVVTVTDENTGEISEKVKLG TKALAGQWLAYGVTRSVTKRSVMTLAYGSKEFGFRQQVLEDTIQPAIDSGK GLMFTQPNQAAGYMAKLIWESVSVTVVAAVEAMNWLKSAAKLLAAEVKDKK TGEILRKRCAVHWVTPDGFPVWQEYKKPIQTRLNLMFLGQFRLQPTININK DSEIDAHKQESGIAPNFVHSQDGSHLRKTVVWAHEKYGIESFALIHDSFGT IPADAANLFKAVRETMVDTYESCDVLADFYDQFADQLHESQLDKMPALPAK GNLNLRDILESDFAFA | |
| R425X | MNTINIAKNDFSDIELAAIPENTLADHYGERLAREQLALEHESYEMGEARF RKMFERQLKAGEVADNAAAKPLITTLLPKMIARINDWFEEVKAKRGKRPTA FQFLQEIKPEAVAYITIKTTLACLTSADNTTVQAVASAIGRAIEDEARFGR IRDLEAKHFKKNVEEQLNKRVGHVYKKAFMQVVEADMLSKGLLGGEAWSSW HKEDSIHVGVRCIEMLIESTGMVSLHRQNAGVVGQDSETIELAPEYAEAIA TRAGALAGISPMFQPCVVPPKPWTGITGGGYWANGRRPLALVRTHSKKALM RYEDVYMPEVYKAINIAQNTAWKINKKVLAVANVITKWKHCPVEDIPAIER EELPMKPEDIDMNPEALTAWKRAAAAVYRKDKARKSRRISLEFMLEQANKE ANHKAIWFPYNMDWRGXVYAVSMFNPQGNDMTKGLLTLAKGKPIGKEGYYW LKIHGANCAGVDKVPFPERIKFIEENHENIMACAKSPLENTWWAEQDSPFC FLAFCFEYAGVQHHGLSYNCSLPLAFDGSCSGIQHFSAMLRDEVGGRAVNL LPSETVQDIYGIVAKKVNEILQADAINGTDNEVVTVTDENTGEISEKVKLG TKALAGQWLAYGVTRSVTKRSVMTLAYGSKEFGFRQQVLEDTIQPAIDSGK GLMFTQPNQAAGYMAKLIWESVSVTVVAAVEAMNWLKSAAKLLAAEVKDKK TGEILRKRCAVHWVTPDGFPVWQEYKKPIQTRLNLMFLGQFRLQPTININK DSEIDAHKQESGIAPNFVHSQDGSHLRKTVVWAHEKYGIESFALIHDSFGT IPADAANLFKAVRETMVDTYESCDVLADFYDQFADQLHESQLDKMPALPAK GNLNLRDILESDFAFA | 7 |
| Y427X | MNTINIAKNDFSDIELAAIPFNTLADHYGERLAREQLALEHESYEMGEARF RKMFERQLKAGEVADNAAAKPLITTLLPKMIARINDWFEEVKAKRGKRPTA FQFLQEIKPEAVAYITIKTTLACLISADNTTVQAVASAIGRAIEDEARFGR IRDLEAKHFKKNVEEQLNKRVGHVYKKAFMQVVEADMLSKGLLGGEAWSSW HKEDSIHVGVRCIEMLIESTGMVSLHRQNAGVVGQDSETIELAPEYAEAIA TRAGALAGISPMFQPCVVPPKPWTGITGGGYWANGRRPLALVRTHSKKALM RYEDVYMPEVYKAINIAQNTAWKINKKVLAVANVITKWKHCPVEDIPAIER EELPMKPEDIDMNPEALTAWKRAAAAVYRKDKARKSRRISLEFMLEQANKE ANHKAIWFPYNMDWRGRVXAVSMFNPQGNDMTKGLLTLAKGKPIGKEGYYW LKIHGANCAGVDKVPFPERIKFIEENHENIMACAKSPLENTWWAEQDSPFC FLAFCFEYAGVQHHGLSYNCSLPLAFDGSCSGIQHFSAMLRDEVGGRAVNL LPSETVQDIYGIVAKKVNEILQADAINGTDNEVVTVTDENTGEISEKVKLG TKALAGQWLAYGVTRSVTKRSVMTLAYGSKEFGFRQQVLEDTIQPAIDSGK GLMFTQPNQAAGYMAKLIWESVSVTVVAAVEAMNWLKSAAKLLAAEVKDKK TGEILRKRCAVHWVTPDGFPVWQEYKKPIQTRLNLMFLGQFRLQPTINTNK DSEIDAHKQESGIAPNFVHSQDGSHLRKTVVWAHEKYGIESFALIHDSFGT IPADAANLFKAVRETMVDTYESCDVLADFYDQFADQLHESQLDKMPALPAK GNLNLRDILESDFAFA | 8 |
| N437X | MNTINIAKNDFSDIELAAIPENTLADHYGERLAREQLALEHESYEMGEARF RKMFERQLKAGEVADNAAAKPLITTLLPKMIARINDWFEEVKAKRGKRPTA FQFLQEIKPEAVAYITIKTTLACLTSADNTTVQAVASAIGRAIEDEARFGR IRDLEAKHFKKNVEEQLNKRVGHVYKKAFMQVVEADMLSKGLLGGEAWSSW HKEDSIHVGVRCIEMLIESTGMVSLHRQNAGVVGQDSETIELAPEYAEAIA TRAGALAGISPMFQPCVVPPKPWTGITGGGYWANGRRPLALVRTHSKKALM RYEDVYMPEVYKAINIAQNTAWKINKKVLAVANVITKWKHCPVEDIPAIER EELPMKPEDIDMNPEALTAWKRAAAAVYRKDKARKSRRISLEFMLEQANKE ANHKAIWFPYNMDWRGRVYAVSMFNPQGXDMTKGLLTLAKGKPIGKEGYYW LKIHGANCAGVDKVPFPERIKFIEENHENIMACAKSPLENTWWAEQDSPFC FLAFCFEYAGVQHHGLSYNCSLPLAFDGSCSGIQHFSAMLRDEVGGRAVNL LPSETVQDIYGIVAKKVNEILQADAINGTDNEVVTVTDENTGEISEKVKLG TKALAGQWLAYGVTRSVTKRSVMTLAYGSKEFGFRQQVLEDTIQPAIDSGK GLMFTQPNQAAGYMAKLIWESVSVTVVAAVEAMNWLKSAAKLLAAEVKDKK TGEILRKRCAVHWVTPDGFPVWQEYKKPIQTRLNLMFLGQFRLQPTININK DSEIDAHKQESGIAPNFVHSQDGSHLRKTVVWAHEKYGIESFALIHDSFGT IPADAANLFKAVRETMVDTYESCDVLADFYDQFADQLHESQLDKMPALPAK GNLNLRDILESDFAFA | 9 |
| K441X | MNTINIAKNDFSDIELAAIPENTLADHYGERLAREQLALEHESYEMGEARF RKMFERQLKAGEVADNAAAKPLITTLLPKMIARINDWFEEVKAKRGKRPTA FQFLQEIKPEAVAYITIKTTLACLTSADNTTVQAVASAIGRAIEDEARFGR IRDLEAKHFKKNVEEQLNKRVGHVYKKAFMQVVEADMLSKGLLGGEAWSSW HKEDSIHVGVRCIEMLIESTGMVSLHRQNAGVVGQDSETIELAPEYAEAIA TRAGALAGISPMFQPCVVPPKPWTGITGGGYWANGRRPLALVRTHSKKALM RYEDVYMPEVYKAINIAQNTAWKINKKVLAVANVITKWKHCPVEDIPAIER | 10 |

TABLE 1-continued

RNA Polymerase Variants

| RNA Polymerase Variants | Amino Acid Sequence | SEQ ID NO |
|---|---|---|
|  | EELPMKPEDIDMNPEALTAWKRAAAAVYRKDKARKSRRISLEFMLEQANKF ANHKAIWFPYNMDWRGRVYAVSMFNPQGNDMTXGLLTLAKGKPIGKEGYYW LKIHGANCAGVDKVPFPERIKFIEENHENIMACAKSPLENTWWAEQDSPFC FLAFCFEYAGVQHHGLSYNCSLPLAFDGSCSGIQHFSAMLRDEVGGRAVNL LPSETVQDIYGIVAKKVNEILQADAINGTDNEVVTVTDENTGEISEKVKLG TKALAGQWLAYGVTRSVTKRSVMTLAYGSKEFGFRQQVLEDTIQPAIDSGK GLMFTQPNQAAGYMAKLIWESVSVTVVAAVEAMNWLKSAAKLLAAEVKDKK TGEILRKRCAVHWVTPDGFPVWQEYKKPIQTRLNLMFLGQFRLQPTININK DSEIDAHKQESGIAPNFVHSQDGSHLRKTVVWAHEKYGIESFALIHDSFGT IPADAANLFKAVRETMVDTYESCDVLADFYDQFADQLHESQLDKMPALPAK GNLNLRDILESDFAFA |  |
| R632X | MNTINIAKNDFSDIELAAIPENTLADHYGERLAREQLALEHESYEMGEARF RKMFERQLKAGEVADNAAAKPLITTLLPKMIARINDWFEEVKAKRGKRPTA FQFLQEIKPEAVAYITIKTTLACLTSADNTTVQAVASAIGRAIEDEARFGR IRDLEAKHFKKNVEEQLNKRVGHVYKKAFMQVVEADMLSKGLLGGEAWSSW HKEDSIHVGVRCIEMLIESTGMVSLHRQNAGVVGQDSETIELAPEYAEAIA TRAGALAGISPMFQPCVVPPKPWTGITGGGYWANGRRPLALVRTHSKKALM RYEDVYMPEVYKAINIAQNTAWKINKKVLAVANVITKWKHCPVEDIPAIER EELPMKPEDIDMNPEALTAWKRAAAAVYRKDKARKSRRISLEFMLEQANKE ANHKAIWFPYNMDWRGRVYAVSMFNPQGNDMTKGLLTLAKGKPIGKEGYYW LKIHGANCAGVDKVPFPERIKFIEENHENIMACAKSPLENTWWAEQDSPFC FLAFCFEYAGVQHHGLSYNCSLPLAFDGSCSGIQHFSAMLRDEVGGRAVNL LPSETVQDIYGIVAKKVNEILQADAINGTDNEVVTVTDENTGEISEKVKLG TKALAGQWLAYGVTRSVTKXSVMTLAYGSKEFGFRQQVLEDTIQPAIDSGK GLMFTQPNQAAGYMAKLIWESVSVTVVAAVEAMNWLKSAAKLLAAEVKDKK TGEILRKRCAVHWVTPDGFPVWQEYKKPIQTRLNLMFLGQFRLQPTININK DSEIDAHKQESGIAPNFVHSQDGSHLRKTVVWAHEKYGIESFALIHDSFGT IPADAANLFKAVRETMVDTYESCDVLADFYDQFADQLHESQLDKMPALPAK GNLNLRDILESDFAFA | 11 |
| H811X | MNTINIAKNDFSDIELAAIPENTLADHYGERLAREQLALEHESYEMGEARF RKMFERQLKAGEVADNAAAKPLITTLLPKMIARINDWFEEVKAKRGKRPTA FQFLQEIKPEAVAYITIKTTLACLTSADNTTVQAVASAIGRAIEDEARFGR IRDLEAKHFKKNVEEQLNKRVGHVYKKAFMQVVEADMLSKGLLGGEAWSSW HKEDSIHVGVRCIEMLIESTGMVSLHRQNAGVVGQDSETIELAPEYAEAIA TRAGALAGISPMFQPCVVPPKPWTGITGGGYWANGRRPLALVRTHSKKALM RYEDVYMPEVYKAINIAQNTAWKINKKVLAVANVITKWKHCPVEDIPAIER EELPMKPEDIDMNPEALTAWKRAAAAVYRKDKARKSRRISLEFMLEQANKE ANHKAIWFPYNMDWRGRVYAVSMFNPQGNDMTKGLLTLAKGKPIGKEGYYW LKIHGANCAGVDKVPFPERIKFIEENHENIMACAKSPLENTWWAEQDSPFC FLAFCFEYAGVQHHGLSYNCSLPLAFDGSCSGIQHFSAMLRDEVGGRAVNL LPSETVQDIYGIVAKKVNEILQADAINGTDNEVVTVTDENTGEISEKVKLG TKALAGQWLAYGVTRSVTKRSVMTLAYGSKEFGFRQQVLEDTIQPAIDSGK GLMFTQPNQAAGYMAKLIWESVSVTVVAAVEAMNWLKSAAKLLAAEVKDKK TGEILRKRCAVHWVTPDGFPVWQEYKKPIQTRLNLMFLGQFRLQPTININK DSEIDAHKQESGIAPNFVHSQDGSHLRKTVVWAHEKYGIESFALIXDSFGT IPADAANLFKAVRETMVDTYESCDVLADFYDQFADQLHESQLDKMPALPAK GNLNLRDILESDFAFA | 12 |
| F880X | MNTINIAKNDFSDIELAAIPENTLADHYGERLAREQLALEHESYEMGEARF RKMFERQLKAGEVADNAAAKPLITTLLPKMIARINDWFEEVKAKRGKRPTA FQFLQEIKPEAVAYITIKTTLACLTSADNTTVQAVASAIGRAIEDEARFGR IRDLEAKHFKKNVEEQLNKRVGHVYKKAFMQVVEADMLSKGLLGGEAWSSW HKEDSIHVGVRCIEMLIESTGMVSLHRQNAGVVGQDSETIELAPEYAEAIA TRAGALAGISPMFQPCVVPPKPWTGITGGGYWANGRRPLALVRTHSKKALM RYEDVYMPEVYKAINIAQNTAWKINKKVLAVANVITKWKHCPVEDIPAIER EELPMKPEDIDMNPEALTAWKRAAAAVYRKDKARKSRRISLEFMLEQANKF ANHKAIWFPYNMDWRGRVYAVSMFNPQGNDMTKGLLTLAKGKPIGKEGYYW LKIHGANCAGVDKVPFPERIKFIEENHENIMACAKSPLENTWWAEQDSPFC FLAFCFEYAGVQHHGLSYNCSLPLAFDGSCSGIQHFSAMLRDEVGGRAVNL LPSETVQDIYGIVAKKVNEILQADAINGTDNEVVTVTDENTGEISEKVKLG TKALAGQWLAYGVTRSVTKRSVMTLAYGSKEFGFRQQVLEDTIQPAIDSGK GLMFTQPNQAAGYMAKLIWESVSVTVVAAVEAMNWLKSAAKLLAAEVKDKK TGEILRKRCAVHWVTPDGFPVWQEYKKPIQTRLNLMFLGQFRLQPTININK DSEIDAHKQESGIAPNFVHSQDGSHLRKTVVWAHEKYGIESFALIHDSFGT IPADAANLFKAVRETMVDTYESCDVLADFYDQFADQLHESQLDKMPALPAK GNLNLRDILESDXAFA | 13 |
| 884X | MNTINIAKNDFSDIELAAIPENTLADHYGERLAREQLALEHESYEMGEARF RKMFERQLKAGEVADNAAAKPLITTLLPKMIARINDWFEEVKAKRGKRPTA FQFLQEIKPEAVAYITIKTTLACLTSADNTTVQAVASAIGRAIEDEARFGR IRDLEAKHFKKNVEEQLNKRVGHVYKKAFMQVVEADMLSKGLLGGEAWSSW HKEDSIHVGVRCIEMLIESTGMVSLHRQNAGVVGQDSETIELAPEYAEAIA TRAGALAGISPMFQPCVVPPKPWTGITGGGYWANGRRPLALVRTHSKKALM RYEDVYMPEVYKAINIAQNTAWKINKKVLAVANVITKWKHCPVEDIPAIER EELPMKPEDIDMNPEALTAWKRAAAAVYRKDKARKSRRISLEFMLEQANKE ANHKAIWFPYNMDWRGRVYAVSMFNPQGNDMTKGLLTLAKGKPIGKEGYYW | 14 |

TABLE 1-continued

RNA Polymerase Variants

| RNA Polymerase Variants | Amino Acid Sequence | SEQ ID NO |
|---|---|---|
| | LKIHGANCAGVDKVPFPERIKFIEENHENIMACAKSPLENTWWAEQDSPFC FLAFCFEYAGVQHHGLSYNCSLPLAFDGSCSGIQHFSAMLRDEVGGRAVNL LPSETVQDIYGIVAKKVNEILQADAINGTDNEVVTVTDENTGEISEKVKLG TKALAGQWLAYGVTRSVTKRSVMTLAYGSKEFGFRQQVLEDTIQPAIDSGK GLMFTQPNQAAGYMAKLIWESVSVTVVAAVEAMNWLKSAAKLLAAEVKDKK TGEILRKRCAVHWVTPDGFPVWQEYKKPIQTRLNLMFLGQFRLQPTININK DSEIDAHKQESGIAPNFVHSQDGSHLRKTVVWAHEKYGIESFALIHDSFGT IPADAANLFKAVRETMVDTYESCDVLADFYDQFADQLHESQLDKMPALPAK GNLNLRDILESDFAFAX | |
| G47A | MNTINIAKNDFSDIELAAIPFNTLADHYGERLAREQLALEHESYEMAEARF RKMFERQLKAGEVADNAAAKPLITTLLPKMIARINDWFEEVKAKRGKRPTA FQFLQEIKPEAVAYITIKTTLACLTSADNTTVQAVASAIGRAIEDEARFGR IRDLEAKHFKKNVEEQLNKRVGHVYKKAFMQVVEADMLSKGLLGGEAWSSW HKEDSIHVGVRCIEMLIESTGMVSLHRQNAGVVGQDSETIELAPEYAEAIA TRAGALAGISPMFQPCVVPPKPWTGITGGGYWANGRRPLALVRTHSKKALM RYEDVYMPEVYKAINIAQNTAWKINKKVLAVANVITKWKHCPVEDIPAIER EELPMKPEDIDMNPEALTAWKRAAAAVYRKDKARKSRRISLEFMLEQANKE ANHKAIWFPYNMDWRGRVYAVSMFNPQGNDMTKGLLTLAKGKPIGKEGYYW LKIHGANCAGVDKVPFPERIKFIEENHENIMACAKSPLENTWWAEQDSPFC FLAFCFEYAGVQHHGLSYNCSLPLAFDGSCSGIQHFSAMLRDEVGGRAVNL LPSETVQDIYGIVAKKVNEILQADAINGTDNEVVTVTDENTGEISEKVKLG TKALAGQWLAYGVTRSVTKRSVMTLAYGSKEFGFRQQVLEDTIQPAIDSGK GLMFTQPNQAAGYMAKLIWESVSVTVVAAVEAMNWLKSAAKLLAAEVKDKK TGEILRKRCAVHWVTPDGFPVWQEYKKPIQTRLNLMFLGQFRLQPTININK DSEIDAHKQESGIAPNFVHSQDGSHLRKTVVWAHEKYGIESFALIHDSFGT IPADAANLFKAVRETMVDTYESCDVLADFYDQFADQLHESQLDKMPALPAK GNLNLRDILESDFAFA | 15 |
| E350K | MNTINIAKNDFSDIELAAIPFNTLADHYGERLAREQLALEHESYEMGEARF RKMFERQLKAGEVADNAAAKPLITTLLPKMIARINDWFEEVKAKRGKRPTA FQFLQEIKPEAVAYITIKTTLACLTSADNTTVQAVASAIGRAIEDEARFGR IRDLEAKHFKKNVEEQLNKRVGHVYKKAFMQVVEADMLSKGLLGGEAWSSW HKEDSIHVGVRCIEMLIESTGMVSLHRQNAGVVGQDSETIELAPEYAEAIA TRAGALAGISPMFQPCVVPPKPWTGITGGGYWANGRRPLALVRTHSKKALM RYEDVYMPEVYKAINIAQNTAWKINKKVLAVANVITKWKHCPVKDIPAIER EELPMKPEDIDMNPEALTAWKRAAAAVYRKDKARKSRRISLEFMLEQANKF ANHKAIWFPYNMDWRGRVYAVSMFNPQGNDMTKGLLTLAKGKPIGKEGYYW LKIHGANCAGVDKVPFPERIKFIEENHENIMACAKSPLENTWWAEQDSPFC FLAFCFEYAGVQHHGLSYNCSLPLAFDGSCSGIQHFSAMLRDEVGGRAVNL LPSETVQDIYGIVAKKVNEILQADAINGTDNEVVTVTDENTGEISEKVKLG TKALAGQWLAYGVTRSVTKRSVMTLAYGSKEFGFRQQVLEDTIQPAIDSGK GLMFTQPNQAAGYMAKLIWESVSVTVVAAVEAMNWLKSAAKLLAAEVKDKK TGEILRKRCAVHWVTPDGFPVWQEYKKPIQTRLNLMFLGQFRLQPTININK DSEIDAHKQESGIAPNFVHSQDGSHLRKTVVWAHEKYGIESFALIHDSFGT IPADAANLFKAVRETMVDTYESCDVLADFYDQFADQLHESQLDKMPALPAK GNLNLRDILESDFAFA | 16 |
| E350N | MNTINIAKNDFSDIELAAIPENTLADHYGERLAREQLALEHESYEMGEARF RKMFERQLKAGEVADNAAAKPLITTLLPKMIARINDWFEEVKAKRGKRPTA FQFLQEIKPEAVAYITIKTTLACLTSADNTTVQAVASAIGRAIEDEARFGR IRDLEAKHFKKNVEEQLNKRVGHVYKKAFMQVVEADMLSKGLLGGEAWSSW HKEDSIHVGVRCIEMLIESTGMVSLHRQNAGVVGQDSETIELAPEYAEAIA TRAGALAGISPMFQPCVVPPKPWTGITGGGYWANGRRPLALVRTHSKKALM RYEDVYMPEVYKAINIAQNTAWKINKKVLAVANVITKWKHCPVNDIPAIER EELPMKPEDIDMNPEALTAWKRAAAAVYRKDKARKSRRISLEFMLEQANKE ANHKAIWFPYNMDWRGRVYAVSMFNPQGNDMTKGLLTLAKGKPIGKEGYYW LKIHGANCAGVDKVPFPERIKFIEENHENIMACAKSPLENTWWAEQDSPFC FLAFCFEYAGVQHHGLSYNCSLPLAFDGSCSGIQHFSAMLRDEVGGRAVNL LPSETVQDIYGIVAKKVNEILQADAINGTDNEVVTVTDENTGEISEKVKLG TKALAGQWLAYGVTRSVTKRSVMTLAYGSKEFGFRQQVLEDTIQPAIDSGK GLMFTQPNQAAGYMAKLIWESVSVTVVAAVEAMNWLKSAAKLLAAEVKDKK TGEILRKRCAVHWVTPDGFPVWQEYKKPIQTRLNLMFLGQFRLQPTINTNK DSEIDAHKQESGIAPNFVHSQDGSHLRKTVVWAHEKYGIESFALIHDSFGT IPADAANLFKAVRETMVDTYESCDVLADFYDQFADQLHESQLDKMPALPAK GNLNLRDILESDFAFA | 17 |
| E350A | MNTINIAKNDFSDIELAAIPENTLADHYGERLAREQLALEHESYEMGEARF RKMFERQLKAGEVADNAAAKPLITTLLPKMIARINDWFEEVKAKRGKRPTA FQFLQEIKPEAVAYITIKTTLACLTSADNTTVQAVASAIGRAIEDEARFGR IRDLEAKHFKKNVEEQLNKRVGHVYKKAFMQVVEADMLSKGLLGGEAWSSW HKEDSIHVGVRCIEMLIESTGMVSLHRQNAGVVGQDSETIELAPEYAEAIA TRAGALAGISPMFQPCVVPPKPWTGITGGGYWANGRRPLALVRTHSKKALM RYEDVYMPEVYKAINIAQNTAWKINKKVLAVANVITKWKHCPVADIPAIER EELPMKPEDIDMNPEALTAWKRAAAAVYRKDKARKSRRISLEFMLEQANKE ANHKAIWFPYNMDWRGRVYAVSMFNPQGNDMTKGLLTLAKGKPIGKEGYYW LKIHGANCAGVDKVPFPERIKFIEENHENIMACAKSPLENTWWAEQDSPFC FLAFCFEYAGVQHHGLSYNCSLPLAFDGSCSGIQHFSAMLRDEVGGRAVNL | 18 |

TABLE 1-continued

RNA Polymerase Variants

| RNA Polymerase Variants | Amino Acid Sequence | SEQ ID NO |
|---|---|---|
| | LPSETVQDIYGIVAKKVNEILQADAINGTDNEVVTVTDENTGEISEKVKLG TKALAGQWLAYGVTRSVTKRSVMTLAYGSKEFGFRQQVLEDTIQPAIDSGK GLMFTQPNQAAGYMAKLIWESVSVTVVAAVEAMNWLKSAAKLLAAEVKDKK TGEILRKRCAVHWVTPDGFPVWQEYKKPIQTRLNLMFLGQFRLQPTININK DSEIDAHKQESGIAPNFVHSQDGSHLRKTVVWAHEKYGIESFALIHDSFGT IPADAANLFKAVRETMVDTYESCDVLADFYDQFADQLHESQLDKMPALPAK GNLNLRDILESDFAFA | |
| E350W | MNTINIAKNDFSDIELAAIPENTLADHYGERLAREQLALEHESYEMGEARF RKMFERQLKAGEVADNAAAKPLITTLLPKMIARINDWFEEVKAKRGKRPTA FQFLQEIKPEAVAYITIKTTLACLTSADNTTVQAVASAIGRAIEDEARFGR IRDLEAKHFKKNVEEQLNKRVGHVYKKAFMQVVEADMLSKGLLGGEAWSSW HKEDSIHVGVRCIEMLIESTGMVSLHRQNAGVVGQDSETIELAPEYAEAIA TRAGALAGISPMFQPCVVPPKPWTGITGGGYWANGRRPLALVRTHSKKALM RYEDVYMPEVYKAINIAQNTAWKINKKVLAVANVITKWKHCPVWDIPAIER EELPMKPEDIDMNPEALTAWKRAAAAVYRKDKARKSRRISLEFMLEQANKE ANHKAIWFPYNMDWRGRVYAVSMFNPQGNDMTKGLLTLAKGKPIGKEGYYW LKIHGANCAGVDKVPFPERIKFIEENHENIMACAKSPLENTWWAEQDSPFC FLAFCFEYAGVQHHGLSYNCSLPLAFDGSCSGIQHFSAMLRDEVGGRAVNL LPSETVQDIYGIVAKKVNEILQADAINGTDNEVVTVTDENTGEISEKVKLG TKALAGQWLAYGVTRSVTKRSVMTLAYGSKEFGFRQQVLEDTIQPAIDSGK GLMFTQPNQAAGYMAKLIWESVSVTVVAAVEAMNWLKSAAKLLAAEVKDKK TGEILRKRCAVHWVTPDGFPVWQEYKKPIQTRLNLMFLGQFRLQPTINTNK DSEIDAHKQESGIAPNFVHSQDGSHLRKTVVWAHEKYGIESFALIHDSFGT IPADAANLFKAVRETMVDTYESCDVLADFYDQFADQLHESQLDKMPALPAK GNLNLRDILESDFAFA | 19 |
| D351V | MNTINIAKNDFSDIELAAIPENTLADHYGERLAREQLALEHESYEMGEARF RKMFERQLKAGEVADNAAAKPLITTLLPKMIARINDWFEEVKAKRGKRPTA FQFLQEIKPEAVAYITIKTTLACLTSADNITVQAVASAIGRAIEDEARFGR IRDLEAKHFKKNVEEQLNKRVGHVYKKAFMQVVEADMLSKGLLGGEAWSSW HKEDSIHVGVRCIEMLIESTGMVSLHRQNAGVVGQDSETIELAPEYAEAIA TRAGALAGISPMFQPCVVPPKPWTGITGGGYWANGRRPLALVRTHSKKALM RYEDVYMPEVYKAINIAQNTAWKINKKVLAVANVITKWKHCPVEVIPAIER EELPMKPEDIDMNPEALTAWKRAAAAVYRKDKARKSRRISLEFMLEQANKE ANHKAIWFPYNMDWRGRVYAVSMFNPQGNDMTKGLLTLAKGKPIGKEGYYW LKIHGANCAGVDKVPFPERIKFIEENHENIMACAKSPLENTWWAEQDSPFC FLAFCFEYAGVQHHGLSYNCSLPLAFDGSCSGIQHFSAMLRDEVGGRAVNL LPSETVQDIYGIVAKKVNEILQADAINGTDNEVVTVTDENTGEISEKVKLG TKALAGQWLAYGVTRSVTKRSVMTLAYGSKEFGFRQQVLEDTIQPAIDSGK GLMFTQPNQAAGYMAKLIWESVSVTVVAAVEAMNWLKSAAKLLAAEVKDKK TGEILRKRCAVHWVTPDGFPVWQEYKKPIQTRLNLMFLGQFRLQPTININK DSEIDAHKQESGIAPNFVHSQDGSHLRKTVVWAHEKYGIESFALIHDSFGT IPADAANLFKAVRETMVDTYESCDVLADFYDQFADQLHESQLDKMPALPAK GNLNLRDILESDFAFA | 20 |
| K387S | MNTINIAKNDFSDIELAAIPENTLADHYGERLAREQLALEHESYEMGEARF RKMFERQLKAGEVADNAAAKPLITTLLPKMIARINDWFEEVKAKRGKRPTA FQFLQEIKPEAVAYITIKTTLACLTSADNTTVQAVASAIGRAIEDEARFGR IRDLEAKHFKKNVEEQLNKRVGHVYKKAFMQVVEADMLSKGLLGGEAWSSW HKEDSIHVGVRCIEMLIESTGMVSLHRQNAGVVGQDSETIELAPEYAEAIA TRAGALAGISPMFQPCVVPPKPWTGITGGGYWANGRRPLALVRTHSKKALM RYEDVYMPEVYKAINIAQNTAWKINKKVLAVANVITKWKHCPVEDIPAIER EELPMKPEDIDMNPEALTAWKRAAAAVYRSDKARKSRRISLEFMLEQANKF ANHKAIWFPYNMDWRGRVYAVSMFNPQGNDMTKGLLTLAKGKPIGKEGYYW LKIHGANCAGVDKVPFPERIKFIEENHENIMACAKSPLENTWWAEQDSPFC FLAFCFEYAGVQHHGLSYNCSLPLAFDGSCSGIQHFSAMLRDEVGGRAVNL LPSETVQDIYGIVAKKVNEILQADAINGTDNEVVTVTDENTGEISEKVKLG TKALAGQWLAYGVTRSVTKRSVMTLAYGSKEFGFRQQVLEDTIQPAIDSGK GLMFTQPNQAAGYMAKLIWESVSVTVVAAVEAMNWLKSAAKLLAAEVKDKK TGEILRKRCAVHWVTPDGFPVWQEYKKPIQTRLNLMFLGQFRLQPTININK DSEIDAHKQESGIAPNFVHSQDGSHLRKTVVWAHEKYGIESFALIHDSFGT IPADAANLFKAVRETMVDTYESCDVLADFYDQFADQLHESQLDKMPALPAK GNLNLRDILESDFAFA | 21 |
| K387H | MNTINIAKNDFSDIELAAIPENTLADHYGERLAREQLALEHESYEMGEARF RKMFERQLKAGEVADNAAAKPLITTLLPKMIARINDWFEEVKAKRGKRPTA FQFLQEIKPEAVAYITIKTTLACLTSADNTTVQAVASAIGRAIEDEARFGR IRDLEAKHFKKNVEEQLNKRVGHVYKKAFMQVVEADMLSKGLLGGEAWSSW HKEDSIHVGVRCIEMLIESTGMVSLHRQNAGVVGQDSETIELAPEYAEAIA TRAGALAGISPMFQPCVVPPKPWTGITGGGYWANGRRPLALVRTHSKKALM RYEDVYMPEVYKAINIAQNTAWKINKKVLAVANVITKWKHCPVEDIPAIER EELPMKPEDIDMNPEALTAWKRAAAAVYRHDKARKSRRISLEFMLEQANKE ANHKAIWFPYNMDWRGRVYAVSMFNPQGNDMTKGLLTLAKGKPIGKEGYYW LKIHGANCAGVDKVPFPERIKFIEENHENIMACAKSPLENTWWAEQDSPFC FLAFCFEYAGVQHHGLSYNCSLPLAFDGSCSGIQHFSAMLRDEVGGRAVNL LPSETVQDIYGIVAKKVNEILQADAINGTDNEVVTVTDENTGEISEKVKLG TKALAGQWLAYGVTRSVTKRSVMTLAYGSKEFGFRQQVLEDTIQPAIDSGK | 22 |

TABLE 1-continued

RNA Polymerase Variants

| RNA Polymerase Variants | Amino Acid Sequence | SEQ ID NO |
|---|---|---|
| | GLMFTQPNQAAGYMAKLIWESVSVTVVAAVEAMNWLKSAAKLLAAEVKDKK TGEILRKRCAVHWVTPDGFPVWQEYKKPIQTRLNLMFLGQFRLQPTININK DSEIDAHKQESGIAPNFVHSQDGSHLRKTVVWAHEKYGIESFALIHDSFGT IPADAANLFKAVRETMVDTYESCDVLADFYDQFADQLHESQLDKMPALPAK GNLNLRDILESDFAFA | |
| K387N | MNTINIAKNDFSDIELAAIPFNTLADHYGERLAREQLALEHESYEMGEARF RKMFERQLKAGEVADNAAAKPLITTLLPKMIARINDWFEEVKAKRGKRPTA FQFLQEIKPEAVAYITIKTTLACLTSADNTTVQAVASAIGRAIEDEARFGR IRDLEAKHFKKNVEEQLNKRVGHVYKKAFMQVVEADMLSKGLLGGEAWSSW HKEDSIHVGVRCIEMLIESTGMVSLHRQNAGVVGQDSETIELAPEYAEAIA TRAGALAGISPMFQPCVVPPKPWTGITGGGYWANGRRPLALVRTHSKKALM RYEDVYMPEVYKAINIAQNTAWKINKKVLAVANVITKWKHCPVEDIPAIER EELPMKPEDIDMNPEALTAWKRAAAAVYRNDKARKSRRISLEFMLEQANKE ANHKAIWFPYNMDWRGRVYAVSMFNPQGNDMTKGLLTLAKGKPIGKEGYYW LKIHGANCAGVDKVPFPERIKFIEENHENIMACAKSPLENTWWAEQDSPFC FLAFCFEYAGVQHHGLSYNCSLPLAFDGSCSGIQHFSAMLRDEVGGRAVNL LPSETVQDIYGIVAKKVNEILQADAINGTDNEVVTVTDENTGEISEKVKLG TKALAGQWLAYGVTRSVTKRSVMTLAYGSKEFGFRQQVLEDTIQPAIDSGK GLMFTQPNQAAGYMAKLIWESVSVTVVAAVEAMNWLKSAAKLLAAEVKDKK TGEILRKRCAVHWVTPDGFPVWQEYKKPIQTRLNLMFLGQFRLQPTININK DSEIDAHKQESGIAPNFVHSQDGSHLRKTVVWAHEKYGIESFALIHDSFGT IPADAANLFKAVRETMVDTYESCDVLADFYDQFADQLHESQLDKMPALPAK GNLNLRDILESDFAFA | 23 |
| G47A E350K | MNTINIAKNDFSDIELAAIPENTLADHYGERLAREQLALEHESYEMAEARF RKMFERQLKAGEVADNAAAKPLITTLLPKMIARINDWFEEVKAKRGKRPTA FQFLQEIKPEAVAYITIKTTLACLTSADNTTVQAVASAIGRAIEDEARFGR IRDLEAKHFKKNVEEQLNKRVGHVYKKAFMQVVEADMLSKGLLGGEAWSSW HKEDSIHVGVRCIEMLIESTGMVSLHRQNAGVVGQDSETIELAPEYAEAIA TRAGALAGISPMFQPCVVPPKPWTGITGGGYWANGRRPLALVRTHSKKALM RYEDVYMPEVYKAINIAQNTAWKINKKVLAVANVITKWKHCPVKDIPAIER EELPMKPEDIDMNPEALTAWKRAAAAVYRKDKARKSRRISLEFMLEQANKE ANHKAIWFPYNMDWRGRVYAVSMFNPQGNDMTKGLLTLAKGKPIGKEGYYW LKIHGANCAGVDKVPFPERIKFIEENHENIMACAKSPLENTWWAEQDSPFC FLAFCFEYAGVQHHGLSYNCSLPLAFDGSCSGIQHFSAMLRDEVGGRAVNL LPSETVQDIYGIVAKKVNEILQADAINGTDNEVVTVTDENTGEISEKVKLG TKALAGQWLAYGVTRSVTKRSVMTLAYGSKEFGFRQQVLEDTIQPAIDSGK GLMFTQPNQAAGYMAKLIWESVSVTVVAAVEAMNWLKSAAKLLAAEVKDKK TGEILRKRCAVHWVTPDGFPVWQEYKKPIQTRLNLMFLGQFRLQPTININK DSEIDAHKQESGIAPNFVHSQDGSHLRKTVVWAHEKYGIESFALIHDSFGT IPADAANLFKAVRETMVDTYESCDVLADFYDQFADQLHESQLDKMPALPAK GNLNLRDILESDFAFA | 24 |
| G47A E350N | MNTINIAKNDESDIELAAIPENTLADHYGERLAREQLALEHESYEMAEARF RKMFERQLKAGEVADNAAAKPLITTLLPKMIARINDWFEEVKAKRGKRPTA FQFLQEIKPEAVAYITIKTTLACLTSADNTTVQAVASAIGRAIEDEARFGR IRDLEAKHFKKNVEEQLNKRVGHVYKKAFMQVVEADMLSKGLLGGEAWSSW HKEDSIHVGVRCIEMLIESTGMVSLHRQNAGVVGQDSETIELAPEYAEAIA TRAGALAGISPMFQPCVVPPKPWTGITGGGYWANGRRPLALVRTHSKKALM RYEDVYMPEVYKAINIAQNTAWKINKKVLAVANVITKWKHCPVNDIPAIER EELPMKPEDIDMNPEALTAWKRAAAAVYRKDKARKSRRISLEFMLEQANKE ANHKAIWFPYNMDWRGRVYAVSMFNPQGNDMTKGLLTLAKGKPIGKEGYYW LKIHGANCAGVDKVPFPERIKFIEENHENIMACAKSPLENTWWAEQDSPFC FLAFCFEYAGVQHHGLSYNCSLPLAFDGSCSGIQHFSAMLRDEVGGRAVNL LPSETVQDIYGIVAKKVNEILQADAINGTDNEVVTVTDENTGEISEKVKLG TKALAGQWLAYGVTRSVTKRSVMTLAYGSKEFGFRQQVLEDTIQPAIDSGK GLMFTQPNQAAGYMAKLIWESVSVTVVAAVEAMNWLKSAAKLLAAEVKDKK TGEILRKRCAVHWVTPDGFPVWQEYKKPIQTRLNLMFLGQFRLQPTININK DSEIDAHKQESGIAPNFVHSQDGSHLRKTVVWAHEKYGIESFALIHDSFGT IPADAANLFKAVRETMVDTYESCDVLADFYDQFADQLHESQLDKMPALPAK GNLNLRDILESDFAFA | 25 |
| G47A E350A | MNTINIAKNDFSDIELAAIPENTLADHYGERLAREQLALEHESYEMAEARF RKMFERQLKAGEVADNAAAKPLITTLLPKMIARINDWFEEVKAKRGKRPTA FQFLQEIKPEAVAYITIKTTLACLTSADNTTVQAVASAIGRAIEDEARFGR IRDLEAKHFKKNVEEQLNKRVGHVYKKAFMQVVEADMLSKGLLGGEAWSSW HKEDSIHVGVRCIEMLIESTGMVSLHRQNAGVVGQDSETIELAPEYAEAIA TRAGALAGISPMFQPCVVPPKPWTGITGGGYWANGRRPLALVRTHSKKALM RYEDVYMPEVYKAINIAQNTAWKINKKVLAVANVITKWKHCPVADIPAIER EELPMKPEDIDMNPEALTAWKRAAAAVYRKDKARKSRRISLEFMLEQANKE ANHKAIWFPYNMDWRGRVYAVSMFNPQGNDMTKGLLTLAKGKPIGKEGYYW LKIHGANCAGVDKVPFPERIKFIEENHENIMACAKSPLENTWWAEQDSPFC FLAFCFEYAGVQHHGLSYNCSLPLAFDGSCSGIQHFSAMLRDEVGGRAVNL LPSETVQDIYGIVAKKVNEILQADAINGTDNEVVTVTDENTGEISEKVKLG TKALAGQWLAYGVTRSVTKRSVMTLAYGSKEFGFRQQVLEDTIQPAIDSGK GLMFTQPNQAAGYMAKLIWESVSVTVVAAVEAMNWLKSAAKLLAAEVKDKK TGEILRKRCAVHWVTPDGFPVWQEYKKPIQTRLNLMFLGQFRLQPTININK | 26 |

TABLE 1-continued

RNA Polymerase Variants

| RNA Polymerase Variants | Amino Acid Sequence | SEQ ID NO |
|---|---|---|
| | DSEIDAHKQESGIAPNFVHSQDGSHLRKTVVWAHEKYGIESFALIHDSFGT IPADAANLFKAVRETMVDTYESCDVLADFYDQFADQLHESQLDKMPALPAK GNLNLRDILESDFAFA | |
| G47A E350W | MNTINIAKNDFSDIELAAIPENTLADHYGERLAREQLALEHESYEMAEARF RKMFERQLKAGEVADNAAAKPLITTLLPKMIARINDWFEEVKAKRGKRPTA FQFLQEIKPEAVAYITIKTTLACLTSADNTTVQAVASAIGRAIEDEARFGR IRDLEAKHFKKNVEEQLNKRVGHVYKKAFMQVVEADMLSKGLLGGEAWSSW HKEDSIHVGVRCIEMLIESTGMVSLHRQNAGVVGQDSETIELAPEYAEAIA TRAGALAGISPMFQPCVVPPKPWTGITGGGYWANGRRPLALVRTHSKKALM RYEDVYMPEVYKAINIAQNTAWKINKKVLAVANVITKWKHCPVWDIPAIER EELPMKPEDIDMNPEALTAWKRAAAAVYRKDKARKSRRISLEFMLEQANKE ANHKAIWFPYNMDWRGRVYAVSMFNPQGNDMTKGLLTLAKGKPIGKEGYYW LKIHGANCAGVDKVPFPERIKFIEENHENIMACAKSPLENTWWAEQDSPFC FLAFCFEYAGVQHHGLSYNCSLPLAFDGSCSGIQHFSAMLRDEVGGRAVNL LPSETVQDIYGIVAKKVNEILQADAINGTDNEVVTVTDENTGEISEKVKLG TKALAGQWLAYGVTRSVTKRSVMTLAYGSKEFGFRQQVLEDTIQPAIDSGK GLMFTQPNQAAGYMAKLIWESVSVTVVAAVEAMNWLKSAAKLLAAEVKDKK TGEILRKRCAVHWVTPDGFPVWQEYKKPIQTRLNLMFLGQFRLQPTININK DSEIDAHKQESGIAPNFVHSQDGSHLRKTVVWAHEKYGIESFALIHDSFGT IPADAANLFKAVRETMVDTYESCDVLADFYDQFADQLHESQLDKMPALPAK GNLNLRDILESDFAFA | 27 |
| G47A D351V | MNTINIAKNDFSDIELAAIPENTLADHYGERLAREQLALEHESYEMAEARF RKMFERQLKAGEVADNAAAKPLITTLLPKMIARINDWFEEVKAKRGKRPTA FQFLQEIKPEAVAYITIKTTLACLTSADNTTVQAVASAIGRAIEDEARFGR IRDLEAKHFKKNVEEQLNKRVGHVYKKAFMQVVEADMLSKGLLGGEAWSSW HKEDSIHVGVRCIEMLIESTGMVSLHRQNAGVVGQDSETIELAPEYAEAIA TRAGALAGISPMFQPCVVPPKPWTGITGGGYWANGRRPLALVRTHSKKALM RYEDVYMPEVYKAINIAQNTAWKINKKVLAVANVITKWKHCPVEVIPAIER EELPMKPEDIDMNPEALTAWKRAAAAVYRKDKARKSRRISLEFMLEQANKE ANHKAIWFPYNMDWRGRVYAVSMFNPQGNDMTKGLLTLAKGKPIGKEGYYW LKIHGANCAGVDKVPFPERIKFIEENHENIMACAKSPLENTWWAEQDSPFC FLAFCFEYAGVQHHGLSYNCSLPLAFDGSCSGIQHFSAMLRDEVGGRAVNL LPSETVQDIYGIVAKKVNEILQADAINGTDNEVVTVTDENTGEISEKVKLG TKALAGQWLAYGVTRSVTKRSVMTLAYGSKEFGFRQQVLEDTIQPAIDSGK GLMFTQPNQAAGYMAKLIWESVSVTVVAAVEAMNWLKSAAKLLAAEVKDKK TGEILRKRCAVHWVTPDGFPVWQEYKKPIQTRLNLMFLGQFRLQPTININK DSEIDAHKQESGIAPNFVHSQDGSHLRKTVVWAHEKYGIESFALIHDSFGT IPADAANLFKAVRETMVDTYESCDVLADFYDQFADQLHESQLDKMPALPAK GNLNLRDILESDFAFA | 28 |
| G47A K387S | MNTINIAKNDFSDIELAAIPFNTLADHYGERLAREQLALEHESYEMAEARF RKMFERQLKAGEVADNAAAKPLITTLLPKMIARINDWFEEVKAKRGKRPTA FQFLQEIKPEAVAYITIKTTLACLTSADNTTVQAVASAIGRAIEDEARFGR IRDLEAKHFKKNVEEQLNKRVGHVYKKAFMQVVEADMLSKGLLGGEAWSSW HKEDSIHVGVRCIEMLIESTGMVSLHRQNAGVVGQDSETIELAPEYAEAIA TRAGALAGISPMFQPCVVPPKPWTGITGGGYWANGRRPLALVRTHSKKALM RYEDVYMPEVYKAINIAQNTAWKINKKVLAVANVITKWKHCPVEDIPAIER EELPMKPEDIDMNPEALTAWKRAAAAVYRSDKARKSRRISLEFMLEQANKE ANHKAIWFPYNMDWRGRVYAVSMFNPQGNDMTKGLLTLAKGKPIGKEGYYW LKIHGANCAGVDKVPFPERIKFIEENHENIMACAKSPLENTWWAEQDSPFC FLAFCFEYAGVQHHGLSYNCSLPLAFDGSCSGIQHFSAMLRDEVGGRAVNL LPSETVQDIYGIVAKKVNEILQADAINGTDNEVVTVTDENTGEISEKVKLG TKALAGQWLAYGVTRSVTKRSVMTLAYGSKEFGFRQQVLEDTIQPAIDSGK GLMFTQPNQAAGYMAKLIWESVSVTVVAAVEAMNWLKSAAKLLAAEVKDKK TGEILRKRCAVHWVTPDGFPVWQEYKKPIQTRLNLMFLGQFRLQPTININK DSEIDAHKQESGIAPNFVHSQDGSHLRKTVVWAHEKYGIESFALIHDSFGT IPADAANLFKAVRETMVDTYESCDVLADFYDQFADQLHESQLDKMPALPAK GNLNLRDILESDFAFA | 29 |
| G47A K387H | MNTINIAKNDFSDIELAAIPENTLADHYGERLAREQLALEHESYEMAEARF RKMFERQLKAGEVADNAAAKPLITTLLPKMIARINDWFEEVKAKRGKRPTA FQFLQEIKPEAVAYITIKTTLACLTSADNTTVQAVASAIGRAIEDEARFGR IRDLEAKHFKKNVEEQLNKRVGHVYKKAFMQVVEADMLSKGLLGGEAWSSW HKEDSIHVGVRCIEMLIESTGMVSLHRQNAGVVGQDSETIELAPEYAEAIA TRAGALAGISPMFQPCVVPPKPWTGITGGGYWANGRRPLALVRTHSKKALM RYEDVYMPEVYKAINIAQNTAWKINKKVLAVANVITKWKHCPVEDIPAIER EELPMKPEDIDMNPEALTAWKRAAAAVYRHDKARKSRRISLEFMLEQANKF ANHKAIWFPYNMDWRGRVYAVSMFNPQGNDMTKGLLTLAKGKPIGKEGYYW LKIHGANCAGVDKVPFPERIKFIEENHENIMACAKSPLENTWWAEQDSPFC FLAFCFEYAGVQHHGLSYNCSLPLAFDGSCSGIQHFSAMLRDEVGGRAVNL LPSETVQDIYGIVAKKVNEILQADAINGTDNEVVTVTDENTGEISEKVKLG TKALAGQWLAYGVTRSVTKRSVMTLAYGSKEFGFRQQVLEDTIQPAIDSGK GLMFTQPNQAAGYMAKLIWESVSVTVVAAVEAMNWLKSAAKLLAAEVKDKK | 30 |

TABLE 1-continued

RNA Polymerase Variants

| RNA Polymerase Variants | Amino Acid Sequence | SEQ ID NO |
|---|---|---|
| | TGEILRKRCAVHWVTPDGFPVWQEYKKPIQTRLNLMFLGQFRLQPTININK DSEIDAHKQESGIAPNFVHSQDGSHLRKTVVWAHEKYGIESFALIHDSFGT IPADAANLFKAVRETMVDTYESCDVLADFYDQFADQLHESQLDKMPALPAK GNLNLRDILESDFAFA | |
| G47A K387N | MNTINIAKNDFSDIELAAIPFNTLADHYGERLAREQLALEHESYEMAEARF RKMFERQLKAGEVADNAAAKPLITTLLPKMIARINDWFEEVKAKRGKRPTA FQFLQEIKPEAVAYITIKTTLACLTSADNTTVQAVASAIGRAIEDEARFGR IRDLEAKHFKKNVEEQLNKRVGHVYKKAFMQVVEADMLSKGLLGGEAWSSW HKEDSIHVGVRCIEMLIESTGMVSLHRQNAGVVGQDSETIELAPEYAEAIA TRAGALAGISPMFQPCVVPPKPWTGITGGGYWANGRRPLALVRTHSKKALM RYEDVYMPEVYKAINIAQNTAWKINKKVLAVANVITKWKHCPVEDIPAIER EELPMKPEDIDMNPEALTAWKRAAAAVYRNDKARKSRRISLEFMLEQANKE ANHKAIWFPYNMDWRGRVYAVSMFNPQGNDMTKGLLTLAKGKPIGKEGYYW LKIHGANCAGVDKVPFPERIKFIEENHENIMACAKSPLENTWWAEQDSPFC FLAFCFEYAGVQHHGLSYNCSLPLAFDGSCSGIQHFSAMLRDEVGGRAVNL LPSETVQDIYGIVAKKVNEILQADAINGTDNEVVTVTDENTGEISEKVKLG TKALAGQWLAYGVTRSVTKRSVMTLAYGSKEFGFRQQVLEDTIQPAIDSGK GLMFTQPNQAAGYMAKLIWESVSVTVVAAVEAMNWLKSAAKLLAAEVKDKK TGEILRKRCAVHWVTPDGFPVWQEYKKPIQTRLNLMFLGQFRLQPTININK DSEIDAHKQESGIAPNFVHSQDGSHLRKTVVWAHEKYGIESFALIHDSFGT IPADAANLFKAVRETMVDTYESCDVLADFYDQFADQLHESQLDKMPALPAK GNLNLRDILESDFAFA | 31 |
| G47A E350K C-Terminal G | MNTINIAKNDFSDIELAAIPFNTLADHYGERLAREQLALEHESYEMAEARF RKMFERQLKAGEVADNAAAKPLITTLLPKMIARINDWFEEVKAKRGKRPTA FQFLQEIKPEAVAYITIKTTLACLTSADNTTVQAVASAIGRAIEDEARFGR IRDLEAKHFKKNVEEQLNKRVGHVYKKAFMQVVEADMLSKGLLGGEAWSSW HKEDSIHVGVRCIEMLIESTGMVSLHRQNAGVVGQDSETIELAPEYAEAIA TRAGALAGISPMFQPCVVPPKPWTGITGGGYWANGRRPLALVRTHSKKALM RYEDVYMPEVYKAINIAQNTAWKINKKVLAVANVITKWKHCPVKDIPAIER EELPMKPEDIDMNPEALTAWKRAAAAVYRKDKARKSRRISLEFMLEQANKE ANHKAIWFPYNMDWRGRVYAVSMFNPQGNDMTKGLLTLAKGKPIGKEGYYW LKIHGANCAGVDKVPFPERIKFIEENHENIMACAKSPLENTWWAEQDSPFC FLAFCFEYAGVQHHGLSYNCSLPLAFDGSCSGIQHFSAMLRDEVGGRAVNL LPSETVQDIYGIVAKKVNEILQADAINGTDNEVVTVTDENTGEISEKVKLG TKALAGQWLAYGVTRSVTKRSVMTLAYGSKEFGFRQQVLEDTIQPAIDSGK GLMFTQPNQAAGYMAKLIWESVSVTVVAAVEAMNWLKSAAKLLAAEVKDKK TGEILRKRCAVHWVTPDGFPVWQEYKKPIQTRLNLMFLGQFRLQPTININK DSEIDAHKQESGIAPNFVHSQDGSHLRKTVVWAHEKYGIESFALIHDSFGT IPADAANLFKAVRETMVDTYESCDVLADFYDQFADQLHESQLDKMPALPAK GNLNLRDILESDFAFAG | 32 |
| G47A E350N C-Terminal G | MNTINIAKNDFSDIELAAIPENTLADHYGERLAREQLALEHESYEMAEARF RKMFERQLKAGEVADNAAAKPLITTLLPKMIARINDWFEEVKAKRGKRPTA FQFLQEIKPEAVAYITIKTTLACLTSADNTTVQAVASAIGRAIEDEARFGR IRDLEAKHFKKNVEEQLNKRVGHVYKKAFMQVVEADMLSKGLLGGEAWSSW HKEDSIHVGVRCIEMLIESTGMVSLHRQNAGVVGQDSETIELAPEYAEAIA TRAGALAGISPMFQPCVVPPKPWTGITGGGYWANGRRPLALVRTHSKKALM RYEDVYMPEVYKAINIAQNTAWKINKKVLAVANVITKWKHCPVNDIPAIER EELPMKPEDIDMNPEALTAWKRAAAAVYRKDKARKSRRISLEFMLEQANKF ANHKAIWFPYNMDWRGRVYAVSMFNPQGNDMTKGLLTLAKGKPIGKEGYYW LKIHGANCAGVDKVPFPERIKFIEENHENIMACAKSPLENTWWAEQDSPFC FLAFCFEYAGVQHHGLSYNCSLPLAFDGSCSGIQHFSAMLRDEVGGRAVNL LPSETVQDIYGIVAKKVNEILQADAINGTDNEVVTVTDENTGEISEKVKLG TKALAGQWLAYGVTRSVTKRSVMTLAYGSKEFGFRQQVLEDTIQPAIDSGK GLMFTQPNQAAGYMAKLIWESVSVTVVAAVEAMNWLKSAAKLLAAEVKDKK TGEILRKRCAVHWVTPDGFPVWQEYKKPIQTRLNLMFLGQFRLQPTININK DSEIDAHKQESGIAPNFVHSQDGSHLRKTVVWAHEKYGIESFALIHDSFGT IPADAANLFKAVRETMVDTYESCDVLADFYDQFADQLHESQLDKMPALPAK GNLNLRDILESDFAFAG | 33 |
| G47A E350A C-Terminal G | MNTINIAKNDFSDIELAAIPENTLADHYGERLAREQLALEHESYEMAEARF RKMFERQLKAGEVADNAAAKPLITTLLPKMIARINDWFEEVKAKRGKRPTA FQFLQEIKPEAVAYITIKTTLACLTSADNTTVQAVASAIGRAIEDEARFGR IRDLEAKHFKKNVEEQLNKRVGHVYKKAFMQVVEADMLSKGLLGGEAWSSW HKEDSIHVGVRCIEMLIESTGMVSLHRQNAGVVGQDSETIELAPEYAEAIA TRAGALAGISPMFQPCVVPPKPWTGITGGGYWANGRRPLALVRTHSKKALM RYEDVYMPEVYKAINIAQNTAWKINKKVLAVANVITKWKHCPVADIPAIER EELPMKPEDIDMNPEALTAWKRAAAAVYRKDKARKSRRISLEFMLEQANKE ANHKAIWFPYNMDWRGRVYAVSMFNPQGNDMTKGLLTLAKGKPIGKEGYYW LKIHGANCAGVDKVPFPERIKFIEENHENIMACAKSPLENTWWAEQDSPFC FLAFCFEYAGVQHHGLSYNCSLPLAFDGSCSGIQHFSAMLRDEVGGRAVNL LPSETVQDIYGIVAKKVNEILQADAINGTDNEVVTVTDENTGEISEKVKLG TKALAGQWLAYGVTRSVTKRSVMTLAYGSKEFGFRQQVLEDTIQPAIDSGK GLMFTQPNQAAGYMAKLIWESVSVTVVAAVEAMNWLKSAAKLLAAEVKDKK TGEILRKRCAVHWVTPDGFPVWQEYKKPIQTRLNLMFLGQFRLQPTININK DSEIDAHKQESGIAPNFVHSQDGSHLRKTVVWAHEKYGIESFALIHDSFGT | 34 |

TABLE 1-continued

RNA Polymerase Variants

| RNA Polymerase Variants | Amino Acid Sequence | SEQ ID NO |
|---|---|---|
| | IPADAANLFKAVRETMVDTYESCDVLADFYDQFADQLHESQLDKMPALPAK GNLNLRDILESDFAFAG | |
| G47A E350W C-Terminal G | MNTINIAKNDFSDIELAAIPENTLADHYGERLAREQLALEHESYEMAEARF RKMFERQLKAGEVADNAAAKPLITTLLPKMIARINDWFEEVKAKRGKRPTA FQFLQEIKPEAVAYITIKTTLACLTSADNTTVQAVASAIGRAIEDEARFGR IRDLEAKHFKKNVEEQLNKRVGHVYKKAFMQVVEADMLSKGLLGGEAWSSW HKEDSIHVGVRCIEMLIESTGMVSLHRQNAGVVGQDSETIELAPEYAEAIA TRAGALAGISPMFQPCVVPPKPWTGITGGGYWANGRRPLALVRTHSKKALM RYEDVYMPEVYKAINIAQNTAWKINKKVLAVANVITKWKHCPVWDIPAIER EELPMKPEDIDMNPEALTAWKRAAAAVYRKDKARKSRRISLEFMLEQANKE ANHKAIWFPYNMDWRGRVYAVSMFNPQGNDMTKGLLTLAKGKPIGKEGYYW LKIHGANCAGVDKVPFPERIKFIEENHENIMACAKSPLENTWWAEQDSPFC FLAFCFEYAGVQHHGLSYNCSLPLAFDGSCSGIQHFSAMLRDEVGGRAVNL LPSETVQDIYGIVAKKVNEILQADAINGTDNEVVTVTDENTGEISEKVKLG TKALAGQWLAYGVTRSVTKRSVMTLAYGSKEFGFRQQVLEDTIQPAIDSGK GLMFTQPNQAAGYMAKLIWESVSVTVVAAVEAMNWLKSAAKLLAAEVKDKK TGEILRKRCAVHWVTPDGFPVWQEYKKPIQTRLNLMFLGQFRLQPTINTNK DSEIDAHKQESGIAPNFVHSQDGSHLRKTVVWAHEKYGIESFALIHDSFGT IPADAANLFKAVRETMVDTYESCDVLADFYDQFADQLHESQLDKMPALPAK GNLNLRDILESDFAFAG | 35 |
| G47A D351V C-Terminal G | MNTINIAKNDFSDIELAAIPENTLADHYGERLAREQLALEHESYEMAEARF RKMFERQLKAGEVADNAAAKPLITTLLPKMIARINDWFEEVKAKRGKRPTA FQFLQEIKPEAVAYITIKTTLACLTSADNTTVQAVASAIGRAIEDEARFGR IRDLEAKHFKKNVEEQLNKRVGHVYKKAFMQVVEADMLSKGLLGGEAWSSW HKEDSIHVGVRCIEMLIESTGMVSLHRQNAGVVGQDSETIELAPEYAEAIA TRAGALAGISPMFQPCVVPPKPWTGITGGGYWANGRRPLALVRTHSKKALM RYEDVYMPEVYKAINIAQNTAWKINKKVLAVANVITKWKHCPVEVIPAIER EELPMKPEDIDMNPEALTAWKRAAAAVYRKDKARKSRRISLEFMLEQANKE ANHKAIWFPYNMDWRGRVYAVSMFNPQGNDMTKGLLTLAKGKPIGKEGYYW LKIHGANCAGVDKVPFPERIKFIEENHENIMACAKSPLENTWWAEQDSPFC FLAFCFEYAGVQHHGLSYNCSLPLAFDGSCSGIQHFSAMLRDEVGGRAVNL LPSETVQDIYGIVAKKVNEILQADAINGTDNEVVTVTDENTGEISEKVKLG TKALAGQWLAYGVTRSVTKRSVMTLAYGSKEFGFRQQVLEDTIQPAIDSGK GLMFTQPNQAAGYMAKLIWESVSVTVVAAVEAMNWLKSAAKLLAAEVKDKK TGEILRKRCAVHWVTPDGFPVWQEYKKPIQTRLNLMFLGQFRLQPTININK DSEIDAHKQESGIAPNFVHSQDGSHLRKTVVWAHEKYGIESFALIHDSFGT IPADAANLFKAVRETMVDTYESCDVLADFYDQFADQLHESQLDKMPALPAK GNLNLRDILESDFAFAG | 36 |
| G47A K387S C-Terminal G | MNTINIAKNDFSDIELAAIPENTLADHYGERLAREQLALEHESYEMAEARF RKMFERQLKAGEVADNAAAKPLITTLLPKMIARINDWFEEVKAKRGKRPTA FQFLQEIKPEAVAYITIKTTLACLTSADNTTVQAVASAIGRAIEDEARFGR IRDLEAKHFKKNVEEQLNKRVGHVYKKAFMQVVEADMLSKGLLGGEAWSSW HKEDSIHVGVRCIEMLIESTGMVSLHRQNAGVVGQDSETIELAPEYAEAIA TRAGALAGISPMFQPCVVPPKPWTGITGGGYWANGRRPLALVRTHSKKALM RYEDVYMPEVYKAINIAQNTAWKINKKVLAVANVITKWKHCPVEDIPAIER EELPMKPEDIDMNPEALTAWKRAAAAVYRSDKARKSRRISLEFMLEQANKE ANHKAIWFPYNMDWRGRVYAVSMFNPQGNDMTKGLLTLAKGKPIGKEGYYW LKIHGANCAGVDKVPFPERIKFIEENHENIMACAKSPLENTWWAEQDSPFC FLAFCFEYAGVQHHGLSYNCSLPLAFDGSCSGIQHFSAMLRDEVGGRAVNL LPSETVQDIYGIVAKKVNEILQADAINGTDNEVVTVTDENTGEISEKVKLG TKALAGQWLAYGVTRSVTKRSVMTLAYGSKEFGFRQQVLEDTIQPAIDSGK GLMFTQPNQAAGYMAKLIWESVSVTVVAAVEAMNWLKSAAKLLAAEVKDKK TGEILRKRCAVHWVTPDGFPVWQEYKKPIQTRLNLMFLGQFRLQPTINTNK DSEIDAHKQESGIAPNFVHSQDGSHLRKTVVWAHEKYGIESFALIHDSFGT IPADAANLFKAVRETMVDTYESCDVLADFYDQFADQLHESQLDKMPALPAK GNLNLRDILESDFAFAG | 37 |
| G47A K387H C-Terminal G | MNTINIAKNDFSDIELAAIPENTLADHYGERLAREQLALEHESYEMAEARF RKMFERQLKAGEVADNAAAKPLITTLLPKMIARINDWFEEVKAKRGKRPTA FQFLQEIKPEAVAYITIKTTLACLTSADNTTVQAVASAIGRAIEDEARFGR IRDLEAKHFKKNVEEQLNKRVGHVYKKAFMQVVEADMLSKGLLGGEAWSSW HKEDSIHVGVRCIEMLIESTGMVSLHRQNAGVVGQDSETIELAPEYAEAIA TRAGALAGISPMFQPCVVPPKPWTGITGGGYWANGRRPLALVRTHSKKALM RYEDVYMPEVYKAINIAQNTAWKINKKVLAVANVITKWKHCPVEDIPAIER EELPMKPEDIDMNPEALTAWKRAAAAVYRHDKARKSRRISLEFMLEQANKE ANHKAIWFPYNMDWRGRVYAVSMFNPQGNDMTKGLLTLAKGKPIGKEGYYW LKIHGANCAGVDKVPFPERIKFIEENHENIMACAKSPLENTWWAEQDSPFC FLAFCFEYAGVQHHGLSYNCSLPLAFDGSCSGIQHFSAMLRDEVGGRAVNL LPSETVQDIYGIVAKKVNEILQADAINGTDNEVVTVTDENTGEISEKVKLG TKALAGQWLAYGVTRSVTKRSVMTLAYGSKEFGFRQQVLEDTIQPAIDSGK GLMFTQPNQAAGYMAKLIWESVSVTVVAAVEAMNWLKSAAKLLAAEVKDKK TGEILRKRCAVHWVTPDGFPVWQEYKKPIQTRLNLMFLGQFRLQPTININK DSEIDAHKQESGIAPNFVHSQDGSHLRKTVVWAHEKYGIESFALIHDSFGT IPADAANLFKAVRETMVDTYESCDVLADFYDQFADQLHESQLDKMPALPAK GNLNLRDILESDFAFAG | 38 |

TABLE 1-continued

RNA Polymerase Variants

| RNA Polymerase Variants | Amino Acid Sequence | SEQ ID NO |
|---|---|---|
| G47A K387N C-Terminal G | MNTINIAKNDFSDIELAAIPENTLADHYGERLAREQLALEHESYEMAEARF RKMFERQLKAGEVADNAAAKPLITTLLPKMIARINDWFEEVKAKRGKRPTA FQFLQEIKPEAVAYITIKTTLACLTSADNTTVQAVASAIGRAIEDEARFGR IRDLEAKHFKKNVEEQLNKRVGHVYKKAFMQVVEADMLSKGLLGGEAWSSW HKEDSIHVGVRCIEMLIESTGMVSLHRQNAGVVGQDSETIELAPEYAEAIA TRAGALAGISPMFQPCVVPPKPWTGITGGGYWANGRRPLALVRTHSKKALM RYEDVYMPEVYKAINIAQNTAWKINKKVLAVANVITKWKHCPVEDIPAIER EELPMKPEDIDMNPEALTAWKRAAAAVYRNDKARKSRRISLEFMLEQANKE ANHKAIWFPYNMDWRGRVYAVSMFNPQGNDMTKGLLTLAKGKPIGKEGYYW LKIHGANCAGVDKVPFPERIKFIEENHENIMACAKSPLENTWWAEQDSPFC FLAFCFEYAGVQHHGLSYNCSLPLAFDGSCSGIQHFSAMLRDEVGGRAVNL LPSETVQDIYGIVAKKVNEILQADAINGTDNEVVTVTDENTGEISEKVKLG TKALAGQWLAYGVTRSVTKRSVMTLAYGSKEFGFRQQVLEDTIQPAIDSGK GLMFTQPNQAAGYMAKLIWESVSVTVVAAVEAMNWLKSAAKLLAAEVKDKK TGEILRKRCAVHWVTPDGFPVWQEYKKPIQTRLNLMFLGQFRLQPTININK DSEIDAHKQESGIAPNFVHSQDGSHLRKTVVWAHEKYGIESFALIHDSFGT IPADAANLFKAVRETMVDTYESCDVLADFYDQFADQLHESQLDKMPALPAK GNLNLRDILESDFAFAG | 39 |
| G47A E350X1, wherein X1 is A, K, N, or W D351V K387X2, wherein X2 is S, H, or N C-Terminal G | MNTINIAKNDFSDIELAAIPFNTLADHYGERLAREQLALEHESYEMAEARF RKMFERQLKAGEVADNAAAKPLITTLLPKMIARINDWFEEVKAKRGKRPTA FQFLQEIKPEAVAYITIKTTLACLTSADNTTVQAVASAIGRAIEDEARFGR IRDLEAKHFKKNVEEQLNKRVGHVYKKAFMQVVEADMLSKGLLGGEAWSSW HKEDSIHVGVRCIEMLIESTGMVSLHRQNAGVVGQDSETIELAPEYAEAIA TRAGALAGISPMFQPCVVPPKPWTGITGGGYWANGRRPLALVRTHSKKALM RYEDVYMPEVYKAINIAQNTAWKINKKVLAVANVITKWKHCPVX1VIPAIE REELPMKPEDIDMNPEALTAWKRAAAAVYRX2DKARKSRRISLEFMLEQAN KFANHKAIWFPYNMDWRGRVYAVSMFNPQGNDMTKGLLTLAKGKPIGKEGY YWLKIHGANCAGVDKVPFPERIKFIEENHENIMACAKSPLENTWWAEQDSP FCFLAFCFEYAGVQHHGLSYNCSLPLAFDGSCSGIQHFSAMLRDEVGGRAV NLLPSETVQDIYGIVAKKVNEILQADAINGTDNEVVTVTDENTGEISEKVK LGTKALAGQWLAYGVTRSVTKRSVMTLAYGSKEFGFRQQVLEDTIQPAIDS GKGLMFTQPNQAAGYMAKLIWESVSVTVVAAVEAMNWLKSAAKLLAAEVKD KKTGEILRKRCAVHWVTPDGFPVWQEYKKPIQTRLNLMFLGQFRLQPTINT NKDSEIDAHKQESGIAPNFVHSQDGSHLRKTVVWAHEKYGIESFALIHDSF GTIPADAANLFKAVRETMVDTYESCDVLADFYDQFADQLHESQLDKMPALP AKGNLNLRDILESDFAFAG | 40 |
| G47A N437X1, wherein X1 is T, Y, I, or F K441R C-Terminal G | MNTINIAKNDESDIELAAIPENTLADHYGERLAREQLALEHESYEMAEARF RKMFERQLKAGEVADNAAAKPLITTLLPKMIARINDWFEEVKAKRGKRPTA FQFLQEIKPEAVAYITIKTTLACLTSADNTTVQAVASAIGRAIEDEARFGR IRDLEAKHFKKNVEEQLNKRVGHVYKKAFMQVVEADMLSKGLLGGEAWSSW HKEDSIHVGVRCIEMLIESTGMVSLHRQNAGVVGQDSETIELAPEYAEAIA TRAGALAGISPMFQPCVVPPKPWTGITGGGYWANGRRPLALVRTHSKKALM RYEDVYMPEVYKAINIAQNTAWKINKKVLAVANVITKWKHCPVEDIPAIER EELPMKPEDIDMNPEALTAWKRAAAAVYRKDKARKSRRISLEFMLEQANKF ANHKAIWFPYNMDWRGRVYAVSMFNPQGXDMTRGLLTLAKGKPIGKEGYYW LKIHGANCAGVDKVPFPERIKFIEENHENIMACAKSPLENTWWAEQDSPFC FLAFCFEYAGVQHHGLSYNCSLPLAFDGSCSGIQHFSAMLRDEVGGRAVNL LPSETVQDIYGIVAKKVNEILQADAINGTDNEVVTVTDENTGEISEKVKLG TKALAGQWLAYGVTRSVTKRSVMTLAYGSKEFGFRQQVLEDTIQPAIDSGK GLMFTQPNQAAGYMAKLIWESVSVTVVAAVEAMNWLKSAAKLLAAEVKDKK TGEILRKRCAVHWVTPDGFPVWQEYKKPIQTRLNLMFLGQFRLQPTININK DSEIDAHKQESGIAPNFVHSQDGSHLRKTVVWAHEKYGIESFALIHDSFGT IPADAANLFKAVRETMVDTYESCDVLADFYDQFADQLHESQLDKMPALPAK GNLNLRDILESDFAFAG | 41 |
| G47A F880Y C-Terminal X, wherein X is A, S, T, or P | MNTINIAKNDFSDIELAAIPFNTLADHYGERLAREQLALEHESYEMAEARF RKMFERQLKAGEVADNAAAKPLITTLLPKMIARINDWFEEVKAKRGKRPTA FQFLQEIKPEAVAYITIKTTLACLTSADNTTVQAVASAIGRAIEDEARFGR IRDLEAKHFKKNVEEQLNKRVGHVYKKAFMQVVEADMLSKGLLGGEAWSSW HKEDSIHVGVRCIEMLIESTGMVSLHRQNAGVVGQDSETIELAPEYAEAIA TRAGALAGISPMFQPCVVPPKPWTGITGGGYWANGRRPLALVRTHSKKALM RYEDVYMPEVYKAINIAQNTAWKINKKVLAVANVITKWKHCPVEDIPAIER EELPMKPEDIDMNPEALTAWKRAAAAVYRKDKARKSRRISLEFMLEQANKE ANHKAIWFPYNMDWRGRVYAVSMFNPQGNDMTKGLLTLAKGKPIGKEGYYW LKIHGANCAGVDKVPFPERIKFIEENHENIMACAKSPLENTWWAEQDSPFC FLAFCFEYAGVQHHGLSYNCSLPLAFDGSCSGIQHFSAMLRDEVGGRAVNL LPSETVQDIYGIVAKKVNEILQADAINGTDNEVVTVTDENTGEISEKVKLG TKALAGQWLAYGVTRSVTKRSVMTLAYGSKEFGFRQQVLEDTIQPAIDSGK GLMFTQPNQAAGYMAKLIWESVSVTVVAAVEAMNWLKSAAKLLAAEVKDKK TGEILRKRCAVHWVTPDGFPVWQEYKKPIQTRLNLMFLGQFRLQPTINTNK DSEIDAHKQESGIAPNFVHSQDGSHLRKTVVWAHEKYGIESFALIHDSFGT IPADAANLFKAVRETMVDTYESCDVLADFYDQFADQLHESQLDKMPALPAK GNLNLRDILESDYAFAX | 42 |

TABLE 1-continued

RNA Polymerase Variants

| RNA Polymerase Variants | Amino Acid Sequence | SEQ ID NO |
|---|---|---|
| G47A R632X$_1$, wherein X$_1$ is K or T D653X$_2$, wherein X$_2$ is T or K P657X$_3$, wherein X$_3$ is W, R, or A C-Terminal G | MNTINIAKNDFSDIELAAIPENTLADHYGERLAREQLALEHESYEMAEARF RKMFERQLKAGEVADNAAAKPLITTLLPKMIARINDWFEEVKAKRGKRPTA FQFLQEIKPEAVAYITIKTTLACLTSADNTTVQAVASAIGRAIEDEARFGR IRDLEAKHFKKNVEEQLNKRVGHVYKKAFMQVVEADMLSKGLLGGEAWSSW HKEDSIHVGVRCIEMLIESTGMVSLHRQNAGVVGQDSETIELAPEYAEAIA TRAGALAGISPMFQPCVVPPKPWTGITGGGYWANGRRPLALVRTHSKKALM RYEDVYMPEVYKAINIAQNTAWKINKKVLAVANVITKWKHCPVEDIPAIER EELPMKPEDIDMNPEALTAWKRAAAAVYRKDKARKSRRISLEFMLEQANKE ANHKAIWFPYNMDWRGRVYAVSMFNPQGNDMTKGLLTLAKGKPIGKEGYYW LKIHGANCAGVDKVPFPERIKFIEENHENIMACAKSPLENTWWAEQDSPFC FLAFCFEYAGVQHHGLSYNCSLPLAFDGSCSGIQHFSAMLRDEVGGRAVNL LPSETVQDIYGIVAKKVNEILQADAINGTDNEVVTVTDENTGEISEKVKLG TKALAGQWLAYGVTRSVTKX1SVMTLAYGSKEFGFRQQVLEX2TIQX3AIDS GKGLMFTQPNQAAGYMAKLIWESVSVTVVAAVEAMNWLKSAAKLLAAEVKD KKTGEILRKRCAVHWVTPDGFPVWQEYKKPIQTRLNLMFLGQFRLQPTINT NKDSEIDAHKQESGIAPNFVHSQDGSHLRKTVVWAHEKYGIESFALIHDSF GTIPADAANLFKAVRETMVDTYESCDVLADFYDQFADQLHESQLDKMPALP AKGNLNLRDILESDFAFAG | 43 |
| C-terminal G T7 RNA polymerase | MNTINIAKNDFSDIELAAIPFNTLADHYGERLAREQLALEHESYEMGEARF RKMFERQLKAGEVADNAAAKPLITTLLPKMIARINDWFEEVKAKRGKRPTA FQFLQEIKPEAVAYITIKTTLACLTSADNTTVQAVASAIGRAIEDEARFGR IRDLEAKHFKKNVEEQLNKRVGHVYKKAFMQVVEADMLSKGLLGGEAWSSW HKEDSIHVGVRCIEMLIESTGMVSLHRQNAGVVGQDSETIELAPEYAEAIA TRAGALAGISPMFQPCVVPPKPWTGITGGGYWANGRRPLALVRTHSKKALM RYEDVYMPEVYKAINIAQNTAWKINKKVLAVANVITKWKHCPVEDIPAIER EELPMKPEDIDMNPEALTAWKRAAAAVYRKDKARKSRRISLEFMLEQANKE ANHKAIWFPYNMDWRGRVYAVSMFNPQGNDMTKGLLTLAKGKPIGKEGYYW LKIHGANCAGVDKVPFPERIKFIEENHENIMACAKSPLENTWWAEQDSPFC FLAFCFEYAGVQHHGLSYNCSLPLAFDGSCSGIQHFSAMLRDEVGGRAVNL LPSETVQDIYGIVAKKVNEILQADAINGTDNEVVTVTDENTGEISEKVKLG TKALAGQWLAYGVTRSVTKRSVMTLAYGSKEFGFRQQVLEDTIQPAIDSGK GLMFTQPNQAAGYMAKLIWESVSVTVVAAVEAMNWLKSAAKLLAAEVKDKK TGEILRKRCAVHWVTPDGFPVWQEYKKPIQTRLNLMFLGQFRLQPTININK DSEIDAHKQESGIAPNFVHSQDGSHLRKTVVWAHEKYGIESFALIHDSFGT IPADAANLFKAVRETMVDTYESCDVLADFYDQFADQLHESQLDKMPALPAK GNLNLRDILESDFAFAG | 44 |

EXAMPLES

Example 1. Production of Truncated RNA Products Using a DNA Template Comprising a Non-Canonical Terminator Sequence In vitro transcription (IVT) reactions were performed using a DNA template comprising a non-canonical terminator sequence (ATCTGTT) and (1) Wild-type (WT) T7 RNA polymerase (SEQ ID NO: 1), (2) a G47A T7 RNA polymerase variant (SEQ ID NO: 15), (3) a C-terminal G T7 RNA polymerase variant (SE ID NO: 44), and (4) G47A+ C-terminal G T7 RNA polymerase variant (SEQ ID NO: 45).

Figure 1B:
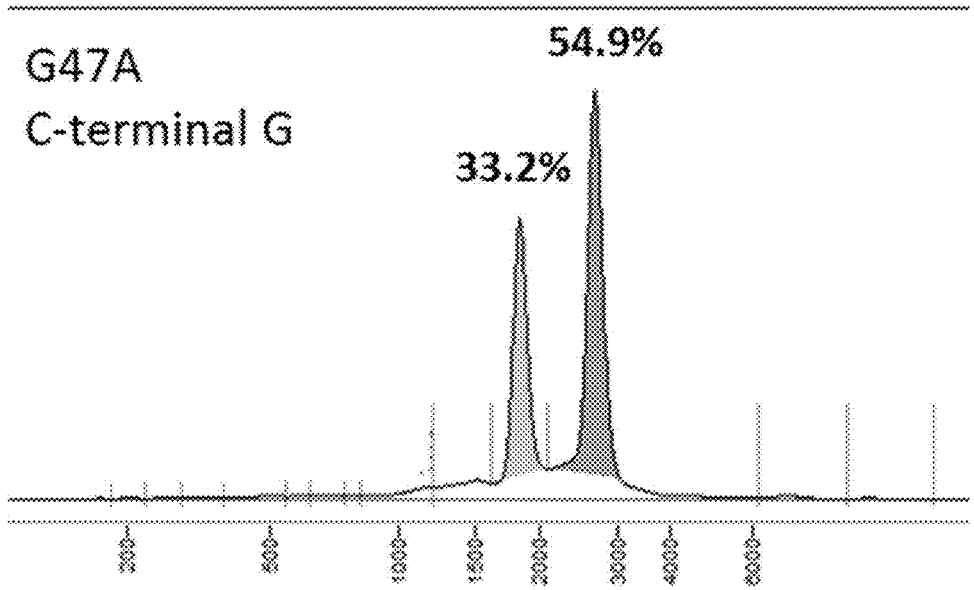
Figure 2:
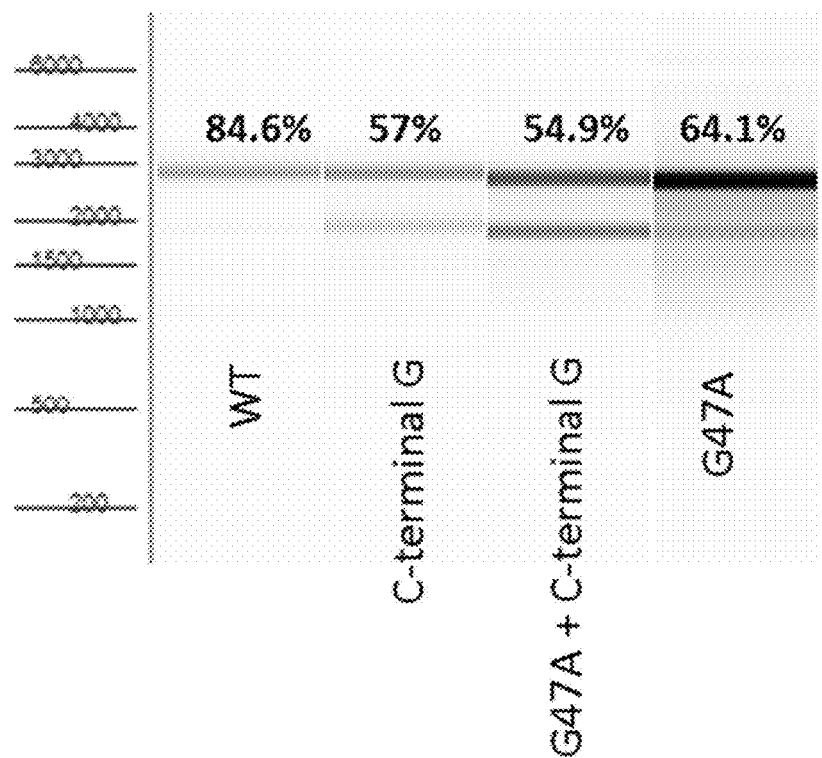
FIG. 2 shows a capillary electropherogram of RNA products following in vitro transcription of a DNA template (Template A) comprising a non-canonical terminator sequence (ATCTGTT) using the WT T7 polymerase or T7 polymerase variants (C-terminal G T7 polymerase variant, G47A+C-terminal G T7 polymerase variant, and G47A T7 polymerase variant). 84.6% of total RNA products generated using WT polymerase were full-length RNA transcripts (~2800 nucleotides); and 57-64.1% of total RNA products generated using T7 polymerase variants were full-length RNA transcripts.

Capillary electrophoresis analysis of these IVT reactions demonstrated that the T7 polymerase variants produced significantly greater amounts of truncated RNA products relative to WT T7 polymerase. As shown in FIG. 1A, 84.6% of total RNA products generated using WT polymerase were full-length RNA transcripts (~2800 nucleotides) and that only 7.2% of total RNA products were truncated transcripts (~2000 nucleotides). In contrast, as shown in FIG. 1B, 54.9% of total RNA products generated using G47A+C-terminal G polymerase were full-length RNA transcripts (~2800 nucleotides) and 33.2% of total RNA products were truncated transcripts (~2000 nucleotides). Further, as shown in FIG. 2, an electropherogram of all IVT reactions demonstrated that while 84.6% of total RNA products generated using WT polymerase were full-length RNA transcripts (~2800 nucleotides), only 57-64.1% of total RNA products generated using T7 polymerase variants were full-length RNA transcripts (~57% for C-terminal G variant; 54.9% for G47A+C-terminal variant; 64.1% for G47A).

Figure 3:
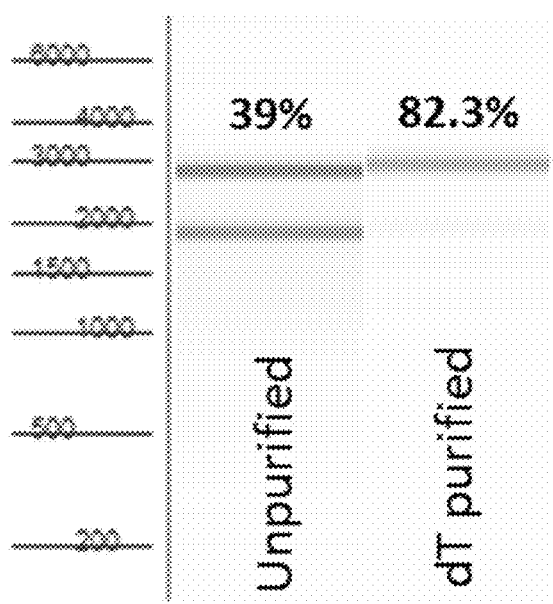
FIG. 3 shows a capillary electropherogram of RNA products following in vitro transcription of a DNA template (Template A) comprising a non-canonical terminator sequence (ATCTGTT) using G47A+C-terminal G T7 polymerase before (unpurified) and after (dT purified) purification of full-length RNA products away from truncated RNA products.

Crude or unpurified IVT reaction mixtures were purified using reverse-phase (RP) HPLC and oligo dT to isolate full-length RNA and truncated RNA products, as shown in FIG. 3.

Collectively, these data show that IVT reactions using WT polymerase and T7 polymerase variants as described herein are capable of transcribing DNA constructs that comprise a non-canonical terminator sequence, ATCTGTT.

Example 2. Rapid Amplification of cDNA Ends (RACE) to Precisely Determine Sequences of Truncated RNA Products As described in Example 1, in vitro transcription (IVT) reactions were performed using two discrete DNA templates (Template A and Template B) comprising a non-canonical terminator sequence (ATCTGTT) and (1) Wild-type (WT) T7 RNA polymerase (SEQ ID NO: 1) and (2) G47A+C-terminal G T7 RNA polymerase variant (SEQ ID NO: 45).

Following an IVT reaction, the transcribed RNA products were subjected to a 3' 'rapid amplification of cDNA ends' (RACE) procedure. Briefly, the 3' RACE procedure involves the synthesis of cDNAs. The cDNA is then treated with RNAse H to remove remaining RNA products before the cDNA is circularized by CircLigase into a circular DNA. The circular DNA is subsequently amplified using PCR before being re-linearized, treated with polynucleotide kinase (PNK), and appended with a RACE adaptor sequence. The resulting linear sequences are then subjected to next-generation sequencing.

Figure 4:
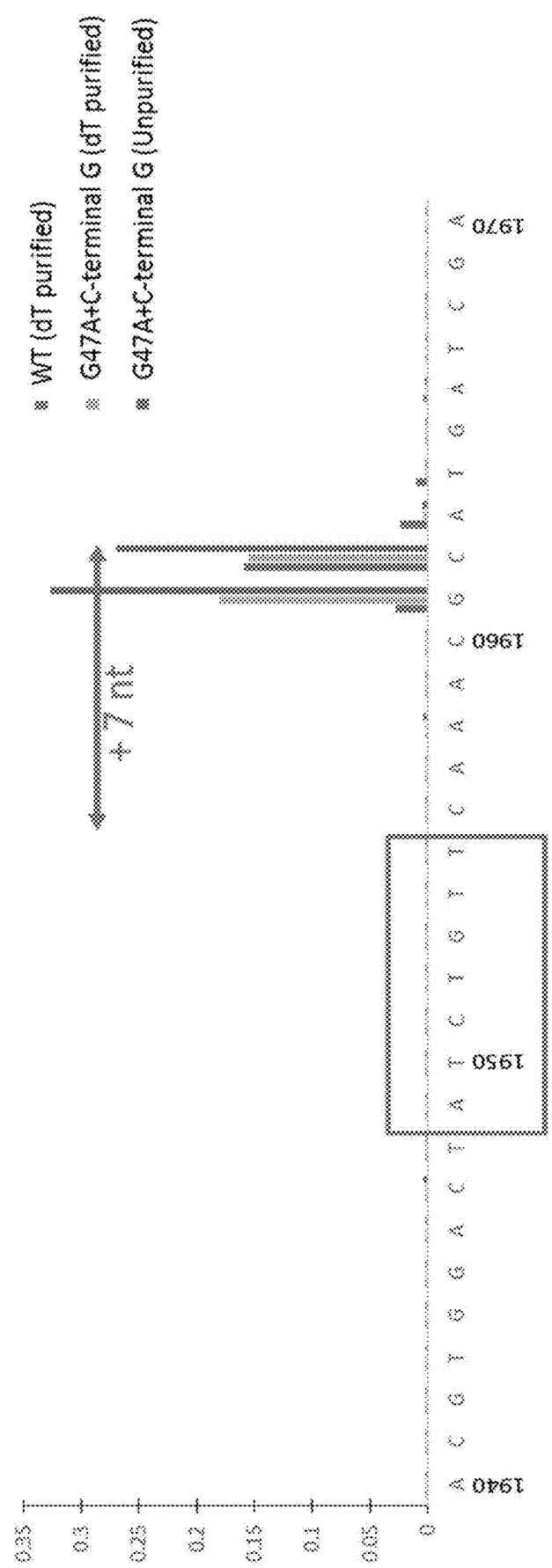
FIG. 4 shows a graph depicting the relative amounts of truncated RNA products following in vitro transcription of a DNA template (Template A) comprising a non-canonical terminator sequence (ATCTGTT) using WT T7 polymerase or G47A+C-terminal G T7 polymerase (SEQ ID NO: 46). Truncated RNA products are amplified using a 'rapid amplification of cDNA ends' (RACE) procedure to enable precise next-generation sequencing. The majority of truncated RNA products were truncated at nucleotide G1961 or C1962, which correspond to the +6 and +7 positions relative to the ATCTGTT sequence motif.

IVT reactions involving Template A and either WT polymerase or the G47A+C-terminal G polymerase variant produced RNA truncations that were primarily truncated at either nucleotide G1961 or C1962 (FIG. 4). These two nucleotide positions correspond to the +6 and +7 positions relative to the ATCTGTT sequence motif that is present in Template A. Note that the ability to identify RNA truncation species was indifferent as to whether the IVT reaction products were purified or unpurified prior to the RACE procedure, as evidenced by the identification of RNA truncation products in oligo dT-purified G47A+C-terminal G polymerase variant reaction samples and unpurified G47A+C-terminal G polymerase variant reaction samples.

Figure 5:
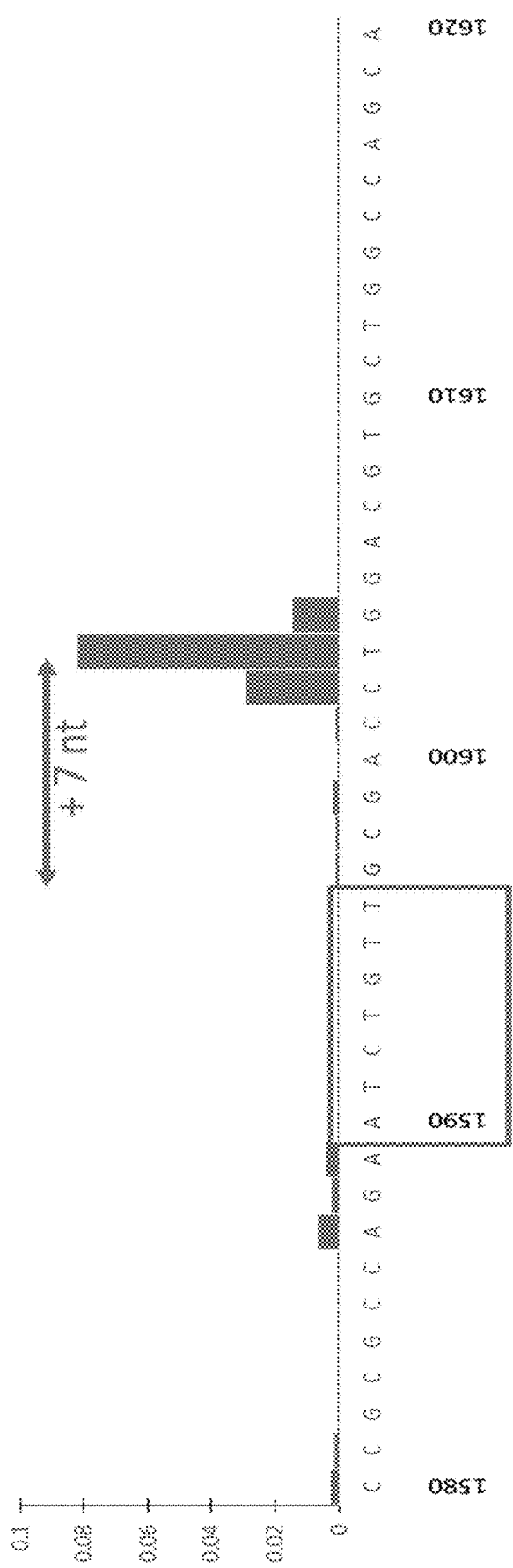
FIG. 5 shows a graph depicting the relative amounts of truncated RNA products following in vitro transcription of a DNA template (Template B) comprising a non-canonical terminator sequence (ATCTGTT) using G47A+C-terminal G T7 polymerase (SEQ ID NO: 47). Truncated RNA products are amplified using a 'rapid amplification of cDNA ends' (RACE) procedure to enable precise next-generation sequencing. The majority of truncated RNA products were truncated at nucleotide C1601, T1602, or G1603, which correspond to the +6, +7, and +8 positions relative to the ATCTGTT sequence motif.

In a similar manner, IVT reactions involving Template B and G47A+C-terminal G polymerase variant produced RNA truncations that were primarily truncated at +6 and +7 positions relative to the ATCTGTT sequence motif (C1601 or T1602) (FIG. 5). In addition, a lesser amount of truncated RNA products were truncated at the +8 position of Template B (G1603).

Example 3. Mutation of the Non-Canonical ATCTGTT Terminator Motif Prevents Early Termination A DNA template comprising a ATCTGTT terminator sequence motif (Template B) was genetically mutated using site-directed mutagenesis to generate a modified DNA template (Modified Template B) comprising a disrupted terminator sequence. Specifically, the ATCTGTT sequence motif of Template B was mutated to ATTTGCT in Modified Template C.

Figure 6:
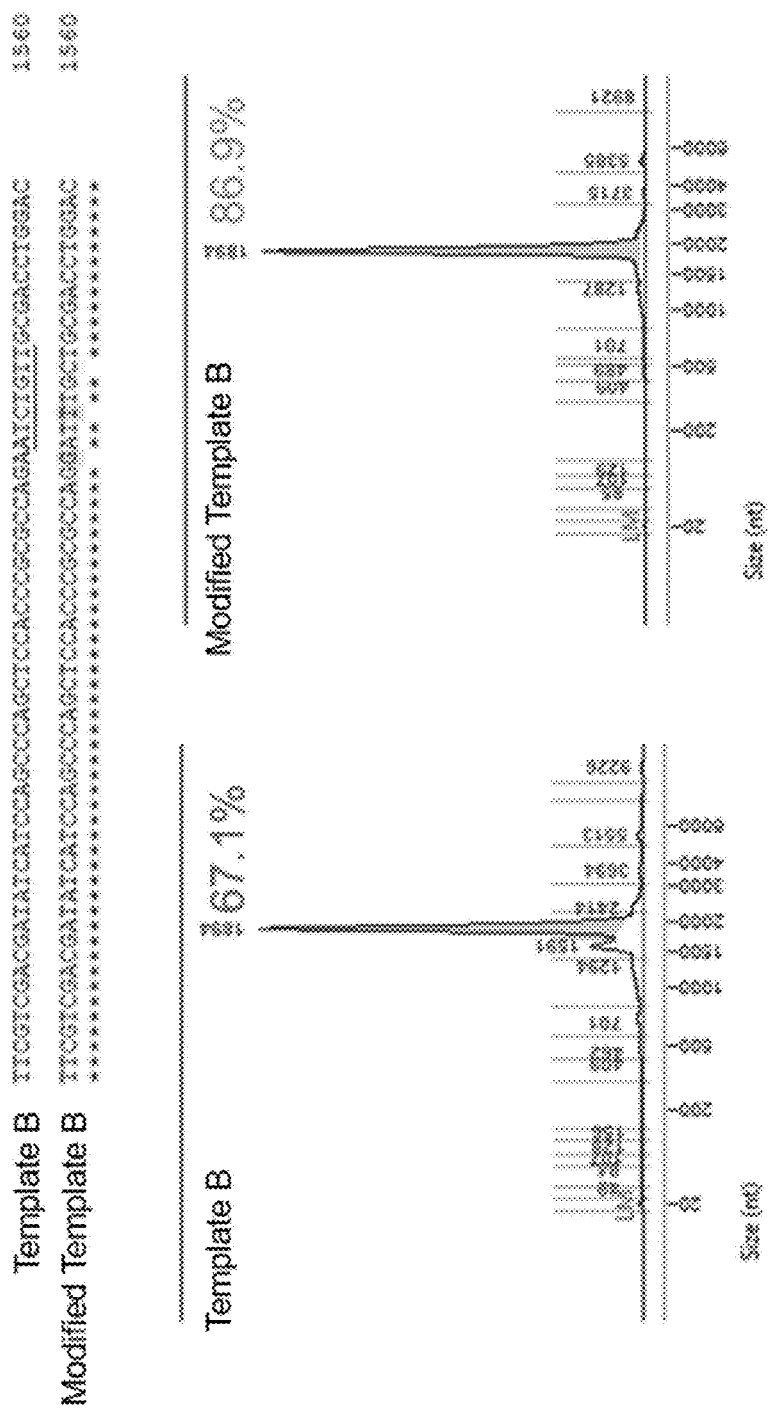
FIG. 6 shows capillary electropherograms of RNA products following in vitro transcription of two DNA templates (Template B (SEQ ID NO: 48) and Modified Template B (SEQ ID NO: 49)) using G47A+C-terminal G T7 polymerase. Template B comprises a ATCTGTT sequence motif while modified Template B has been mutated to eliminate the ATCTGTT motif while preserving the amino acid sequence of the polypeptide encoded by Template B.

In vitro transcription (IVT) reactions of Template B and Modified Template B were independently performed using the G47A+C-terminal G T7 polymerase variant. Resultant IVT products were analyzed using reverse-phase HPLC (FIG. 6). 67.1% of the total RNA products produced using Template B, which comprises the ATCTGTT terminator sequence, were full-length transcripts (1894 nucleotides). Approximately 10% of the total RNA products produced using Template B were truncated transcripts (1591 nucleotides). Conversely, 86.9% of the total RNA products produced using Modified Template B, which does not comprise the ATCTGTT terminator sequence, were full-length transcripts (1894 nucleotides). Further, no truncated RNA transcripts of 1591 nucleotides were observed to have been produced using Modified Template B.

Further various additional Template A and Template B constructs were made by making 1-2 nucleotide mutations in the non-canonical terminator motif. RNA was produced in vitro using either WT T7 RNA polymerase or the G47A+C-terminal G T7 polymerase variant. Table 2 (Template A) and Table 3 (Template B) show the modifications to the non-canonical terminator motif do not result in early termination and that the G47A+C-terminal G T7 polymerase variant is more sensitive to the specific 7-nucleotide non-canonical terminator motif, relative to the WT T7 RNA polymerase.

TABLE 2

Template A Variants (Percent full-length mRNA)

| Template A mRNA | DNA terminator motif | G47A+C-terminal G T7 RNA Polymerase Variant | WT T7 RNA Polymerase Variant |
| --- | --- | --- | --- |
| 1 | ACCTTTT | 71.2 | 77.5 |
| 2 | ATCTTTT | 74.6 | 77.8 |
| 3 | ACTTGTT | 83.6 | 86.4 |
| 4 | ATCTGTT | 38.1 | 77.5 |
| 5 | ATCTCTT | 85.2 | 85.8 |
| 6 | ACCTCTT | 81.6 | 81.7 |
| 7 | ACCTTTT | 77.7 | 86.9 |
| 8 | ACTTGTT | 74.6 | 85.9 |
| 9 | ACCTGTT | 70 | 84.3 |
| 10 | ATCTGTT | 52.7 | 73.9 |

TABLE 3

Template B Variants (Percent full-length mRNA)

| Template B mRNA | DNA terminator motif | G47A+C-terminal G T7 RNA Polymerase Variant | WT T7 RNA Polymerase Variant |
| --- | --- | --- | --- |
| 1 | ATCTGCT | 84.3 | 81.7 |
| 2 | ATATGCT | 76 | 62.5 |
| 3 | ATCTGTT | 55.6 | 74.7 |
| 4 | ATATGCT | 87.1 | 80.4 |
| 5 | ATCTGCT | 82.7 | 82.1 |
| 6 | ATCTGCT | 62.7 | 62.2 |
| 7 | ATCTGTT | 66.4 | 78 |
| 8 | ATTTGCT | 72.3 | 78.8 |

These data demonstrate that the presence of an ATCTGTT terminator sequence in a DNA template is sufficiently capable of inducing early termination of in vitro transcription reactions to produce truncated RNA templates. Similarly, these data demonstrate that simple mutation of an ATCTGTT terminator sequence is sufficient to reduce and/or prevent early termination of desired RNA products.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method of producing a messenger RNA (mRNA), the method comprising
   (a) identifying a non-canonical terminator motif NNATCTGTTNN (SEQ ID NO: 50) in a DNA encoding a mRNA that encodes a polypeptide, wherein N at each position of the non-canonical terminator motif is any nucleotide selected from A, T, C, and G;
   (b) producing a modified DNA comprising at least one codon substitution in the non-canonical terminator motif that preserves the amino acid sequence of the polypeptide; and
   (c) producing a modified mRNA in an in vitro transcription reaction that comprises the modified DNA, nucleoside triphosphates, and a T7 RNA polymerase.

2. The method of claim 1, wherein:
   the polypeptide comprises an amino acid sequence X1-Ser-Val, and X1 is selected from the group consisting of Ile, Leu, Val, Ala, Gly, Pro, Thr, Ser, Gln, Glu, Lys, and Arg;
   the polypeptide comprises an amino acid sequence X2-Leu-Phe, and X2 is selected from the group consisting of Tyr, His, Asn, and Asp;
   the polypeptide comprises an amino acid sequence X2-Leu-Leu, and X2 is selected from the group consisting of Tyr, His, Asn, and Asp;
   the polypeptide comprises an amino acid sequence Ile-Cys-X3, and X3 is selected from the group consisting of Leu, Phe, Cys, Ser, Tyr, and Trp.

3. The method of claim 1, wherein the T7 RNA polymerase comprises the amino acid sequence of SEQ ID NO: 1.

4. The method of claim 1, wherein the T7 RNA polymerase comprises an amino acid substitution at position 47, relative to a T7 RNA polymerase comprising the amino acid sequence of SEQ ID NO: 1.

5. The method of claim 4, wherein the amino acid substitution at position 47 is G47A.

6. The method of claim 5, wherein the amino acid modification comprises an additional C-terminal amino acid, relative to the T7 RNA polymerase comprising the amino acid sequence of SEQ ID NO: 1.

7. The method of claim 6, wherein the additional C-terminal amino acid is selected from glycine, threonine, serine, alanine, and proline.

8. The method of claim 1, wherein the T7 RNA polymerase comprises an amino acid substitution at a position selected from positions 350, 351, 387, 394, 425, 427, 437, 441, 632, 811, and 880, relative to T7 RNA polymerase comprising the amino acid sequence of SEQ ID NO: 1.

9. The method of claim 8, wherein the amino acid substitution is at position 350, and the amino acid substitution at position 350 is selected from E350K, E350N, E350A, and E350W.

10. A method of producing a modified DNA encoding a messenger RNA (mRNA), the method comprising
    (a) identifying a non-canonical terminator motif NNATCTGTTNN (SEQ ID NO: 50) in a DNA encoding a mRNA that encodes a polypeptide, wherein N at each position of the non-canonical terminator motif is any nucleotide selected from A, T, C, and G; and
    (b) producing a modified DNA encoding the mRNA, wherein the modified DNA comprises at least one codon substitution in the non-canonical terminator motif that preserves the amino acid sequence of the polypeptide encoded by the mRNA.

11. The method of claim 8, wherein the amino acid substitution is at position 351, and the amino acid substitution at position 351 is D351V.

12. The method of claim 8, wherein the amino acid substitution is at position 387, and the amino acid substitution at position 387 is K387H, K387N, and K387S.

13. The method of claim 8, wherein the amino acid substitution is at position 437, and the amino acid substitution at position 437 is N437T, N437I, N437Y and N437F.

14. The method of claim 8, wherein the amino acid substitution is at position 441, and the amino acid substitution at position 441 is K441R.

15. The method of claim 8, wherein the amino acid substitution is at position 880, and the amino acid substitution at position 880 is F880Y.

* * * * *

SEQUENCE LISTING

<160> NUMBER OF SEQ ID NOS: 51

<210> SEQ ID NO 1
<211> LENGTH: 883
<212> TYPE: PRT
<213> ORGANISM: Unknown
<220> FEATURE:
<223> OTHER INFORMATION: wild-type T7 RNA polymerase

<400> SEQUENCE: 1

```
Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
    210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Gly Tyr Trp Ala
        275                 280                 285

Asn Gly Arg Arg Pro Leu Ala Leu Val Arg Thr His Ser Lys Lys Ala
    290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
            340                 345                 350

Pro Ala Ile Glu Arg Glu Glu Leu Pro Met Lys Pro Glu Asp Ile Asp
```

-continued

```
            355                 360                 365
Met Asn Pro Glu Ala Leu Thr Ala Trp Lys Arg Ala Ala Ala Val
            370                 375                 380
Tyr Arg Lys Asp Lys Ala Arg Lys Ser Arg Ile Ser Leu Glu Phe
385                 390                 395                 400
Met Leu Glu Gln Ala Asn Lys Phe Ala Asn His Lys Ala Ile Trp Phe
                    405                 410                 415
Pro Tyr Asn Met Asp Trp Arg Gly Arg Val Tyr Ala Val Ser Met Phe
                420                 425                 430
Asn Pro Gln Gly Asn Asp Met Thr Lys Gly Leu Leu Thr Leu Ala Lys
                    435                 440                 445
Gly Lys Pro Ile Gly Lys Glu Gly Tyr Tyr Trp Leu Lys Ile His Gly
                450                 455                 460
Ala Asn Cys Ala Gly Val Asp Lys Val Pro Phe Pro Glu Arg Ile Lys
465                 470                 475                 480
Phe Ile Glu Glu Asn His Glu Asn Ile Met Ala Cys Ala Lys Ser Pro
                    485                 490                 495
Leu Glu Asn Thr Trp Trp Ala Glu Gln Asp Ser Pro Phe Cys Phe Leu
                500                 505                 510
Ala Phe Cys Phe Glu Tyr Ala Gly Val Gln His His Gly Leu Ser Tyr
                515                 520                 525
Asn Cys Ser Leu Pro Leu Ala Phe Asp Gly Ser Cys Ser Gly Ile Gln
                530                 535                 540
His Phe Ser Ala Met Leu Arg Asp Glu Val Gly Gly Arg Ala Val Asn
545                 550                 555                 560
Leu Leu Pro Ser Glu Thr Val Gln Asp Ile Tyr Gly Ile Val Ala Lys
                    565                 570                 575
Lys Val Asn Glu Ile Leu Gln Ala Asp Ala Ile Asn Gly Thr Asp Asn
                580                 585                 590
Glu Val Val Thr Val Thr Asp Glu Asn Thr Gly Glu Ile Ser Glu Lys
                    595                 600                 605
Val Lys Leu Gly Thr Lys Ala Leu Ala Gly Gln Trp Leu Ala Tyr Gly
                610                 615                 620
Val Thr Arg Ser Val Thr Lys Arg Ser Val Met Thr Leu Ala Tyr Gly
625                 630                 635                 640
Ser Lys Glu Phe Gly Phe Arg Gln Gln Val Leu Glu Asp Thr Ile Gln
                    645                 650                 655
Pro Ala Ile Asp Ser Gly Lys Gly Leu Met Phe Thr Gln Pro Asn Gln
                660                 665                 670
Ala Ala Gly Tyr Met Ala Lys Leu Ile Trp Glu Ser Val Ser Val Thr
                    675                 680                 685
Val Val Ala Ala Val Glu Ala Met Asn Trp Leu Lys Ser Ala Ala Lys
                690                 695                 700
Leu Leu Ala Ala Glu Val Lys Asp Lys Lys Thr Gly Glu Ile Leu Arg
705                 710                 715                 720
Lys Arg Cys Ala Val His Trp Val Thr Pro Asp Gly Phe Pro Val Trp
                    725                 730                 735
Gln Glu Tyr Lys Lys Pro Ile Gln Thr Arg Leu Asn Leu Met Phe Leu
                740                 745                 750
Gly Gln Phe Arg Leu Gln Pro Thr Ile Asn Thr Asn Lys Asp Ser Glu
                755                 760                 765
Ile Asp Ala His Lys Gln Glu Ser Gly Ile Ala Pro Asn Phe Val His
                770                 775                 780
```

```
Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
            805                 810                 815

Ile Pro Ala Asp Ala Ala Asn Leu Phe Lys Ala Val Arg Glu Thr Met
                820                 825                 830

Val Asp Thr Tyr Glu Ser Cys Asp Val Leu Ala Asp Phe Tyr Asp Gln
            835                 840                 845

Phe Ala Asp Gln Leu His Glu Ser Gln Leu Asp Lys Met Pro Ala Leu
850                 855                 860

Pro Ala Lys Gly Asn Leu Asn Leu Arg Asp Ile Leu Glu Ser Asp Phe
865                 870                 875                 880

Ala Phe Ala

<210> SEQ ID NO 2
<211> LENGTH: 883
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (47)..(47)
<223> OTHER INFORMATION: Xaa can be any naturally occurring amino acid

<400> SEQUENCE: 2

Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Xaa Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
    210                 215                 220

Gly Met Val Ser Leu His Arg Gln Asn Ala Gly Val Val Gly Gln Asp
225                 230                 235                 240
```

```
Ser Glu Thr Ile Glu Leu Ala Pro Glu Tyr Ala Glu Ala Ile Ala Thr
            245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Gly Tyr Trp Ala
            275                 280                 285

Asn Gly Arg Arg Pro Leu Ala Leu Val Arg Thr His Ser Lys Lys Ala
            290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
            325                 330                 335

Val Ala Asn Val Ile Thr Lys Trp Lys His Cys Pro Val Glu Asp Ile
            340                 345                 350

Pro Ala Ile Glu Arg Glu Leu Pro Met Lys Pro Glu Asp Ile Asp
            355                 360                 365

Met Asn Pro Glu Ala Leu Thr Ala Trp Lys Arg Ala Ala Ala Val
            370                 375                 380

Tyr Arg Lys Asp Lys Ala Arg Lys Ser Arg Ile Ser Leu Glu Phe
385                 390                 395                 400

Met Leu Glu Gln Ala Asn Lys Phe Ala Asn His Lys Ala Ile Trp Phe
            405                 410                 415

Pro Tyr Asn Met Asp Trp Arg Gly Arg Val Tyr Ala Val Ser Met Phe
            420                 425                 430

Asn Pro Gln Gly Asn Asp Met Thr Lys Gly Leu Leu Thr Leu Ala Lys
            435                 440                 445

Gly Lys Pro Ile Gly Lys Glu Gly Tyr Tyr Trp Leu Lys Ile His Gly
            450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
            485                 490                 495

Leu Glu Asn Thr Trp Trp Ala Glu Gln Asp Ser Pro Phe Cys Phe Leu
            500                 505                 510

Ala Phe Cys Phe Glu Tyr Ala Gly Val Gln His His Gly Leu Ser Tyr
            515                 520                 525

Asn Cys Ser Leu Pro Leu Ala Phe Asp Gly Ser Cys Ser Gly Ile Gln
            530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
            565                 570                 575

Lys Val Asn Glu Ile Leu Gln Ala Asp Ala Ile Asn Gly Thr Asp Asn
            580                 585                 590

Glu Val Val Thr Val Thr Asp Glu Asn Thr Gly Glu Ile Ser Glu Lys
            595                 600                 605

Val Lys Leu Gly Thr Lys Ala Leu Ala Gly Gln Trp Leu Ala Tyr Gly
            610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Asp Thr Ile Gln
            645                 650                 655
```

```
Pro Ala Ile Asp Ser Gly Lys Gly Leu Met Phe Thr Gln Pro Asn Gln
            660                 665                 670

Ala Ala Gly Tyr Met Ala Lys Leu Ile Trp Glu Ser Val Ser Val Thr
        675                 680                 685

Val Val Ala Ala Val Glu Ala Met Asn Trp Leu Lys Ser Ala Ala Lys
    690                 695                 700

Leu Leu Ala Ala Glu Val Lys Asp Lys Lys Thr Gly Glu Ile Leu Arg
705                 710                 715                 720

Lys Arg Cys Ala Val His Trp Val Thr Pro Asp Gly Phe Pro Val Trp
                725                 730                 735

Gln Glu Tyr Lys Lys Pro Ile Gln Thr Arg Leu Asn Leu Met Phe Leu
            740                 745                 750

Gly Gln Phe Arg Leu Gln Pro Thr Ile Asn Thr Asn Lys Asp Ser Glu
        755                 760                 765

Ile Asp Ala His Lys Gln Glu Ser Gly Ile Ala Pro Asn Phe Val His
    770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
            820                 825                 830

Val Asp Thr Tyr Glu Ser Cys Asp Val Leu Ala Asp Phe Tyr Asp Gln
        835                 840                 845

Phe Ala Asp Gln Leu His Glu Ser Gln Leu Asp Lys Met Pro Ala Leu
    850                 855                 860

Pro Ala Lys Gly Asn Leu Asn Leu Arg Asp Ile Leu Glu Ser Asp Phe
865                 870                 875                 880

Ala Phe Ala

<210> SEQ ID NO 3
<211> LENGTH: 883
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (350)..(350)
<223> OTHER INFORMATION: Xaa can be any naturally occurring amino acid

<400> SEQUENCE: 3

Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110
```

```
Ala Val Ala Tyr Ile Thr Ile Lys Thr Thr Leu Ala Cys Leu Thr Ser
            115                 120                 125

Ala Asp Asn Thr Thr Val Gln Ala Val Ala Ser Ala Ile Gly Arg Ala
130                 135                 140

Ile Glu Asp Glu Ala Arg Phe Gly Arg Ile Arg Asp Leu Glu Ala Lys
145                 150                 155                 160

His Phe Lys Lys Asn Val Glu Gln Leu Asn Lys Arg Val Gly His
                165                 170                 175

Val Tyr Lys Lys Ala Phe Met Gln Val Glu Ala Asp Met Leu Ser
            180                 185                 190

Lys Gly Leu Leu Gly Gly Glu Ala Trp Ser Ser Trp His Lys Glu Asp
            195                 200                 205

Ser Ile His Val Gly Val Arg Cys Ile Glu Met Leu Ile Glu Ser Thr
    210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Tyr Trp Ala
275                 280                 285

Asn Gly Arg Arg Pro Leu Ala Leu Val Arg Thr His Ser Lys Lys Ala
290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
            325                 330                 335

Val Ala Asn Val Ile Thr Lys Trp Lys His Cys Pro Val Xaa Asp Ile
            340                 345                 350

Pro Ala Ile Glu Arg Glu Glu Leu Pro Met Lys Pro Glu Asp Ile Asp
            355                 360                 365

Met Asn Pro Glu Ala Leu Thr Ala Trp Lys Arg Ala Ala Ala Val
370                 375                 380

Tyr Arg Lys Asp Lys Ala Arg Lys Ser Arg Ile Ser Leu Glu Phe
385                 390                 395                 400

Met Leu Glu Gln Ala Asn Lys Phe Ala Asn His Lys Ala Ile Trp Phe
                405                 410                 415

Pro Tyr Asn Met Asp Trp Arg Gly Arg Val Tyr Ala Val Ser Met Phe
            420                 425                 430

Asn Pro Gln Gly Asn Asp Met Thr Lys Gly Leu Leu Thr Leu Ala Lys
            435                 440                 445

Gly Lys Pro Ile Gly Lys Glu Gly Tyr Tyr Trp Leu Lys Ile His Gly
    450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
            500                 505                 510

Ala Phe Cys Phe Glu Tyr Ala Gly Val Gln His His Gly Leu Ser Tyr
            515                 520                 525

Asn Cys Ser Leu Pro Leu Ala Phe Asp Gly Ser Cys Ser Gly Ile Gln
```

```
                530                 535                 540
His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                565                 570                 575

Lys Val Asn Glu Ile Leu Gln Ala Asp Ala Ile Asn Gly Thr Asp Asn
            580                 585                 590

Glu Val Val Thr Val Thr Asp Glu Asn Thr Gly Glu Ile Ser Glu Lys
        595                 600                 605

Val Lys Leu Gly Thr Lys Ala Leu Ala Gly Gln Trp Leu Ala Tyr Gly
610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Asp Thr Ile Gln
                645                 650                 655

Pro Ala Ile Asp Ser Gly Lys Gly Leu Met Phe Thr Gln Pro Asn Gln
            660                 665                 670

Ala Ala Gly Tyr Met Ala Lys Leu Ile Trp Glu Ser Val Ser Val Thr
        675                 680                 685

Val Val Ala Ala Val Glu Ala Met Asn Trp Leu Lys Ser Ala Ala Lys
690                 695                 700

Leu Leu Ala Ala Glu Val Lys Asp Lys Thr Gly Glu Ile Leu Arg
705                 710                 715                 720

Lys Arg Cys Ala Val His Trp Val Thr Pro Asp Gly Phe Pro Val Trp
                725                 730                 735

Gln Glu Tyr Lys Lys Pro Ile Gln Thr Arg Leu Asn Leu Met Phe Leu
            740                 745                 750

Gly Gln Phe Arg Leu Gln Pro Thr Ile Asn Thr Asn Lys Asp Ser Glu
        755                 760                 765

Ile Asp Ala His Lys Gln Glu Ser Gly Ile Ala Pro Asn Phe Val His
770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
            820                 825                 830

Val Asp Thr Tyr Glu Ser Cys Asp Val Leu Ala Asp Phe Tyr Asp Gln
        835                 840                 845

Phe Ala Asp Gln Leu His Glu Ser Gln Leu Asp Lys Met Pro Ala Leu
850                 855                 860

Pro Ala Lys Gly Asn Leu Asn Leu Arg Asp Ile Leu Glu Ser Asp Phe
865                 870                 875                 880

Ala Phe Ala

<210> SEQ ID NO 4
<211> LENGTH: 883
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (351)..(351)
<223> OTHER INFORMATION: Xaa can be any naturally occurring amino acid
```

<400> SEQUENCE: 4

```
Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
    210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Gly Tyr Trp Ala
        275                 280                 285

Asn Gly Arg Arg Pro Leu Ala Leu Val Arg Thr His Ser Lys Lys Ala
    290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Xaa Ile
            340                 345                 350

Pro Ala Ile Glu Arg Glu Glu Leu Pro Met Lys Pro Glu Asp Ile Asp
        355                 360                 365

Met Asn Pro Glu Ala Leu Thr Ala Trp Lys Arg Ala Ala Ala Ala Val
    370                 375                 380

Tyr Arg Lys Asp Lys Ala Arg Lys Ser Arg Arg Ile Ser Leu Glu Phe
385                 390                 395                 400

Met Leu Glu Gln Ala Asn Lys Phe Ala Asn His Lys Ala Ile Trp Phe
                405                 410                 415
```

```
Pro Tyr Asn Met Asp Trp Arg Gly Arg Val Tyr Ala Val Ser Met Phe
            420                 425                 430

Asn Pro Gln Gly Asn Asp Met Thr Lys Gly Leu Leu Thr Leu Ala Lys
            435                 440                 445

Gly Lys Pro Ile Gly Lys Glu Gly Tyr Tyr Trp Leu Lys Ile His Gly
450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
            500                 505                 510

Ala Phe Cys Phe Glu Tyr Ala Gly Val Gln His His Gly Leu Ser Tyr
            515                 520                 525

Asn Cys Ser Leu Pro Leu Ala Phe Asp Gly Ser Cys Ser Gly Ile Gln
            530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                565                 570                 575

Lys Val Asn Glu Ile Leu Gln Ala Asp Ala Ile Asn Gly Thr Asp Asn
            580                 585                 590

Glu Val Val Thr Val Thr Asp Glu Asn Thr Gly Glu Ile Ser Glu Lys
            595                 600                 605

Val Lys Leu Gly Thr Lys Ala Leu Ala Gly Gln Trp Leu Ala Tyr Gly
610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Asp Thr Ile Gln
                645                 650                 655

Pro Ala Ile Asp Ser Gly Lys Gly Leu Met Phe Thr Gln Pro Asn Gln
            660                 665                 670

Ala Ala Gly Tyr Met Ala Lys Leu Ile Trp Glu Ser Val Ser Val Thr
            675                 680                 685

Val Val Ala Ala Val Glu Ala Met Asn Trp Leu Lys Ser Ala Ala Lys
            690                 695                 700

Leu Leu Ala Ala Glu Val Lys Asp Lys Lys Thr Gly Glu Ile Leu Arg
705                 710                 715                 720

Lys Arg Cys Ala Val His Trp Val Thr Pro Asp Gly Phe Pro Val Trp
                725                 730                 735

Gln Glu Tyr Lys Lys Pro Ile Gln Thr Arg Leu Asn Leu Met Phe Leu
            740                 745                 750

Gly Gln Phe Arg Leu Gln Pro Thr Ile Asn Thr Asn Lys Asp Ser Glu
            755                 760                 765

Ile Asp Ala His Lys Gln Glu Ser Gly Ile Ala Pro Asn Phe Val His
            770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
            820                 825                 830
```

-continued

```
Val Asp Thr Tyr Glu Ser Cys Asp Val Leu Ala Asp Phe Tyr Asp Gln
            835                 840                 845

Phe Ala Asp Gln Leu His Glu Ser Gln Leu Asp Lys Met Pro Ala Leu
            850                 855                 860

Pro Ala Lys Gly Asn Leu Asn Leu Arg Asp Ile Leu Glu Ser Asp Phe
865                 870                 875                 880

Ala Phe Ala

<210> SEQ ID NO 5
<211> LENGTH: 883
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (387)..(387)
<223> OTHER INFORMATION: Xaa can be any naturally occurring amino acid

<400> SEQUENCE: 5

Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
    210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Gly Tyr Trp Ala
        275                 280                 285
```

```
Asn Gly Arg Arg Pro Leu Ala Leu Val Arg Thr His Ser Lys Lys Ala
    290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
            340                 345                 350

Pro Ala Ile Glu Arg Glu Glu Leu Pro Met Lys Pro Glu Asp Ile Asp
        355                 360                 365

Met Asn Pro Glu Ala Leu Thr Ala Trp Lys Arg Ala Ala Ala Ala Val
    370                 375                 380

Tyr Arg Xaa Asp Lys Ala Arg Lys Ser Arg Arg Ile Ser Leu Glu Phe
385                 390                 395                 400

Met Leu Glu Gln Ala Asn Lys Phe Ala Asn His Lys Ala Ile Trp Phe
                405                 410                 415

Pro Tyr Asn Met Asp Trp Arg Gly Arg Val Tyr Ala Val Ser Met Phe
            420                 425                 430

Asn Pro Gln Gly Asn Asp Met Thr Lys Gly Leu Leu Thr Leu Ala Lys
        435                 440                 445

Gly Lys Pro Ile Gly Lys Glu Gly Tyr Tyr Trp Leu Lys Ile His Gly
    450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
            500                 505                 510

Ala Phe Cys Phe Glu Tyr Ala Gly Val Gln His His Gly Leu Ser Tyr
        515                 520                 525

Asn Cys Ser Leu Pro Leu Ala Phe Asp Gly Ser Cys Ser Gly Ile Gln
    530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                565                 570                 575

Lys Val Asn Glu Ile Leu Gln Ala Asp Ala Ile Asn Gly Thr Asp Asn
            580                 585                 590

Glu Val Val Thr Val Thr Asp Glu Asn Thr Gly Glu Ile Ser Glu Lys
        595                 600                 605

Val Lys Leu Gly Thr Lys Ala Leu Ala Gly Gln Trp Leu Ala Tyr Gly
    610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Asp Thr Ile Gln
                645                 650                 655

Pro Ala Ile Asp Ser Gly Lys Gly Leu Met Phe Thr Gln Pro Asn Gln
            660                 665                 670

Ala Ala Gly Tyr Met Ala Lys Leu Ile Trp Glu Ser Val Ser Val Thr
        675                 680                 685

Val Val Ala Ala Val Glu Ala Met Asn Trp Leu Lys Ser Ala Ala Lys
    690                 695                 700

Leu Leu Ala Ala Glu Val Lys Asp Lys Lys Thr Gly Glu Ile Leu Arg
```

```
                705                 710                 715                 720
Lys Arg Cys Ala Val His Trp Val Thr Pro Asp Gly Phe Pro Val Trp
                    725                 730                 735

Gln Glu Tyr Lys Lys Pro Ile Gln Thr Arg Leu Asn Leu Met Phe Leu
                740                 745                 750

Gly Gln Phe Arg Leu Gln Pro Thr Ile Asn Thr Asn Lys Asp Ser Glu
                755                 760                 765

Ile Asp Ala His Lys Gln Glu Ser Gly Ile Ala Pro Asn Phe Val His
            770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
                    805                 810                 815

Ile Pro Ala Asp Ala Asn Leu Phe Lys Ala Val Arg Glu Thr Met
                820                 825                 830

Val Asp Thr Tyr Glu Ser Cys Asp Val Leu Ala Asp Phe Tyr Asp Gln
                835                 840                 845

Phe Ala Asp Gln Leu His Glu Ser Gln Leu Asp Lys Met Pro Ala Leu
            850                 855                 860

Pro Ala Lys Gly Asn Leu Asn Leu Arg Asp Ile Leu Glu Ser Asp Phe
865                 870                 875                 880

Ala Phe Ala

<210> SEQ ID NO 6
<211> LENGTH: 883
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (394)..(394)
<223> OTHER INFORMATION: Xaa can be any naturally occurring amino acid

<400> SEQUENCE: 6

Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
                20                  25                  30

Ala Arg Glu Gln Leu Ala Leu Glu His Glu Ser Tyr Glu Met Gly Glu
            35                  40                  45

Ala Arg Phe Arg Lys Met Phe Glu Arg Gln Leu Lys Ala Gly Glu Val
        50                  55                  60

Ala Asp Asn Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
```

```
            165                 170                 175
Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
            195                 200                 205

Ser Ile His Val Gly Val Arg Cys Ile Glu Met Leu Ile Glu Ser Thr
            210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Tyr Trp Ala
            275                 280                 285

Asn Gly Arg Arg Pro Leu Ala Leu Val Arg Thr His Ser Lys Lys Ala
            290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
            340                 345                 350

Pro Ala Ile Glu Arg Glu Leu Pro Met Lys Pro Glu Asp Ile Asp
            355                 360                 365

Met Asn Pro Glu Ala Leu Thr Ala Trp Lys Arg Ala Ala Ala Val
370                 375                 380

Tyr Arg Lys Asp Lys Ala Arg Lys Ser Xaa Arg Ile Ser Leu Glu Phe
385                 390                 395                 400

Met Leu Glu Gln Ala Asn Lys Phe Ala Asn His Lys Ala Ile Trp Phe
                405                 410                 415

Pro Tyr Asn Met Asp Trp Arg Gly Arg Val Tyr Ala Val Ser Met Phe
            420                 425                 430

Asn Pro Gln Gly Asn Asp Met Thr Lys Gly Leu Leu Thr Leu Ala Lys
            435                 440                 445

Gly Lys Pro Ile Gly Lys Glu Gly Tyr Tyr Trp Leu Lys Ile His Gly
            450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
            500                 505                 510

Ala Phe Cys Phe Glu Tyr Ala Gly Val Gln His His Gly Leu Ser Tyr
            515                 520                 525

Asn Cys Ser Leu Pro Leu Ala Phe Asp Gly Ser Cys Ser Gly Ile Gln
            530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                565                 570                 575

Lys Val Asn Glu Ile Leu Gln Ala Asp Ala Ile Asn Gly Thr Asp Asn
            580                 585                 590
```

```
Glu Val Val Thr Val Thr Asp Glu Asn Thr Gly Glu Ile Ser Glu Lys
            595                 600                 605

Val Lys Leu Gly Thr Lys Ala Leu Ala Gly Gln Trp Leu Ala Tyr Gly
    610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Asp Thr Ile Gln
                645                 650                 655

Pro Ala Ile Asp Ser Gly Lys Gly Leu Met Phe Thr Gln Pro Asn Gln
            660                 665                 670

Ala Ala Gly Tyr Met Ala Lys Leu Ile Trp Glu Ser Val Ser Val Thr
        675                 680                 685

Val Val Ala Ala Val Glu Ala Met Asn Trp Leu Lys Ser Ala Ala Lys
    690                 695                 700

Leu Leu Ala Ala Glu Val Lys Asp Lys Lys Thr Gly Glu Ile Leu Arg
705                 710                 715                 720

Lys Arg Cys Ala Val His Trp Val Thr Pro Asp Gly Phe Pro Val Trp
                725                 730                 735

Gln Glu Tyr Lys Lys Pro Ile Gln Thr Arg Leu Asn Leu Met Phe Leu
            740                 745                 750

Gly Gln Phe Arg Leu Gln Pro Thr Ile Asn Thr Asn Lys Asp Ser Glu
        755                 760                 765

Ile Asp Ala His Lys Gln Glu Ser Gly Ile Ala Pro Asn Phe Val His
    770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
            820                 825                 830

Val Asp Thr Tyr Glu Ser Cys Asp Val Leu Ala Asp Phe Tyr Asp Gln
        835                 840                 845

Phe Ala Asp Gln Leu His Glu Ser Gln Leu Asp Lys Met Pro Ala Leu
    850                 855                 860

Pro Ala Lys Gly Asn Leu Asn Leu Arg Asp Ile Leu Glu Ser Asp Phe
865                 870                 875                 880

Ala Phe Ala

<210> SEQ ID NO 7
<211> LENGTH: 883
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (425)..(425)
<223> OTHER INFORMATION: Xaa can be any naturally occurring amino acid

<400> SEQUENCE: 7

Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45
```

```
Ala Arg Phe Arg Lys Met Phe Glu Arg Gln Leu Lys Ala Gly Glu Val
    50                  55                  60

Ala Asp Asn Ala Ala Lys Pro Leu Ile Thr Thr Leu Leu Pro Lys
 65              70                  75                  80

Met Ile Ala Arg Ile Asn Asp Trp Phe Glu Glu Val Lys Ala Lys Arg
                 85                  90                  95

Gly Lys Arg Pro Thr Ala Phe Gln Phe Leu Gln Glu Ile Lys Pro Glu
                100                 105                 110

Ala Val Ala Tyr Ile Thr Ile Lys Thr Thr Leu Ala Cys Leu Thr Ser
                115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
                180                 185                 190

Lys Gly Leu Leu Gly Gly Glu Ala Trp Ser Ser Trp His Lys Glu Asp
                195                 200                 205

Ser Ile His Val Gly Val Arg Cys Ile Glu Met Leu Ile Glu Ser Thr
    210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
                260                 265                 270

Val Pro Pro Lys Pro Trp Thr Gly Ile Thr Gly Gly Tyr Trp Ala
                275                 280                 285

Asn Gly Arg Arg Pro Leu Ala Leu Val Arg Thr His Ser Lys Lys Ala
    290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
                340                 345                 350

Pro Ala Ile Glu Arg Glu Glu Leu Pro Met Lys Pro Glu Asp Ile Asp
                355                 360                 365

Met Asn Pro Glu Ala Leu Thr Ala Trp Lys Arg Ala Ala Ala Val
    370                 375                 380

Tyr Arg Lys Asp Lys Ala Arg Lys Ser Arg Arg Ile Ser Leu Glu Phe
385                 390                 395                 400

Met Leu Glu Gln Ala Asn Lys Phe Ala Asn His Lys Ala Ile Trp Phe
                405                 410                 415

Pro Tyr Asn Met Asp Trp Arg Gly Xaa Val Tyr Ala Val Ser Met Phe
                420                 425                 430

Asn Pro Gln Gly Asn Asp Met Thr Lys Gly Leu Leu Thr Leu Ala Lys
    435                 440                 445

Gly Lys Pro Ile Gly Lys Glu Gly Tyr Tyr Trp Leu Lys Ile His Gly
    450                 455                 460
```

```
Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
            500                 505                 510

Ala Phe Cys Phe Glu Tyr Ala Gly Val Gln His His Gly Leu Ser Tyr
        515                 520                 525

Asn Cys Ser Leu Pro Leu Ala Phe Asp Gly Ser Cys Ser Gly Ile Gln
    530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                565                 570                 575

Lys Val Asn Glu Ile Leu Gln Ala Asp Ala Ile Asn Gly Thr Asp Asn
            580                 585                 590

Glu Val Val Thr Val Thr Asp Glu Asn Thr Gly Glu Ile Ser Glu Lys
        595                 600                 605

Val Lys Leu Gly Thr Lys Ala Leu Ala Gly Gln Trp Leu Ala Tyr Gly
    610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Asp Thr Ile Gln
                645                 650                 655

Pro Ala Ile Asp Ser Gly Lys Gly Leu Met Phe Thr Gln Pro Asn Gln
            660                 665                 670

Ala Ala Gly Tyr Met Ala Lys Leu Ile Trp Glu Ser Val Ser Val Thr
        675                 680                 685

Val Val Ala Ala Val Glu Ala Met Asn Trp Leu Lys Ser Ala Ala Lys
    690                 695                 700

Leu Leu Ala Ala Glu Val Lys Asp Lys Lys Thr Gly Glu Ile Leu Arg
705                 710                 715                 720

Lys Arg Cys Ala Val His Trp Val Thr Pro Asp Gly Phe Pro Val Trp
                725                 730                 735

Gln Glu Tyr Lys Lys Pro Ile Gln Thr Arg Leu Asn Leu Met Phe Leu
            740                 745                 750

Gly Gln Phe Arg Leu Gln Pro Thr Ile Asn Thr Asn Lys Asp Ser Glu
        755                 760                 765

Ile Asp Ala His Lys Gln Glu Ser Gly Ile Ala Pro Asn Phe Val His
    770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
            820                 825                 830

Val Asp Thr Tyr Glu Ser Cys Asp Val Leu Ala Asp Phe Tyr Asp Gln
        835                 840                 845

Phe Ala Asp Gln Leu His Glu Ser Gln Leu Asp Lys Met Pro Ala Leu
    850                 855                 860

Pro Ala Lys Gly Asn Leu Asn Leu Arg Asp Ile Leu Glu Ser Asp Phe
865                 870                 875                 880

Ala Phe Ala
```

```
<210> SEQ ID NO 8
<211> LENGTH: 883
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (427)..(427)
<223> OTHER INFORMATION: Xaa can be any naturally occurring amino acid

<400> SEQUENCE: 8

Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
    210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Gly Tyr Trp Ala
        275                 280                 285

Asn Gly Arg Arg Pro Leu Ala Leu Val Arg Thr His Ser Lys Lys Ala
    290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
```

```
            340                 345                 350
Pro Ala Ile Glu Arg Glu Leu Pro Met Lys Pro Glu Asp Ile Asp
            355                 360                 365
Met Asn Pro Glu Ala Leu Thr Ala Trp Lys Arg Ala Ala Ala Val
            370                 375                 380
Tyr Arg Lys Asp Lys Ala Arg Lys Ser Arg Arg Ile Ser Leu Glu Phe
385                 390                 395                 400
Met Leu Glu Gln Ala Asn Lys Phe Ala Asn His Lys Ala Ile Trp Phe
            405                 410                 415
Pro Tyr Asn Met Asp Trp Arg Gly Arg Val Xaa Ala Val Ser Met Phe
            420                 425                 430
Asn Pro Gln Gly Asn Asp Met Thr Lys Gly Leu Leu Thr Leu Ala Lys
            435                 440                 445
Gly Lys Pro Ile Gly Lys Glu Gly Tyr Tyr Trp Leu Lys Ile His Gly
            450                 455                 460
Ala Asn Cys Ala Gly Val Asp Lys Val Pro Phe Pro Glu Arg Ile Lys
465                 470                 475                 480
Phe Ile Glu Glu Asn His Glu Asn Ile Met Ala Cys Ala Lys Ser Pro
            485                 490                 495
Leu Glu Asn Thr Trp Trp Ala Glu Gln Asp Ser Pro Phe Cys Phe Leu
            500                 505                 510
Ala Phe Cys Phe Glu Tyr Ala Gly Val Gln His His Gly Leu Ser Tyr
            515                 520                 525
Asn Cys Ser Leu Pro Leu Ala Phe Asp Gly Ser Cys Ser Gly Ile Gln
            530                 535                 540
His Phe Ser Ala Met Leu Arg Asp Glu Val Gly Gly Arg Ala Val Asn
545                 550                 555                 560
Leu Leu Pro Ser Glu Thr Val Gln Asp Ile Tyr Gly Ile Val Ala Lys
            565                 570                 575
Lys Val Asn Glu Ile Leu Gln Ala Asp Ala Ile Asn Gly Thr Asp Asn
            580                 585                 590
Glu Val Val Thr Val Thr Asp Glu Asn Thr Gly Glu Ile Ser Glu Lys
            595                 600                 605
Val Lys Leu Gly Thr Lys Ala Leu Ala Gly Gln Trp Leu Ala Tyr Gly
            610                 615                 620
Val Thr Arg Ser Val Thr Lys Arg Ser Val Met Thr Leu Ala Tyr Gly
625                 630                 635                 640
Ser Lys Glu Phe Gly Phe Arg Gln Gln Val Leu Glu Asp Thr Ile Gln
            645                 650                 655
Pro Ala Ile Asp Ser Gly Lys Gly Leu Met Phe Thr Gln Pro Asn Gln
            660                 665                 670
Ala Ala Gly Tyr Met Ala Lys Leu Ile Trp Glu Ser Val Ser Val Thr
            675                 680                 685
Val Val Ala Ala Val Glu Ala Met Asn Trp Leu Lys Ser Ala Ala Lys
            690                 695                 700
Leu Leu Ala Ala Glu Val Lys Asp Lys Lys Thr Gly Glu Ile Leu Arg
705                 710                 715                 720
Lys Arg Cys Ala Val His Trp Val Thr Pro Asp Gly Phe Pro Val Trp
            725                 730                 735
Gln Glu Tyr Lys Lys Pro Ile Gln Thr Arg Leu Asn Leu Met Phe Leu
            740                 745                 750
Gly Gln Phe Arg Leu Gln Pro Thr Ile Asn Thr Asn Lys Asp Ser Glu
            755                 760                 765
```

```
Ile Asp Ala His Lys Gln Glu Ser Gly Ile Ala Pro Asn Phe Val His
        770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
            820                 825                 830

Val Asp Thr Tyr Glu Ser Cys Asp Val Leu Ala Asp Phe Tyr Asp Gln
        835                 840                 845

Phe Ala Asp Gln Leu His Glu Ser Gln Leu Asp Lys Met Pro Ala Leu
    850                 855                 860

Pro Ala Lys Gly Asn Leu Asn Leu Arg Asp Ile Leu Glu Ser Asp Phe
865                 870                 875                 880

Ala Phe Ala

<210> SEQ ID NO 9
<211> LENGTH: 883
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (437)..(437)
<223> OTHER INFORMATION: Xaa can be any naturally occurring amino acid

<400> SEQUENCE: 9

Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
    210                 215                 220
```

```
Gly Met Val Ser Leu His Arg Gln Asn Ala Gly Val Gly Gln Asp
225                 230                 235                 240

Ser Glu Thr Ile Glu Leu Ala Pro Glu Tyr Ala Glu Ala Ile Ala Thr
        245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Tyr Trp Ala
        275                 280                 285

Asn Gly Arg Arg Pro Leu Ala Leu Val Arg Thr His Ser Lys Lys Ala
    290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
            340                 345                 350

Pro Ala Ile Glu Arg Glu Leu Pro Met Lys Pro Glu Asp Ile Asp
        355                 360                 365

Met Asn Pro Glu Ala Leu Thr Ala Trp Lys Arg Ala Ala Ala Val
370                 375                 380

Tyr Arg Lys Asp Lys Ala Arg Lys Ser Arg Ile Ser Leu Glu Phe
385                 390                 395                 400

Met Leu Glu Gln Ala Asn Lys Phe Ala Asn His Lys Ala Ile Trp Phe
                405                 410                 415

Pro Tyr Asn Met Asp Trp Arg Gly Arg Val Tyr Ala Val Ser Met Phe
            420                 425                 430

Asn Pro Gln Gly Xaa Asp Met Thr Lys Gly Leu Leu Thr Leu Ala Lys
        435                 440                 445

Gly Lys Pro Ile Gly Lys Glu Gly Tyr Tyr Trp Leu Lys Ile His Gly
    450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
            500                 505                 510

Ala Phe Cys Phe Glu Tyr Ala Gly Val Gln His His Gly Leu Ser Tyr
        515                 520                 525

Asn Cys Ser Leu Pro Leu Ala Phe Asp Gly Ser Cys Ser Gly Ile Gln
    530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                565                 570                 575

Lys Val Asn Glu Ile Leu Gln Ala Asp Ala Ile Asn Gly Thr Asp Asn
            580                 585                 590

Glu Val Val Thr Val Thr Asp Glu Asn Thr Gly Glu Ile Ser Glu Lys
        595                 600                 605

Val Lys Leu Gly Thr Lys Ala Leu Ala Gly Gln Trp Leu Ala Tyr Gly
    610                 615                 620

Val Thr Arg Ser Val Thr Lys Arg Ser Val Met Thr Leu Ala Tyr Gly
625                 630                 635                 640
```

```
Ser Lys Glu Phe Gly Phe Arg Gln Gln Val Leu Glu Asp Thr Ile Gln
                645                 650                 655

Pro Ala Ile Asp Ser Gly Lys Gly Leu Met Phe Thr Gln Pro Asn Gln
            660                 665                 670

Ala Ala Gly Tyr Met Ala Lys Leu Ile Trp Glu Ser Val Ser Val Thr
        675                 680                 685

Val Val Ala Ala Val Glu Ala Met Asn Trp Leu Lys Ser Ala Ala Lys
    690                 695                 700

Leu Leu Ala Ala Glu Val Lys Asp Lys Lys Thr Gly Glu Ile Leu Arg
705                 710                 715                 720

Lys Arg Cys Ala Val His Trp Val Thr Pro Asp Gly Phe Pro Val Trp
                725                 730                 735

Gln Glu Tyr Lys Lys Pro Ile Gln Thr Arg Leu Asn Leu Met Phe Leu
            740                 745                 750

Gly Gln Phe Arg Leu Gln Pro Thr Ile Asn Thr Asn Lys Asp Ser Glu
        755                 760                 765

Ile Asp Ala His Lys Gln Glu Ser Gly Ile Ala Pro Asn Phe Val His
    770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
            820                 825                 830

Val Asp Thr Tyr Glu Ser Cys Asp Val Leu Ala Asp Phe Tyr Asp Gln
        835                 840                 845

Phe Ala Asp Gln Leu His Glu Ser Gln Leu Asp Lys Met Pro Ala Leu
    850                 855                 860

Pro Ala Lys Gly Asn Leu Asn Leu Arg Asp Ile Leu Glu Ser Asp Phe
865                 870                 875                 880

Ala Phe Ala

<210> SEQ ID NO 10
<211> LENGTH: 883
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (441)..(441)
<223> OTHER INFORMATION: Xaa can be any naturally occurring amino acid

<400> SEQUENCE: 10

Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95
```

```
Gly Lys Arg Pro Thr Ala Phe Gln Phe Leu Gln Glu Ile Lys Pro Glu
             100                 105                 110

Ala Val Ala Tyr Ile Thr Ile Lys Thr Thr Leu Ala Cys Leu Thr Ser
         115                 120                 125

Ala Asp Asn Thr Thr Val Gln Ala Val Ala Ser Ala Ile Gly Arg Ala
     130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                 165                 170                 175

Val Tyr Lys Lys Ala Phe Met Gln Val Glu Ala Asp Met Leu Ser
         180                 185                 190

Lys Gly Leu Leu Gly Gly Glu Ala Trp Ser Ser Trp His Lys Glu Asp
         195                 200                 205

Ser Ile His Val Gly Val Arg Cys Ile Glu Met Leu Ile Glu Ser Thr
         210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                 245                 250                 255

Arg Ala Gly Ala Leu Ala Gly Ile Ser Pro Met Phe Gln Pro Cys Val
             260                 265                 270

Val Pro Pro Lys Pro Trp Thr Gly Ile Thr Gly Gly Tyr Trp Ala
             275                 280                 285

Asn Gly Arg Arg Pro Leu Ala Leu Val Arg Thr His Ser Lys Lys Ala
     290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                 325                 330                 335

Val Ala Asn Val Ile Thr Lys Trp Lys His Cys Pro Val Glu Asp Ile
             340                 345                 350

Pro Ala Ile Glu Arg Glu Glu Leu Pro Met Lys Pro Glu Asp Ile Asp
         355                 360                 365

Met Asn Pro Glu Ala Leu Thr Ala Trp Lys Arg Ala Ala Ala Val
     370                 375                 380

Tyr Arg Lys Asp Lys Ala Arg Lys Ser Arg Arg Ile Ser Leu Glu Phe
385                 390                 395                 400

Met Leu Glu Gln Ala Asn Lys Phe Ala Asn His Lys Ala Ile Trp Phe
                 405                 410                 415

Pro Tyr Asn Met Asp Trp Arg Gly Arg Val Tyr Ala Val Ser Met Phe
             420                 425                 430

Asn Pro Gln Gly Asn Asp Met Thr Xaa Gly Leu Leu Thr Leu Ala Lys
     435                 440                 445

Gly Lys Pro Ile Gly Lys Glu Gly Tyr Tyr Trp Leu Lys Ile His Gly
     450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                 485                 490                 495

Leu Glu Asn Thr Trp Trp Ala Glu Gln Asp Ser Pro Phe Cys Phe Leu
             500                 505                 510

Ala Phe Cys Phe Glu Tyr Ala Gly Val Gln His His Gly Leu Ser Tyr
```

```
                515                 520                 525
Asn Cys Ser Leu Pro Leu Ala Phe Asp Gly Ser Cys Ser Gly Ile Gln
    530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                565                 570                 575

Lys Val Asn Glu Ile Leu Gln Ala Asp Ala Ile Asn Gly Thr Asp Asn
            580                 585                 590

Glu Val Val Thr Val Thr Asp Glu Asn Thr Gly Glu Ile Ser Glu Lys
        595                 600                 605

Val Lys Leu Gly Thr Lys Ala Leu Ala Gly Gln Trp Leu Ala Tyr Gly
    610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Asp Thr Ile Gln
                645                 650                 655

Pro Ala Ile Asp Ser Gly Lys Gly Leu Met Phe Thr Gln Pro Asn Gln
            660                 665                 670

Ala Ala Gly Tyr Met Ala Lys Leu Ile Trp Glu Ser Val Ser Val Thr
        675                 680                 685

Val Val Ala Ala Val Glu Ala Met Asn Trp Leu Lys Ser Ala Ala Lys
    690                 695                 700

Leu Leu Ala Ala Glu Val Lys Asp Lys Lys Thr Gly Glu Ile Leu Arg
705                 710                 715                 720

Lys Arg Cys Ala Val His Trp Val Thr Pro Asp Gly Phe Pro Val Trp
                725                 730                 735

Gln Glu Tyr Lys Lys Pro Ile Gln Thr Arg Leu Asn Leu Met Phe Leu
            740                 745                 750

Gly Gln Phe Arg Leu Gln Pro Thr Ile Asn Thr Asn Lys Asp Ser Glu
        755                 760                 765

Ile Asp Ala His Lys Gln Glu Ser Gly Ile Ala Pro Asn Phe Val His
    770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
            820                 825                 830

Val Asp Thr Tyr Glu Ser Cys Asp Val Leu Ala Asp Phe Tyr Asp Gln
        835                 840                 845

Phe Ala Asp Gln Leu His Glu Ser Gln Leu Asp Lys Met Pro Ala Leu
    850                 855                 860

Pro Ala Lys Gly Asn Leu Asn Leu Arg Asp Ile Leu Glu Ser Asp Phe
865                 870                 875                 880

Ala Phe Ala

<210> SEQ ID NO 11
<211> LENGTH: 883
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
```

<222> LOCATION: (632)..(632)
<223> OTHER INFORMATION: Xaa can be any naturally occurring amino acid

<400> SEQUENCE: 11

```
Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
    210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Gly Tyr Trp Ala
        275                 280                 285

Asn Gly Arg Arg Pro Leu Ala Leu Val Arg Thr His Ser Lys Lys Ala
    290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
            340                 345                 350

Pro Ala Ile Glu Arg Glu Glu Leu Pro Met Lys Pro Glu Asp Ile Asp
        355                 360                 365

Met Asn Pro Glu Ala Leu Thr Ala Trp Lys Arg Ala Ala Ala Ala Val
    370                 375                 380

Tyr Arg Lys Asp Lys Ala Arg Lys Ser Arg Arg Ile Ser Leu Glu Phe
385                 390                 395                 400
```

-continued

Met Leu Glu Gln Ala Asn Lys Phe Ala Asn His Lys Ala Ile Trp Phe
                405                 410                 415

Pro Tyr Asn Met Asp Trp Arg Gly Arg Val Tyr Ala Val Ser Met Phe
            420                 425                 430

Asn Pro Gln Gly Asn Asp Met Thr Lys Gly Leu Leu Thr Leu Ala Lys
        435                 440                 445

Gly Lys Pro Ile Gly Lys Glu Gly Tyr Tyr Trp Leu Lys Ile His Gly
    450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
            500                 505                 510

Ala Phe Cys Phe Glu Tyr Ala Gly Val Gln His His Gly Leu Ser Tyr
        515                 520                 525

Asn Cys Ser Leu Pro Leu Ala Phe Asp Gly Ser Cys Ser Gly Ile Gln
    530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                565                 570                 575

Lys Val Asn Glu Ile Leu Gln Ala Asp Ala Ile Asn Gly Thr Asp Asn
            580                 585                 590

Glu Val Thr Val Thr Asp Glu Asn Thr Gly Glu Ile Ser Glu Lys
        595                 600                 605

Val Lys Leu Gly Thr Lys Ala Leu Ala Gly Gln Trp Leu Ala Tyr Gly
    610                 615                 620

Val Thr Arg Ser Val Thr Lys Xaa Ser Val Met Thr Leu Ala Tyr Gly
625                 630                 635                 640

Ser Lys Glu Phe Gly Phe Arg Gln Gln Val Leu Glu Asp Thr Ile Gln
                645                 650                 655

Pro Ala Ile Asp Ser Gly Lys Gly Leu Met Phe Thr Gln Pro Asn Gln
            660                 665                 670

Ala Ala Gly Tyr Met Ala Lys Leu Ile Trp Glu Ser Val Ser Val Thr
        675                 680                 685

Val Val Ala Ala Val Glu Ala Met Asn Trp Leu Lys Ser Ala Ala Lys
    690                 695                 700

Leu Leu Ala Ala Glu Val Lys Asp Lys Lys Thr Gly Glu Ile Leu Arg
705                 710                 715                 720

Lys Arg Cys Ala Val His Trp Val Thr Pro Asp Gly Phe Pro Val Trp
                725                 730                 735

Gln Glu Tyr Lys Lys Pro Ile Gln Thr Arg Leu Asn Leu Met Phe Leu
            740                 745                 750

Gly Gln Phe Arg Leu Gln Pro Thr Ile Asn Thr Asn Lys Asp Ser Glu
        755                 760                 765

Ile Asp Ala His Lys Gln Glu Ser Gly Ile Ala Pro Asn Phe Val His
    770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
                805                 810                 815

```
Ile Pro Ala Asp Ala Ala Asn Leu Phe Lys Ala Val Arg Glu Thr Met
            820                 825                 830

Val Asp Thr Tyr Glu Ser Cys Asp Val Leu Ala Asp Phe Tyr Asp Gln
        835                 840                 845

Phe Ala Asp Gln Leu His Glu Ser Gln Leu Asp Lys Met Pro Ala Leu
    850                 855                 860

Pro Ala Lys Gly Asn Leu Asn Leu Arg Asp Ile Leu Glu Ser Asp Phe
865                 870                 875                 880

Ala Phe Ala

<210> SEQ ID NO 12
<211> LENGTH: 883
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (811)..(811)
<223> OTHER INFORMATION: Xaa can be any naturally occurring amino acid

<400> SEQUENCE: 12

Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
    210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270
```

```
Val Pro Pro Lys Pro Trp Thr Gly Ile Thr Gly Gly Tyr Trp Ala
        275                 280                 285

Asn Gly Arg Arg Pro Leu Ala Leu Val Arg Thr His Ser Lys Lys Ala
    290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
            340                 345                 350

Pro Ala Ile Glu Arg Glu Leu Pro Met Lys Pro Glu Asp Ile Asp
        355                 360                 365

Met Asn Pro Glu Ala Leu Thr Ala Trp Lys Arg Ala Ala Ala Val
    370                 375                 380

Tyr Arg Lys Asp Lys Ala Arg Lys Ser Arg Ile Ser Leu Glu Phe
385                 390                 395                 400

Met Leu Glu Gln Ala Asn Lys Phe Ala Asn His Lys Ala Ile Trp Phe
                405                 410                 415

Pro Tyr Asn Met Asp Trp Arg Gly Arg Val Tyr Ala Val Ser Met Phe
            420                 425                 430

Asn Pro Gln Gly Asn Asp Met Thr Lys Gly Leu Leu Thr Leu Ala Lys
        435                 440                 445

Gly Lys Pro Ile Gly Lys Glu Gly Tyr Tyr Trp Leu Lys Ile His Gly
    450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
            500                 505                 510

Ala Phe Cys Phe Glu Tyr Ala Gly Val Gln His His Gly Leu Ser Tyr
        515                 520                 525

Asn Cys Ser Leu Pro Leu Ala Phe Asp Gly Ser Cys Ser Gly Ile Gln
    530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                565                 570                 575

Lys Val Asn Glu Ile Leu Gln Ala Asp Ala Ile Asn Gly Thr Asp Asn
            580                 585                 590

Glu Val Val Thr Val Thr Asp Glu Asn Thr Gly Glu Ile Ser Glu Lys
        595                 600                 605

Val Lys Leu Gly Thr Lys Ala Leu Ala Gly Gln Trp Leu Ala Tyr Gly
    610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Asp Thr Ile Gln
                645                 650                 655

Pro Ala Ile Asp Ser Gly Lys Gly Leu Met Phe Thr Gln Pro Asn Gln
            660                 665                 670

Ala Ala Gly Tyr Met Ala Lys Leu Ile Trp Glu Ser Val Ser Val Thr
        675                 680                 685

Val Val Ala Ala Val Glu Ala Met Asn Trp Leu Lys Ser Ala Ala Lys
```

```
                690                 695                 700
Leu Leu Ala Ala Glu Val Lys Asp Lys Lys Thr Gly Glu Ile Leu Arg
705                 710                 715                 720

Lys Arg Cys Ala Val His Trp Val Thr Pro Asp Gly Phe Pro Val Trp
                725                 730                 735

Gln Glu Tyr Lys Lys Pro Ile Gln Thr Arg Leu Asn Leu Met Phe Leu
                740                 745                 750

Gly Gln Phe Arg Leu Gln Pro Thr Ile Asn Thr Asn Lys Asp Ser Glu
                755                 760                 765

Ile Asp Ala His Lys Gln Glu Ser Gly Ile Ala Pro Asn Phe Val His
                770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile Xaa Asp Ser Phe Gly Thr
                805                 810                 815

Ile Pro Ala Asp Ala Ala Asn Leu Phe Lys Ala Val Arg Glu Thr Met
                820                 825                 830

Val Asp Thr Tyr Glu Ser Cys Asp Val Leu Ala Asp Phe Tyr Asp Gln
                835                 840                 845

Phe Ala Asp Gln Leu His Glu Ser Gln Leu Asp Lys Met Pro Ala Leu
                850                 855                 860

Pro Ala Lys Gly Asn Leu Asn Leu Arg Asp Ile Leu Glu Ser Asp Phe
865                 870                 875                 880

Ala Phe Ala

<210> SEQ ID NO 13
<211> LENGTH: 883
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (880)..(880)
<223> OTHER INFORMATION: Xaa can be any naturally occurring amino acid

<400> SEQUENCE: 13

Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
                20                  25                  30

Ala Arg Glu Gln Leu Ala Leu Glu His Glu Ser Tyr Glu Met Gly Glu
            35                  40                  45

Ala Arg Phe Arg Lys Met Phe Glu Arg Gln Leu Lys Ala Gly Glu Val
        50                  55                  60

Ala Asp Asn Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
                100                 105                 110

Ala Val Ala Tyr Ile Thr Ile Lys Thr Thr Leu Ala Cys Leu Thr Ser
            115                 120                 125

Ala Asp Asn Thr Thr Val Gln Ala Val Ala Ser Ala Ile Gly Arg Ala
        130                 135                 140

Ile Glu Asp Glu Ala Arg Phe Gly Arg Ile Arg Asp Leu Glu Ala Lys
```

```
            145                 150                 155                 160
        His Phe Lys Lys Asn Val Glu Glu Gln Leu Asn Lys Arg Val Gly His
                        165                 170                 175

Val Tyr Lys Lys Ala Phe Met Gln Val Val Glu Ala Asp Met Leu Ser
                        180                 185                 190

Lys Gly Leu Gly Gly Glu Ala Trp Ser Ser Trp His Lys Glu Asp
                        195                 200                 205

Ser Ile His Val Gly Val Arg Cys Ile Glu Met Leu Ile Glu Ser Thr
                        210                 215                 220

Gly Met Val Ser Leu His Arg Gln Asn Ala Gly Val Val Gly Gln Asp
        225                 230                 235                 240

Ser Glu Thr Ile Glu Leu Ala Pro Glu Tyr Ala Glu Ala Ile Ala Thr
                        245                 250                 255

Arg Ala Gly Ala Leu Ala Gly Ile Ser Pro Met Phe Gln Pro Cys Val
                        260                 265                 270

Val Pro Pro Lys Pro Trp Thr Gly Ile Thr Gly Gly Tyr Trp Ala
                        275                 280                 285

Asn Gly Arg Arg Pro Leu Ala Leu Val Arg Thr His Ser Lys Lys Ala
                        290                 295                 300

Leu Met Arg Tyr Glu Asp Val Tyr Met Pro Glu Val Tyr Lys Ala Ile
        305                 310                 315                 320

Asn Ile Ala Gln Asn Thr Ala Trp Lys Ile Asn Lys Lys Val Leu Ala
                        325                 330                 335

Val Ala Asn Val Ile Thr Lys Trp Lys His Cys Pro Val Glu Asp Ile
                        340                 345                 350

Pro Ala Ile Glu Arg Glu Leu Pro Met Lys Pro Glu Asp Ile Asp
                        355                 360                 365

Met Asn Pro Glu Ala Leu Thr Ala Trp Lys Arg Ala Ala Ala Val
                        370                 375                 380

Tyr Arg Lys Asp Lys Ala Arg Lys Ser Arg Ile Ser Leu Glu Phe
        385                 390                 395                 400

Met Leu Glu Gln Ala Asn Lys Phe Ala Asn His Lys Ala Ile Trp Phe
                        405                 410                 415

Pro Tyr Asn Met Asp Trp Arg Gly Arg Val Tyr Ala Val Ser Met Phe
                        420                 425                 430

Asn Pro Gln Gly Asn Asp Met Thr Lys Gly Leu Leu Thr Leu Ala Lys
                        435                 440                 445

Gly Lys Pro Ile Gly Lys Glu Gly Tyr Tyr Trp Leu Lys Ile His Gly
                        450                 455                 460

Ala Asn Cys Ala Gly Val Asp Lys Val Pro Phe Pro Glu Arg Ile Lys
        465                 470                 475                 480

Phe Ile Glu Glu Asn His Glu Asn Ile Met Ala Cys Ala Lys Ser Pro
                        485                 490                 495

Leu Glu Asn Thr Trp Trp Ala Glu Gln Asp Ser Pro Phe Cys Phe Leu
                        500                 505                 510

Ala Phe Cys Phe Glu Tyr Ala Gly Val Gln His His Gly Leu Ser Tyr
                        515                 520                 525

Asn Cys Ser Leu Pro Leu Ala Phe Asp Gly Ser Cys Ser Gly Ile Gln
                        530                 535                 540

His Phe Ser Ala Met Leu Arg Asp Glu Val Gly Gly Arg Ala Val Asn
        545                 550                 555                 560

Leu Leu Pro Ser Glu Thr Val Gln Asp Ile Tyr Gly Ile Val Ala Lys
                        565                 570                 575
```

Lys Val Asn Glu Ile Leu Gln Ala Asp Ala Ile Asn Gly Thr Asp Asn
            580                 585                 590

Glu Val Val Thr Val Thr Asp Glu Asn Thr Gly Glu Ile Ser Glu Lys
            595                 600                 605

Val Lys Leu Gly Thr Lys Ala Leu Ala Gly Gln Trp Leu Ala Tyr Gly
610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Asp Thr Ile Gln
            645                 650                 655

Pro Ala Ile Asp Ser Gly Lys Gly Leu Met Phe Thr Gln Pro Asn Gln
            660                 665                 670

Ala Ala Gly Tyr Met Ala Lys Leu Ile Trp Glu Ser Val Ser Val Thr
            675                 680                 685

Val Val Ala Ala Val Glu Ala Met Asn Trp Leu Lys Ser Ala Ala Lys
            690                 695                 700

Leu Leu Ala Ala Glu Val Lys Asp Lys Lys Thr Gly Glu Ile Leu Arg
705                 710                 715                 720

Lys Arg Cys Ala Val His Trp Val Thr Pro Asp Gly Phe Pro Val Trp
            725                 730                 735

Gln Glu Tyr Lys Lys Pro Ile Gln Thr Arg Leu Asn Leu Met Phe Leu
            740                 745                 750

Gly Gln Phe Arg Leu Gln Pro Thr Ile Asn Thr Asn Lys Asp Ser Glu
            755                 760                 765

Ile Asp Ala His Lys Gln Glu Ser Gly Ile Ala Pro Asn Phe Val His
            770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
            805                 810                 815

Ile Pro Ala Asp Ala Ala Asn Leu Phe Lys Ala Val Arg Glu Thr Met
            820                 825                 830

Val Asp Thr Tyr Glu Ser Cys Asp Val Leu Ala Asp Phe Tyr Asp Gln
            835                 840                 845

Phe Ala Asp Gln Leu His Glu Ser Gln Leu Asp Lys Met Pro Ala Leu
            850                 855                 860

Pro Ala Lys Gly Asn Leu Asn Leu Arg Asp Ile Leu Glu Ser Asp Xaa
865                 870                 875                 880

Ala Phe Ala

<210> SEQ ID NO 14
<211> LENGTH: 884
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (884)..(884)
<223> OTHER INFORMATION: Xaa can be any naturally occurring amino acid

<400> SEQUENCE: 14

Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

```
Ala Arg Glu Gln Leu Ala Leu Glu His Glu Ser Tyr Glu Met Gly Glu
            35                  40                  45

Ala Arg Phe Arg Lys Met Phe Glu Arg Gln Leu Lys Ala Gly Glu Val
        50                  55                  60

Ala Asp Asn Ala Ala Lys Pro Leu Ile Thr Thr Leu Leu Pro Lys
65              70                  75                  80

Met Ile Ala Arg Ile Asn Asp Trp Phe Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
            115                 120                 125

Ala Asp Asn Thr Thr Val Gln Ala Val Ala Ser Ala Ile Gly Arg Ala
            130                 135                 140

Ile Glu Asp Glu Ala Arg Phe Gly Arg Ile Arg Asp Leu Glu Ala Lys
145                 150                 155                 160

His Phe Lys Lys Asn Val Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
            195                 200                 205

Ser Ile His Val Gly Val Arg Cys Ile Glu Met Leu Ile Glu Ser Thr
        210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Tyr Trp Ala
        275                 280                 285

Asn Gly Arg Arg Pro Leu Ala Leu Val Arg Thr His Ser Lys Lys Ala
        290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
            340                 345                 350

Pro Ala Ile Glu Arg Glu Glu Leu Pro Met Lys Pro Glu Asp Ile Asp
            355                 360                 365

Met Asn Pro Glu Ala Leu Thr Ala Trp Lys Arg Ala Ala Ala Val
370                 375                 380

Tyr Arg Lys Asp Lys Ala Arg Lys Ser Arg Ile Ser Leu Glu Phe
385                 390                 395                 400

Met Leu Glu Gln Ala Asn Lys Phe Ala Asn His Lys Ala Ile Trp Phe
                405                 410                 415

Pro Tyr Asn Met Asp Trp Arg Gly Arg Val Tyr Ala Val Ser Met Phe
            420                 425                 430

Asn Pro Gln Gly Asn Asp Met Thr Lys Gly Leu Leu Thr Leu Ala Lys
            435                 440                 445
```

-continued

```
Gly Lys Pro Ile Gly Lys Glu Gly Tyr Tyr Trp Leu Lys Ile His Gly
    450             455                 460
Ala Asn Cys Ala Gly Val Asp Lys Val Pro Phe Pro Glu Arg Ile Lys
465             470                 475                 480
Phe Ile Glu Glu Asn His Glu Asn Ile Met Ala Cys Ala Lys Ser Pro
                485                 490                 495
Leu Glu Asn Thr Trp Trp Ala Glu Gln Asp Ser Pro Phe Cys Phe Leu
            500                 505                 510
Ala Phe Cys Phe Glu Tyr Ala Gly Val Gln His His Gly Leu Ser Tyr
        515                 520                 525
Asn Cys Ser Leu Pro Leu Ala Phe Asp Gly Ser Cys Ser Gly Ile Gln
530                 535                 540
His Phe Ser Ala Met Leu Arg Asp Glu Val Gly Gly Arg Ala Val Asn
545                 550                 555                 560
Leu Leu Pro Ser Glu Thr Val Gln Asp Ile Tyr Gly Ile Val Ala Lys
                565                 570                 575
Lys Val Asn Glu Ile Leu Gln Ala Asp Ala Ile Asn Gly Thr Asp Asn
            580                 585                 590
Glu Val Val Thr Val Thr Asp Glu Asn Thr Gly Glu Ile Ser Glu Lys
        595                 600                 605
Val Lys Leu Gly Thr Lys Ala Leu Ala Gly Gln Trp Leu Ala Tyr Gly
    610                 615                 620
Val Thr Arg Ser Val Thr Lys Arg Ser Val Met Thr Leu Ala Tyr Gly
625                 630                 635                 640
Ser Lys Glu Phe Gly Phe Arg Gln Gln Val Leu Glu Asp Thr Ile Gln
                645                 650                 655
Pro Ala Ile Asp Ser Gly Lys Gly Leu Met Phe Thr Gln Pro Asn Gln
            660                 665                 670
Ala Ala Gly Tyr Met Ala Lys Leu Ile Trp Glu Ser Val Ser Val Thr
        675                 680                 685
Val Val Ala Ala Val Glu Ala Met Asn Trp Leu Lys Ser Ala Ala Lys
    690                 695                 700
Leu Leu Ala Ala Glu Val Lys Asp Lys Lys Thr Gly Glu Ile Leu Arg
705                 710                 715                 720
Lys Arg Cys Ala Val His Trp Val Thr Pro Asp Gly Phe Pro Val Trp
                725                 730                 735
Gln Glu Tyr Lys Lys Pro Ile Gln Thr Arg Leu Asn Leu Met Phe Leu
            740                 745                 750
Gly Gln Phe Arg Leu Gln Pro Thr Ile Asn Thr Asn Lys Asp Ser Glu
        755                 760                 765
Ile Asp Ala His Lys Gln Glu Ser Gly Ile Ala Pro Asn Phe Val His
    770                 775                 780
Ser Gln Asp Gly Ser His Leu Arg Lys Thr Val Val Trp Ala His Glu
785                 790                 795                 800
Lys Tyr Gly Ile Glu Ser Phe Ala Leu Ile His Asp Ser Phe Gly Thr
                805                 810                 815
Ile Pro Ala Asp Ala Ala Asn Leu Phe Lys Ala Val Arg Glu Thr Met
            820                 825                 830
Val Asp Thr Tyr Glu Ser Cys Asp Val Leu Ala Asp Phe Tyr Asp Gln
        835                 840                 845
Phe Ala Asp Gln Leu His Glu Ser Gln Leu Asp Lys Met Pro Ala Leu
    850                 855                 860
Pro Ala Lys Gly Asn Leu Asn Leu Arg Asp Ile Leu Glu Ser Asp Phe
```

```
865                 870                 875                 880

Ala Phe Ala Xaa

<210> SEQ ID NO 15
<211> LENGTH: 883
<212> TYPE: PRT
<213> ORGANISM: Artificial Sequence
<220> FEATURE:
<223> OTHER INFORMATION: Synthetic Polypeptide

<400> SEQUENCE: 15

Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Ala Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
    210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Gly Tyr Trp Ala
        275                 280                 285

Asn Gly Arg Arg Pro Leu Ala Leu Val Arg Thr His Ser Lys Lys Ala
    290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
            340                 345                 350
```

```
Pro Ala Ile Glu Arg Glu Glu Leu Pro Met Lys Pro Glu Asp Ile Asp
        355                 360                 365
Met Asn Pro Glu Ala Leu Thr Ala Trp Lys Arg Ala Ala Ala Ala Val
        370                 375                 380
Tyr Arg Lys Asp Lys Ala Arg Lys Ser Arg Arg Ile Ser Leu Glu Phe
385                 390                 395                 400
Met Leu Glu Gln Ala Asn Lys Phe Ala Asn His Lys Ala Ile Trp Phe
                405                 410                 415
Pro Tyr Asn Met Asp Trp Arg Gly Arg Val Tyr Ala Val Ser Met Phe
                420                 425                 430
Asn Pro Gln Gly Asn Asp Met Thr Lys Gly Leu Leu Thr Leu Ala Lys
                435                 440                 445
Gly Lys Pro Ile Gly Lys Glu Gly Tyr Tyr Trp Leu Lys Ile His Gly
                450                 455                 460
Ala Asn Cys Ala Gly Val Asp Lys Val Pro Phe Pro Glu Arg Ile Lys
465                 470                 475                 480
Phe Ile Glu Glu Asn His Glu Asn Ile Met Ala Cys Ala Lys Ser Pro
                485                 490                 495
Leu Glu Asn Thr Trp Trp Ala Glu Gln Asp Ser Pro Phe Cys Phe Leu
                500                 505                 510
Ala Phe Cys Phe Glu Tyr Ala Gly Val Gln His His Gly Leu Ser Tyr
                515                 520                 525
Asn Cys Ser Leu Pro Leu Ala Phe Asp Gly Ser Cys Ser Gly Ile Gln
                530                 535                 540
His Phe Ser Ala Met Leu Arg Asp Glu Val Gly Gly Arg Ala Val Asn
545                 550                 555                 560
Leu Leu Pro Ser Glu Thr Val Gln Asp Ile Tyr Gly Ile Val Ala Lys
                565                 570                 575
Lys Val Asn Glu Ile Leu Gln Ala Asp Ala Ile Asn Gly Thr Asp Asn
                580                 585                 590
Glu Val Val Thr Val Thr Asp Glu Asn Thr Gly Glu Ile Ser Glu Lys
                595                 600                 605
Val Lys Leu Gly Thr Lys Ala Leu Ala Gly Gln Trp Leu Ala Tyr Gly
                610                 615                 620
Val Thr Arg Ser Val Thr Lys Arg Ser Val Met Thr Leu Ala Tyr Gly
625                 630                 635                 640
Ser Lys Glu Phe Gly Phe Arg Gln Gln Val Leu Glu Asp Thr Ile Gln
                645                 650                 655
Pro Ala Ile Asp Ser Gly Lys Gly Leu Met Phe Thr Gln Pro Asn Gln
                660                 665                 670
Ala Ala Gly Tyr Met Ala Lys Leu Ile Trp Glu Ser Val Ser Val Thr
                675                 680                 685
Val Val Ala Ala Val Glu Ala Met Asn Trp Leu Lys Ser Ala Ala Lys
                690                 695                 700
Leu Leu Ala Ala Glu Val Lys Asp Lys Lys Thr Gly Glu Ile Leu Arg
705                 710                 715                 720
Lys Arg Cys Ala Val His Trp Val Thr Pro Asp Gly Phe Pro Val Trp
                725                 730                 735
Gln Glu Tyr Lys Lys Pro Ile Gln Thr Arg Leu Asn Leu Met Phe Leu
                740                 745                 750
Gly Gln Phe Arg Leu Gln Pro Thr Ile Asn Thr Asn Lys Asp Ser Glu
                755                 760                 765
```

```
Ile Asp Ala His Lys Gln Glu Ser Gly Ile Ala Pro Asn Phe Val His
        770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
                820                 825                 830

Val Asp Thr Tyr Glu Ser Cys Asp Val Leu Ala Asp Phe Tyr Asp Gln
            835                 840                 845

Phe Ala Asp Gln Leu His Glu Ser Gln Leu Asp Lys Met Pro Ala Leu
        850                 855                 860

Pro Ala Lys Gly Asn Leu Asn Leu Arg Asp Ile Leu Glu Ser Asp Phe
865                 870                 875                 880

Ala Phe Ala

<210> SEQ ID NO 16
<211> LENGTH: 883
<212> TYPE: PRT
<213> ORGANISM: Artificial Sequence
<220> FEATURE:
<223> OTHER INFORMATION: Synthetic Polypeptide

<400> SEQUENCE: 16

Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
    210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
```

-continued

```
            245                 250                 255
Arg Ala Gly Ala Leu Ala Gly Ile Ser Pro Met Phe Gln Pro Cys Val
            260                 265                 270
Val Pro Pro Lys Pro Trp Thr Gly Ile Thr Gly Gly Tyr Trp Ala
            275                 280             285
Asn Gly Arg Arg Pro Leu Ala Leu Val Arg Thr His Ser Lys Lys Ala
            290                 295                 300
Leu Met Arg Tyr Glu Asp Val Tyr Met Pro Glu Val Tyr Lys Ala Ile
305                 310                 315                 320
Asn Ile Ala Gln Asn Thr Ala Trp Lys Ile Asn Lys Val Leu Ala
                325                 330                 335
Val Ala Asn Val Ile Thr Lys Trp Lys His Cys Pro Val Lys Asp Ile
                340                 345                 350
Pro Ala Ile Glu Arg Glu Leu Pro Met Lys Pro Glu Asp Ile Asp
                355                 360                 365
Met Asn Pro Glu Ala Leu Thr Ala Trp Lys Arg Ala Ala Ala Val
        370                 375                 380
Tyr Arg Lys Asp Lys Ala Arg Lys Ser Arg Ile Ser Leu Glu Phe
385                 390                 395                 400
Met Leu Glu Gln Ala Asn Lys Phe Ala Asn His Lys Ala Ile Trp Phe
                    405                 410                 415
Pro Tyr Asn Met Asp Trp Arg Gly Arg Val Tyr Ala Val Ser Met Phe
                420                 425                 430
Asn Pro Gln Gly Asn Asp Met Thr Lys Gly Leu Leu Thr Leu Ala Lys
                435                 440                 445
Gly Lys Pro Ile Gly Lys Glu Gly Tyr Tyr Trp Leu Lys Ile His Gly
            450                 455                 460
Ala Asn Cys Ala Gly Val Asp Lys Val Pro Phe Pro Glu Arg Ile Lys
465                 470                 475                 480
Phe Ile Glu Glu Asn His Glu Asn Ile Met Ala Cys Ala Lys Ser Pro
                    485                 490                 495
Leu Glu Asn Thr Trp Trp Ala Glu Gln Asp Ser Pro Phe Cys Phe Leu
                500                 505                 510
Ala Phe Cys Phe Glu Tyr Ala Gly Val Gln His His Gly Leu Ser Tyr
            515                 520                 525
Asn Cys Ser Leu Pro Leu Ala Phe Asp Gly Ser Cys Ser Gly Ile Gln
            530                 535                 540
His Phe Ser Ala Met Leu Arg Asp Glu Val Gly Gly Arg Ala Val Asn
545                 550                 555                 560
Leu Leu Pro Ser Glu Thr Val Gln Asp Ile Tyr Gly Ile Val Ala Lys
                    565                 570                 575
Lys Val Asn Glu Ile Leu Gln Ala Asp Ala Ile Asn Gly Thr Asp Asn
                580                 585                 590
Glu Val Val Thr Val Thr Asp Glu Asn Thr Gly Glu Ile Ser Glu Lys
                595                 600                 605
Val Lys Leu Gly Thr Lys Ala Leu Ala Gly Gln Trp Leu Ala Tyr Gly
            610                 615                 620
Val Thr Arg Ser Val Thr Lys Arg Ser Val Met Thr Leu Ala Tyr Gly
625                 630                 635                 640
Ser Lys Glu Phe Gly Phe Arg Gln Gln Val Leu Glu Asp Thr Ile Gln
                    645                 650                 655
Pro Ala Ile Asp Ser Gly Lys Gly Leu Met Phe Thr Gln Pro Asn Gln
                660                 665                 670
```

```
Ala Ala Gly Tyr Met Ala Lys Leu Ile Trp Glu Ser Val Ser Val Thr
            675                 680                 685

Val Val Ala Ala Val Glu Ala Met Asn Trp Leu Lys Ser Ala Ala Lys
690                 695                 700

Leu Leu Ala Ala Glu Val Lys Asp Lys Thr Gly Glu Ile Leu Arg
705                 710                 715                 720

Lys Arg Cys Ala Val His Trp Val Thr Pro Asp Gly Phe Pro Val Trp
                725                 730                 735

Gln Glu Tyr Lys Lys Pro Ile Gln Thr Arg Leu Asn Leu Met Phe Leu
            740                 745                 750

Gly Gln Phe Arg Leu Gln Pro Thr Ile Asn Thr Asn Lys Asp Ser Glu
        755                 760                 765

Ile Asp Ala His Lys Gln Glu Ser Gly Ile Ala Pro Asn Phe Val His
    770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
            820                 825                 830

Val Asp Thr Tyr Glu Ser Cys Asp Val Leu Ala Asp Phe Tyr Asp Gln
        835                 840                 845

Phe Ala Asp Gln Leu His Glu Ser Gln Leu Asp Lys Met Pro Ala Leu
    850                 855                 860

Pro Ala Lys Gly Asn Leu Asn Leu Arg Asp Ile Leu Glu Ser Asp Phe
865                 870                 875                 880

Ala Phe Ala

<210> SEQ ID NO 17
<211> LENGTH: 883
<212> TYPE: PRT
<213> ORGANISM: Artificial Sequence
<220> FEATURE:
<223> OTHER INFORMATION: Synthetic Polypeptide

<400> SEQUENCE: 17

Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140
```

```
Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
    210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Tyr Trp Ala
        275                 280                 285

Asn Gly Arg Arg Pro Leu Ala Leu Val Arg Thr His Ser Lys Lys Ala
290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Asn Asp Ile
            340                 345                 350

Pro Ala Ile Glu Arg Glu Leu Pro Met Lys Pro Glu Asp Ile Asp
        355                 360                 365

Met Asn Pro Glu Ala Leu Thr Ala Trp Lys Arg Ala Ala Ala Val
370                 375                 380

Tyr Arg Lys Asp Lys Ala Arg Lys Ser Arg Arg Ile Ser Leu Glu Phe
385                 390                 395                 400

Met Leu Glu Gln Ala Asn Lys Phe Ala Asn His Lys Ala Ile Trp Phe
                405                 410                 415

Pro Tyr Asn Met Asp Trp Arg Gly Arg Val Tyr Ala Val Ser Met Phe
            420                 425                 430

Asn Pro Gln Gly Asn Asp Met Thr Lys Gly Leu Leu Thr Leu Ala Lys
        435                 440                 445

Gly Lys Pro Ile Gly Lys Glu Gly Tyr Tyr Trp Leu Lys Ile His Gly
450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
            500                 505                 510

Ala Phe Cys Phe Glu Tyr Ala Gly Val Gln His His Gly Leu Ser Tyr
        515                 520                 525

Asn Cys Ser Leu Pro Leu Ala Phe Asp Gly Ser Cys Ser Gly Ile Gln
530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
```

565                 570                 575

Lys Val Asn Glu Ile Leu Gln Ala Asp Ala Ile Asn Gly Thr Asp Asn
            580                 585                 590

Glu Val Val Thr Val Thr Asp Glu Asn Thr Gly Glu Ile Ser Glu Lys
            595                 600                 605

Val Lys Leu Gly Thr Lys Ala Leu Ala Gly Gln Trp Leu Ala Tyr Gly
            610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Asp Thr Ile Gln
            645                 650                 655

Pro Ala Ile Asp Ser Gly Lys Gly Leu Met Phe Thr Gln Pro Asn Gln
            660                 665                 670

Ala Ala Gly Tyr Met Ala Lys Leu Ile Trp Glu Ser Val Ser Val Thr
            675                 680                 685

Val Val Ala Ala Val Glu Ala Met Asn Trp Leu Lys Ser Ala Ala Lys
            690                 695                 700

Leu Leu Ala Ala Glu Val Lys Asp Lys Lys Thr Gly Glu Ile Leu Arg
705                 710                 715                 720

Lys Arg Cys Ala Val His Trp Val Thr Pro Asp Gly Phe Pro Val Trp
            725                 730                 735

Gln Glu Tyr Lys Lys Pro Ile Gln Thr Arg Leu Asn Leu Met Phe Leu
            740                 745                 750

Gly Gln Phe Arg Leu Gln Pro Thr Ile Asn Thr Asn Lys Asp Ser Glu
            755                 760                 765

Ile Asp Ala His Lys Gln Glu Ser Gly Ile Ala Pro Asn Phe Val His
            770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
            805                 810                 815

Ile Pro Ala Asp Ala Ala Asn Leu Phe Lys Ala Val Arg Glu Thr Met
            820                 825                 830

Val Asp Thr Tyr Glu Ser Cys Asp Val Leu Ala Asp Phe Tyr Asp Gln
            835                 840                 845

Phe Ala Asp Gln Leu His Glu Ser Gln Leu Asp Lys Met Pro Ala Leu
            850                 855                 860

Pro Ala Lys Gly Asn Leu Asn Leu Arg Asp Ile Leu Glu Ser Asp Phe
865                 870                 875                 880

Ala Phe Ala

<210> SEQ ID NO 18
<211> LENGTH: 883
<212> TYPE: PRT
<213> ORGANISM: Artificial Sequence
<220> FEATURE:
<223> OTHER INFORMATION: Synthetic Polypeptide

<400> SEQUENCE: 18

Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
            35                  40                  45

```
Ala Arg Phe Arg Lys Met Phe Glu Arg Gln Leu Lys Ala Gly Glu Val
         50                  55                  60

Ala Asp Asn Ala Ala Lys Pro Leu Ile Thr Thr Leu Leu Pro Lys
 65              70                  75                  80

Met Ile Ala Arg Ile Asn Asp Trp Phe Glu Glu Val Lys Ala Lys Arg
                 85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
             115                 120                 125

Ala Asp Asn Thr Thr Val Gln Ala Val Ala Ser Ala Ile Gly Arg Ala
            130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
            195                 200                 205

Ser Ile His Val Gly Val Arg Cys Ile Glu Met Leu Ile Glu Ser Thr
    210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Tyr Trp Ala
            275                 280                 285

Asn Gly Arg Arg Pro Leu Ala Leu Val Arg Thr His Ser Lys Lys Ala
    290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Ala Asp Ile
            340                 345                 350

Pro Ala Ile Glu Arg Glu Glu Leu Pro Met Lys Pro Glu Asp Ile Asp
            355                 360                 365

Met Asn Pro Glu Ala Leu Thr Ala Trp Lys Arg Ala Ala Ala Val
    370                 375                 380

Tyr Arg Lys Asp Lys Ala Arg Lys Ser Arg Arg Ile Ser Leu Glu Phe
385                 390                 395                 400

Met Leu Glu Gln Ala Asn Lys Phe Ala Asn His Lys Ala Ile Trp Phe
                405                 410                 415

Pro Tyr Asn Met Asp Trp Arg Gly Arg Val Tyr Ala Val Ser Met Phe
            420                 425                 430

Asn Pro Gln Gly Asn Asp Met Thr Lys Gly Leu Leu Thr Leu Ala Lys
            435                 440                 445

Gly Lys Pro Ile Gly Lys Glu Gly Tyr Tyr Trp Leu Lys Ile His Gly
    450                 455                 460
```

```
Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
            485                 490                 495

Leu Glu Asn Thr Trp Trp Ala Glu Gln Asp Ser Pro Phe Cys Phe Leu
            500                 505                 510

Ala Phe Cys Phe Glu Tyr Ala Gly Val Gln His His Gly Leu Ser Tyr
            515                 520                 525

Asn Cys Ser Leu Pro Leu Ala Phe Asp Gly Ser Cys Ser Gly Ile Gln
            530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
            565                 570                 575

Lys Val Asn Glu Ile Leu Gln Ala Asp Ala Ile Asn Gly Thr Asp Asn
            580                 585                 590

Glu Val Val Thr Val Thr Asp Glu Asn Thr Gly Glu Ile Ser Glu Lys
            595                 600                 605

Val Lys Leu Gly Thr Lys Ala Leu Ala Gly Gln Trp Leu Ala Tyr Gly
610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Asp Thr Ile Gln
            645                 650                 655

Pro Ala Ile Asp Ser Gly Lys Gly Leu Met Phe Thr Gln Pro Asn Gln
            660                 665                 670

Ala Ala Gly Tyr Met Ala Lys Leu Ile Trp Glu Ser Val Ser Val Thr
            675                 680                 685

Val Val Ala Ala Val Glu Ala Met Asn Trp Leu Lys Ser Ala Ala Lys
            690                 695                 700

Leu Leu Ala Ala Glu Val Lys Asp Lys Lys Thr Gly Glu Ile Leu Arg
705                 710                 715                 720

Lys Arg Cys Ala Val His Trp Val Thr Pro Asp Gly Phe Pro Val Trp
            725                 730                 735

Gln Glu Tyr Lys Lys Pro Ile Gln Thr Arg Leu Asn Leu Met Phe Leu
            740                 745                 750

Gly Gln Phe Arg Leu Gln Pro Thr Ile Asn Thr Asn Lys Asp Ser Glu
            755                 760                 765

Ile Asp Ala His Lys Gln Glu Ser Gly Ile Ala Pro Asn Phe Val His
            770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
            805                 810                 815

Ile Pro Ala Asp Ala Ala Asn Leu Phe Lys Ala Val Arg Glu Thr Met
            820                 825                 830

Val Asp Thr Tyr Glu Ser Cys Asp Val Leu Ala Asp Phe Tyr Asp Gln
            835                 840                 845

Phe Ala Asp Gln Leu His Glu Ser Gln Leu Asp Lys Met Pro Ala Leu
            850                 855                 860

Pro Ala Lys Gly Asn Leu Asn Leu Arg Asp Ile Leu Glu Ser Asp Phe
865                 870                 875                 880

Ala Phe Ala
```

```
<210> SEQ ID NO 19
<211> LENGTH: 883
<212> TYPE: PRT
<213> ORGANISM: Artificial Sequence
<220> FEATURE:
<223> OTHER INFORMATION: Synthetic Polypeptide

<400> SEQUENCE: 19
```

| | | | | | | | | | | | | | | |
|---|---|---|---|---|---|---|---|---|---|---|---|---|---|---|
| Met | Asn | Thr | Ile | Asn | Ile | Ala | Lys | Asn | Asp | Phe | Ser | Asp | Ile | Glu | Leu |
| 1 | | | | 5 | | | | | 10 | | | | | 15 | |
| Ala | Ala | Ile | Pro | Phe | Asn | Thr | Leu | Ala | Asp | His | Tyr | Gly | Glu | Arg | Leu |
| | | | 20 | | | | | 25 | | | | | 30 | | |
| Ala | Arg | Glu | Gln | Leu | Ala | Leu | Glu | His | Glu | Ser | Tyr | Glu | Met | Gly | Glu |
| | | 35 | | | | | 40 | | | | | 45 | | | |
| Ala | Arg | Phe | Arg | Lys | Met | Phe | Glu | Arg | Gln | Leu | Lys | Ala | Gly | Glu | Val |
| | 50 | | | | | 55 | | | | | 60 | | | | |
| Ala | Asp | Asn | Ala | Ala | Lys | Pro | Leu | Ile | Thr | Thr | Leu | Leu | Pro | Lys | |
| 65 | | | | | 70 | | | | | 75 | | | | | 80 |
| Met | Ile | Ala | Arg | Ile | Asn | Asp | Trp | Phe | Glu | Glu | Val | Lys | Ala | Lys | Arg |
| | | | | 85 | | | | | 90 | | | | | 95 | |
| Gly | Lys | Arg | Pro | Thr | Ala | Phe | Gln | Phe | Leu | Gln | Glu | Ile | Lys | Pro | Glu |
| | | | 100 | | | | | 105 | | | | | 110 | | |
| Ala | Val | Ala | Tyr | Ile | Thr | Ile | Lys | Thr | Thr | Leu | Ala | Cys | Leu | Thr | Ser |
| | | | 115 | | | | | 120 | | | | | 125 | | |
| Ala | Asp | Asn | Thr | Thr | Val | Gln | Ala | Val | Ala | Ser | Ala | Ile | Gly | Arg | Ala |
| | 130 | | | | | 135 | | | | | 140 | | | | |
| Ile | Glu | Asp | Glu | Ala | Arg | Phe | Gly | Arg | Ile | Arg | Asp | Leu | Glu | Ala | Lys |
| 145 | | | | | 150 | | | | | 155 | | | | | 160 |
| His | Phe | Lys | Lys | Asn | Val | Glu | Glu | Gln | Leu | Asn | Lys | Arg | Val | Gly | His |
| | | | | 165 | | | | | 170 | | | | | 175 | |
| Val | Tyr | Lys | Lys | Ala | Phe | Met | Gln | Val | Val | Glu | Ala | Asp | Met | Leu | Ser |
| | | | 180 | | | | | 185 | | | | | 190 | | |
| Lys | Gly | Leu | Leu | Gly | Gly | Glu | Ala | Trp | Ser | Ser | Trp | His | Lys | Glu | Asp |
| | | | 195 | | | | | 200 | | | | | 205 | | |
| Ser | Ile | His | Val | Gly | Val | Arg | Cys | Ile | Glu | Met | Leu | Ile | Glu | Ser | Thr |
| | 210 | | | | | 215 | | | | | 220 | | | | |
| Gly | Met | Val | Ser | Leu | His | Arg | Gln | Asn | Ala | Gly | Val | Val | Gly | Gln | Asp |
| 225 | | | | | 230 | | | | | 235 | | | | | 240 |
| Ser | Glu | Thr | Ile | Glu | Leu | Ala | Pro | Glu | Tyr | Ala | Glu | Ala | Ile | Ala | Thr |
| | | | | 245 | | | | | 250 | | | | | 255 | |
| Arg | Ala | Gly | Ala | Leu | Ala | Gly | Ile | Ser | Pro | Met | Phe | Gln | Pro | Cys | Val |
| | | | 260 | | | | | 265 | | | | | 270 | | |
| Val | Pro | Pro | Lys | Pro | Trp | Thr | Gly | Ile | Thr | Gly | Gly | Gly | Tyr | Trp | Ala |
| | | | 275 | | | | | 280 | | | | | 285 | | |
| Asn | Gly | Arg | Arg | Pro | Leu | Ala | Leu | Val | Arg | Thr | His | Ser | Lys | Lys | Ala |
| | 290 | | | | | 295 | | | | | 300 | | | | |
| Leu | Met | Arg | Tyr | Glu | Asp | Val | Tyr | Met | Pro | Glu | Val | Tyr | Lys | Ala | Ile |
| 305 | | | | | 310 | | | | | 315 | | | | | 320 |
| Asn | Ile | Ala | Gln | Asn | Thr | Ala | Trp | Lys | Ile | Asn | Lys | Lys | Val | Leu | Ala |
| | | | | 325 | | | | | 330 | | | | | 335 | |
| Val | Ala | Asn | Val | Ile | Thr | Lys | Trp | Lys | His | Cys | Pro | Val | Trp | Asp | Ile |
| | | | 340 | | | | | 345 | | | | | 350 | | |
| Pro | Ala | Ile | Glu | Arg | Glu | Glu | Leu | Pro | Met | Lys | Pro | Glu | Asp | Ile | Asp |
| | | | | 355 | | | | | 360 | | | | | 365 | |

```
Met Asn Pro Glu Ala Leu Thr Ala Trp Lys Arg Ala Ala Ala Val
    370                 375                 380

Tyr Arg Lys Asp Lys Ala Arg Lys Ser Arg Arg Ile Ser Leu Glu Phe
385                 390                 395                 400

Met Leu Glu Gln Ala Asn Lys Phe Ala Asn His Lys Ala Ile Trp Phe
                405                 410                 415

Pro Tyr Asn Met Asp Trp Arg Gly Arg Val Tyr Ala Val Ser Met Phe
            420                 425                 430

Asn Pro Gln Gly Asn Asp Met Thr Lys Gly Leu Leu Thr Leu Ala Lys
        435                 440                 445

Gly Lys Pro Ile Gly Lys Glu Gly Tyr Tyr Trp Leu Lys Ile His Gly
    450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
            500                 505                 510

Ala Phe Cys Phe Glu Tyr Ala Gly Val Gln His His Gly Leu Ser Tyr
        515                 520                 525

Asn Cys Ser Leu Pro Leu Ala Phe Asp Gly Ser Cys Ser Gly Ile Gln
    530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                565                 570                 575

Lys Val Asn Glu Ile Leu Gln Ala Asp Ala Ile Asn Gly Thr Asp Asn
            580                 585                 590

Glu Val Val Thr Val Thr Asp Glu Asn Thr Gly Glu Ile Ser Glu Lys
        595                 600                 605

Val Lys Leu Gly Thr Lys Ala Leu Ala Gly Gln Trp Leu Ala Tyr Gly
    610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Asp Thr Ile Gln
                645                 650                 655

Pro Ala Ile Asp Ser Gly Lys Gly Leu Met Phe Thr Gln Pro Asn Gln
            660                 665                 670

Ala Ala Gly Tyr Met Ala Lys Leu Ile Trp Glu Ser Val Ser Val Thr
        675                 680                 685

Val Val Ala Ala Val Glu Ala Met Asn Trp Leu Lys Ser Ala Ala Lys
    690                 695                 700

Leu Leu Ala Ala Glu Val Lys Asp Lys Lys Thr Gly Glu Ile Leu Arg
705                 710                 715                 720

Lys Arg Cys Ala Val His Trp Val Thr Pro Asp Gly Phe Pro Val Trp
                725                 730                 735

Gln Glu Tyr Lys Lys Pro Ile Gln Thr Arg Leu Asn Leu Met Phe Leu
            740                 745                 750

Gly Gln Phe Arg Leu Gln Pro Thr Ile Asn Thr Asn Lys Asp Ser Glu
        755                 760                 765

Ile Asp Ala His Lys Gln Glu Ser Gly Ile Ala Pro Asn Phe Val His
    770                 775                 780
```

-continued

```
Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
            805                 810                 815

Ile Pro Ala Asp Ala Ala Asn Leu Phe Lys Ala Val Arg Glu Thr Met
        820                 825                 830

Val Asp Thr Tyr Glu Ser Cys Asp Val Leu Ala Asp Phe Tyr Asp Gln
    835                 840                 845

Phe Ala Asp Gln Leu His Glu Ser Gln Leu Asp Lys Met Pro Ala Leu
850                 855                 860

Pro Ala Lys Gly Asn Leu Asn Leu Arg Asp Ile Leu Glu Ser Asp Phe
865                 870                 875                 880

Ala Phe Ala

<210> SEQ ID NO 20
<211> LENGTH: 883
<212> TYPE: PRT
<213> ORGANISM: Artificial Sequence
<220> FEATURE:
<223> OTHER INFORMATION: Synthetic Polypeptide

<400> SEQUENCE: 20

Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
    210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
```

```
                260                 265                 270
Val Pro Pro Lys Pro Trp Thr Gly Ile Thr Gly Gly Tyr Trp Ala
            275                 280                 285

Asn Gly Arg Arg Pro Leu Ala Leu Val Arg Thr His Ser Lys Lys Ala
            290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Val Ile
            340                 345                 350

Pro Ala Ile Glu Arg Glu Leu Pro Met Lys Pro Glu Asp Ile Asp
            355                 360                 365

Met Asn Pro Glu Ala Leu Thr Ala Trp Lys Arg Ala Ala Ala Val
370                 375                 380

Tyr Arg Lys Asp Lys Ala Arg Lys Ser Arg Arg Ile Ser Leu Glu Phe
385                 390                 395                 400

Met Leu Glu Gln Ala Asn Lys Phe Ala Asn His Lys Ala Ile Trp Phe
                405                 410                 415

Pro Tyr Asn Met Asp Trp Arg Gly Arg Val Tyr Ala Val Ser Met Phe
                420                 425                 430

Asn Pro Gln Gly Asn Asp Met Thr Lys Gly Leu Leu Thr Leu Ala Lys
                435                 440                 445

Gly Lys Pro Ile Gly Lys Glu Gly Tyr Tyr Trp Leu Lys Ile His Gly
            450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
                500                 505                 510

Ala Phe Cys Phe Glu Tyr Ala Gly Val Gln His His Gly Leu Ser Tyr
            515                 520                 525

Asn Cys Ser Leu Pro Leu Ala Phe Asp Gly Ser Cys Ser Gly Ile Gln
            530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                565                 570                 575

Lys Val Asn Glu Ile Leu Gln Ala Asp Ala Ile Asn Gly Thr Asp Asn
                580                 585                 590

Glu Val Thr Val Thr Asp Glu Asn Thr Gly Glu Ile Ser Glu Lys
            595                 600                 605

Val Lys Leu Gly Thr Lys Ala Leu Ala Gly Gln Trp Leu Ala Tyr Gly
            610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Asp Thr Ile Gln
                645                 650                 655

Pro Ala Ile Asp Ser Gly Lys Gly Leu Met Phe Thr Gln Pro Asn Gln
                660                 665                 670

Ala Ala Gly Tyr Met Ala Lys Leu Ile Trp Glu Ser Val Ser Val Thr
                675                 680                 685
```

Val Val Ala Ala Val Glu Ala Met Asn Trp Leu Lys Ser Ala Ala Lys
690                 695                 700

Leu Leu Ala Ala Glu Val Lys Asp Lys Lys Thr Gly Glu Ile Leu Arg
705                 710                 715                 720

Lys Arg Cys Ala Val His Trp Val Thr Pro Asp Gly Phe Pro Val Trp
            725                 730                 735

Gln Glu Tyr Lys Lys Pro Ile Gln Thr Arg Leu Asn Leu Met Phe Leu
        740                 745                 750

Gly Gln Phe Arg Leu Gln Pro Thr Ile Asn Thr Asn Lys Asp Ser Glu
        755                 760                 765

Ile Asp Ala His Lys Gln Glu Ser Gly Ile Ala Pro Asn Phe Val His
770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
            805                 810                 815

Ile Pro Ala Asp Ala Ala Asn Leu Phe Lys Ala Val Arg Glu Thr Met
        820                 825                 830

Val Asp Thr Tyr Glu Ser Cys Asp Val Leu Ala Asp Phe Tyr Asp Gln
        835                 840                 845

Phe Ala Asp Gln Leu His Glu Ser Gln Leu Asp Lys Met Pro Ala Leu
850                 855                 860

Pro Ala Lys Gly Asn Leu Asn Leu Arg Asp Ile Leu Glu Ser Asp Phe
865                 870                 875                 880

Ala Phe Ala

<210> SEQ ID NO 21
<211> LENGTH: 883
<212> TYPE: PRT
<213> ORGANISM: Artificial Sequence
<220> FEATURE:
<223> OTHER INFORMATION: Synthetic Polypeptide

<400> SEQUENCE: 21

Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

-continued

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
    210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Tyr Trp Ala
        275                 280                 285

Asn Gly Arg Arg Pro Leu Ala Leu Val Arg Thr His Ser Lys Lys Ala
    290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
            340                 345                 350

Pro Ala Ile Glu Arg Glu Leu Pro Met Lys Pro Glu Asp Ile Asp
        355                 360                 365

Met Asn Pro Glu Ala Leu Thr Ala Trp Lys Arg Ala Ala Ala Val
    370                 375                 380

Tyr Arg Ser Asp Lys Ala Arg Lys Ser Arg Arg Ile Ser Leu Glu Phe
385                 390                 395                 400

Met Leu Glu Gln Ala Asn Lys Phe Ala Asn His Lys Ala Ile Trp Phe
                405                 410                 415

Pro Tyr Asn Met Asp Trp Arg Gly Arg Val Tyr Ala Val Ser Met Phe
            420                 425                 430

Asn Pro Gln Gly Asn Asp Met Thr Lys Gly Leu Leu Thr Leu Ala Lys
        435                 440                 445

Gly Lys Pro Ile Gly Lys Glu Gly Tyr Tyr Trp Leu Lys Ile His Gly
    450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
            500                 505                 510

Ala Phe Cys Phe Glu Tyr Ala Gly Val Gln His His Gly Leu Ser Tyr
        515                 520                 525

Asn Cys Ser Leu Pro Leu Ala Phe Asp Gly Ser Cys Ser Gly Ile Gln
    530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                565                 570                 575

Lys Val Asn Glu Ile Leu Gln Ala Asp Ala Ile Asn Gly Thr Asp Asn

```
                580             585             590
    Glu Val Val Thr Val Thr Asp Glu Asn Thr Gly Glu Ile Ser Glu Lys
                    595                 600                 605

Val Lys Leu Gly Thr Lys Ala Leu Ala Gly Gln Trp Leu Ala Tyr Gly
                610                 615                 620

Val Thr Arg Ser Val Thr Lys Arg Ser Val Met Thr Leu Ala Tyr Gly
    625                 630                 635                 640

Ser Lys Glu Phe Gly Phe Arg Gln Gln Val Leu Glu Asp Thr Ile Gln
                    645                 650                 655

Pro Ala Ile Asp Ser Gly Lys Gly Leu Met Phe Thr Gln Pro Asn Gln
                    660                 665                 670

Ala Ala Gly Tyr Met Ala Lys Leu Ile Trp Glu Ser Val Ser Val Thr
                675                 680                 685

Val Val Ala Ala Val Glu Ala Met Asn Trp Leu Lys Ser Ala Ala Lys
                690                 695                 700

Leu Leu Ala Ala Glu Val Lys Asp Lys Lys Thr Gly Glu Ile Leu Arg
    705                 710                 715                 720

Lys Arg Cys Ala Val His Trp Val Thr Pro Asp Gly Phe Pro Val Trp
                    725                 730                 735

Gln Glu Tyr Lys Lys Pro Ile Gln Thr Arg Leu Asn Leu Met Phe Leu
                    740                 745                 750

Gly Gln Phe Arg Leu Gln Pro Thr Ile Asn Thr Asn Lys Asp Ser Glu
                    755                 760                 765

Ile Asp Ala His Lys Gln Glu Ser Gly Ile Ala Pro Asn Phe Val His
                770                 775                 780

Ser Gln Asp Gly Ser His Leu Arg Lys Thr Val Val Trp Ala His Glu
    785                 790                 795                 800

Lys Tyr Gly Ile Glu Ser Phe Ala Leu Ile His Asp Ser Phe Gly Thr
                    805                 810                 815

Ile Pro Ala Asp Ala Ala Asn Leu Phe Lys Ala Val Arg Glu Thr Met
                    820                 825                 830

Val Asp Thr Tyr Glu Ser Cys Asp Val Leu Ala Asp Phe Tyr Asp Gln
                835                 840                 845

Phe Ala Asp Gln Leu His Glu Ser Gln Leu Asp Lys Met Pro Ala Leu
                850                 855                 860

Pro Ala Lys Gly Asn Leu Asn Leu Arg Asp Ile Leu Glu Ser Asp Phe
    865                 870                 875                 880

Ala Phe Ala

<210> SEQ ID NO 22
<211> LENGTH: 883
<212> TYPE: PRT
<213> ORGANISM: Artificial Sequence
<220> FEATURE:
<223> OTHER INFORMATION: Synthetic Polypeptide

<400> SEQUENCE: 22

Met Asn Thr Ile Asn Ile Ala Lys Asn Asp Phe Ser Asp Ile Glu Leu
    1               5                   10                  15

Ala Ala Ile Pro Phe Asn Thr Leu Ala Asp His Tyr Gly Glu Arg Leu
                    20                  25                  30

Ala Arg Glu Gln Leu Ala Leu Glu His Glu Ser Tyr Glu Met Gly Glu
                35                  40                  45

Ala Arg Phe Arg Lys Met Phe Glu Arg Gln Leu Lys Ala Gly Glu Val
            50                  55                  60
```

```
Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
                115                 120                 125

Ala Asp Asn Thr Thr Val Gln Ala Val Ala Ser Ala Ile Gly Arg Ala
            130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
                180                 185                 190

Lys Gly Leu Leu Gly Gly Glu Ala Trp Ser Ser Trp His Lys Glu Asp
            195                 200                 205

Ser Ile His Val Gly Val Arg Cys Ile Glu Met Leu Ile Glu Ser Thr
210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Tyr Trp Ala
            275                 280                 285

Asn Gly Arg Arg Pro Leu Ala Leu Val Arg Thr His Ser Lys Lys Ala
    290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
                340                 345                 350

Pro Ala Ile Glu Arg Glu Glu Leu Pro Met Lys Pro Glu Asp Ile Asp
            355                 360                 365

Met Asn Pro Glu Ala Leu Thr Ala Trp Lys Arg Ala Ala Ala Val
    370                 375                 380

Tyr Arg His Asp Lys Ala Arg Lys Ser Arg Arg Ile Ser Leu Glu Phe
385                 390                 395                 400

Met Leu Glu Gln Ala Asn Lys Phe Ala Asn His Lys Ala Ile Trp Phe
                405                 410                 415

Pro Tyr Asn Met Asp Trp Arg Gly Arg Val Tyr Ala Val Ser Met Phe
            420                 425                 430

Asn Pro Gln Gly Asn Asp Met Thr Lys Gly Leu Leu Thr Leu Ala Lys
                435                 440                 445

Gly Lys Pro Ile Gly Lys Glu Gly Tyr Tyr Trp Leu Lys Ile His Gly
            450                 455                 460

Ala Asn Cys Ala Gly Val Asp Lys Val Pro Phe Pro Glu Arg Ile Lys
465                 470                 475                 480
```

```
Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
            500                 505                 510

Ala Phe Cys Phe Glu Tyr Ala Gly Val Gln His His Gly Leu Ser Tyr
        515                 520                 525

Asn Cys Ser Leu Pro Leu Ala Phe Asp Gly Ser Cys Ser Gly Ile Gln
    530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                565                 570                 575

Lys Val Asn Glu Ile Leu Gln Ala Asp Ala Ile Asn Gly Thr Asp Asn
            580                 585                 590

Glu Val Thr Val Thr Asp Glu Asn Thr Gly Glu Ile Ser Glu Lys
        595                 600                 605

Val Lys Leu Gly Thr Lys Ala Leu Ala Gly Gln Trp Leu Ala Tyr Gly
    610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Asp Thr Ile Gln
                645                 650                 655

Pro Ala Ile Asp Ser Gly Lys Gly Leu Met Phe Thr Gln Pro Asn Gln
            660                 665                 670

Ala Ala Gly Tyr Met Ala Lys Leu Ile Trp Glu Ser Val Ser Val Thr
        675                 680                 685

Val Val Ala Ala Val Glu Ala Met Asn Trp Leu Lys Ser Ala Ala Lys
    690                 695                 700

Leu Leu Ala Ala Glu Val Lys Asp Lys Lys Thr Gly Glu Ile Leu Arg
705                 710                 715                 720

Lys Arg Cys Ala Val His Trp Val Thr Pro Asp Gly Phe Pro Val Trp
                725                 730                 735

Gln Glu Tyr Lys Lys Pro Ile Gln Thr Arg Leu Asn Leu Met Phe Leu
            740                 745                 750

Gly Gln Phe Arg Leu Gln Pro Thr Ile Asn Thr Asn Lys Asp Ser Glu
        755                 760                 765

Ile Asp Ala His Lys Gln Glu Ser Gly Ile Ala Pro Asn Phe Val His
    770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
            820                 825                 830

Val Asp Thr Tyr Glu Ser Cys Asp Val Leu Ala Asp Phe Tyr Asp Gln
        835                 840                 845

Phe Ala Asp Gln Leu His Glu Ser Gln Leu Asp Lys Met Pro Ala Leu
    850                 855                 860

Pro Ala Lys Gly Asn Leu Asn Leu Arg Asp Ile Leu Glu Ser Asp Phe
865                 870                 875                 880

Ala Phe Ala

<210> SEQ ID NO 23
```

```
<211> LENGTH: 883
<212> TYPE: PRT
<213> ORGANISM: Artificial Sequence
<220> FEATURE:
<223> OTHER INFORMATION: Synthetic Polypeptide

<400> SEQUENCE: 23
```

| | | | | | | | | | | | | | | |
|---|---|---|---|---|---|---|---|---|---|---|---|---|---|---|
| Met | Asn | Thr | Ile | Asn | Ile | Ala | Lys | Asn | Asp | Phe | Ser | Asp | Ile | Glu | Leu |
| 1 | | | | 5 | | | | | 10 | | | | | 15 | |
| Ala | Ala | Ile | Pro | Phe | Asn | Thr | Leu | Ala | Asp | His | Tyr | Gly | Glu | Arg | Leu |
| | | | 20 | | | | | 25 | | | | | 30 | | |
| Ala | Arg | Glu | Gln | Leu | Ala | Leu | Glu | His | Glu | Ser | Tyr | Glu | Met | Gly | Glu |
| | | 35 | | | | | 40 | | | | | 45 | | | |
| Ala | Arg | Phe | Arg | Lys | Met | Phe | Glu | Arg | Gln | Leu | Lys | Ala | Gly | Glu | Val |
| | 50 | | | | | 55 | | | | | 60 | | | | |
| Ala | Asp | Asn | Ala | Ala | Ala | Lys | Pro | Leu | Ile | Thr | Thr | Leu | Leu | Pro | Lys |
| 65 | | | | | 70 | | | | | 75 | | | | | 80 |
| Met | Ile | Ala | Arg | Ile | Asn | Asp | Trp | Phe | Glu | Glu | Val | Lys | Ala | Lys | Arg |
| | | | | 85 | | | | | 90 | | | | | 95 | |
| Gly | Lys | Arg | Pro | Thr | Ala | Phe | Gln | Phe | Leu | Gln | Glu | Ile | Lys | Pro | Glu |
| | | | 100 | | | | | 105 | | | | | 110 | | |
| Ala | Val | Ala | Tyr | Ile | Thr | Ile | Lys | Thr | Thr | Leu | Ala | Cys | Leu | Thr | Ser |
| | | 115 | | | | | 120 | | | | | 125 | | | |
| Ala | Asp | Asn | Thr | Thr | Val | Gln | Ala | Val | Ala | Ser | Ala | Ile | Gly | Arg | Ala |
| | 130 | | | | | 135 | | | | | 140 | | | | |
| Ile | Glu | Asp | Glu | Ala | Arg | Phe | Gly | Arg | Ile | Arg | Asp | Leu | Glu | Ala | Lys |
| 145 | | | | | 150 | | | | | 155 | | | | | 160 |
| His | Phe | Lys | Lys | Asn | Val | Glu | Glu | Gln | Leu | Asn | Lys | Arg | Val | Gly | His |
| | | | | 165 | | | | | 170 | | | | | 175 | |
| Val | Tyr | Lys | Lys | Ala | Phe | Met | Gln | Val | Val | Glu | Ala | Asp | Met | Leu | Ser |
| | | | 180 | | | | | 185 | | | | | 190 | | |
| Lys | Gly | Leu | Leu | Gly | Gly | Glu | Ala | Trp | Ser | Ser | Trp | His | Lys | Glu | Asp |
| | | 195 | | | | | 200 | | | | | 205 | | | |
| Ser | Ile | His | Val | Gly | Val | Arg | Cys | Ile | Glu | Met | Leu | Ile | Glu | Ser | Thr |
| | 210 | | | | | 215 | | | | | 220 | | | | |
| Gly | Met | Val | Ser | Leu | His | Arg | Gln | Asn | Ala | Gly | Val | Val | Gly | Gln | Asp |
| 225 | | | | | 230 | | | | | 235 | | | | | 240 |
| Ser | Glu | Thr | Ile | Glu | Leu | Ala | Pro | Glu | Tyr | Ala | Glu | Ala | Ile | Ala | Thr |
| | | | | 245 | | | | | 250 | | | | | 255 | |
| Arg | Ala | Gly | Ala | Leu | Ala | Gly | Ile | Ser | Pro | Met | Phe | Gln | Pro | Cys | Val |
| | | | 260 | | | | | 265 | | | | | 270 | | |
| Val | Pro | Pro | Lys | Pro | Trp | Thr | Gly | Ile | Thr | Gly | Gly | Gly | Tyr | Trp | Ala |
| | | 275 | | | | | 280 | | | | | 285 | | | |
| Asn | Gly | Arg | Arg | Pro | Leu | Ala | Leu | Val | Arg | Thr | His | Ser | Lys | Lys | Ala |
| | 290 | | | | | 295 | | | | | 300 | | | | |
| Leu | Met | Arg | Tyr | Glu | Asp | Val | Tyr | Met | Pro | Glu | Val | Tyr | Lys | Ala | Ile |
| 305 | | | | | 310 | | | | | 315 | | | | | 320 |
| Asn | Ile | Ala | Gln | Asn | Thr | Ala | Trp | Lys | Ile | Asn | Lys | Lys | Val | Leu | Ala |
| | | | | 325 | | | | | 330 | | | | | 335 | |
| Val | Ala | Asn | Val | Ile | Thr | Lys | Trp | Lys | His | Cys | Pro | Val | Glu | Asp | Ile |
| | | | 340 | | | | | 345 | | | | | 350 | | |
| Pro | Ala | Ile | Glu | Arg | Glu | Glu | Leu | Pro | Met | Lys | Pro | Glu | Asp | Ile | Asp |
| | | 355 | | | | | 360 | | | | | 365 | | | |
| Met | Asn | Pro | Glu | Ala | Leu | Thr | Ala | Trp | Lys | Arg | Ala | Ala | Ala | Ala | Val |
| | 370 | | | | | 375 | | | | | 380 | | | | |

```
Tyr Arg Asn Asp Lys Ala Arg Lys Ser Arg Arg Ile Ser Leu Glu Phe
385                 390                 395                 400

Met Leu Glu Gln Ala Asn Lys Phe Ala Asn His Lys Ala Ile Trp Phe
            405                 410                 415

Pro Tyr Asn Met Asp Trp Arg Gly Arg Val Tyr Ala Val Ser Met Phe
        420                 425                 430

Asn Pro Gln Gly Asn Asp Met Thr Lys Gly Leu Leu Thr Leu Ala Lys
        435                 440                 445

Gly Lys Pro Ile Gly Lys Glu Gly Tyr Tyr Trp Leu Lys Ile His Gly
        450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
            500                 505                 510

Ala Phe Cys Phe Glu Tyr Ala Gly Val Gln His His Gly Leu Ser Tyr
        515                 520                 525

Asn Cys Ser Leu Pro Leu Ala Phe Asp Gly Ser Cys Ser Gly Ile Gln
530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                565                 570                 575

Lys Val Asn Glu Ile Leu Gln Ala Asp Ala Ile Asn Gly Thr Asp Asn
            580                 585                 590

Glu Val Val Thr Val Thr Asp Glu Asn Thr Gly Glu Ile Ser Glu Lys
        595                 600                 605

Val Lys Leu Gly Thr Lys Ala Leu Ala Gly Gln Trp Leu Ala Tyr Gly
        610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Asp Thr Ile Gln
                645                 650                 655

Pro Ala Ile Asp Ser Gly Lys Gly Leu Met Phe Thr Gln Pro Asn Gln
            660                 665                 670

Ala Ala Gly Tyr Met Ala Lys Leu Ile Trp Glu Ser Val Ser Val Thr
        675                 680                 685

Val Val Ala Ala Val Glu Ala Met Asn Trp Leu Lys Ser Ala Ala Lys
        690                 695                 700

Leu Leu Ala Ala Glu Val Lys Asp Lys Lys Thr Gly Glu Ile Leu Arg
705                 710                 715                 720

Lys Arg Cys Ala Val His Trp Val Thr Pro Asp Gly Phe Pro Val Trp
                725                 730                 735

Gln Glu Tyr Lys Lys Pro Ile Gln Thr Arg Leu Asn Leu Met Phe Leu
            740                 745                 750

Gly Gln Phe Arg Leu Gln Pro Thr Ile Asn Thr Asn Lys Asp Ser Glu
        755                 760                 765

Ile Asp Ala His Lys Gln Glu Ser Gly Ile Ala Pro Asn Phe Val His
        770                 775                 780

Ser Gln Asp Gly Ser His Leu Arg Lys Thr Val Val Trp Ala His Glu
785                 790                 795                 800
```

```
Lys Tyr Gly Ile Glu Ser Phe Ala Leu Ile His Asp Ser Phe Gly Thr
                    805                 810                 815

Ile Pro Ala Asp Ala Ala Asn Leu Phe Lys Ala Val Arg Glu Thr Met
                820                 825                 830

Val Asp Thr Tyr Glu Ser Cys Asp Val Leu Ala Asp Phe Tyr Asp Gln
                835                 840                 845

Phe Ala Asp Gln Leu His Glu Ser Gln Leu Asp Lys Met Pro Ala Leu
850                 855                 860

Pro Ala Lys Gly Asn Leu Asn Leu Arg Asp Ile Leu Glu Ser Asp Phe
865                 870                 875                 880

Ala Phe Ala

<210> SEQ ID NO 24
<211> LENGTH: 883
<212> TYPE: PRT
<213> ORGANISM: Artificial Sequence
<220> FEATURE:
<223> OTHER INFORMATION: Synthetic Polypeptide

<400> SEQUENCE: 24

Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
                20                  25                  30

Ala Arg Glu Gln Leu Ala Leu Glu His Glu Ser Tyr Glu Met Ala Glu
            35                  40                  45

Ala Arg Phe Arg Lys Met Phe Glu Arg Gln Leu Lys Ala Gly Glu Val
        50                  55                  60

Ala Asp Asn Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
                100                 105                 110

Ala Val Ala Tyr Ile Thr Ile Lys Thr Thr Leu Ala Cys Leu Thr Ser
            115                 120                 125

Ala Asp Asn Thr Thr Val Gln Ala Val Ala Ser Ala Ile Gly Arg Ala
        130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
                180                 185                 190

Lys Gly Leu Leu Gly Gly Glu Ala Trp Ser Ser Trp His Lys Glu Asp
            195                 200                 205

Ser Ile His Val Gly Val Arg Cys Ile Glu Met Leu Ile Glu Ser Thr
        210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
                260                 265                 270

Val Pro Pro Lys Pro Trp Thr Gly Ile Thr Gly Gly Gly Tyr Trp Ala
```

-continued

```
                275                 280                 285
Asn Gly Arg Arg Pro Leu Ala Leu Val Arg Thr His Ser Lys Lys Ala
290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Lys Asp Ile
                340                 345                 350

Pro Ala Ile Glu Arg Glu Leu Pro Met Lys Pro Glu Asp Ile Asp
                355                 360                 365

Met Asn Pro Glu Ala Leu Thr Ala Trp Lys Arg Ala Ala Ala Val
370                 375                 380

Tyr Arg Lys Asp Lys Ala Arg Lys Ser Arg Ile Ser Leu Glu Phe
385                 390                 395                 400

Met Leu Glu Gln Ala Asn Lys Phe Ala Asn His Lys Ala Ile Trp Phe
                405                 410                 415

Pro Tyr Asn Met Asp Trp Arg Gly Arg Val Tyr Ala Val Ser Met Phe
                420                 425                 430

Asn Pro Gln Gly Asn Asp Met Thr Lys Gly Leu Leu Thr Leu Ala Lys
                435                 440                 445

Gly Lys Pro Ile Gly Lys Glu Gly Tyr Tyr Trp Leu Lys Ile His Gly
450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
                500                 505                 510

Ala Phe Cys Phe Glu Tyr Ala Gly Val Gln His His Gly Leu Ser Tyr
                515                 520                 525

Asn Cys Ser Leu Pro Leu Ala Phe Asp Gly Ser Cys Ser Gly Ile Gln
                530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                565                 570                 575

Lys Val Asn Glu Ile Leu Gln Ala Asp Ala Ile Asn Gly Thr Asp Asn
                580                 585                 590

Glu Val Val Thr Val Thr Asp Glu Asn Thr Gly Glu Ile Ser Glu Lys
                595                 600                 605

Val Lys Leu Gly Thr Lys Ala Leu Ala Gly Gln Trp Leu Ala Tyr Gly
                610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Asp Thr Ile Gln
                645                 650                 655

Pro Ala Ile Asp Ser Gly Lys Gly Leu Met Phe Thr Gln Pro Asn Gln
                660                 665                 670

Ala Ala Gly Tyr Met Ala Lys Leu Ile Trp Glu Ser Val Ser Val Thr
                675                 680                 685

Val Val Ala Ala Val Glu Ala Met Asn Trp Leu Lys Ser Ala Ala Lys
                690                 695                 700
```

```
Leu Leu Ala Ala Glu Val Lys Asp Lys Thr Gly Glu Ile Leu Arg
705                 710                 715                 720

Lys Arg Cys Ala Val His Trp Val Thr Pro Asp Gly Phe Pro Val Trp
            725                 730                 735

Gln Glu Tyr Lys Lys Pro Ile Gln Thr Arg Leu Asn Leu Met Phe Leu
        740                 745                 750

Gly Gln Phe Arg Leu Gln Pro Thr Ile Asn Thr Asn Lys Asp Ser Glu
    755                 760                 765

Ile Asp Ala His Lys Gln Glu Ser Gly Ile Ala Pro Asn Phe Val His
770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
            820                 825                 830

Val Asp Thr Tyr Glu Ser Cys Asp Val Leu Ala Asp Phe Tyr Asp Gln
        835                 840                 845

Phe Ala Asp Gln Leu His Glu Ser Gln Leu Asp Lys Met Pro Ala Leu
    850                 855                 860

Pro Ala Lys Gly Asn Leu Asn Leu Arg Asp Ile Leu Glu Ser Asp Phe
865                 870                 875                 880

Ala Phe Ala

<210> SEQ ID NO 25
<211> LENGTH: 883
<212> TYPE: PRT
<213> ORGANISM: Artificial Sequence
<220> FEATURE:
<223> OTHER INFORMATION: Synthetic Polypeptide

<400> SEQUENCE: 25

Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Ala Glu
        35                  40                  45

Ala Arg Phe Arg Lys Met Phe Glu Arg Gln Leu Lys Ala Gly Glu Val
    50                  55                  60

Ala Asp Asn Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175
```

```
Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
    210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Tyr Trp Ala
        275                 280                 285

Asn Gly Arg Arg Pro Leu Ala Leu Val Arg Thr His Ser Lys Lys Ala
    290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Asn Asp Ile
            340                 345                 350

Pro Ala Ile Glu Arg Glu Glu Leu Pro Met Lys Pro Glu Asp Ile Asp
        355                 360                 365

Met Asn Pro Glu Ala Leu Thr Ala Trp Lys Arg Ala Ala Ala Val
370                 375                 380

Tyr Arg Lys Asp Lys Ala Arg Lys Ser Arg Ile Ser Leu Glu Phe
385                 390                 395                 400

Met Leu Glu Gln Ala Asn Lys Phe Ala Asn His Lys Ala Ile Trp Phe
                405                 410                 415

Pro Tyr Asn Met Asp Trp Arg Gly Arg Val Tyr Ala Val Ser Met Phe
            420                 425                 430

Asn Pro Gln Gly Asn Asp Met Thr Lys Gly Leu Leu Thr Leu Ala Lys
        435                 440                 445

Gly Lys Pro Ile Gly Lys Glu Gly Tyr Tyr Trp Leu Lys Ile His Gly
    450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
            500                 505                 510

Ala Phe Cys Phe Glu Tyr Ala Gly Val Gln His His Gly Leu Ser Tyr
        515                 520                 525

Asn Cys Ser Leu Pro Leu Ala Phe Asp Gly Ser Cys Ser Gly Ile Gln
    530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                565                 570                 575

Lys Val Asn Glu Ile Leu Gln Ala Asp Ala Ile Asn Gly Thr Asp Asn
            580                 585                 590

Glu Val Val Thr Val Thr Asp Glu Asn Thr Gly Glu Ile Ser Glu Lys
```

```
                595                 600                 605
Val Lys Leu Gly Thr Lys Ala Leu Ala Gly Gln Trp Leu Ala Tyr Gly
        610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Asp Thr Ile Gln
                645                 650                 655

Pro Ala Ile Asp Ser Gly Lys Gly Leu Met Phe Thr Gln Pro Asn Gln
            660                 665                 670

Ala Ala Gly Tyr Met Ala Lys Leu Ile Trp Glu Ser Val Ser Val Thr
        675                 680                 685

Val Val Ala Ala Val Glu Ala Met Asn Trp Leu Lys Ser Ala Ala Lys
690                 695                 700

Leu Leu Ala Ala Glu Val Lys Asp Lys Thr Gly Glu Ile Leu Arg
705                 710                 715                 720

Lys Arg Cys Ala Val His Trp Val Thr Pro Asp Gly Phe Pro Val Trp
                725                 730                 735

Gln Glu Tyr Lys Lys Pro Ile Gln Thr Arg Leu Asn Leu Met Phe Leu
            740                 745                 750

Gly Gln Phe Arg Leu Gln Pro Thr Ile Asn Thr Asn Lys Asp Ser Glu
        755                 760                 765

Ile Asp Ala His Lys Gln Glu Ser Gly Ile Ala Pro Asn Phe Val His
770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
            820                 825                 830

Val Asp Thr Tyr Glu Ser Cys Asp Val Leu Ala Asp Phe Tyr Asp Gln
        835                 840                 845

Phe Ala Asp Gln Leu His Glu Ser Gln Leu Asp Lys Met Pro Ala Leu
850                 855                 860

Pro Ala Lys Gly Asn Leu Asn Leu Arg Asp Ile Leu Glu Ser Asp Phe
865                 870                 875                 880

Ala Phe Ala

<210> SEQ ID NO 26
<211> LENGTH: 883
<212> TYPE: PRT
<213> ORGANISM: Artificial Sequence
<220> FEATURE:
<223> OTHER INFORMATION: Synthetic Polypeptide

<400> SEQUENCE: 26

Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Ala Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80
```

```
Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
            115                 120                 125

Ala Asp Asn Thr Thr Val Gln Ala Val Ala Ser Ala Ile Gly Arg Ala
130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
            195                 200                 205

Ser Ile His Val Gly Val Arg Cys Ile Glu Met Leu Ile Glu Ser Thr
            210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Tyr Trp Ala
            275                 280                 285

Asn Gly Arg Arg Pro Leu Ala Leu Val Arg Thr His Ser Lys Lys Ala
290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Ala Asp Ile
            340                 345                 350

Pro Ala Ile Glu Arg Glu Leu Pro Met Lys Pro Glu Asp Ile Asp
            355                 360                 365

Met Asn Pro Glu Ala Leu Thr Ala Trp Lys Arg Ala Ala Ala Val
370                 375                 380

Tyr Arg Lys Asp Lys Ala Arg Lys Ser Arg Arg Ile Ser Leu Glu Phe
385                 390                 395                 400

Met Leu Glu Gln Ala Asn Lys Phe Ala Asn His Lys Ala Ile Trp Phe
                405                 410                 415

Pro Tyr Asn Met Asp Trp Arg Gly Arg Val Tyr Ala Val Ser Met Phe
            420                 425                 430

Asn Pro Gln Gly Asn Asp Met Thr Lys Gly Leu Leu Thr Leu Ala Lys
            435                 440                 445

Gly Lys Pro Ile Gly Lys Glu Gly Tyr Tyr Trp Leu Lys Ile His Gly
            450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                485                 490                 495
```

```
Leu Glu Asn Thr Trp Trp Ala Glu Gln Asp Ser Pro Phe Cys Phe Leu
            500                 505                 510

Ala Phe Cys Phe Glu Tyr Ala Gly Val Gln His His Gly Leu Ser Tyr
        515                 520                 525

Asn Cys Ser Leu Pro Leu Ala Phe Asp Gly Ser Cys Ser Gly Ile Gln
    530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                565                 570                 575

Lys Val Asn Glu Ile Leu Gln Ala Asp Ala Ile Asn Gly Thr Asp Asn
            580                 585                 590

Glu Val Val Thr Val Thr Asp Glu Asn Thr Gly Glu Ile Ser Glu Lys
        595                 600                 605

Val Lys Leu Gly Thr Lys Ala Leu Ala Gly Gln Trp Leu Ala Tyr Gly
    610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Asp Thr Ile Gln
                645                 650                 655

Pro Ala Ile Asp Ser Gly Lys Gly Leu Met Phe Thr Gln Pro Asn Gln
            660                 665                 670

Ala Ala Gly Tyr Met Ala Lys Leu Ile Trp Glu Ser Val Ser Val Thr
        675                 680                 685

Val Val Ala Ala Val Glu Ala Met Asn Trp Leu Lys Ser Ala Ala Lys
690                 695                 700

Leu Leu Ala Ala Glu Val Lys Asp Lys Lys Thr Gly Glu Ile Leu Arg
705                 710                 715                 720

Lys Arg Cys Ala Val His Trp Val Thr Pro Asp Gly Phe Pro Val Trp
                725                 730                 735

Gln Glu Tyr Lys Lys Pro Ile Gln Thr Arg Leu Asn Leu Met Phe Leu
            740                 745                 750

Gly Gln Phe Arg Leu Gln Pro Thr Ile Asn Thr Asn Lys Asp Ser Glu
        755                 760                 765

Ile Asp Ala His Lys Gln Glu Ser Gly Ile Ala Pro Asn Phe Val His
770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
            820                 825                 830

Val Asp Thr Tyr Glu Ser Cys Asp Val Leu Ala Asp Phe Tyr Asp Gln
        835                 840                 845

Phe Ala Asp Gln Leu His Glu Ser Gln Leu Asp Lys Met Pro Ala Leu
850                 855                 860

Pro Ala Lys Gly Asn Leu Asn Leu Arg Asp Ile Leu Glu Ser Asp Phe
865                 870                 875                 880

Ala Phe Ala

<210> SEQ ID NO 27
<211> LENGTH: 883
<212> TYPE: PRT
<213> ORGANISM: Artificial Sequence
```

```
<220> FEATURE:
<223> OTHER INFORMATION: Synthetic Polypeptide

<400> SEQUENCE: 27

Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Ala Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
    210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Gly Tyr Trp Ala
        275                 280                 285

Asn Gly Arg Arg Pro Leu Ala Leu Val Arg Thr His Ser Lys Lys Ala
    290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Trp Asp Ile
            340                 345                 350

Pro Ala Ile Glu Arg Glu Glu Leu Pro Met Lys Pro Glu Asp Ile Asp
        355                 360                 365

Met Asn Pro Glu Ala Leu Thr Ala Trp Lys Arg Ala Ala Ala Ala Val
    370                 375                 380

Tyr Arg Lys Asp Lys Ala Arg Lys Ser Arg Arg Ile Ser Leu Glu Phe
385                 390                 395                 400
```

```
Met Leu Glu Gln Ala Asn Lys Phe Ala Asn His Lys Ala Ile Trp Phe
                405                 410                 415
Pro Tyr Asn Met Asp Trp Arg Gly Arg Val Tyr Ala Val Ser Met Phe
            420                 425                 430
Asn Pro Gln Gly Asn Asp Met Thr Lys Gly Leu Leu Thr Leu Ala Lys
        435                 440                 445
Gly Lys Pro Ile Gly Lys Glu Gly Tyr Tyr Trp Leu Lys Ile His Gly
    450                 455                 460
Ala Asn Cys Ala Gly Val Asp Lys Val Pro Phe Pro Glu Arg Ile Lys
465                 470                 475                 480
Phe Ile Glu Glu Asn His Glu Asn Ile Met Ala Cys Ala Lys Ser Pro
                485                 490                 495
Leu Glu Asn Thr Trp Trp Ala Glu Gln Asp Ser Pro Phe Cys Phe Leu
            500                 505                 510
Ala Phe Cys Phe Glu Tyr Ala Gly Val Gln His His Gly Leu Ser Tyr
        515                 520                 525
Asn Cys Ser Leu Pro Leu Ala Phe Asp Gly Ser Cys Ser Gly Ile Gln
    530                 535                 540
His Phe Ser Ala Met Leu Arg Asp Glu Val Gly Gly Arg Ala Val Asn
545                 550                 555                 560
Leu Leu Pro Ser Glu Thr Val Gln Asp Ile Tyr Gly Ile Val Ala Lys
                565                 570                 575
Lys Val Asn Glu Ile Leu Gln Ala Asp Ala Ile Asn Gly Thr Asp Asn
            580                 585                 590
Glu Val Thr Val Thr Asp Glu Asn Thr Gly Glu Ile Ser Glu Lys
        595                 600                 605
Val Lys Leu Gly Thr Lys Ala Leu Ala Gly Gln Trp Leu Ala Tyr Gly
    610                 615                 620
Val Thr Arg Ser Val Thr Lys Arg Ser Val Met Thr Leu Ala Tyr Gly
625                 630                 635                 640
Ser Lys Glu Phe Gly Phe Arg Gln Gln Val Leu Glu Asp Thr Ile Gln
                645                 650                 655
Pro Ala Ile Asp Ser Gly Lys Gly Leu Met Phe Thr Gln Pro Asn Gln
            660                 665                 670
Ala Ala Gly Tyr Met Ala Lys Leu Ile Trp Glu Ser Val Ser Val Thr
        675                 680                 685
Val Val Ala Ala Val Glu Ala Met Asn Trp Leu Lys Ser Ala Ala Lys
    690                 695                 700
Leu Leu Ala Ala Glu Val Lys Asp Lys Lys Thr Gly Glu Ile Leu Arg
705                 710                 715                 720
Lys Arg Cys Ala Val His Trp Val Thr Pro Asp Gly Phe Pro Val Trp
                725                 730                 735
Gln Glu Tyr Lys Lys Pro Ile Gln Thr Arg Leu Asn Leu Met Phe Leu
            740                 745                 750
Gly Gln Phe Arg Leu Gln Pro Thr Ile Asn Thr Asn Lys Asp Ser Glu
        755                 760                 765
Ile Asp Ala His Lys Gln Glu Ser Gly Ile Ala Pro Asn Phe Val His
    770                 775                 780
Ser Gln Asp Gly Ser His Leu Arg Lys Thr Val Val Trp Ala His Glu
785                 790                 795                 800
Lys Tyr Gly Ile Glu Ser Phe Ala Leu Ile His Asp Ser Phe Gly Thr
                805                 810                 815
```

```
Ile Pro Ala Asp Ala Ala Asn Leu Phe Lys Ala Val Arg Glu Thr Met
                820                 825                 830

Val Asp Thr Tyr Glu Ser Cys Asp Val Leu Ala Asp Phe Tyr Asp Gln
            835                 840                 845

Phe Ala Asp Gln Leu His Glu Ser Gln Leu Asp Lys Met Pro Ala Leu
        850                 855                 860

Pro Ala Lys Gly Asn Leu Asn Leu Arg Asp Ile Leu Glu Ser Asp Phe
865                 870                 875                 880

Ala Phe Ala

<210> SEQ ID NO 28
<211> LENGTH: 883
<212> TYPE: PRT
<213> ORGANISM: Artificial Sequence
<220> FEATURE:
<223> OTHER INFORMATION: Synthetic Polypeptide

<400> SEQUENCE: 28

Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Ala Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
    210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Gly Tyr Trp Ala
        275                 280                 285

Asn Gly Arg Arg Pro Leu Ala Leu Val Arg Thr His Ser Lys Lys Ala
```

```
              290                 295                 300
Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Val Ile
                340                 345                 350

Pro Ala Ile Glu Arg Glu Leu Pro Met Lys Pro Glu Asp Ile Asp
            355                 360                 365

Met Asn Pro Glu Ala Leu Thr Ala Trp Lys Arg Ala Ala Ala Val
370                 375                 380

Tyr Arg Lys Asp Lys Ala Arg Lys Ser Arg Ile Ser Leu Glu Phe
385                 390                 395                 400

Met Leu Glu Gln Ala Asn Lys Phe Ala Asn His Lys Ala Ile Trp Phe
            405                 410                 415

Pro Tyr Asn Met Asp Trp Arg Gly Arg Val Tyr Ala Val Ser Met Phe
                420                 425                 430

Asn Pro Gln Gly Asn Asp Met Thr Lys Gly Leu Leu Thr Leu Ala Lys
            435                 440                 445

Gly Lys Pro Ile Gly Lys Glu Gly Tyr Tyr Trp Leu Lys Ile His Gly
    450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
                500                 505                 510

Ala Phe Cys Phe Glu Tyr Ala Gly Val Gln His His Gly Leu Ser Tyr
            515                 520                 525

Asn Cys Ser Leu Pro Leu Ala Phe Asp Gly Ser Cys Ser Gly Ile Gln
        530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                565                 570                 575

Lys Val Asn Glu Ile Leu Gln Ala Asp Ala Ile Asn Gly Thr Asp Asn
            580                 585                 590

Glu Val Val Thr Val Thr Asp Glu Asn Thr Gly Glu Ile Ser Glu Lys
        595                 600                 605

Val Lys Leu Gly Thr Lys Ala Leu Ala Gly Gln Trp Leu Ala Tyr Gly
    610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Asp Thr Ile Gln
                645                 650                 655

Pro Ala Ile Asp Ser Gly Lys Gly Leu Met Phe Thr Gln Pro Asn Gln
            660                 665                 670

Ala Ala Gly Tyr Met Ala Lys Leu Ile Trp Glu Ser Val Ser Val Thr
            675                 680                 685

Val Val Ala Ala Val Glu Ala Met Asn Trp Leu Lys Ser Ala Ala Lys
        690                 695                 700

Leu Leu Ala Ala Glu Val Lys Asp Lys Thr Gly Glu Ile Leu Arg
705                 710                 715                 720
```

```
Lys Arg Cys Ala Val His Trp Val Thr Pro Asp Gly Phe Pro Val Trp
                725                 730                 735

Gln Glu Tyr Lys Lys Pro Ile Gln Thr Arg Leu Asn Leu Met Phe Leu
            740                 745                 750

Gly Gln Phe Arg Leu Gln Pro Thr Ile Asn Thr Asn Lys Asp Ser Glu
        755                 760                 765

Ile Asp Ala His Lys Gln Glu Ser Gly Ile Ala Pro Asn Phe Val His
    770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
            820                 825                 830

Val Asp Thr Tyr Glu Ser Cys Asp Val Leu Ala Asp Phe Tyr Asp Gln
        835                 840                 845

Phe Ala Asp Gln Leu His Glu Ser Gln Leu Asp Lys Met Pro Ala Leu
    850                 855                 860

Pro Ala Lys Gly Asn Leu Asn Leu Arg Asp Ile Leu Glu Ser Asp Phe
865                 870                 875                 880

Ala Phe Ala

<210> SEQ ID NO 29
<211> LENGTH: 883
<212> TYPE: PRT
<213> ORGANISM: Artificial Sequence
<220> FEATURE:
<223> OTHER INFORMATION: Synthetic Polypeptide

<400> SEQUENCE: 29

Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
                20                  25                  30

Ala Arg Glu Gln Leu Ala Leu Glu His Glu Ser Tyr Glu Met Ala Glu
            35                  40                  45

Ala Arg Phe Arg Lys Met Phe Glu Arg Gln Leu Lys Ala Gly Glu Val
        50                  55                  60

Ala Asp Asn Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Gln Leu Asn Lys Arg Val Gly His
                165                 170                 175

Val Tyr Lys Lys Ala Phe Met Gln Val Val Glu Ala Asp Met Leu Ser
            180                 185                 190
```

-continued

```
Lys Gly Leu Leu Gly Gly Glu Ala Trp Ser Ser Trp His Lys Glu Asp
            195                 200                 205

Ser Ile His Val Gly Val Arg Cys Ile Glu Met Leu Ile Glu Ser Thr
        210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Tyr Trp Ala
        275                 280                 285

Asn Gly Arg Arg Pro Leu Ala Leu Val Arg Thr His Ser Lys Lys Ala
        290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
            340                 345                 350

Pro Ala Ile Glu Arg Glu Leu Pro Met Lys Pro Glu Asp Ile Asp
            355                 360                 365

Met Asn Pro Glu Ala Leu Thr Ala Trp Lys Arg Ala Ala Ala Val
370                 375                 380

Tyr Arg Ser Asp Lys Ala Arg Lys Ser Arg Ile Ser Leu Glu Phe
385                 390                 395                 400

Met Leu Glu Gln Ala Asn Lys Phe Ala Asn His Lys Ala Ile Trp Phe
                405                 410                 415

Pro Tyr Asn Met Asp Trp Arg Gly Arg Val Tyr Ala Val Ser Met Phe
            420                 425                 430

Asn Pro Gln Gly Asn Asp Met Thr Lys Gly Leu Leu Thr Leu Ala Lys
            435                 440                 445

Gly Lys Pro Ile Gly Lys Glu Gly Tyr Tyr Trp Leu Lys Ile His Gly
450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
            500                 505                 510

Ala Phe Cys Phe Glu Tyr Ala Gly Val Gln His His Gly Leu Ser Tyr
            515                 520                 525

Asn Cys Ser Leu Pro Leu Ala Phe Asp Gly Ser Cys Ser Gly Ile Gln
        530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                565                 570                 575

Lys Val Asn Glu Ile Leu Gln Ala Asp Ala Ile Asn Gly Thr Asp Asn
            580                 585                 590

Glu Val Val Thr Val Thr Asp Glu Asn Thr Gly Glu Ile Ser Glu Lys
        595                 600                 605

Val Lys Leu Gly Thr Lys Ala Leu Ala Gly Gln Trp Leu Ala Tyr Gly
```

```
            610                 615                 620
Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Asp Thr Ile Gln
                645                 650                 655

Pro Ala Ile Asp Ser Gly Lys Gly Leu Met Phe Thr Gln Pro Asn Gln
            660                 665                 670

Ala Ala Gly Tyr Met Ala Lys Leu Ile Trp Glu Ser Val Ser Val Thr
        675                 680                 685

Val Val Ala Ala Val Glu Ala Met Asn Trp Leu Lys Ser Ala Ala Lys
    690                 695                 700

Leu Leu Ala Ala Glu Val Lys Asp Lys Lys Thr Gly Glu Ile Leu Arg
705                 710                 715                 720

Lys Arg Cys Ala Val His Trp Val Thr Pro Asp Gly Phe Pro Val Trp
                725                 730                 735

Gln Glu Tyr Lys Lys Pro Ile Gln Thr Arg Leu Asn Leu Met Phe Leu
            740                 745                 750

Gly Gln Phe Arg Leu Gln Pro Thr Ile Asn Thr Asn Lys Asp Ser Glu
        755                 760                 765

Ile Asp Ala His Lys Gln Glu Ser Gly Ile Ala Pro Asn Phe Val His
    770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
            820                 825                 830

Val Asp Thr Tyr Glu Ser Cys Asp Val Leu Ala Asp Phe Tyr Asp Gln
        835                 840                 845

Phe Ala Asp Gln Leu His Glu Ser Gln Leu Asp Lys Met Pro Ala Leu
    850                 855                 860

Pro Ala Lys Gly Asn Leu Asn Leu Arg Asp Ile Leu Glu Ser Asp Phe
865                 870                 875                 880

Ala Phe Ala

<210> SEQ ID NO 30
<211> LENGTH: 883
<212> TYPE: PRT
<213> ORGANISM: Artificial Sequence
<220> FEATURE:
<223> OTHER INFORMATION: Synthetic Polypeptide

<400> SEQUENCE: 30

Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Ala Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95
```

```
Gly Lys Arg Pro Thr Ala Phe Gln Phe Leu Gln Ile Lys Pro Glu
            100                 105                 110

Ala Val Ala Tyr Ile Thr Ile Lys Thr Thr Leu Ala Cys Leu Thr Ser
            115                 120                 125

Ala Asp Asn Thr Thr Val Gln Ala Val Ala Ser Ala Ile Gly Arg Ala
            130                 135                 140

Ile Glu Asp Glu Ala Arg Phe Gly Arg Ile Arg Asp Leu Glu Ala Lys
145                 150                 155                 160

His Phe Lys Lys Asn Val Glu Gln Leu Asn Lys Arg Val Gly His
            165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
            195                 200                 205

Ser Ile His Val Gly Val Arg Cys Ile Glu Met Leu Ile Glu Ser Thr
            210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
            245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Tyr Trp Ala
            275                 280                 285

Asn Gly Arg Arg Pro Leu Ala Leu Val Arg Thr His Ser Lys Lys Ala
            290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
            325                 330                 335

Val Ala Asn Val Ile Thr Lys Trp Lys His Cys Pro Val Glu Asp Ile
            340                 345                 350

Pro Ala Ile Glu Arg Glu Leu Pro Met Lys Pro Glu Asp Ile Asp
            355                 360                 365

Met Asn Pro Glu Ala Leu Thr Ala Trp Lys Arg Ala Ala Ala Val
370                 375                 380

Tyr Arg His Asp Lys Ala Arg Lys Ser Arg Arg Ile Ser Leu Glu Phe
385                 390                 395                 400

Met Leu Glu Gln Ala Asn Lys Phe Ala Asn His Lys Ala Ile Trp Phe
            405                 410                 415

Pro Tyr Asn Met Asp Trp Arg Gly Arg Val Tyr Ala Val Ser Met Phe
            420                 425                 430

Asn Pro Gln Gly Asn Asp Met Thr Lys Gly Leu Leu Thr Leu Ala Lys
            435                 440                 445

Gly Lys Pro Ile Gly Lys Glu Gly Tyr Tyr Trp Leu Lys Ile His Gly
            450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
            485                 490                 495

Leu Glu Asn Thr Trp Trp Ala Glu Gln Asp Ser Pro Phe Cys Phe Leu
            500                 505                 510
```

Ala Phe Cys Phe Glu Tyr Ala Gly Val Gln His His Gly Leu Ser Tyr
515                 520                 525

Asn Cys Ser Leu Pro Leu Ala Phe Asp Gly Ser Cys Ser Gly Ile Gln
530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
            565                 570                 575

Lys Val Asn Glu Ile Leu Gln Ala Asp Ala Ile Asn Gly Thr Asp Asn
            580                 585                 590

Glu Val Val Thr Val Thr Asp Glu Asn Thr Gly Glu Ile Ser Glu Lys
            595                 600                 605

Val Lys Leu Gly Thr Lys Ala Leu Ala Gly Gln Trp Leu Ala Tyr Gly
610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Asp Thr Ile Gln
            645                 650                 655

Pro Ala Ile Asp Ser Gly Lys Gly Leu Met Phe Thr Gln Pro Asn Gln
            660                 665                 670

Ala Ala Gly Tyr Met Ala Lys Leu Ile Trp Glu Ser Val Ser Val Thr
            675                 680                 685

Val Val Ala Ala Val Glu Ala Met Asn Trp Leu Lys Ser Ala Ala Lys
            690                 695                 700

Leu Leu Ala Ala Glu Val Lys Asp Lys Lys Thr Gly Glu Ile Leu Arg
705                 710                 715                 720

Lys Arg Cys Ala Val His Trp Val Thr Pro Asp Gly Phe Pro Val Trp
                725                 730                 735

Gln Glu Tyr Lys Lys Pro Ile Gln Thr Arg Leu Asn Leu Met Phe Leu
            740                 745                 750

Gly Gln Phe Arg Leu Gln Pro Thr Ile Asn Thr Asn Lys Asp Ser Glu
            755                 760                 765

Ile Asp Ala His Lys Gln Glu Ser Gly Ile Ala Pro Asn Phe Val His
770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
            820                 825                 830

Val Asp Thr Tyr Glu Ser Cys Asp Val Leu Ala Asp Phe Tyr Asp Gln
            835                 840                 845

Phe Ala Asp Gln Leu His Glu Ser Gln Leu Asp Lys Met Pro Ala Leu
850                 855                 860

Pro Ala Lys Gly Asn Leu Asn Leu Arg Asp Ile Leu Glu Ser Asp Phe
865                 870                 875                 880

Ala Phe Ala

<210> SEQ ID NO 31
<211> LENGTH: 883
<212> TYPE: PRT
<213> ORGANISM: Artificial Sequence
<220> FEATURE:
<223> OTHER INFORMATION: Synthetic Polypeptide

```
<400> SEQUENCE: 31

Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Ala Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
    210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Gly Tyr Trp Ala
        275                 280                 285

Asn Gly Arg Arg Pro Leu Ala Leu Val Arg Thr His Ser Lys Lys Ala
    290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
            340                 345                 350

Pro Ala Ile Glu Arg Glu Glu Leu Pro Met Lys Pro Glu Asp Ile Asp
        355                 360                 365

Met Asn Pro Glu Ala Leu Thr Ala Trp Lys Arg Ala Ala Ala Ala Val
    370                 375                 380

Tyr Arg Asn Asp Lys Ala Arg Lys Ser Arg Arg Ile Ser Leu Glu Phe
385                 390                 395                 400

Met Leu Glu Gln Ala Asn Lys Phe Ala Asn His Lys Ala Ile Trp Phe
                405                 410                 415
```

```
Pro Tyr Asn Met Asp Trp Arg Gly Arg Val Tyr Ala Val Ser Met Phe
            420                 425                 430

Asn Pro Gln Gly Asn Asp Met Thr Lys Gly Leu Leu Thr Leu Ala Lys
            435                 440                 445

Gly Lys Pro Ile Gly Lys Glu Gly Tyr Tyr Trp Leu Lys Ile His Gly
            450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
            500                 505                 510

Ala Phe Cys Phe Glu Tyr Ala Gly Val Gln His His Gly Leu Ser Tyr
            515                 520                 525

Asn Cys Ser Leu Pro Leu Ala Phe Asp Gly Ser Cys Ser Gly Ile Gln
            530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                565                 570                 575

Lys Val Asn Glu Ile Leu Gln Ala Asp Ala Ile Asn Gly Thr Asp Asn
            580                 585                 590

Glu Val Val Thr Val Thr Asp Glu Asn Thr Gly Glu Ile Ser Glu Lys
            595                 600                 605

Val Lys Leu Gly Thr Lys Ala Leu Ala Gly Gln Trp Leu Ala Tyr Gly
            610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Asp Thr Ile Gln
                645                 650                 655

Pro Ala Ile Asp Ser Gly Lys Gly Leu Met Phe Thr Gln Pro Asn Gln
            660                 665                 670

Ala Ala Gly Tyr Met Ala Lys Leu Ile Trp Glu Ser Val Ser Val Thr
            675                 680                 685

Val Val Ala Ala Val Glu Ala Met Asn Trp Leu Lys Ser Ala Ala Lys
            690                 695                 700

Leu Leu Ala Ala Glu Val Lys Asp Lys Lys Thr Gly Glu Ile Leu Arg
705                 710                 715                 720

Lys Arg Cys Ala Val His Trp Val Thr Pro Asp Gly Phe Pro Val Trp
                725                 730                 735

Gln Glu Tyr Lys Lys Pro Ile Gln Thr Arg Leu Asn Leu Met Phe Leu
            740                 745                 750

Gly Gln Phe Arg Leu Gln Pro Thr Ile Asn Thr Asn Lys Asp Ser Glu
            755                 760                 765

Ile Asp Ala His Lys Gln Glu Ser Gly Ile Ala Pro Asn Phe Val His
            770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
            820                 825                 830
```

```
Val Asp Thr Tyr Glu Ser Cys Asp Val Leu Ala Asp Phe Tyr Asp Gln
            835                 840                 845

Phe Ala Asp Gln Leu His Glu Ser Gln Leu Asp Lys Met Pro Ala Leu
850                 855                 860

Pro Ala Lys Gly Asn Leu Asn Leu Arg Asp Ile Leu Glu Ser Asp Phe
865                 870                 875                 880

Ala Phe Ala

<210> SEQ ID NO 32
<211> LENGTH: 884
<212> TYPE: PRT
<213> ORGANISM: Artificial Sequence
<220> FEATURE:
<223> OTHER INFORMATION: Synthetic Polypeptide

<400> SEQUENCE: 32

Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
                20                  25                  30

Ala Arg Glu Gln Leu Ala Leu Glu His Glu Ser Tyr Glu Met Ala Glu
        35                  40                  45

Ala Arg Phe Arg Lys Met Phe Glu Arg Gln Leu Lys Ala Gly Glu Val
50                  55                  60

Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
    210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Gly Tyr Trp Ala
        275                 280                 285

Asn Gly Arg Arg Pro Leu Ala Leu Val Arg Thr His Ser Lys Lys Ala
    290                 295                 300

Leu Met Arg Tyr Glu Asp Val Tyr Met Pro Glu Val Tyr Lys Ala Ile
```

-continued

```
305                 310                 315                 320
Asn Ile Ala Gln Asn Thr Ala Trp Lys Ile Asn Lys Lys Val Leu Ala
                325                 330                 335
Val Ala Asn Val Ile Thr Lys Trp Lys His Cys Pro Val Lys Asp Ile
                340                 345                 350
Pro Ala Ile Glu Arg Glu Glu Leu Pro Met Lys Pro Glu Asp Ile Asp
                355                 360                 365
Met Asn Pro Glu Ala Leu Thr Ala Trp Lys Arg Ala Ala Ala Val
    370                 375                 380
Tyr Arg Lys Asp Lys Ala Arg Lys Ser Arg Ile Ser Leu Glu Phe
385                 390                 395                 400
Met Leu Glu Gln Ala Asn Lys Phe Ala Asn His Lys Ala Ile Trp Phe
                405                 410                 415
Pro Tyr Asn Met Asp Trp Arg Gly Arg Val Tyr Ala Val Ser Met Phe
                420                 425                 430
Asn Pro Gln Gly Asn Asp Met Thr Lys Gly Leu Leu Thr Leu Ala Lys
                435                 440                 445
Gly Lys Pro Ile Gly Lys Glu Gly Tyr Tyr Trp Leu Lys Ile His Gly
    450                 455                 460
Ala Asn Cys Ala Gly Val Asp Lys Val Pro Phe Pro Glu Arg Ile Lys
465                 470                 475                 480
Phe Ile Glu Glu Asn His Glu Asn Ile Met Ala Cys Ala Lys Ser Pro
                485                 490                 495
Leu Glu Asn Thr Trp Trp Ala Glu Gln Asp Ser Pro Phe Cys Phe Leu
                500                 505                 510
Ala Phe Cys Phe Glu Tyr Ala Gly Val Gln His His Gly Leu Ser Tyr
                515                 520                 525
Asn Cys Ser Leu Pro Leu Ala Phe Asp Gly Ser Cys Ser Gly Ile Gln
                530                 535                 540
His Phe Ser Ala Met Leu Arg Asp Glu Val Gly Gly Arg Ala Val Asn
545                 550                 555                 560
Leu Leu Pro Ser Glu Thr Val Gln Asp Ile Tyr Gly Ile Val Ala Lys
                565                 570                 575
Lys Val Asn Glu Ile Leu Gln Ala Asp Ala Ile Asn Gly Thr Asp Asn
                580                 585                 590
Glu Val Val Thr Val Thr Asp Glu Asn Thr Gly Glu Ile Ser Glu Lys
                595                 600                 605
Val Lys Leu Gly Thr Lys Ala Leu Ala Gly Gln Trp Leu Ala Tyr Gly
    610                 615                 620
Val Thr Arg Ser Val Thr Lys Arg Ser Val Met Thr Leu Ala Tyr Gly
625                 630                 635                 640
Ser Lys Glu Phe Gly Phe Arg Gln Gln Val Leu Glu Asp Thr Ile Gln
                645                 650                 655
Pro Ala Ile Asp Ser Gly Lys Gly Leu Met Phe Thr Gln Pro Asn Gln
                660                 665                 670
Ala Ala Gly Tyr Met Ala Lys Leu Ile Trp Glu Ser Val Ser Val Thr
                675                 680                 685
Val Val Ala Ala Val Glu Ala Met Asn Trp Leu Lys Ser Ala Ala Lys
                690                 695                 700
Leu Leu Ala Ala Glu Val Lys Asp Lys Lys Thr Gly Glu Ile Leu Arg
705                 710                 715                 720
Lys Arg Cys Ala Val His Trp Val Thr Pro Asp Gly Phe Pro Val Trp
                725                 730                 735
```

```
Gln Glu Tyr Lys Lys Pro Ile Gln Thr Arg Leu Asn Leu Met Phe Leu
                740                 745                 750

Gly Gln Phe Arg Leu Gln Pro Thr Ile Asn Thr Asn Lys Asp Ser Glu
            755                 760                 765

Ile Asp Ala His Lys Gln Glu Ser Gly Ile Ala Pro Asn Phe Val His
770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
            820                 825                 830

Val Asp Thr Tyr Glu Ser Cys Asp Val Leu Ala Asp Phe Tyr Asp Gln
        835                 840                 845

Phe Ala Asp Gln Leu His Glu Ser Gln Leu Asp Lys Met Pro Ala Leu
850                 855                 860

Pro Ala Lys Gly Asn Leu Asn Leu Arg Asp Ile Leu Glu Ser Asp Phe
865                 870                 875                 880

Ala Phe Ala Gly

<210> SEQ ID NO 33
<211> LENGTH: 884
<212> TYPE: PRT
<213> ORGANISM: Artificial Sequence
<220> FEATURE:
<223> OTHER INFORMATION: Synthetic Polypeptide

<400> SEQUENCE: 33

Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Ala Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205
```

```
Ser Ile His Val Gly Val Arg Cys Ile Glu Met Leu Ile Glu Ser Thr
210                 215                 220

Gly Met Val Ser Leu His Arg Gln Asn Ala Gly Val Val Gly Gln Asp
225                 230                 235                 240

Ser Glu Thr Ile Glu Leu Ala Pro Tyr Ala Glu Ala Ile Ala Thr
            245                 250                 255

Arg Ala Gly Ala Leu Ala Gly Ile Ser Pro Met Phe Gln Pro Cys Val
        260                 265                 270

Val Pro Pro Lys Pro Trp Thr Gly Ile Thr Gly Gly Tyr Trp Ala
        275                 280                 285

Asn Gly Arg Arg Pro Leu Ala Leu Val Arg Thr His Ser Lys Lys Ala
290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
            325                 330                 335

Val Ala Asn Val Ile Thr Lys Trp Lys His Cys Pro Val Asn Asp Ile
        340                 345                 350

Pro Ala Ile Glu Arg Glu Leu Pro Met Lys Pro Glu Asp Ile Asp
        355                 360                 365

Met Asn Pro Glu Ala Leu Thr Ala Trp Lys Arg Ala Ala Ala Val
370                 375                 380

Tyr Arg Lys Asp Lys Ala Arg Lys Ser Arg Arg Ile Ser Leu Glu Phe
385                 390                 395                 400

Met Leu Glu Gln Ala Asn Lys Phe Ala Asn His Lys Ala Ile Trp Phe
            405                 410                 415

Pro Tyr Asn Met Asp Trp Arg Gly Arg Val Tyr Ala Val Ser Met Phe
        420                 425                 430

Asn Pro Gln Gly Asn Asp Met Thr Lys Gly Leu Leu Thr Leu Ala Lys
        435                 440                 445

Gly Lys Pro Ile Gly Lys Glu Gly Tyr Tyr Trp Leu Lys Ile His Gly
450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
            485                 490                 495

Leu Glu Asn Thr Trp Trp Ala Glu Gln Asp Ser Pro Phe Cys Phe Leu
        500                 505                 510

Ala Phe Cys Phe Glu Tyr Ala Gly Val Gln His His Gly Leu Ser Tyr
        515                 520                 525

Asn Cys Ser Leu Pro Leu Ala Phe Asp Gly Ser Cys Ser Gly Ile Gln
530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
            565                 570                 575

Lys Val Asn Glu Ile Leu Gln Ala Asp Ala Ile Asn Gly Thr Asp Asn
        580                 585                 590

Glu Val Val Thr Val Thr Asp Glu Asn Thr Gly Glu Ile Ser Glu Lys
        595                 600                 605

Val Lys Leu Gly Thr Lys Ala Leu Ala Gly Gln Trp Leu Ala Tyr Gly
610                 615                 620

Val Thr Arg Ser Val Thr Lys Arg Ser Val Met Thr Leu Ala Tyr Gly
```

```
                   625                 630                 635                 640

Ser Lys Glu Phe Gly Phe Arg Gln Gln Val Leu Glu Asp Thr Ile Gln
                645                 650                 655

Pro Ala Ile Asp Ser Gly Lys Gly Leu Met Phe Thr Gln Pro Asn Gln
            660                 665                 670

Ala Ala Gly Tyr Met Ala Lys Leu Ile Trp Glu Ser Val Ser Val Thr
            675                 680                 685

Val Val Ala Ala Val Glu Ala Met Asn Trp Leu Lys Ser Ala Ala Lys
        690                 695                 700

Leu Leu Ala Ala Glu Val Lys Asp Lys Lys Thr Gly Glu Ile Leu Arg
705                 710                 715                 720

Lys Arg Cys Ala Val His Trp Val Thr Pro Asp Gly Phe Pro Val Trp
                725                 730                 735

Gln Glu Tyr Lys Lys Pro Ile Gln Thr Arg Leu Asn Leu Met Phe Leu
            740                 745                 750

Gly Gln Phe Arg Leu Gln Pro Thr Ile Asn Thr Asn Lys Asp Ser Glu
            755                 760                 765

Ile Asp Ala His Lys Gln Glu Ser Gly Ile Ala Pro Asn Phe Val His
        770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
            820                 825                 830

Val Asp Thr Tyr Glu Ser Cys Asp Val Leu Ala Asp Phe Tyr Asp Gln
            835                 840                 845

Phe Ala Asp Gln Leu His Glu Ser Gln Leu Asp Lys Met Pro Ala Leu
        850                 855                 860

Pro Ala Lys Gly Asn Leu Asn Leu Arg Asp Ile Leu Glu Ser Asp Phe
865                 870                 875                 880

Ala Phe Ala Gly

<210> SEQ ID NO 34
<211> LENGTH: 884
<212> TYPE: PRT
<213> ORGANISM: Artificial Sequence
<220> FEATURE:
<223> OTHER INFORMATION: Synthetic Polypeptide

<400> SEQUENCE: 34

Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Ala Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110
```

```
Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
        130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
                180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
        210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
        260                 265                 270

Val Pro Pro Lys Pro Trp Thr Gly Ile Thr Gly Gly Tyr Trp Ala
        275                 280                 285

Asn Gly Arg Arg Pro Leu Ala Leu Val Arg Thr His Ser Lys Lys Ala
        290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Ala Asp Ile
                340                 345                 350

Pro Ala Ile Glu Arg Glu Leu Pro Met Lys Pro Glu Asp Ile Asp
        355                 360                 365

Met Asn Pro Glu Ala Leu Thr Ala Trp Lys Arg Ala Ala Ala Val
        370                 375                 380

Tyr Arg Lys Asp Lys Ala Arg Lys Ser Arg Arg Ile Ser Leu Glu Phe
385                 390                 395                 400

Met Leu Glu Gln Ala Asn Lys Phe Ala Asn His Lys Ala Ile Trp Phe
                405                 410                 415

Pro Tyr Asn Met Asp Trp Arg Gly Arg Val Tyr Ala Val Ser Met Phe
                420                 425                 430

Asn Pro Gln Gly Asn Asp Met Thr Lys Gly Leu Leu Thr Leu Ala Lys
        435                 440                 445

Gly Lys Pro Ile Gly Lys Glu Gly Tyr Tyr Trp Leu Lys Ile His Gly
        450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
                500                 505                 510

Ala Phe Cys Phe Glu Tyr Ala Gly Val Gln His His Gly Leu Ser Tyr
        515                 520                 525
```

```
Asn Cys Ser Leu Pro Leu Ala Phe Asp Gly Ser Cys Ser Gly Ile Gln
    530                 535                 540
His Phe Ser Ala Met Leu Arg Asp Glu Val Gly Gly Arg Ala Val Asn
545                 550                 555                 560
Leu Leu Pro Ser Glu Thr Val Gln Asp Ile Tyr Gly Ile Val Ala Lys
                565                 570                 575
Lys Val Asn Glu Ile Leu Gln Ala Asp Ala Ile Asn Gly Thr Asp Asn
            580                 585                 590
Glu Val Thr Val Thr Asp Glu Asn Thr Gly Glu Ile Ser Glu Lys
        595                 600                 605
Val Lys Leu Gly Thr Lys Ala Leu Ala Gly Gln Trp Leu Ala Tyr Gly
610                 615                 620
Val Thr Arg Ser Val Thr Lys Arg Ser Val Met Thr Leu Ala Tyr Gly
625                 630                 635                 640
Ser Lys Glu Phe Gly Phe Arg Gln Gln Val Leu Glu Asp Thr Ile Gln
                645                 650                 655
Pro Ala Ile Asp Ser Gly Lys Gly Leu Met Phe Thr Gln Pro Asn Gln
            660                 665                 670
Ala Ala Gly Tyr Met Ala Lys Leu Ile Trp Glu Ser Val Ser Val Thr
        675                 680                 685
Val Val Ala Ala Val Glu Ala Met Asn Trp Leu Lys Ser Ala Ala Lys
690                 695                 700
Leu Leu Ala Ala Glu Val Lys Asp Lys Lys Thr Gly Glu Ile Leu Arg
705                 710                 715                 720
Lys Arg Cys Ala Val His Trp Val Thr Pro Asp Gly Phe Pro Val Trp
                725                 730                 735
Gln Glu Tyr Lys Lys Pro Ile Gln Thr Arg Leu Asn Leu Met Phe Leu
            740                 745                 750
Gly Gln Phe Arg Leu Gln Pro Thr Ile Asn Thr Asn Lys Asp Ser Glu
        755                 760                 765
Ile Asp Ala His Lys Gln Glu Ser Gly Ile Ala Pro Asn Phe Val His
770                 775                 780
Ser Gln Asp Gly Ser His Leu Arg Lys Thr Val Val Trp Ala His Glu
785                 790                 795                 800
Lys Tyr Gly Ile Glu Ser Phe Ala Leu Ile His Asp Ser Phe Gly Thr
                805                 810                 815
Ile Pro Ala Asp Ala Ala Asn Leu Phe Lys Ala Val Arg Glu Thr Met
            820                 825                 830
Val Asp Thr Tyr Glu Ser Cys Asp Val Leu Ala Asp Phe Tyr Asp Gln
        835                 840                 845
Phe Ala Asp Gln Leu His Glu Ser Gln Leu Asp Lys Met Pro Ala Leu
850                 855                 860
Pro Ala Lys Gly Asn Leu Asn Leu Arg Asp Ile Leu Glu Ser Asp Phe
865                 870                 875                 880
Ala Phe Ala Gly

<210> SEQ ID NO 35
<211> LENGTH: 884
<212> TYPE: PRT
<213> ORGANISM: Artificial Sequence
<220> FEATURE:
<223> OTHER INFORMATION: Synthetic Polypeptide

<400> SEQUENCE: 35

Met Asn Thr Ile Asn Ile Ala Lys Asn Asp Phe Ser Asp Ile Glu Leu
```

-continued

```
1               5                   10                  15
Ala Ala Ile Pro Phe Asn Thr Leu Ala Asp His Tyr Gly Glu Arg Leu
                20                  25                  30
Ala Arg Glu Gln Leu Ala Leu Glu His Glu Ser Tyr Glu Met Ala Glu
                35                  40                  45
Ala Arg Phe Arg Lys Met Phe Glu Arg Gln Leu Lys Ala Gly Glu Val
                50                  55                  60
Ala Asp Asn Ala Ala Lys Pro Leu Ile Thr Thr Leu Leu Pro Lys
65              70                  75                  80
Met Ile Ala Arg Ile Asn Asp Trp Phe Glu Val Lys Ala Lys Arg
                85                  90                  95
Gly Lys Arg Pro Thr Ala Phe Gln Phe Leu Gln Glu Ile Lys Pro Glu
                100                 105                 110
Ala Val Ala Tyr Ile Thr Ile Lys Thr Thr Leu Ala Cys Leu Thr Ser
                115                 120                 125
Ala Asp Asn Thr Thr Val Gln Ala Val Ala Ser Ala Ile Gly Arg Ala
                130                 135                 140
Ile Glu Asp Glu Ala Arg Phe Gly Arg Ile Arg Asp Leu Glu Ala Lys
145                 150                 155                 160
His Phe Lys Lys Asn Val Glu Glu Gln Leu Asn Lys Arg Val Gly His
                165                 170                 175
Val Tyr Lys Lys Ala Phe Met Gln Val Val Glu Ala Asp Met Leu Ser
                180                 185                 190
Lys Gly Leu Leu Gly Gly Glu Ala Trp Ser Ser Trp His Lys Glu Asp
                195                 200                 205
Ser Ile His Val Gly Val Arg Cys Ile Glu Met Leu Ile Glu Ser Thr
                210                 215                 220
Gly Met Val Ser Leu His Arg Gln Asn Ala Gly Val Val Gly Gln Asp
225                 230                 235                 240
Ser Glu Thr Ile Glu Leu Ala Pro Glu Tyr Ala Glu Ala Ile Ala Thr
                245                 250                 255
Arg Ala Gly Ala Leu Ala Gly Ile Ser Pro Met Phe Gln Pro Cys Val
                260                 265                 270
Val Pro Pro Lys Pro Trp Thr Gly Ile Thr Gly Gly Gly Tyr Trp Ala
                275                 280                 285
Asn Gly Arg Arg Pro Leu Ala Leu Val Arg Thr His Ser Lys Lys Ala
                290                 295                 300
Leu Met Arg Tyr Glu Asp Val Tyr Met Pro Glu Val Tyr Lys Ala Ile
305                 310                 315                 320
Asn Ile Ala Gln Asn Thr Ala Trp Lys Ile Asn Lys Lys Val Leu Ala
                325                 330                 335
Val Ala Asn Val Ile Thr Lys Trp Lys His Cys Pro Val Trp Asp Ile
                340                 345                 350
Pro Ala Ile Glu Arg Glu Glu Leu Pro Met Lys Pro Glu Asp Ile Asp
                355                 360                 365
Met Asn Pro Glu Ala Leu Thr Ala Trp Lys Arg Ala Ala Ala Val
                370                 375                 380
Tyr Arg Lys Asp Lys Ala Arg Lys Ser Arg Arg Ile Ser Leu Glu Phe
385                 390                 395                 400
Met Leu Glu Gln Ala Asn Lys Phe Ala Asn His Lys Ala Ile Trp Phe
                405                 410                 415
Pro Tyr Asn Met Asp Trp Arg Gly Arg Val Tyr Ala Val Ser Met Phe
                420                 425                 430
```

```
Asn Pro Gln Gly Asn Asp Met Thr Lys Gly Leu Leu Thr Leu Ala Lys
        435                 440                 445

Gly Lys Pro Ile Gly Lys Glu Gly Tyr Tyr Trp Leu Lys Ile His Gly
        450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
            500                 505                 510

Ala Phe Cys Phe Glu Tyr Ala Gly Val Gln His His Gly Leu Ser Tyr
        515                 520                 525

Asn Cys Ser Leu Pro Leu Ala Phe Asp Gly Ser Cys Ser Gly Ile Gln
        530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                565                 570                 575

Lys Val Asn Glu Ile Leu Gln Ala Asp Ala Ile Asn Gly Thr Asp Asn
            580                 585                 590

Glu Val Val Thr Val Thr Asp Glu Asn Thr Gly Glu Ile Ser Glu Lys
        595                 600                 605

Val Lys Leu Gly Thr Lys Ala Leu Ala Gly Gln Trp Leu Ala Tyr Gly
        610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Asp Thr Ile Gln
                645                 650                 655

Pro Ala Ile Asp Ser Gly Lys Gly Leu Met Phe Thr Gln Pro Asn Gln
            660                 665                 670

Ala Ala Gly Tyr Met Ala Lys Leu Ile Trp Glu Ser Val Ser Val Thr
        675                 680                 685

Val Val Ala Ala Val Glu Ala Met Asn Trp Leu Lys Ser Ala Ala Lys
        690                 695                 700

Leu Leu Ala Ala Glu Val Lys Asp Lys Lys Thr Gly Glu Ile Leu Arg
705                 710                 715                 720

Lys Arg Cys Ala Val His Trp Val Thr Pro Asp Gly Phe Pro Val Trp
                725                 730                 735

Gln Glu Tyr Lys Lys Pro Ile Gln Thr Arg Leu Asn Leu Met Phe Leu
            740                 745                 750

Gly Gln Phe Arg Leu Gln Pro Thr Ile Asn Thr Asn Lys Asp Ser Glu
        755                 760                 765

Ile Asp Ala His Lys Gln Glu Ser Gly Ile Ala Pro Asn Phe Val His
        770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
            820                 825                 830

Val Asp Thr Tyr Glu Ser Cys Asp Val Leu Ala Asp Phe Tyr Asp Gln
        835                 840                 845
```

```
Phe Ala Asp Gln Leu His Glu Ser Gln Leu Asp Lys Met Pro Ala Leu
            850                 855                 860

Pro Ala Lys Gly Asn Leu Asn Leu Arg Asp Ile Leu Glu Ser Asp Phe
865                 870                 875                 880

Ala Phe Ala Gly

<210> SEQ ID NO 36
<211> LENGTH: 884
<212> TYPE: PRT
<213> ORGANISM: Artificial Sequence
<220> FEATURE:
<223> OTHER INFORMATION: Synthetic Polypeptide

<400> SEQUENCE: 36

Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Ala Glu
        35                  40                  45

Ala Arg Phe Arg Lys Met Phe Glu Arg Gln Leu Lys Ala Gly Glu Val
    50                  55                  60

Ala Asp Asn Ala Ala Lys Pro Leu Ile Thr Thr Leu Leu Pro Lys
65                  70                  75                  80

Met Ile Ala Arg Ile Asn Asp Trp Phe Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
    210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Gly Tyr Trp Ala
        275                 280                 285

Asn Gly Arg Arg Pro Leu Ala Leu Val Arg Thr His Ser Lys Lys Ala
    290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
```

```
            325                 330                 335
Val Ala Asn Val Ile Thr Lys Trp Lys His Cys Pro Val Glu Val Ile
            340                 345                 350
Pro Ala Ile Glu Arg Glu Glu Leu Pro Met Lys Pro Glu Asp Ile Asp
            355                 360                 365
Met Asn Pro Glu Ala Leu Thr Ala Trp Lys Arg Ala Ala Ala Val
            370                 375                 380
Tyr Arg Lys Asp Lys Ala Arg Lys Ser Arg Arg Ile Ser Leu Glu Phe
385                 390                 395                 400
Met Leu Glu Gln Ala Asn Lys Phe Ala Asn His Lys Ala Ile Trp Phe
            405                 410                 415
Pro Tyr Asn Met Asp Trp Arg Gly Arg Val Tyr Ala Val Ser Met Phe
            420                 425                 430
Asn Pro Gln Gly Asn Asp Met Thr Lys Gly Leu Leu Thr Leu Ala Lys
            435                 440                 445
Gly Lys Pro Ile Gly Lys Glu Gly Tyr Tyr Trp Leu Lys Ile His Gly
            450                 455                 460
Ala Asn Cys Ala Gly Val Asp Lys Val Pro Phe Pro Glu Arg Ile Lys
465                 470                 475                 480
Phe Ile Glu Glu Asn His Glu Asn Ile Met Ala Cys Ala Lys Ser Pro
            485                 490                 495
Leu Glu Asn Thr Trp Trp Ala Glu Gln Asp Ser Pro Phe Cys Phe Leu
            500                 505                 510
Ala Phe Cys Phe Glu Tyr Ala Gly Val Gln His His Gly Leu Ser Tyr
            515                 520                 525
Asn Cys Ser Leu Pro Leu Ala Phe Asp Gly Ser Cys Ser Gly Ile Gln
            530                 535                 540
His Phe Ser Ala Met Leu Arg Asp Glu Val Gly Gly Arg Ala Val Asn
545                 550                 555                 560
Leu Leu Pro Ser Glu Thr Val Gln Asp Ile Tyr Gly Ile Val Ala Lys
            565                 570                 575
Lys Val Asn Glu Ile Leu Gln Ala Asp Ala Ile Asn Gly Thr Asp Asn
            580                 585                 590
Glu Val Val Thr Val Thr Asp Glu Asn Thr Gly Glu Ile Ser Glu Lys
            595                 600                 605
Val Lys Leu Gly Thr Lys Ala Leu Ala Gly Gln Trp Leu Ala Tyr Gly
            610                 615                 620
Val Thr Arg Ser Val Thr Lys Arg Ser Val Met Thr Leu Ala Tyr Gly
625                 630                 635                 640
Ser Lys Glu Phe Gly Phe Arg Gln Gln Val Leu Glu Asp Thr Ile Gln
            645                 650                 655
Pro Ala Ile Asp Ser Gly Lys Gly Leu Met Phe Thr Gln Pro Asn Gln
            660                 665                 670
Ala Ala Gly Tyr Met Ala Lys Leu Ile Trp Glu Ser Val Ser Val Thr
            675                 680                 685
Val Val Ala Ala Val Glu Ala Met Asn Trp Leu Lys Ser Ala Ala Lys
            690                 695                 700
Leu Leu Ala Ala Glu Val Lys Asp Lys Thr Gly Glu Ile Leu Arg
705                 710                 715                 720
Lys Arg Cys Ala Val His Trp Val Thr Pro Asp Gly Phe Pro Val Trp
            725                 730                 735
Gln Glu Tyr Lys Lys Pro Ile Gln Thr Arg Leu Asn Leu Met Phe Leu
            740                 745                 750
```

Gly Gln Phe Arg Leu Gln Pro Thr Ile Asn Thr Asn Lys Asp Ser Glu
            755                 760                 765

Ile Asp Ala His Lys Gln Glu Ser Gly Ile Ala Pro Asn Phe Val His
        770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
            820                 825                 830

Val Asp Thr Tyr Glu Ser Cys Asp Val Leu Ala Asp Phe Tyr Asp Gln
        835                 840                 845

Phe Ala Asp Gln Leu His Glu Ser Gln Leu Asp Lys Met Pro Ala Leu
850                 855                 860

Pro Ala Lys Gly Asn Leu Asn Leu Arg Asp Ile Leu Glu Ser Asp Phe
865                 870                 875                 880

Ala Phe Ala Gly

<210> SEQ ID NO 37
<211> LENGTH: 884
<212> TYPE: PRT
<213> ORGANISM: Artificial Sequence
<220> FEATURE:
<223> OTHER INFORMATION: Synthetic Polypeptide

<400> SEQUENCE: 37

Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Ala Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
    210                 215                 220

```
Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
            245                 250                 255

Arg Ala Gly Ala Leu Ala Gly Ile Ser Pro Met Phe Gln Pro Cys Val
        260                 265                 270

Val Pro Pro Lys Pro Trp Thr Gly Ile Thr Gly Gly Tyr Trp Ala
    275                 280                 285

Asn Gly Arg Arg Pro Leu Ala Leu Val Arg Thr His Ser Lys Lys Ala
290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
            340                 345                 350

Pro Ala Ile Glu Arg Glu Leu Pro Met Lys Pro Glu Asp Ile Asp
        355                 360                 365

Met Asn Pro Glu Ala Leu Thr Ala Trp Lys Arg Ala Ala Ala Val
370                 375                 380

Tyr Arg Ser Asp Lys Ala Arg Lys Ser Arg Arg Ile Ser Leu Glu Phe
385                 390                 395                 400

Met Leu Glu Gln Ala Asn Lys Phe Ala Asn His Lys Ala Ile Trp Phe
                405                 410                 415

Pro Tyr Asn Met Asp Trp Arg Gly Arg Val Tyr Ala Val Ser Met Phe
            420                 425                 430

Asn Pro Gln Gly Asn Asp Met Thr Lys Gly Leu Leu Thr Leu Ala Lys
                435                 440                 445

Gly Lys Pro Ile Gly Lys Glu Gly Tyr Tyr Trp Leu Lys Ile His Gly
        450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
            500                 505                 510

Ala Phe Cys Phe Glu Tyr Ala Gly Val Gln His His Gly Leu Ser Tyr
                515                 520                 525

Asn Cys Ser Leu Pro Leu Ala Phe Asp Gly Ser Cys Ser Gly Ile Gln
530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
            565                 570                 575

Lys Val Asn Glu Ile Leu Gln Ala Asp Ala Ile Asn Gly Thr Asp Asn
        580                 585                 590

Glu Val Val Thr Val Thr Asp Glu Asn Thr Gly Glu Ile Ser Glu Lys
            595                 600                 605

Val Lys Leu Gly Thr Lys Ala Leu Ala Gly Gln Trp Leu Ala Tyr Gly
        610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Asp Thr Ile Gln
```

```
                    645                 650                 655

Pro Ala Ile Asp Ser Gly Lys Gly Leu Met Phe Thr Gln Pro Asn Gln
                660                 665                 670

Ala Ala Gly Tyr Met Ala Lys Leu Ile Trp Glu Ser Val Ser Val Thr
            675                 680                 685

Val Val Ala Ala Val Glu Ala Met Asn Trp Leu Lys Ser Ala Ala Lys
        690                 695                 700

Leu Leu Ala Ala Glu Val Lys Asp Lys Thr Gly Glu Ile Leu Arg
705                 710                 715                 720

Lys Arg Cys Ala Val His Trp Val Thr Pro Asp Gly Phe Pro Val Trp
                725                 730                 735

Gln Glu Tyr Lys Lys Pro Ile Gln Thr Arg Leu Asn Leu Met Phe Leu
            740                 745                 750

Gly Gln Phe Arg Leu Gln Pro Thr Ile Asn Thr Asn Lys Asp Ser Glu
        755                 760                 765

Ile Asp Ala His Lys Gln Glu Ser Gly Ile Ala Pro Asn Phe Val His
    770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
            820                 825                 830

Val Asp Thr Tyr Glu Ser Cys Asp Val Leu Ala Asp Phe Tyr Asp Gln
        835                 840                 845

Phe Ala Asp Gln Leu His Glu Ser Gln Leu Asp Lys Met Pro Ala Leu
    850                 855                 860

Pro Ala Lys Gly Asn Leu Asn Leu Arg Asp Ile Leu Glu Ser Asp Phe
865                 870                 875                 880

Ala Phe Ala Gly

<210> SEQ ID NO 38
<211> LENGTH: 884
<212> TYPE: PRT
<213> ORGANISM: Artificial Sequence
<220> FEATURE:
<223> OTHER INFORMATION: Synthetic Polypeptide

<400> SEQUENCE: 38

Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Ala Glu
        35                  40                  45

Ala Arg Phe Arg Lys Met Phe Glu Arg Gln Leu Lys Ala Gly Glu Val
    50                  55                  60

Ala Asp Asn Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125
```

```
Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Glu Ala Asp Met Leu Ser
                180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
    210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
                260                 265                 270

Val Pro Pro Lys Pro Trp Thr Gly Ile Thr Gly Gly Tyr Trp Ala
                275                 280                 285

Asn Gly Arg Arg Pro Leu Ala Leu Val Arg Thr His Ser Lys Lys Ala
    290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
                340                 345                 350

Pro Ala Ile Glu Arg Glu Leu Pro Met Lys Pro Glu Asp Ile Asp
                355                 360                 365

Met Asn Pro Glu Ala Leu Thr Ala Trp Lys Arg Ala Ala Ala Val
370                 375                 380

Tyr Arg His Asp Lys Ala Arg Lys Ser Arg Arg Ile Ser Leu Glu Phe
385                 390                 395                 400

Met Leu Glu Gln Ala Asn Lys Phe Ala Asn His Lys Ala Ile Trp Phe
                405                 410                 415

Pro Tyr Asn Met Asp Trp Arg Gly Arg Val Tyr Ala Val Ser Met Phe
                420                 425                 430

Asn Pro Gln Gly Asn Asp Met Thr Lys Gly Leu Leu Thr Leu Ala Lys
                435                 440                 445

Gly Lys Pro Ile Gly Lys Glu Gly Tyr Tyr Trp Leu Lys Ile His Gly
450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
                500                 505                 510

Ala Phe Cys Phe Glu Tyr Ala Gly Val Gln His His Gly Leu Ser Tyr
                515                 520                 525

Asn Cys Ser Leu Pro Leu Ala Phe Asp Gly Ser Cys Ser Gly Ile Gln
    530                 535                 540
```

```
His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
            565                 570                 575

Lys Val Asn Glu Ile Leu Gln Ala Asp Ala Ile Asn Gly Thr Asp Asn
        580                 585                 590

Glu Val Thr Val Thr Asp Glu Asn Thr Gly Glu Ile Ser Glu Lys
    595                 600                 605

Val Lys Leu Gly Thr Lys Ala Leu Ala Gly Gln Trp Leu Ala Tyr Gly
    610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Asp Thr Ile Gln
            645                 650                 655

Pro Ala Ile Asp Ser Gly Lys Gly Leu Met Phe Thr Gln Pro Asn Gln
        660                 665                 670

Ala Ala Gly Tyr Met Ala Lys Leu Ile Trp Glu Ser Val Ser Val Thr
    675                 680                 685

Val Val Ala Ala Val Glu Ala Met Asn Trp Leu Lys Ser Ala Ala Lys
    690                 695                 700

Leu Leu Ala Ala Glu Val Lys Asp Lys Lys Thr Gly Glu Ile Leu Arg
705                 710                 715                 720

Lys Arg Cys Ala Val His Trp Val Thr Pro Asp Gly Phe Pro Val Trp
                725                 730                 735

Gln Glu Tyr Lys Lys Pro Ile Gln Thr Arg Leu Asn Leu Met Phe Leu
            740                 745                 750

Gly Gln Phe Arg Leu Gln Pro Thr Ile Asn Thr Asn Lys Asp Ser Glu
        755                 760                 765

Ile Asp Ala His Lys Gln Glu Ser Gly Ile Ala Pro Asn Phe Val His
    770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
            820                 825                 830

Val Asp Thr Tyr Glu Ser Cys Asp Val Leu Ala Asp Phe Tyr Asp Gln
        835                 840                 845

Phe Ala Asp Gln Leu His Glu Ser Gln Leu Asp Lys Met Pro Ala Leu
    850                 855                 860

Pro Ala Lys Gly Asn Leu Asn Leu Arg Asp Ile Leu Glu Ser Asp Phe
865                 870                 875                 880

Ala Phe Ala Gly

<210> SEQ ID NO 39
<211> LENGTH: 884
<212> TYPE: PRT
<213> ORGANISM: Artificial Sequence
<220> FEATURE:
<223> OTHER INFORMATION: Synthetic Polypeptide

<400> SEQUENCE: 39

Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
```

```
            20                  25                  30
Ala Arg Glu Gln Leu Ala Leu Glu His Glu Ser Tyr Glu Met Ala Glu
         35                  40                  45

Ala Arg Phe Arg Lys Met Phe Glu Arg Gln Leu Lys Ala Gly Glu Val
 50                  55                  60

Ala Asp Asn Ala Ala Lys Pro Leu Ile Thr Thr Leu Leu Pro Lys
 65                  70                  75                  80

Met Ile Ala Arg Ile Asn Asp Trp Phe Glu Val Lys Ala Lys Arg
                     85                  90                  95

Gly Lys Arg Pro Thr Ala Phe Gln Phe Leu Gln Glu Ile Lys Pro Glu
                 100                 105                 110

Ala Val Ala Tyr Ile Thr Ile Lys Thr Thr Leu Ala Cys Leu Thr Ser
             115                 120                 125

Ala Asp Asn Thr Thr Val Gln Ala Val Ala Ser Ala Ile Gly Arg Ala
 130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                 165                 170                 175

Val Tyr Lys Lys Ala Phe Met Gln Val Val Glu Ala Asp Met Leu Ser
             180                 185                 190

Lys Gly Leu Leu Gly Gly Glu Ala Trp Ser Ser Trp His Lys Glu Asp
         195                 200                 205

Ser Ile His Val Gly Val Arg Cys Ile Glu Met Leu Ile Glu Ser Thr
     210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                 245                 250                 255

Arg Ala Gly Ala Leu Ala Gly Ile Ser Pro Met Phe Gln Pro Cys Val
             260                 265                 270

Val Pro Pro Lys Pro Trp Thr Gly Ile Thr Gly Gly Gly Tyr Trp Ala
         275                 280                 285

Asn Gly Arg Arg Pro Leu Ala Leu Val Arg Thr His Ser Lys Lys Ala
 290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                 325                 330                 335

Val Ala Asn Val Ile Thr Lys Trp Lys His Cys Pro Val Glu Asp Ile
             340                 345                 350

Pro Ala Ile Glu Arg Glu Glu Leu Pro Met Lys Pro Glu Asp Ile Asp
         355                 360                 365

Met Asn Pro Glu Ala Leu Thr Ala Trp Lys Arg Ala Ala Ala Val
 370                 375                 380

Tyr Arg Asn Asp Lys Ala Arg Lys Ser Arg Arg Ile Ser Leu Glu Phe
385                 390                 395                 400

Met Leu Glu Gln Ala Asn Lys Phe Ala Asn His Lys Ala Ile Trp Phe
                 405                 410                 415

Pro Tyr Asn Met Asp Trp Arg Gly Arg Val Tyr Ala Val Ser Met Phe
             420                 425                 430

Asn Pro Gln Gly Asn Asp Met Thr Lys Gly Leu Leu Thr Leu Ala Lys
         435                 440                 445
```

Gly Lys Pro Ile Gly Lys Glu Gly Tyr Tyr Trp Leu Lys Ile His Gly
    450             455                 460

Ala Asn Cys Ala Gly Val Asp Lys Val Pro Phe Pro Glu Arg Ile Lys
465             470                 475                 480

Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
            500                 505                 510

Ala Phe Cys Phe Glu Tyr Ala Gly Val Gln His Gly Leu Ser Tyr
        515                 520                 525

Asn Cys Ser Leu Pro Leu Ala Phe Asp Gly Ser Cys Ser Gly Ile Gln
    530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                565                 570                 575

Lys Val Asn Glu Ile Leu Gln Ala Asp Ala Ile Asn Gly Thr Asp Asn
            580                 585                 590

Glu Val Val Thr Val Thr Asp Glu Asn Thr Gly Glu Ile Ser Glu Lys
            595                 600                 605

Val Lys Leu Gly Thr Lys Ala Leu Ala Gly Gln Trp Leu Ala Tyr Gly
    610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Asp Thr Ile Gln
                645                 650                 655

Pro Ala Ile Asp Ser Gly Lys Gly Leu Met Phe Thr Gln Pro Asn Gln
                660                 665                 670

Ala Ala Gly Tyr Met Ala Lys Leu Ile Trp Glu Ser Val Ser Val Thr
            675                 680                 685

Val Val Ala Ala Val Glu Ala Met Asn Trp Leu Lys Ser Ala Ala Lys
            690                 695                 700

Leu Leu Ala Ala Glu Val Lys Asp Lys Thr Gly Glu Ile Leu Arg
705                 710                 715                 720

Lys Arg Cys Ala Val His Trp Val Thr Pro Asp Gly Phe Pro Val Trp
                725                 730                 735

Gln Glu Tyr Lys Lys Pro Ile Gln Thr Arg Leu Asn Leu Met Phe Leu
            740                 745                 750

Gly Gln Phe Arg Leu Gln Pro Thr Ile Asn Thr Asn Lys Asp Ser Glu
        755                 760                 765

Ile Asp Ala His Lys Gln Glu Ser Gly Ile Ala Pro Asn Phe Val His
    770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
            820                 825                 830

Val Asp Thr Tyr Glu Ser Cys Asp Val Leu Ala Asp Phe Tyr Asp Gln
        835                 840                 845

Phe Ala Asp Gln Leu His Glu Ser Gln Leu Asp Lys Met Pro Ala Leu
    850                 855                 860

-continued

```
Pro Ala Lys Gly Asn Leu Asn Leu Arg Asp Ile Leu Glu Ser Asp Phe
865                 870                 875                 880

Ala Phe Ala Gly
```

<210> SEQ ID NO 40
<211> LENGTH: 884
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (350)..(350)
<223> OTHER INFORMATION: Xaa may be Ala, Lys, Asn or Trp
<220> FEATURE:
<221> NAME/KEY: misc_feature
<222> LOCATION: (387)..(387)
<223> OTHER INFORMATION: Xaa may be Ser, His or Asn

<400> SEQUENCE: 40

```
Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
                20                  25                  30

Ala Arg Glu Gln Leu Ala Leu Glu His Glu Ser Tyr Glu Met Ala Glu
            35                  40                  45

Ala Arg Phe Arg Lys Met Phe Glu Arg Gln Leu Lys Ala Gly Glu Val
        50                  55                  60

Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Gly Tyr Trp Ala
        275                 280                 285

Asn Gly Arg Arg Pro Leu Ala Leu Val Arg Thr His Ser Lys Lys Ala
290                 295                 300
```

```
Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
            325                 330                 335

Val Ala Asn Val Ile Thr Lys Trp Lys His Cys Pro Val Xaa Val Ile
        340                 345                 350

Pro Ala Ile Glu Arg Glu Leu Pro Met Lys Pro Glu Asp Ile Asp
            355                 360                 365

Met Asn Pro Glu Ala Leu Thr Ala Trp Lys Arg Ala Ala Ala Val
370                 375                 380

Tyr Arg Xaa Asp Lys Ala Arg Lys Ser Arg Arg Ile Ser Leu Glu Phe
385                 390                 395                 400

Met Leu Glu Gln Ala Asn Lys Phe Ala Asn His Lys Ala Ile Trp Phe
            405                 410                 415

Pro Tyr Asn Met Asp Trp Arg Gly Arg Val Tyr Ala Val Ser Met Phe
            420                 425                 430

Asn Pro Gln Gly Asn Asp Met Thr Lys Gly Leu Leu Thr Leu Ala Lys
            435                 440                 445

Gly Lys Pro Ile Gly Lys Glu Gly Tyr Tyr Trp Leu Lys Ile His Gly
450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
            485                 490                 495

Leu Glu Asn Thr Trp Trp Ala Glu Gln Asp Ser Pro Phe Cys Phe Leu
            500                 505                 510

Ala Phe Cys Phe Glu Tyr Ala Gly Val Gln His His Gly Leu Ser Tyr
            515                 520                 525

Asn Cys Ser Leu Pro Leu Ala Phe Asp Gly Ser Cys Ser Gly Ile Gln
530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
            565                 570                 575

Lys Val Asn Glu Ile Leu Gln Ala Asp Ala Ile Asn Gly Thr Asp Asn
            580                 585                 590

Glu Val Val Thr Val Thr Asp Glu Asn Thr Gly Glu Ile Ser Glu Lys
            595                 600                 605

Val Lys Leu Gly Thr Lys Ala Leu Ala Gly Gln Trp Leu Ala Tyr Gly
            610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Asp Thr Ile Gln
            645                 650                 655

Pro Ala Ile Asp Ser Gly Lys Gly Leu Met Phe Thr Gln Pro Asn Gln
            660                 665                 670

Ala Ala Gly Tyr Met Ala Lys Leu Ile Trp Glu Ser Val Ser Val Thr
            675                 680                 685

Val Val Ala Ala Val Glu Ala Met Asn Trp Leu Lys Ser Ala Ala Lys
            690                 695                 700

Leu Leu Ala Ala Glu Val Lys Asp Lys Lys Thr Gly Glu Ile Leu Arg
705                 710                 715                 720
```

-continued

```
Lys Arg Cys Ala Val His Trp Val Thr Pro Asp Gly Phe Pro Val Trp
                    725                 730                 735

Gln Glu Tyr Lys Lys Pro Ile Gln Thr Arg Leu Asn Leu Met Phe Leu
            740                 745                 750

Gly Gln Phe Arg Leu Gln Pro Thr Ile Asn Thr Asn Lys Asp Ser Glu
        755                 760                 765

Ile Asp Ala His Lys Gln Glu Ser Gly Ile Ala Pro Asn Phe Val His
    770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
            820                 825                 830

Val Asp Thr Tyr Glu Ser Cys Asp Val Leu Ala Asp Phe Tyr Asp Gln
        835                 840                 845

Phe Ala Asp Gln Leu His Glu Ser Gln Leu Asp Lys Met Pro Ala Leu
    850                 855                 860

Pro Ala Lys Gly Asn Leu Asn Leu Arg Asp Ile Leu Glu Ser Asp Phe
865                 870                 875                 880

Ala Phe Ala Gly

<210> SEQ ID NO 41
<211> LENGTH: 884
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (437)..(437)
<223> OTHER INFORMATION: Xaa may be Thr, Tyr, Ile or Phe

<400> SEQUENCE: 41

Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Ala Glu
        35                  40                  45

Ala Arg Phe Arg Lys Met Phe Glu Arg Gln Leu Lys Ala Gly Glu Val
    50                  55                  60

Ala Asp Asn Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175
```

```
Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
    210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Tyr Trp Ala
        275                 280                 285

Asn Gly Arg Arg Pro Leu Ala Leu Val Arg Thr His Ser Lys Lys Ala
    290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
            340                 345                 350

Pro Ala Ile Glu Arg Glu Glu Leu Pro Met Lys Pro Glu Asp Ile Asp
        355                 360                 365

Met Asn Pro Glu Ala Leu Thr Ala Trp Lys Arg Ala Ala Ala Val
370                 375                 380

Tyr Arg Lys Asp Lys Ala Arg Lys Ser Arg Ile Ser Leu Glu Phe
385                 390                 395                 400

Met Leu Glu Gln Ala Asn Lys Phe Ala Asn His Lys Ala Ile Trp Phe
                405                 410                 415

Pro Tyr Asn Met Asp Trp Arg Gly Arg Val Tyr Ala Val Ser Met Phe
            420                 425                 430

Asn Pro Gln Gly Xaa Asp Met Thr Arg Gly Leu Leu Thr Leu Ala Lys
        435                 440                 445

Gly Lys Pro Ile Gly Lys Glu Gly Tyr Tyr Trp Leu Lys Ile His Gly
    450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
            500                 505                 510

Ala Phe Cys Phe Glu Tyr Ala Gly Val Gln His His Gly Leu Ser Tyr
        515                 520                 525

Asn Cys Ser Leu Pro Leu Ala Phe Asp Gly Ser Cys Ser Gly Ile Gln
    530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                565                 570                 575

Lys Val Asn Glu Ile Leu Gln Ala Asp Ala Ile Asn Gly Thr Asp Asn
            580                 585                 590

Glu Val Val Thr Val Thr Asp Glu Asn Thr Gly Glu Ile Ser Glu Lys
```

```
                595                 600                 605
Val Lys Leu Gly Thr Lys Ala Leu Ala Gly Gln Trp Leu Ala Tyr Gly
        610                 615                 620
Val Thr Arg Ser Val Thr Lys Arg Ser Val Met Thr Leu Ala Tyr Gly
625                 630                 635                 640
Ser Lys Glu Phe Gly Phe Arg Gln Gln Val Leu Glu Asp Thr Ile Gln
            645                 650                 655
Pro Ala Ile Asp Ser Gly Lys Gly Leu Met Phe Thr Gln Pro Asn Gln
        660                 665                 670
Ala Ala Gly Tyr Met Ala Lys Leu Ile Trp Glu Ser Val Ser Val Thr
            675                 680                 685
Val Val Ala Ala Val Glu Ala Met Asn Trp Leu Lys Ser Ala Ala Lys
        690                 695                 700
Leu Leu Ala Ala Glu Val Lys Asp Lys Thr Gly Glu Ile Leu Arg
705                 710                 715                 720
Lys Arg Cys Ala Val His Trp Val Thr Pro Asp Gly Phe Pro Val Trp
                725                 730                 735
Gln Glu Tyr Lys Lys Pro Ile Gln Thr Arg Leu Asn Leu Met Phe Leu
            740                 745                 750
Gly Gln Phe Arg Leu Gln Pro Thr Ile Asn Thr Asn Lys Asp Ser Glu
        755                 760                 765
Ile Asp Ala His Lys Gln Glu Ser Gly Ile Ala Pro Asn Phe Val His
    770                 775                 780
Ser Gln Asp Gly Ser His Leu Arg Lys Thr Val Val Trp Ala His Glu
785                 790                 795                 800
Lys Tyr Gly Ile Glu Ser Phe Ala Leu Ile His Asp Ser Phe Gly Thr
                805                 810                 815
Ile Pro Ala Asp Ala Ala Asn Leu Phe Lys Ala Val Arg Glu Thr Met
            820                 825                 830
Val Asp Thr Tyr Glu Ser Cys Asp Val Leu Ala Asp Phe Tyr Asp Gln
        835                 840                 845
Phe Ala Asp Gln Leu His Glu Ser Gln Leu Asp Lys Met Pro Ala Leu
    850                 855                 860
Pro Ala Lys Gly Asn Leu Asn Leu Arg Asp Ile Leu Glu Ser Asp Phe
865                 870                 875                 880
Ala Phe Ala Gly

<210> SEQ ID NO 42
<211> LENGTH: 884
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (884)..(884)
<223> OTHER INFORMATION: Xaa may be Ala, Ser, Thr or Phe

<400> SEQUENCE: 42

Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Ala Glu
        35                  40                  45

Ala Arg Phe Arg Lys Met Phe Glu Arg Gln Leu Lys Ala Gly Glu Val
```

```
                  50                  55                  60

Ala Asp Asn Ala Ala Lys Pro Leu Ile Thr Thr Leu Leu Pro Lys
 65                  70                  75                  80

Met Ile Ala Arg Ile Asn Asp Trp Phe Glu Val Lys Ala Lys Arg
                     85                  90                  95

Gly Lys Arg Pro Thr Ala Phe Gln Phe Leu Gln Glu Ile Lys Pro Glu
                100                 105                 110

Ala Val Ala Tyr Ile Thr Ile Lys Thr Thr Leu Ala Cys Leu Thr Ser
                115                 120                 125

Ala Asp Asn Thr Thr Val Gln Ala Val Ala Ser Ala Ile Gly Arg Ala
130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
                180                 185                 190

Lys Gly Leu Leu Gly Gly Glu Ala Trp Ser Ser Trp His Lys Glu Asp
                195                 200                 205

Ser Ile His Val Gly Val Arg Cys Ile Glu Met Leu Ile Glu Ser Thr
                210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
                260                 265                 270

Val Pro Pro Lys Pro Trp Thr Gly Ile Thr Gly Gly Tyr Trp Ala
                275                 280                 285

Asn Gly Arg Arg Pro Leu Ala Leu Val Arg Thr His Ser Lys Lys Ala
                290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
                340                 345                 350

Pro Ala Ile Glu Arg Glu Leu Pro Met Lys Pro Glu Asp Ile Asp
                355                 360                 365

Met Asn Pro Glu Ala Leu Thr Ala Trp Lys Arg Ala Ala Ala Val
370                 375                 380

Tyr Arg Lys Asp Lys Ala Arg Lys Ser Arg Arg Ile Ser Leu Glu Phe
385                 390                 395                 400

Met Leu Glu Gln Ala Asn Lys Phe Ala Asn His Lys Ala Ile Trp Phe
                405                 410                 415

Pro Tyr Asn Met Asp Trp Arg Gly Arg Val Tyr Ala Val Ser Met Phe
                420                 425                 430

Asn Pro Gln Gly Asn Asp Met Thr Lys Gly Leu Leu Thr Leu Ala Lys
                435                 440                 445

Gly Lys Pro Ile Gly Lys Glu Gly Tyr Tyr Trp Leu Lys Ile His Gly
                450                 455                 460

Ala Asn Cys Ala Gly Val Asp Lys Val Pro Phe Pro Glu Arg Ile Lys
465                 470                 475                 480
```

```
Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
            500                 505                 510

Ala Phe Cys Phe Glu Tyr Ala Gly Val Gln His His Gly Leu Ser Tyr
        515                 520                 525

Asn Cys Ser Leu Pro Leu Ala Phe Asp Gly Ser Cys Ser Gly Ile Gln
    530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                565                 570                 575

Lys Val Asn Glu Ile Leu Gln Ala Asp Ala Ile Asn Gly Thr Asp Asn
            580                 585                 590

Glu Val Val Thr Val Thr Asp Glu Asn Thr Gly Glu Ile Ser Glu Lys
        595                 600                 605

Val Lys Leu Gly Thr Lys Ala Leu Ala Gly Gln Trp Leu Ala Tyr Gly
    610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Asp Thr Ile Gln
                645                 650                 655

Pro Ala Ile Asp Ser Gly Lys Gly Leu Met Phe Thr Gln Pro Asn Gln
            660                 665                 670

Ala Ala Gly Tyr Met Ala Lys Leu Ile Trp Glu Ser Val Ser Val Thr
        675                 680                 685

Val Val Ala Ala Val Glu Ala Met Asn Trp Leu Lys Ser Ala Ala Lys
    690                 695                 700

Leu Leu Ala Ala Glu Val Lys Asp Lys Lys Thr Gly Glu Ile Leu Arg
705                 710                 715                 720

Lys Arg Cys Ala Val His Trp Val Thr Pro Asp Gly Phe Pro Val Trp
                725                 730                 735

Gln Glu Tyr Lys Lys Pro Ile Gln Thr Arg Leu Asn Leu Met Phe Leu
            740                 745                 750

Gly Gln Phe Arg Leu Gln Pro Thr Ile Asn Thr Asn Lys Asp Ser Glu
        755                 760                 765

Ile Asp Ala His Lys Gln Glu Ser Gly Ile Ala Pro Asn Phe Val His
    770                 775                 780

Ser Gln Asp Gly Ser His Leu Arg Lys Thr Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
            820                 825                 830

Val Asp Thr Tyr Glu Ser Cys Asp Val Leu Ala Asp Phe Tyr Asp Gln
        835                 840                 845

Phe Ala Asp Gln Leu His Glu Ser Gln Leu Asp Lys Met Pro Ala Leu
    850                 855                 860

Pro Ala Lys Gly Asn Leu Asn Leu Arg Asp Ile Leu Glu Ser Asp Tyr
865                 870                 875                 880

Ala Phe Ala Xaa
```

```
<210> SEQ ID NO 43
<211> LENGTH: 884
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (632)..(632)
<223> OTHER INFORMATION: Xaa may be Lys or Thr
<220> FEATURE:
<221> NAME/KEY: misc_feature
<222> LOCATION: (653)..(653)
<223> OTHER INFORMATION: Xaa may be Lys or Thr
<220> FEATURE:
<221> NAME/KEY: misc_feature
<222> LOCATION: (657)..(657)
<223> OTHER INFORMATION: Xaa may be Trp, Arg or Ala

<400> SEQUENCE: 43

Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Ala Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
    210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Gly Tyr Trp Ala
        275                 280                 285

Asn Gly Arg Arg Pro Leu Ala Leu Val Arg Thr His Ser Lys Lys Ala
    290                 295                 300

Leu Met Arg Tyr Glu Asp Val Tyr Met Pro Glu Val Tyr Lys Ala Ile
```

```
        305                 310                 315                 320
Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
                340                 345                 350

Pro Ala Ile Glu Arg Glu Glu Leu Pro Met Lys Pro Glu Asp Ile Asp
                355                 360                 365

Met Asn Pro Glu Ala Leu Thr Ala Trp Lys Arg Ala Ala Ala Val
    370                 375                 380

Tyr Arg Lys Asp Lys Ala Arg Lys Ser Arg Ile Ser Leu Glu Phe
385                 390                 395                 400

Met Leu Glu Gln Ala Asn Lys Phe Ala Asn His Lys Ala Ile Trp Phe
                405                 410                 415

Pro Tyr Asn Met Asp Trp Arg Gly Arg Val Tyr Ala Val Ser Met Phe
                420                 425                 430

Asn Pro Gln Gly Asn Asp Met Thr Lys Gly Leu Leu Thr Leu Ala Lys
                435                 440                 445

Gly Lys Pro Ile Gly Lys Glu Gly Tyr Tyr Trp Leu Lys Ile His Gly
                450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
                500                 505                 510

Ala Phe Cys Phe Glu Tyr Ala Gly Val Gln His His Gly Leu Ser Tyr
                515                 520                 525

Asn Cys Ser Leu Pro Leu Ala Phe Asp Gly Ser Cys Ser Gly Ile Gln
                530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                565                 570                 575

Lys Val Asn Glu Ile Leu Gln Ala Asp Ala Ile Asn Gly Thr Asp Asn
                580                 585                 590

Glu Val Val Thr Val Thr Asp Glu Asn Thr Gly Glu Ile Ser Glu Lys
                595                 600                 605

Val Lys Leu Gly Thr Lys Ala Leu Ala Gly Gln Trp Leu Ala Tyr Gly
                610                 615                 620

Val Thr Arg Ser Val Thr Lys Xaa Ser Val Met Thr Leu Ala Tyr Gly
625                 630                 635                 640

Ser Lys Glu Phe Gly Phe Arg Gln Gln Val Leu Glu Xaa Thr Ile Gln
                645                 650                 655

Xaa Ala Ile Asp Ser Gly Lys Gly Leu Met Phe Thr Gln Pro Asn Gln
                660                 665                 670

Ala Ala Gly Tyr Met Ala Lys Leu Ile Trp Glu Ser Val Ser Val Thr
                675                 680                 685

Val Val Ala Ala Val Glu Ala Met Asn Trp Leu Lys Ser Ala Ala Lys
                690                 695                 700

Leu Leu Ala Ala Glu Val Lys Asp Lys Lys Thr Gly Glu Ile Leu Arg
705                 710                 715                 720

Lys Arg Cys Ala Val His Trp Val Thr Pro Asp Gly Phe Pro Val Trp
                725                 730                 735
```

```
Gln Glu Tyr Lys Lys Pro Ile Gln Thr Arg Leu Asn Leu Met Phe Leu
                740                 745                 750

Gly Gln Phe Arg Leu Gln Pro Thr Ile Asn Thr Asn Lys Asp Ser Glu
            755                 760                 765

Ile Asp Ala His Lys Gln Glu Ser Gly Ile Ala Pro Asn Phe Val His
    770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
            820                 825                 830

Val Asp Thr Tyr Glu Ser Cys Asp Val Leu Ala Asp Phe Tyr Asp Gln
        835                 840                 845

Phe Ala Asp Gln Leu His Glu Ser Gln Leu Asp Lys Met Pro Ala Leu
850                 855                 860

Pro Ala Lys Gly Asn Leu Asn Leu Arg Asp Ile Leu Glu Ser Asp Phe
865                 870                 875                 880

Ala Phe Ala Gly

<210> SEQ ID NO 44
<211> LENGTH: 884
<212> TYPE: PRT
<213> ORGANISM: Artificial Sequence
<220> FEATURE:
<223> OTHER INFORMATION: Synthetic Polypeptide

<400> SEQUENCE: 44

Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
                20                  25                  30

Ala Arg Glu Gln Leu Ala Leu Glu His Glu Ser Tyr Glu Met Gly Glu
            35                  40                  45

Ala Arg Phe Arg Lys Met Phe Glu Arg Gln Leu Lys Ala Gly Glu Val
        50                  55                  60

Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205
```

```
Ser Ile His Val Gly Val Arg Cys Ile Glu Met Leu Ile Glu Ser Thr
210                 215                 220
Gly Met Val Ser Leu His Arg Gln Asn Ala Gly Val Val Gly Gln Asp
225                 230                 235                 240
Ser Glu Thr Ile Glu Leu Ala Pro Tyr Ala Glu Ala Ile Ala Thr
            245                 250                 255
Arg Ala Gly Ala Leu Ala Gly Ile Ser Pro Met Phe Gln Pro Cys Val
            260                 265                 270
Val Pro Pro Lys Pro Trp Thr Gly Ile Thr Gly Gly Tyr Trp Ala
            275                 280                 285
Asn Gly Arg Arg Pro Leu Ala Leu Val Arg Thr His Ser Lys Lys Ala
290                 295                 300
Leu Met Arg Tyr Glu Asp Val Tyr Met Pro Glu Val Tyr Lys Ala Ile
305                 310                 315                 320
Asn Ile Ala Gln Asn Thr Ala Trp Lys Ile Asn Lys Lys Val Leu Ala
                325                 330                 335
Val Ala Asn Val Ile Thr Lys Trp Lys His Cys Pro Val Glu Asp Ile
            340                 345                 350
Pro Ala Ile Glu Arg Glu Leu Pro Met Lys Pro Glu Asp Ile Asp
            355                 360                 365
Met Asn Pro Glu Ala Leu Thr Ala Trp Lys Arg Ala Ala Ala Val
370                 375                 380
Tyr Arg Lys Asp Lys Ala Arg Lys Ser Arg Arg Ile Ser Leu Glu Phe
385                 390                 395                 400
Met Leu Glu Gln Ala Asn Lys Phe Ala Asn His Lys Ala Ile Trp Phe
                405                 410                 415
Pro Tyr Asn Met Asp Trp Arg Gly Arg Val Tyr Ala Val Ser Met Phe
            420                 425                 430
Asn Pro Gln Gly Asn Asp Met Thr Lys Gly Leu Leu Thr Leu Ala Lys
            435                 440                 445
Gly Lys Pro Ile Gly Lys Glu Tyr Tyr Trp Leu Lys Ile His Gly
450                 455                 460
Ala Asn Cys Ala Gly Val Asp Lys Val Pro Phe Pro Glu Arg Ile Lys
465                 470                 475                 480
Phe Ile Glu Glu Asn His Glu Asn Ile Met Ala Cys Ala Lys Ser Pro
                485                 490                 495
Leu Glu Asn Thr Trp Trp Ala Glu Gln Asp Ser Pro Phe Cys Phe Leu
            500                 505                 510
Ala Phe Cys Phe Glu Tyr Ala Gly Val Gln His His Gly Leu Ser Tyr
            515                 520                 525
Asn Cys Ser Leu Pro Leu Ala Phe Asp Gly Ser Cys Ser Gly Ile Gln
530                 535                 540
His Phe Ser Ala Met Leu Arg Asp Glu Val Gly Gly Arg Ala Val Asn
545                 550                 555                 560
Leu Leu Pro Ser Glu Thr Val Gln Asp Ile Tyr Gly Ile Val Ala Lys
                565                 570                 575
Lys Val Asn Glu Ile Leu Gln Ala Asp Ala Ile Asn Gly Thr Asp Asn
            580                 585                 590
Glu Val Val Thr Val Thr Asp Glu Asn Thr Gly Glu Ile Ser Glu Lys
            595                 600                 605
Val Lys Leu Gly Thr Lys Ala Leu Ala Gly Gln Trp Leu Ala Tyr Gly
            610                 615                 620
Val Thr Arg Ser Val Thr Lys Arg Ser Val Met Thr Leu Ala Tyr Gly
```

```
            625                 630                 635                 640

Ser Lys Glu Phe Gly Phe Arg Gln Gln Val Leu Glu Asp Thr Ile Gln
                    645                 650                 655

Pro Ala Ile Asp Ser Gly Lys Gly Leu Met Phe Thr Gln Pro Asn Gln
                    660                 665                 670

Ala Ala Gly Tyr Met Ala Lys Leu Ile Trp Glu Ser Val Ser Val Thr
                    675                 680                 685

Val Val Ala Ala Val Glu Ala Met Asn Trp Leu Lys Ser Ala Ala Lys
                690                 695                 700

Leu Leu Ala Ala Glu Val Lys Asp Lys Lys Thr Gly Glu Ile Leu Arg
    705                 710                 715                 720

Lys Arg Cys Ala Val His Trp Val Thr Pro Asp Gly Phe Pro Val Trp
                    725                 730                 735

Gln Glu Tyr Lys Lys Pro Ile Gln Thr Arg Leu Asn Leu Met Phe Leu
                    740                 745                 750

Gly Gln Phe Arg Leu Gln Pro Thr Ile Asn Thr Asn Lys Asp Ser Glu
                    755                 760                 765

Ile Asp Ala His Lys Gln Glu Ser Gly Ile Ala Pro Asn Phe Val His
                    770                 775                 780

Ser Gln Asp Gly Ser His Leu Arg Lys Thr Val Val Trp Ala His Glu
    785                 790                 795                 800

Lys Tyr Gly Ile Glu Ser Phe Ala Leu Ile His Asp Ser Phe Gly Thr
                    805                 810                 815

Ile Pro Ala Asp Ala Ala Asn Leu Phe Lys Ala Val Arg Glu Thr Met
                    820                 825                 830

Val Asp Thr Tyr Glu Ser Cys Asp Val Leu Ala Asp Phe Tyr Asp Gln
                    835                 840                 845

Phe Ala Asp Gln Leu His Glu Ser Gln Leu Asp Lys Met Pro Ala Leu
                    850                 855                 860

Pro Ala Lys Gly Asn Leu Asn Leu Arg Asp Ile Leu Glu Ser Asp Phe
    865                 870                 875                 880

Ala Phe Ala Gly

<210> SEQ ID NO 45
<211> LENGTH: 884
<212> TYPE: PRT
<213> ORGANISM: Artificial Sequence
<220> FEATURE:
<223> OTHER INFORMATION: Synthetic Polypeptide

<400> SEQUENCE: 45

Met Asn Thr Ile Asn Ile Ala Lys Asn Asp Phe Ser Asp Ile Glu Leu
    1               5                   10                  15

Ala Ala Ile Pro Phe Asn Thr Leu Ala Asp His Tyr Gly Glu Arg Leu
                    20                  25                  30

Ala Arg Glu Gln Leu Ala Leu Glu His Glu Ser Tyr Glu Met Ala Glu
                    35                  40                  45

Ala Arg Phe Arg Lys Met Phe Glu Arg Gln Leu Lys Ala Gly Glu Val
                    50                  55                  60

Ala Asp Asn Ala Ala Ala Lys Pro Leu Ile Thr Thr Leu Leu Pro Lys
    65                  70                  75                  80

Met Ile Ala Arg Ile Asn Asp Trp Phe Glu Glu Val Lys Ala Lys Arg
                    85                  90                  95

Gly Lys Arg Pro Thr Ala Phe Gln Phe Leu Gln Glu Ile Lys Pro Glu
                    100                 105                 110
```

```
Ala Val Ala Tyr Ile Thr Ile Lys Thr Thr Leu Ala Cys Leu Thr Ser
            115                 120                 125

Ala Asp Asn Thr Thr Val Gln Ala Val Ala Ser Ala Ile Gly Arg Ala
        130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
            195                 200                 205

Ser Ile His Val Gly Val Arg Cys Ile Glu Met Leu Ile Glu Ser Thr
        210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Tyr Trp Ala
            275                 280                 285

Asn Gly Arg Arg Pro Leu Ala Leu Val Arg Thr His Ser Lys Lys Ala
        290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
            340                 345                 350

Pro Ala Ile Glu Arg Glu Leu Pro Met Lys Pro Glu Asp Ile Asp
        355                 360                 365

Met Asn Pro Glu Ala Leu Thr Ala Trp Lys Arg Ala Ala Ala Val
        370                 375                 380

Tyr Arg Lys Asp Lys Ala Arg Lys Ser Arg Arg Ile Ser Leu Glu Phe
385                 390                 395                 400

Met Leu Glu Gln Ala Asn Lys Phe Ala Asn His Lys Ala Ile Trp Phe
                405                 410                 415

Pro Tyr Asn Met Asp Trp Arg Gly Arg Val Tyr Ala Val Ser Met Phe
            420                 425                 430

Asn Pro Gln Gly Asn Asp Met Thr Lys Gly Leu Leu Thr Leu Ala Lys
        435                 440                 445

Gly Lys Pro Ile Gly Lys Glu Gly Tyr Tyr Trp Leu Lys Ile His Gly
        450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
            500                 505                 510

Ala Phe Cys Phe Glu Tyr Ala Gly Val Gln His His Gly Leu Ser Tyr
            515                 520                 525
```

-continued

Asn Cys Ser Leu Pro Leu Ala Phe Asp Gly Ser Cys Ser Gly Ile Gln
530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
            565                 570                 575

Lys Val Asn Glu Ile Leu Gln Ala Asp Ala Ile Asn Gly Thr Asp Asn
        580                 585                 590

Glu Val Thr Val Thr Asp Glu Asn Thr Gly Glu Ile Ser Glu Lys
    595                 600                 605

Val Lys Leu Gly Thr Lys Ala Leu Ala Gly Gln Trp Leu Ala Tyr Gly
610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Asp Thr Ile Gln
            645                 650                 655

Pro Ala Ile Asp Ser Gly Lys Gly Leu Met Phe Thr Gln Pro Asn Gln
        660                 665                 670

Ala Ala Gly Tyr Met Ala Lys Leu Ile Trp Glu Ser Val Ser Val Thr
    675                 680                 685

Val Val Ala Ala Val Glu Ala Met Asn Trp Leu Lys Ser Ala Ala Lys
690                 695                 700

Leu Leu Ala Ala Glu Val Lys Asp Lys Lys Thr Gly Glu Ile Leu Arg
705                 710                 715                 720

Lys Arg Cys Ala Val His Trp Val Thr Pro Asp Gly Phe Pro Val Trp
            725                 730                 735

Gln Glu Tyr Lys Lys Pro Ile Gln Thr Arg Leu Asn Leu Met Phe Leu
        740                 745                 750

Gly Gln Phe Arg Leu Gln Pro Thr Ile Asn Thr Asn Lys Asp Ser Glu
    755                 760                 765

Ile Asp Ala His Lys Gln Glu Ser Gly Ile Ala Pro Asn Phe Val His
770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
            805                 810                 815

Ile Pro Ala Asp Ala Ala Asn Leu Phe Lys Ala Val Arg Glu Thr Met
        820                 825                 830

Val Asp Thr Tyr Glu Ser Cys Asp Val Leu Ala Asp Phe Tyr Asp Gln
    835                 840                 845

Phe Ala Asp Gln Leu His Glu Ser Gln Leu Asp Lys Met Pro Ala Leu
850                 855                 860

Pro Ala Lys Gly Asn Leu Asn Leu Arg Asp Ile Leu Glu Ser Asp Phe
865                 870                 875                 880

Ala Phe Ala Gly

<210> SEQ ID NO 46
<211> LENGTH: 31
<212> TYPE: DNA
<213> ORGANISM: Artificial Sequence
<220> FEATURE:
<223> OTHER INFORMATION: Synthetic Polynucleotide

<400> SEQUENCE: 46
acgtggacta tctgttcaaa cgcatgatcg a                               31

```
<210> SEQ ID NO 47
<211> LENGTH: 41
<212> TYPE: DNA
<213> ORGANISM: Artificial Sequence
<220> FEATURE:
<223> OTHER INFORMATION: Synthetic Polynucleotide

<400> SEQUENCE: 47
ccgcgccaga atctgttgcg acctggacgt gctggccagc a                    41

<210> SEQ ID NO 48
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 48
ttcgtcgacg atatcatcca gcccagctcc acccgcgcca gaatctgttg cgacctggac    60

<210> SEQ ID NO 49
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 49
ttcgtcgacg atatcatcca gcccagctcc acccgcgcca ggatttgctg cgacctggac    60

<210> SEQ ID NO 50
<211> LENGTH: 11
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: misc_feature
<222> LOCATION: (10)..(11)
<223> OTHER INFORMATION: n is a, c, g, or t

<400> SEQUENCE: 50
nnatctgttn n                                                      11

<210> SEQ ID NO 51
<211> LENGTH: 11
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: n is a, c, g, or u
<220> FEATURE:
<221> NAME/KEY: misc_feature
<222> LOCATION: (10)..(11)
<223> OTHER INFORMATION: n is a, c, g, or u

<400> SEQUENCE: 51
nnaucuguun n                                                      11
```